United States Patent
Benz et al.

(10) Patent No.: US 11,390,610 B2
(45) Date of Patent: Jul. 19, 2022

(54) PIPERAZINE DERIVATIVES AS MAGL INHIBITORS

(71) Applicant: Hoffmann-La Roche Inc., Little Falls, NJ (US)

(72) Inventors: Joerg Benz, Basel (CH); Uwe Grether, Basel (CH); Benoit Hornsperger, Basel (CH); Bernd Kuhn, Basel (CH); Hans Richter, Basel (CH); Buelent Kocer, Basel (CH); Fionn O'Hara, Basel (CH); Martin Ritter, Basel (CH); Satoshi Tsuchiya, Tokyo (JP); Ludovic Collin, Basel (CH); Simon E. Johnson, Basel (CH); Charles Bell, Basel (CH)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 16/827,211

(22) Filed: Mar. 23, 2020

(65) Prior Publication Data

US 2020/0299277 A1 Sep. 24, 2020

Related U.S. Application Data

(63) Continuation of application No. PCT/EP2018/077377, filed on Oct. 9, 2018.

(30) Foreign Application Priority Data

Oct. 10, 2017 (EP) ...................................... 17195653

(51) Int. Cl.
| | | |
|---|---|---|
| *A61K 31/517* | (2006.01) | |
| *C07D 403/14* | (2006.01) | |
| *C07D 401/14* | (2006.01) | |
| *C07D 403/04* | (2006.01) | |
| *C07D 405/14* | (2006.01) | |
| *C07D 413/14* | (2006.01) | |
| *C07D 417/14* | (2006.01) | |
| *C07D 471/04* | (2006.01) | |
| *C07D 471/08* | (2006.01) | |
| *C07D 487/10* | (2006.01) | |
| *C07D 491/107* | (2006.01) | |

(52) U.S. Cl.
CPC ......... *C07D 403/14* (2013.01); *C07D 401/14* (2013.01); *C07D 403/04* (2013.01); *C07D 405/14* (2013.01); *C07D 413/14* (2013.01); *C07D 417/14* (2013.01); *C07D 471/04* (2013.01); *C07D 471/08* (2013.01); *C07D 487/10* (2013.01); *C07D 491/107* (2013.01)

(58) Field of Classification Search
None
See application file for complete search history.

(56) References Cited

U.S. PATENT DOCUMENTS

| | | |
|---|---|---|
| 10,106,556 B2 | 10/2018 | Ikeda et al. |
| 10,610,520 B2 | 4/2020 | Ikeda et al. |
| 2020/0255439 A1 | 8/2020 | Kamata et al. |
| 2020/0299277 A1 | 9/2020 | Benz et al. |
| 2020/0308158 A1 | 10/2020 | Bell et al. |
| 2020/0308190 A1 | 10/2020 | Bell et al. |
| 2020/0392125 A1 | 12/2020 | Benz et al. |
| 2021/0024546 A1 | 1/2021 | Petersen et al. |
| 2021/0094943 A1 | 4/2021 | Benz et al. |
| 2021/0094971 A1 | 4/2021 | Grether et al. |
| 2021/0094972 A1 | 4/2021 | Benz et al. |
| 2021/0094973 A1 | 4/2021 | Gobbi et al. |
| 2021/0107920 A1 | 4/2021 | Bell et al. |
| 2021/0107921 A1 | 4/2021 | Benz et al. |
| 2021/0277020 A1 | 9/2021 | Anselm et al. |
| 2021/0387999 A1 | 12/2021 | Kuhn et al. |

FOREIGN PATENT DOCUMENTS

| | | |
|---|---|---|
| WO | 2007/025897 A3 | 3/2007 |
| WO | 2009/071650 A2 | 6/2009 |
| WO | 2013/132253 A1 | 9/2013 |
| WO | 2016/094730 A1 | 6/2016 |

(Continued)

OTHER PUBLICATIONS

Alpar, A., et al., "Endocannabinoids modulate cortical development by configuring Slit2/Robo1 signaling" Nat Commun 5(4421):1-13 (Jul. 17, 2014).

(Continued)

*Primary Examiner* — Samantha L Shterengarts
(74) *Attorney, Agent, or Firm* — Katherine J. Mackenzie

(57) ABSTRACT

The invention provides new heterocyclic compounds having the general Formula (I), or a pharmaceutically acceptable salt thereof,

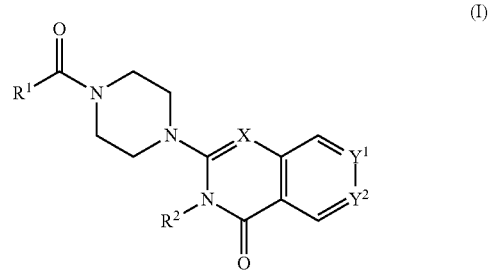

wherein $R^1$, $R^2$, X, $Y^1$ and $Y^2$ are as described herein, compositions including the compounds, processes of manufacturing the compounds and methods of using the compounds.

38 Claims, No Drawings

(56) References Cited

FOREIGN PATENT DOCUMENTS

| WO | 2017/087854 A1 | 5/2017 |
|---|---|---|
| WO | 2017/171100 A1 | 10/2017 |
| WO | 2019/105915 A1 | 6/2019 |
| WO | 2019/115660 A1 | 6/2019 |
| WO | 2019/134985 A1 | 7/2019 |
| WO | 2019/180185 A1 | 9/2019 |
| WO | 2020/035424 A1 | 2/2020 |
| WO | 2020/035425 A1 | 2/2020 |

OTHER PUBLICATIONS

Bernal-Chico, A., et al., "Blockade of Monoacylglycerol Lipase Inhibits Oligodendrocyte Excitotoxicity and Prevents Demyelination In Vivo" GLIA 63(1):163-176 (Jan. 1, 2015).

Caruso et al., "Four Partners, Three-Step, One-Pot Reaction for a Library of New 2-Alkyl(dialkyl)aminoquinazolin-4(3H)-ones" Journal of Heterocyclic Chemistry 51(S1):E282-E293 ( 2014).

Chanda, P.K., et al., "Monoacylglycerol Lipase Activity Is a Critical Modulator of the Tone and Integrity of the Endocannabinoid System" Mol Pharmacol 78(6):996-1003 (Dec. 1, 2010).

Couturier et al., "Identification and optimization of a new series of anti-tubercular quinazolinones" Bioorg. Med. Chem. Lett. 26:5290-5299 ( 2016).

Feliu, A., et al., "2-Arachidonoylglycerol Reduces Proteoglycans and Enhances Remyelination in a Progressive Model of Demyelination" J Neurosci 37(35):8385-8398 (Aug. 30, 2017).

Hou et al., "Evaluation of Novel N-(piperidine-4-yl)benzamide Derivatives as Potential Cell Cycle Inhibitors in HepG2 Cells" Chem Biol Drug Des 86:223-231 ( 2015).

Iannotti, F., et al., "Endocannabinoids and endocannabinoid-related mediators: Targets, metabolism and role in neurological disorders" Prog Lipid Res 62:107-128 (Apr. 1, 2016).

Ignatowska-Jankowska, B., et al., "Selective Monoacylglycerol Lipase Inhibitors: Antinociceptive versus Cannabimimetic Effects in Mice" J Pharmacol Exp Ther 353(2):424-432 (May 1, 2015).

International Search Report and Written Opinion for PCT/EP2018/077377 dated Nov. 6, 2018.

Jacobs et al., "The Synthehis of o-Amino-N-substituted Senzamides arid 3-Substituted 2,4( IH,3H)-Quinazolinediones from Isatoic Anhydride" J. Het. Chem 7(6):1337-1345 ( 1970).

Jonckers et al., "Benzoxazole and benzothiazole amides as novel pharmacokinetic enhancers of HIV protease inhibitors" Bioorg. Med. Chem. Lett. 22:4998-5002 ( 2012).

Korhonen et al., "Piperazine and piperidine carboxamides and carbamates as inhibitors of fatty acid amide hydrolase (FAAH) and monoacylglycerol lipase (MAGL)" Bioorganic & medicinal Chemistry 22:6694-6705 ( 2014).

Li et al., "One-pot synthesis of benzo[a]phenanthridin-5-ones by photoinduced cycloaddition of 3-chloroisoquinolin-1-ones with styrenes" Tetrahedron Letters 51:3748-3751 ( 2010).

Lleo, A., et al., "Molecular targets of non-steroidal anti-inflammatory drugs in neurodegenerative diseases" Cell Mol Life Sci 64(11):1403-1418 (Apr. 20, 2007).

Long, J., et al., "Selective blockade of 2-arachidonoylglycerol hydrolysis produces cannabinoid behavioral effects" Nat Chem Biol 5(1):37-44 (Jan. 1, 2009).

Muccioli, G., et al., "CAY10499, a Novel Monoglyceride Lipase Inhibitor Evidenced by an Expeditious MGL Assay" Chem Bio Chem 9(16):2704-2710 (Nov. 3, 2008).

Mukaiyama et al., "New Synthetic Reactions Based on the Onium Salts of Aza-Arenes" Angew. Chem., Int. Ed. Engl. 18(10):707-808 ( 1979).

Nomura, D.K., et al., "Endocannabinoid Hydrolysis Generates Brain Prostaglandins That Promote Neuroinflammation" Science 334(6057):809-813 (Nov. 11, 2011).

Nomura, D.K., et al., "Monoacylglycerol Lipase Exerts Dual Control over Endocannabinoid and Fatty Acid Pathways to Support Prostate Cancer" Chem Biol 18(7):846-856 (Jul. 29, 2011).

Prabhakar et al., "Palladium catalyzed suzuki couplingreaction for synthesis of novel DI substituted quinazoline-sulphonamide derivatives and their biological screening" Heterocyclic Letters 6(4):775-793 ( 2016).

Qin, Hong, et al., "The role of monoacylglycerol lipase (MAGL) in the cancer progress" Cell Biochem Biophys 70(1):33-36 (Mar. 16, 2014).

Ram et al., "Synthesis and Antihyperglycemic Activity of Suitably Functionalized 3H-quinazolin-4-ones" Bioorg. Med. Chem. 11:2493-2444 ( 2003).

Samrin et al., "Synthesis and Antibacterial Activity of New Diaryldiamines" J. Heterocyclic Chem., 49:1391-1397 ( 2012,).

Sartori and Bigi, "Selected syntheses of ureas through phosgene substitutes" Green Chemistry 2:140-148 ( 2000).

Shen et al., "Highly Reactive, General and Long-Lived Catalysts for Palladium-Catalyzed Amination of Heteroaryl and Aryl Chlorides, Bromides, and Iodides: Scope and Structure-Activity Relationships" J. Am. Chem. Soc 130:6586-6596 ( 2008).

U.S. Appl. No. 16/844,262.

U.S. Appl. No. 16/884,562.

Viader, A., et al., "Reports Article Metabolic Interplay between Astrocytes and Neurons Regulates Endocannabinoid Action" Cell Rep 12(5):798-808 (Aug. 4, 2015).

Wang et al., "One-pot synthesis of benzo[f ]quinolin-3-ones and benzo[a]phenanthridein-5-ones by the photoanuulation of 6-chloropyridin-2-ones and 3-chloroisoquinolin-1-ones to phenylacetylene" Org. Biomol. Chem. 9:5802-5808 ( 2011).

Zhong, P., et al., "Monoacylglycerol Lipase Inhibition Blocks Chronic Stress-Induced Depressive-Like Behaviors via Activation of mTOR Signaling" Neuropsychopharmacology 39(7):1763-1776 (Feb. 19, 2014).

Zunszain et al., "Search for the pharmacophore in prazosin for Transport-P" Bioorganic & Medicinal Chemistry 13:3681-3689 ( 2005).

"U.S. Appl. No. 17/325,934, filed May 20, 2021."

"U.S. Appl. No. 17/174,000, filed Feb. 11, 2021."

Mulvihill, M., et al., "Therapeutic Potential of Monoacylglycerol Lipase Inhibitors" Life Sci 92(8-9):492-497 (Nov. 8, 2013).

"U.S. Appl. No. 17/497,633, filed Oct. 8, 2021."

"U.S. Appl. No. 17/465,536, filed Sep. 2, 2021."

"U.S. Appl. No. 17/552,792, filed Dec. 16, 2021".

"U.S. Appl. No. 17/569,749, filed Jan. 6, 2022".

U.S. Appl. No. 17/692,632, filed Mar. 11, 2022.

U.S. Appl. No. 17/700,987, filed Mar. 22, 2022.

PIPERAZINE DERIVATIVES AS MAGL INHIBITORS

CROSS REFERENCE TO RELATED APPLICATIONS

This application is a continuation of International Application No. PCT/EP2018/077377, filed Oct. 9, 2018, which claims priority to EP Application No. 17195653.5, filed Oct. 10, 2017, the disclosures of each of which are incorporated herein by reference in their entirety.

FIELD OF THE INVENTION

The present invention relates to organic compounds useful for therapy or prophylaxis in a mammal, and in particular to monoacylglycerol lipase (MAGL) inhibitors for the treatment or prophylaxis of neuroinflammation, neurodegenerative diseases, pain, cancer, mental disorders, multiple sclerosis, Alzheimer's disease, Parkinson's disease, amyotrophic lateral sclerosis, traumatic brain injury, neurotoxicity, stroke, epilepsy, anxiety, migraine or depression, or any combination thereof, in a mammal.

BACKGROUND OF THE INVENTION

Endocannabinoids (ECs) are signaling lipids that exert their biological actions by interacting with cannabinoid receptors (CBRs), CB1 and CB2. They modulate multiple physiological processes including neuroinflammation, neurodegeneration and tissue regeneration (Iannotti, F. A., et al., *Progress in lipid research* 2016, 62, 107-28.). In the brain, the main endocannabinoid, 2-arachidonoylglycerol (2-AG), is produced by diacyglycerol lipases (DAGL) and hydrolyzed by the monoacylglycerol lipase, MAGL. MAGL hydrolyses 85% of 2-AG; the remaining 15% being hydrolysed by ABHD6 and ABDH12 (Nomura, D. K., et al., *Science* 2011, 334, 809.). MAGL is expressed throughout the brain and in most brain cell types, including neurons, astrocytes, oligodendrocytes and microglia cells (Chanda, P. K., et al., *Molecular pharmacology* 2010, 78, 996.; Viader, A., et al., *Cell reports* 2015, 72, 798.). 2-AG hydrolysis results in the formation of arachidonic acid (AA), the precursor of prostaglandins (PGs) and leukotrienes (LTs). Oxidative metabolism of AA is increased in inflamed tissues. There are two principal enzyme pathways of arachidonic acid oxygenation involved in inflammatory processes, the cyclo-oxygenase which produces PGs and the 5-lipoxygenase which produces LTs. Of the various cyclooxygenase products formed during inflammation, PGE2 is one of the most important. These products have been detected at sites of inflammation, e.g. in the cerebrospinal fluid of patients suffering from neurodegenerative disorders and are believed to contribute to inflammatory response and disease progression. Mice lacking MAGL (Mgll−/−) exhibit dramatically reduced 2-AG hydrolase activity and elevated 2-AG levels in the nervous system while other arachidonoy-containing phospho- and neutral lipid species including anandamide (AEA), as well as other free fatty acids, are unaltered. Conversely, levels of AA and AA-derived prostaglandins and other eicosanoids, including prostaglandin E2 (PGE2), D2 (PGD2), F2 (PGF2), and thromboxane B2 (TXB2), are strongly decreased. Phospholipase $A_2$ ($PLA_2$) enzymes have been viewed as the principal source of AA, but $cPLA_2$-deficient mice have unaltered AA levels in their brain, reinforcing the key role of MAGL in the brain for AA production and regulation of the brain inflammatory process.

Neuroinflammation is a common pathological change characteristic of diseases of the brain including, but not restricted to, neurodegenerative diseases (e.g. multiple sclerosis, Alzheimer's disease, Parkinson disease, amyotrophic lateral sclerosis, traumatic brain injury, neurotoxicity, stroke, epilepsy and mental disorders such as anxiety and migraine). In the brain, production of eicosanoids and prostaglandins controls the neuroinflammation process. The pro-inflammatory agent lipopolysaccharide (LPS) produces a robust, time-dependent increase in brain eicosanoids that is markedly blunted in Mgll−/− mice. LPS treatment also induces a widespread elevation in pro-inflammatory cytokines including interleukin-1-a (IL-1-a), IL-1b, IL-6, and tumor necrosis factor-a (TNF-α) that is prevented in Mgll−/− mice.

Neuroinflammation is characterized by the activation of the innate immune cells of the central nervous system, the microglia and the astrocytes. It has been reported that anti-inflammatory drugs can suppress in preclinical models the activation of glia cells and the progression of disease including Alzheimer's disease and multiple sclerosis (Lleo A., *Cell Mol Life Sci.* 2007, 64, 1403.). Importantly, genetic and/or pharmacological disruption of MAGL activity also blocks LPS-induced activation of microglial cells in the brain (Nomura, D. K., et al., *Science* 2011, 334, 809.).

In addition, genetic and/or pharmacological disruption of MAGL activity was shown to be protective in several animal models of neurodegeneration including, but not restricted to, Alzheimer's disease, Parkinson's disease and multiple sclerosis. For example, an irreversible MAGL inhibitor has been widely used in preclinical models of neuroinflammation and neurodegeneration (Long, J. Z., et al., *Nature chemical biology* 2009, 5, 37.). Systemic injection of such inhibitor recapitulates the Mgll−/− mice phenotype in the brain, including an increase in 2-AG levels, a reduction in AA levels and related eicosanoids production, as well as the prevention of cytokines production and microglia activation following LPS-induced neuroinflammation (Nomura, D. K., et al., *Science* 2011, 334, 809.), altogether confirming that MAGL is a druggable target.

Consecutive to the genetic and/or pharmacological disruption of MAGL activity, the to endogenous levels of the MAGL natural substrate in the brain, 2-AG, are increased. 2-AG has been reported to show beneficial effects on pain with, for example, anti-nociceptive effects in mice (Ignatowska-Jankowska B. et al., *J. Pharmacol. Exp. Ther.* 2015, 353, 424.) and on mental disorders, such as depression in chronic stress models (Zhong P. et al., *Neuropsychopharmacology* 2014, 39, 1763.).

Furthermore, oligodendrocytes (OLs), the myelinating cells of the central nervous system, and their precursors (OPCs) express the cannabinoid receptor 2 (CB2) on their membrane. 2-AG is the endogenous ligand of CB1 and CB2 receptors. It has been reported that both cannabinoids and pharmacological inhibition of MAGL attenuate OLs's and OPCs's vulnerability to excitotoxic insults and therefore may be neuroprotective (Bernal-Chico, A., et al., *Glia* 2015, 63, 163.). Additionally, pharmacological inhibition of MAGL increases the number of myelinating OLs in the brain of mice, suggesting that MAGL inhibition may promote differentiation of OPCs in myelinating OLs in vivo (Alpar, A., et al., *Nature communications* 2014, 5, 4421.). Inhibition of MAGL was also shown to promote remyelination and functional recovery in a mouse model of progressive multiple sclerosis (Feliu A. et al., *Journal of Neuroscience* 2017, 37 (35), 8385.).

Finally, in recent years, metabolism is talked highly important in cancer research, especially the lipid metabolism. Researchers believe that the de novo fatty acid synthesis plays an important role in tumor development, while many studies illustrated that endocannabinoids have anti-tumorigenic actions, including anti-proliferation, apoptosis induction, and anti-metastatic effects, MAGL as an important decomposing enzyme of both lipid metabolism and endocannabinoids system, additionally as a part of a gene expression signature contributes to different aspects of tumourigenesis (Qin, H., et al., *Cell Biochem. Biophys.* 2014, 70, 33; Nomura D K et al., *Cell* 2009, 140(1), 49-61; Nomura D K et al., *Chem. Biol.* 2011,18(7), 846-856).

Suppressing the action and/or the activation of MAGL is a promising new therapeutic strategy for the treatment or prevention of neuroinflammation, neurodegenerative diseases, pain, cancer and mental disorders. Furthermore, suppressing the action and/or the activation of MAGL is a promising new therapeutic strategy for providing neuroprotection and myelin regeneration. Accordingly, there is a high unmet medical need for new MAGL inhibitors.

SUMMARY OF THE INVENTION

In a first aspect, the present invention provides compounds of Formula (I)

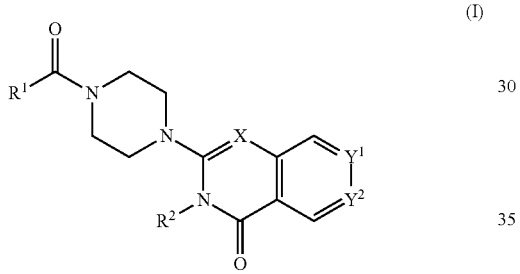

(I)

wherein:
X is C—H or N;
$Y^1$ is selected from the group consisting of C—H, C—F, C-alkyl, C-haloalkyl and N;
$Y^2$ is selected from the group consisting of C—H, C-halogen, C-alkyl and C-haloalkyl;
$R^1$ is selected from the group consisting of:
  i. aryl,
  ii. substituted aryl,
  iii. heteroaryl,
  iv. substituted heteroaryl,
  v. heterocyclyl,
  vi. substituted heterocyclyl,
  vii. cycloalkyl and
  viii. substituted cycloalkyl, wherein:
    each of said substituted aryl, substituted heteroaryl, substituted heterocyclyl and substituted cycloalkyl is independently substituted with one or more substituents selected from the group consisting of aminoalkyl, amino, haloalkylaryl, cycloalkyl, cycloalkylaryl, aryl-alkenyl, haloaryl-alkenyl, cyano(haloaryl), haloarylsulfonyl, alkyl(hydroxyheterocyclyl), alkyl(haloheterocyclyl), arylalkoxyalkylheteroaryl, hydroxyalkynyl, haloalkylaryl-alkoxyalkyl, haloalkylheteroaryl, haloalkylheterocyclyl, alkylheteroaryl, arylcycloalkyl, hydroxyalkylheterocyclyl, alkylsulfanyl, alkoxyheterocyclyl, cycloalkylheteroaryl, alkylcycloalkylheteroaryl, haloalkylcycloalkylheteroaryl, alkoxyalkylheteroaryl, alkoxyalkylheterocyclyl, alkoxyalkylaryl, cycloalkylalkoxy, arylalkoxy, aryloxyalkyl, haloaryloxyalkyl, aryloxyaryl, aryloxyheteroaryl, aryloxy, haloalkylaryloxy, halogen, heterocyclyl, hydroxyheterocyclyl, heterocyclylalkyl, heteroaryl, aryl, aryl-C(O)—, haloaryl, haloheteroaryl, halocycloalkyl, haloalkoxy, hydroxyalkoxy, alkoxyalkoxy, hydroxyalkoxyaryl, hydroxyalkoxyheteroaryl, alkoxy, alkyl, haloalkyl, cyano, cyanoaryl, cyanoheteroaryl, cyanocycloalkyl, cyanoalkylaryl, arylheterocyclyl, alkoxy-(haloalkyl)aryl, alkylaryl, arylalkoxy-(alkyl)aryl, haloaryloxy, hydroxyalkylaryl, hydroxyalkylheteroaryl, alkenyloxy, pentafluoro-lambda6-sulfanyl, heteroarylalkyl, heteroarylalkoxy, haloheteroarylalkoxy, alkoxyaryl, alkoxyheteroaryl, (arylalkoxy)aryl, (arylalkoxy)heteroaryl, carbamoylaryl, alkyl-(alkoxy)aryl, haloalkoxyaryl, haloalkoxyheteroaryl, alkylheterocyclyl, haloheterocyclyl, alkylhaloaryl, haloalkylhaloaryl and haloarylalkoxy, wherein:

said aminoalkyl is substituted on the nitrogen atom with one or two substituents independently selected from the group consisting of H, alkyl, cycloalkyl, alkanoyl, arylalkyl and haloalkylarylalkyl; and said amino is substituted on the nitrogen atom with one or two substituents independently selected from the group consisting of H, alkyl, haloalkyl, cycloalkyl, hydroxyalkyl, alkoxyalkyl, haloarylalkyl, haloalkoxyarylalkyl, benzyl and benzyl substituted with a substituent selected from the group consisting of halogen, alkyl and haloalkyl; and $R^2$ is selected from the group consisting of hydrogen and alkyl;

or a pharmaceutically acceptable salt thereof.

In a further aspect, the present invention provides a process of manufacturing the compounds of Formula (I) as described herein, comprising the steps of:

a) reacting an amine 1, wherein $R^2$, X, $Y^1$ and $Y^2$ are as described herein,

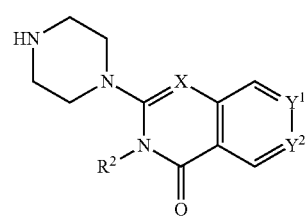

1 with an acid 2, wherein $R^1$ is as described herein

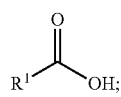

2 or b) reacting an amine 1, wherein $R^2$, X, $Y^1$ and $Y^2$ are as described herein,

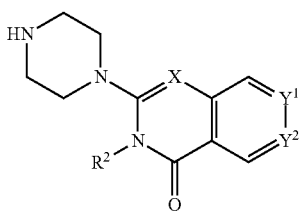

with an acid chloride 2a, wherein R¹ is as described herein

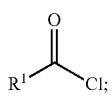

or c) reacting a compound of formula 3, wherein $R^2$, $Y^1$ and $Y^2$ are as described herein

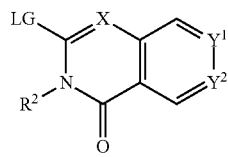

with a piperazine derivative 4, wherein R¹ is as described herein

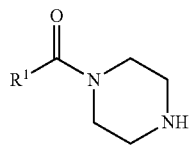

to form said compound of Formula (I).

In a further aspect, the present invention provides a compound according to Formula (I) as described herein, when manufactured according to any one of the described processes.

In a further aspect, the present invention provides compounds of Formula (I) as described herein for use as therapeutically active substance.

In a further aspect, the present invention provides a pharmaceutical composition comprising a compound of Formula (I) as described herein and a pharmaceutically acceptable excipient.

In a further aspect, the present invention provides the use of compounds of Formula (I) as described herein for inhibiting monoacylglycerol lipase (MAGL) in a mammal.

In a further aspect, the present invention provides the use of compounds of Formula (I) as described herein for the treatment or prophylaxis of neuroinflammation, neurodegenerative diseases, pain, cancer or mental disorders, or any combination thereof, in a mammal.

In a further aspect, the present invention provides the use of compounds of Formula (I) as described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer or pain, or any combination thereof, in a mammal.

In a further aspect, the present invention provides compounds of Formula (I) as described herein for use in a method of inhibiting monoacylglycerol lipase (MAGL) in a mammal.

In a further aspect, the present invention provides compounds of Formula (I) as described herein for use in the treatment or prophylaxis of neuroinflammation, neurodegenerative diseases, pain, cancer or mental disorders, or any combination thereof, in a mammal.

In a further aspect, the present invention provides compounds of Formula (I) as described herein for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer or pain, or any combination thereof, in a mammal.

In a further aspect, the present invention provides the use of compounds of Formula (I) as described herein for the preparation of a medicament for inhibiting monoacylglycerol lipase in a mammal.

In a further aspect, the present invention provides the use of compounds of Formula (I) as described herein for the preparation of a medicament for the treatment or prophylaxis of neuroinflammation, neurodegenerative diseases, pain, cancer or mental disorders, or any combination thereof, in a mammal.

In a further aspect, the present invention provides the use of compounds of Formula (I) as described herein for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer or pain, or any combination thereof, in a mammal.

In a further aspect, the present invention provides a method for inhibiting monoacylglycerol lipase in a mammal, which method comprises administering an effective amount of a compound of Formula (I) as described herein to the mammal.

In a further aspect, the present invention provides a method for the treatment or prophylaxis of neuroinflammation, neurodegenerative diseases, pain, cancer or mental disorders, or any combination thereof, in a mammal, which method comprises administering an effective amount of a compound of Formula (I) as described herein to the mammal.

In a further aspect, the present invention provides a method for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer or pain, or any combination thereof, in a mammal, which method comprises administering an effective amount of a compound of Formula (I) as described herein to the mammal.

In a further aspect, the present invention provides compounds of Formula (I) and their pharmaceutically acceptable salts as described herein, wherein said compounds of Formula (I) and their pharmaceutically acceptable salts have $IC_{50}$'s for MAGL inhibition below 25 μM, preferably below 10 µM, more preferably below 5 µM, as measured in the MAGL assay described herein.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., mono-, bi- or trivalent, linear or branched saturated hydrocarbon group of 1 to 12 carbon atoms ("$C_{1-12}$-alkyl"). In some preferred embodiments, the alkyl group contains 1 to 6 carbon atoms ("$C_{1-6}$-alkyl"), e.g., 1, 2, 3, 4, 5, or 6 carbon atoms. In other embodiments, the alkyl group contains 1 to 3 carbon atoms ("$C_{1-3}$-alkyl"), e.g., 1, 2 or 3 carbon atoms. Examples of alkyl groups include, but are not limited to, methyl, ethyl, propyl, 2-propyl (isopropyl), n-butyl, isobutyl, sec-butyl, tert-butyl, and 2,2-dimethylpropyl. In a particularly preferred embodiment, alkyl is methyl, propyl, isopropyl, tert-butyl, or 2,2-dimethylpropyl.

The term "alkenyl" refers to a linear or branched-chain mono- or multivalent, e.g., mono-, bi- or trivalent, hydrocarbon radical of 2 to 12 carbon atoms ("$C_{2-12}$-alkenyl") with at least one site of unsaturation, i.e., a carbon-carbon, sp$^2$ double bond, and includes radicals having "cis" and "trans" orientations, or alternatively, "E" and "Z" orientations. In some embodiments, the alkenyl group contains 2 to 8 carbon atoms ("$C_{2-8}$-alkenyl"). In some preferred embodiments, the alkenyl group contains 2 to 6 carbon atoms ("$C_{2-6}$-alkenyl"), and in still other embodiments, the alkenyl group contains 2 to 4 carbon atoms ("$C_{2-4}$-alkenyl"). Examples of alkenyl groups include, but are not limited to, ethylenyl or vinyl (—CH=CH$_2$), allyl (—CH$_2$CH=CH$_2$), and the like.

The term "alkynyl" refers to a linear or branched-chain mono- or multivalent, e.g., mono-, bi- or trivalent, hydrocarbon radical of 2 to 12 carbon atoms ("$C_{2-12}$-alkynyl") comprising at least one carbon-carbon triple bond. In some embodiments, the alkynyl group contains 2 to 8 carbon atoms ("$C_{2-8}$-alkynyl"). In some preferred embodiments, the alkynyl group contains 2 to 6 carbon atoms ("$C_{%6}$-alkynyl"), and in still other embodiments, the alkynyl group contains 2 to 4 carbon atoms ("$C_{2-4}$-alkynyl"). Examples of alkynyl groups include, but are not limited to, ethynyl, prop-1-ynyl and 3-methylbut-1-ynyl.

The term "alkoxy" refers to an alkyl group, as previously defined, attached to the parent molecular moiety via an oxygen atom. Unless otherwise specified, the alkoxy group contains 1 to 12 carbon atoms ("$C_{1-12}$-alkoxy"). In some preferred embodiments, the alkoxy group contains 1 to 6 carbon atoms ("$C_{1-6}$-alkoxy"). In other embodiments, the alkoxy group contains 1 to 4 carbon atoms ("$C_{1-4}$-alkoxy"). In still other embodiments, the alkoxy group contains 1 to 3 carbon atoms ("$C_{1-3}$-alkoxy"). Some non-limiting examples of alkoxy groups include, but are not limited to, methoxy, ethoxy, n-propoxy, isopropoxy, n-butoxy, isobutoxy and tert-butoxy. In a preferred embodiment, alkoxy is methoxy, ethoxy and isopropoxy. In a particularly preferred embodiment, alkoxy is methoxy.

The term "alkenyloxy" refers to an alkenyl group, as previously defined, attached to the parent molecular moiety via an oxygen atom. In a preferred embodiment, alkenyloxy is allyloxy.

The term "alkoxyalkyl" refers to an alkyl group, wherein at least one of the hydrogen atoms of the alkyl group has been replaced by an alkoxy group. In a preferred embodiment, "alkoxyalkyl" refers to an alkyl group wherein 1 hydrogen atom of the alkyl group has been replaced by an alkoxy group. In a particularly preferred embodiment, alkoxyalkyl is 2-methoxyethyl.

The term "halogen" or "halo" refers to fluoro (F), chloro (Cl), bromo (Br), or iodo (I).

The term "cyano" denotes a —C≡N group.

The term "haloalkyl" or "haloalkoxy", respectively, refers to an alkyl or alkoxy group, as the case may be, substituted with one or more halogen atoms, wherein each of the alkyl or alkoxy is defined as described herein. In a preferred embodiment, the haloalkyl or haloalkoxy group, respectively, contains 1, 2 or 3 halogen atoms, most preferably 1, 2 or 3 F atoms. Examples of such groups include, but are not limited to, fluoromethyl, difluoromethyl, trifluoromethyl (CF$_3$), 2,2,2-trifluoroethyl, trifluoromethoxy, 2,2,2-trifluoroethoxy, 2,2,3,3-tetrafluoropropoxy, and the like.

The term "cyanoalkyl" refers to an alkyl group substituted with one or more cyano (—CN) groups, wherein the alkyl is defined as described herein. In a preferred embodiment, the cyanoalkyl group contains 1, 2 or 3 cyano groups. In a particularly preferred embodiment, the cyanoalkyl group is cyanomethyl.

The term "hydroxyalkyl" refers to an alkyl group substituted with one or more hydroxy (—OH) groups, wherein the alkyl group is defined as described herein. In a preferred embodiment, the hydroxyalkyl group contains 1, 2 or 3 hydroxy groups. In a particularly preferred embodiment, the hydroxyalkyl group is hydroxymethyl.

The term "hydroxyalkynyl" refers to an alkynyl group substituted with one or more hydroxy (—OH) groups, wherein the alkynyl group is defined as described herein. In a preferred embodiment, the hydroxyalkynyl group contains 1, 2 or 3 hydroxy groups, in particular 1 hydroxy group. In a particularly preferred embodiment, the hydroxyalkynyl group is 3-hydroxy-3-methyl-but-1-ynyl.

The term "cycloalkyl" refers to a monocyclic or bicyclic hydrocarbon group of 3 to ring carbon atoms ("$C_{3-10}$-cycloalkyl"). In some embodiments, the cycloalkyl group is a saturated monocyclic hydrocarbon group of 3 to 8 ring carbon atoms ("$C_{3-8}$-cycloalkyl"). "Bicyclic cycloalkyl" means a cycloalkyl moiety consisting of two saturated carbocycles having two carbon atoms in common. In a preferred embodiment, the cycloalkyl group is a monocyclic hydrocarbon group of 3 to 6 ring carbon atoms ("$C_{3-6}$-cycloalkyl"), e.g., of 3, 4, 5 or 6 carbon atoms. Examples for monocyclic cycloalkyl groups include, but are not limited to, cyclopropyl, cyclobutyl, cyclopentyl, cyclohexyl or cycloheptyl. Examples for bicyclic cycloalkyl groups include, but are not limited to, bicyclo[1.1.1]pentanyl, bicyclo[2.2.1]heptanyl and bicyclo[2.2.2]octanyl. In a particularly preferred embodiment, the cycloalkyl group is a bicyclo[1.1.1]pentanyl, cyclopropyl, cyclopentyl or cyclohexyl group. "Substituted cycloalkyl" means that the cycloalkyl radical is substituted with one or more substituents described herein, preferably with 1, 2 or 3 substituents described herein, most preferably with 1 or 2 substituents described herein.

The term "heterocyclyl" refers to a saturated or partly unsaturated mono- or bicyclic ring system of 3 to 12 ring atoms ("$C_{2-11}$-heterocyclyl"), preferably 3 to 10 ring atoms ("$C_{1-9}$-heterocyclyl"), more preferably 3-8 ring atoms ("$C_{1-7}$-heterocyclyl"), most preferably 3-6 ring atoms ("$C_{1-5}$-heterocyclyl"), wherein 1, 2, or 3 of said ring atoms are heteroatoms selected from the group consisting of N, O and S, the remaining ring atoms being carbon. "Bicyclic heterocyclyl", which is encompassed by the term "heterocyclyl" as indicated above, refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. In a preferred embodiment, the heterocyclyl group is a saturated, mono- or bicyclic heterocyclyl group of 3 to 7 ring atoms, e.g., of 3, 4, 5, 6 or 7 ring atoms ("$C_{1-6}$-heterocyclyl"). Examples for monocyclic saturated heterocyclyl include, but are not limited to, oxetanyl, azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocyclyl include, but are not limited to, 3,9-diazaspiro[5.5]undecan-3-yl, 8-oxa-2-azaspiro[4.5]decan-2-yl, 2,7-diazaspiro[4.4]nonan-7-yl, 2-azabicyclo[2.2.1]heptanyl, 8-aza-bicyclo[3.2.1]octyl, 2-azaspiro[3.3]heptan-2-yl, 1-azaspiro[3.3]heptan-1-yl, 1-azaspiro[3.4]octan-1-yl, 2-azaspiro[3.4]octan-2-yl, 1-azaspiro[3.5]nonan-1-yl, 2-azaspiro[3.5]nonan-2-yl, 4-azaspiro[2.4]heptan-4-yl, 5-azaspiro[2.4]heptan-5-yl, 6-azaspiro[3.4]octan-6-yl, 5-azaspiro[3.4]octan-5-yl, 1-azaspiro[4.4]nonane-1-yl, 2-azaspiro[4.4]nonane-2-yl, 5-azaspiro[2.5]octane-5-yl, 6-azaspiro[2.5]octane-6-yl, 6-azaspiro[3.5]nonane-6-yl, and 7-azaspiro[3.5]nonane-7-yl, 2-oxa-6-azaspiro[3.3]heptanyl, 6,6-difluoro-2-azaspiro[3.3]heptanyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocyclyl include, but are not limited to dihydrofuryl, imidazolinyl, dihydrooxazolyl, tetrahydro-pyridyl, or dihydropyranyl. In a preferred embodiment, a heterocyclyl group is piperidinyl, pyrrolidinyl, morpholinyl, azepanyl, azetidinyl, 2-azabicyclo[2.2.1]heptanyl, 2-azaspiro[3.4]octanyl, 2-azaspiro[3.3]heptanyl, 2-oxa-6-azaspiro[3.3]heptanyl, 3,9-diazaspiro[5.5]undecan-3-yl, 6-hydroxy-2-azaspiro[3.3]heptan-2-yl, or 6,6-difluoro-2-azaspiro[3.3]heptanyl (e.g., 6,6-difluoro-2-azaspiro[3.3]heptan-2-yl). "Substituted heterocyclyl" means that the heterocyclyl radical is substituted with one or more substituents described herein, preferably with 1, 2 or 3 substituents described herein, most preferably with 1 or 2 substituents described herein.

The term "aryl" refers to a monocyclic, bicyclic, or tricyclic carbocyclic ring system having a total of 6 to 14 ring members ("$C_{6-14}$-aryl"), preferably, 6 to 12 ring members ("$C_{6-12}$-aryl"), and more preferably 6 to 10 ring members ("$C_{6-10}$-aryl"), and wherein at least one ring in the system is aromatic. Examples of aryl rings may include phenyl, naphthyl, indanyl and anthracenyl. In a particularly preferred embodiment, "aryl" refers to phenyl. "Substituted aryl" means that the aryl radical is substituted with one or more substituents described herein, preferably with 1 to 3 substituents described herein, e.g., with 1 or 2 substituents described herein.

The term "heteroaryl" refers to a mono- or multivalent, monocyclic, bicyclic or tricyclic ring system having a total of 5 to 12 ring members ("$C_{1-11}$-heteroaryl"), preferably, 5 to 10 ring members ("$C_{1-9}$-heteroaryl"), and more preferably 5 to 6 ring members ("$C_{1-5}$-heteroaryl"), wherein at least one ring in the system is aromatic, and at least one ring in the system contains one or more heteroatoms, preferably 1-4 heteroatoms, more preferably 1-3 heteroatoms, most preferably 1-2 heteroatoms. In a preferred embodiment, "heteroaryl" means a 5-10 membered heteroaryl ("$C_{1-9}$-heteroaryl"), comprising 1, 2, 3 or 4 heteroatoms independently selected from the group consisting of O, S and N, preferably 1, 2 or 3 heteroatoms independently selected from the group consisting of O, S and N. Some non-limiting examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles, but are not limited to: benzimidazolyl, benzofuryl, benzothiophenyl, indolyl (e.g., 1H-indol-5-yl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, [1,2,4]triazolo[1,5-a]pyridyl, 2,3-dihydro-1H-pyrrolo[2,3-b]pyridyl or 2,3-dihydropyrrolo[2,3-b]pyrid-1-yl and the like. In one embodiment, "heteroaryl" refers to 1,3-benzoxazolyl, indolyl (e.g., 1H-indol-5-yl), isoxazolyl, indazolyl, furanyl, benzimidazolyl, quinolinyl, oxazolo[4,5-b]pyridyl or pyridyl. In a preferred embodiment, "heteroaryl" refers to indolyl (e.g., 1H-indol-5-yl), indazolyl, benzoxazolyl or pyridyl. In a particularly preferred embodiment, "heteroaryl" refers to benzoxazolyl. In the particular case of $R^1$ being aryl, heteroaryl, heterocyclyl or cycloalkyl, each being independently substituted with heteroaryl, the heteroaryl substituent is selected from the group consisting of thiazol-2-yl, indolin-1-yl, pyridyl and 2,3-dihydropyrrolo[2,3-b]pyridin-1-yl. In the particular case of $R^1$, "Substituted heteroaryl" means that the heteroaryl radical is substituted with one or more substituents described herein, preferably with 1 to 3 substituents described herein, e.g., with 1 or 2 substituents described herein.

The term "amino" refers to a —NH$_2$ group.

The term "aminoalkyl" refers to an alkyl group, wherein at least one of the hydrogen atoms of the alkyl group has been replaced by an amino group. Examples of aminoalkyl include aminomethyl, aminoethyl, aminopropyl, aminomethylpropyl and diaminopropyl.

The term "hydroxyalkoxy" refers to an alkoxy group, wherein at least one of the hydrogen atoms of the alkoxy group has been replaced by a hydroxy group (—OH).

The term "alkoxyalkoxy" refers to an alkoxy group, wherein at least one of the hydrogen atoms of the alkoxy group has been replaced by an alkoxy group.

The term "alkylaryl" refers to an aryl group, wherein at least one of the hydrogen atoms of the aryl group has been replaced by an alkyl group. In one embodiment, "alkylaryl" refers to an aryl group wherein 1, 2 or 3 hydrogen atoms, preferably 1 or 2 hydrogen atoms of the aryl group have been replaced by an alkyl group. In a preferred embodiment, alkylaryl is 4-tert-butylphenyl.

The term "haloalkylaryl" refers to an aryl group, wherein at least one of the hydrogen atoms of the aryl group has been replaced by a haloalkyl group. In one embodiment, "haloalkylaryl" refers to an aryl group wherein 1, 2 or 3 hydrogen atoms, preferably 1 or 2 hydrogen atoms of the aryl group have been replaced by a haloalkyl group. In a preferred embodiment, haloalkylaryl is 3-(trifluoromethyl)phenyl, 4-(trifluoromethyl)phenyl or bis(trifluoromethyl)phenyl (in particular 3,5-bis(trifluoromethyl)phenyl).

The term "alkoxyalkylaryl" refers to an aryl group, wherein at least one of the hydrogen atoms of the aryl group has been replaced by an alkoxyalkyl group. In one embodiment, "alkoxyalkylaryl" refers to an aryl group wherein 1, 2 or 3 hydrogen atoms, preferably 1 or 2 hydrogen atoms of the aryl group have been replaced by an alkoxyalkyl group.

The term "alkoxyalkylheteroaryl" refers to a heteroaryl group, wherein at least one of the hydrogen atoms of the heteroaryl group has been replaced by an alkoxyalkyl group. In one embodiment, "alkoxyalkylheteroaryl" refers to a heteroaryl group wherein 1, 2 or 3 hydrogen atoms, preferably 1 or 2 hydrogen atoms of the heteroaryl group have been replaced by an alkoxyalkyl group. In a preferred embodiment, alkoxyalkylheteroaryl is 5-(alkoxyalkyl)-1,2,4-oxadiazol-3-yl.

The term "alkoxyalkylheterocyclyl" refers to a heterocyclyl group, wherein at least one of the hydrogen atoms of the heterocyclyl group has been replaced by an alkoxyalkyl group. In one embodiment, "alkoxyalkylheterocyclyl" refers to a heterocyclyl group wherein 1, 2 or 3 hydrogen atoms, preferably 1 or 2 hydrogen atoms of the heterocyclyl group have been replaced by an alkoxyalkyl group. In a preferred embodiment, alkoxyalkylheterocyclyl is 3-(methoxymethyl)pyrrolidin-1-yl.

The term "hydroxyalkoxyaryl" refers to an aryl group, wherein at least one of the hydrogen atoms of the aryl group has been replaced by a hydroxyalkoxy group. In one embodiment, "hydroxyalkoxyaryl" refers to an aryl group wherein 1, 2 or 3 hydrogen atoms, preferably 1 or 2 hydrogen atoms of the aryl group have been replaced by a hydroxyalkoxy group.

The term "hydroxyalkoxyheteroaryl" refers to a heteroaryl group, wherein at least one of the hydrogen atoms of the heteroaryl group has been replaced by a hydroxyalkoxy group. In one embodiment, "hydroxyalkoxyheteroaryl" refers to a heteroaryl group wherein 1, 2 or 3 hydrogen atoms, preferably 1 or 2 hydrogen atoms of the heteroaryl group have been replaced by a hydroxyalkoxy group.

The term "haloaryl" refers to an aryl group, wherein at least one of the hydrogen atoms of the aryl group has been replaced by a halogen atom. In one embodiment, "haloaryl" refers to an aryl group wherein 1, 2 or 3 hydrogen atoms, preferably 1 or 2 hydrogen atoms of the aryl group have been replaced by a halogen atom. In a preferred embodiment, haloaryl is selected from the group consisting of 3-fluorophenyl, 4-fluorophenyl, 2,6-difluorophenyl, 3,5-difluorophenyl, 3,4-difluorophenyl, 2-iodophenyl, 3-chlorophenyl, 3,4-dichlorophenyl, 4-bromo-3-fluoro-phenyl and 3-bromophenyl.

The term "cyano(haloaryl)" refers to a haloaryl group, wherein at least one of the hydrogen atoms of the haloaryl group has been replaced by a cyano group. In one embodiment, "cyano(haloaryl)" refers to a haloaryl group wherein 1, 2 or 3 hydrogen atoms, preferably 1 or 2 hydrogen atoms, most preferably 1 hydrogen atom of the haloaryl group have been replaced by a cyano group. In a particularly preferred embodiment, cyano(haloaryl) is 3-chloro-4-cyano-phenyl.

The term "haloheteroaryl" refers to a heteroaryl group, wherein at least one of the hydrogen atoms of the heteroaryl group has been replaced by a halogen atom. In one embodiment, "haloheteroaryl" refers to a heteroaryl group wherein 1, 2 or 3 hydrogen atoms, preferably 1 or 2 hydrogen atoms of the heteroaryl group have been replaced by a halogen atom. In a preferred embodiment, haloheteroaryl is selected from the group consisting of fluorothiazol-2-yl, fluoroindolin-1-yl, fluoropyridyl and fluoro-2,3-dihydropyrrolo[2,3-b]pyridin-1-yl.

The term "haloheterocyclyl" refers to a heterocyclyl group, wherein at least one of the hydrogen atoms of the heterocyclyl group has been replaced by a halogen atom. In one embodiment, "haloheterocyclyl" refers to a heterocyclyl group wherein 1, 2 or 3 hydrogen atoms, preferably 1 or 2 hydrogen atoms of the heterocyclyl group have been replaced by a halogen atom. In a preferred embodiment, "haloheterocyclyl" is 7,7-difluoro-2-azaspiro[3.3]heptan-2-yl.

The term "hydroxyheterocyclyl" refers to a heterocyclyl group, wherein at least one of the hydrogen atoms of the heterocyclyl group has been replaced by a hydroxy group (—OH). In one embodiment, "hydroxyheterocyclyl" refers to a heterocyclyl group wherein 1, 2 or 3 hydrogen atoms, preferably 1 or 2 hydrogen atoms of the heterocyclyl group have been replaced by a hydroxy group.

The term "alkyl(hydroxyheterocyclyl)" refers to a heterocyclyl group, wherein at least one of the hydrogen atoms of the heterocyclyl group has been replaced by a hydroxy group (—OH) and at least a further one the hydrogen atoms of the heterocyclyl group has been replaced by an alkyl group. In one embodiment, "alkyl(hydroxyheterocyclyl)" refers to a heterocyclyl substituted with one hydroxy group and with one alkyl group. A particular, yet non-limiting example of alkyl(hydroxyheterocyclyl) is 3-hydroxy-3-methyl-pyrrolidin-1-yl.

The term "alkyl(haloheterocyclyl)" refers to a heterocyclyl group, wherein at least one of the hydrogen atoms of the heterocyclyl group has been replaced by a halogen atom and at least a further one the hydrogen atoms of the heterocyclyl group has been replaced by an alkyl group. In one embodiment, "alkyl(haloheterocyclyl)" refers to a heterocyclyl substituted with one halogen atom and with one alkyl group. A particular, yet non-limiting example of alkyl(haloheterocyclyl) is 3-fluoro-3-methyl-pyrrolidin-1-yl.

The term "halocycloalkyl" refers to a cycloalkyl group, wherein at least one of the hydrogen atoms of the cycloalkyl group has been replaced by a halogen atom. In one embodiment, "halocycloalkyl" refers to a cycloalkyl group wherein 1, 2 or 3 hydrogen atoms, preferably 1 or 2 hydrogen atoms of the cycloalkyl group have been replaced by a halogen atom. In a preferred embodiment, "halocycloalkyl" is selected from the group consisting of fluorocyclopropyl, fluorocyclobutyl, fluorocyclopentyl and fluorocyclohexyl.

The term "haloaryl-alkenyl" refers to an alkenyl group, wherein at least one of the hydrogen atoms of the alkenyl group has been replaced by a haloaryl group. In a preferred embodiment, "haloaryl-alkenyl" refers to an alkenyl group wherein 1 hydrogen atom of the alkenyl group has been replaced by a haloaryl group. In a particularly preferred embodiment, haloaryl-alkenyl is (Z)-2-(3-fluorophenyl)vinyl.

The term "haloalkylaryl-alkoxyalkyl" refers to an alkoxyalkyl group, wherein at least one of the hydrogen atoms of the alkoxyalkyl group has been replaced by a haloalkylaryl group. In a preferred embodiment, "haloalkylaryl-alkoxyalkyl" refers to an alkoxyalkyl group wherein 1 hydrogen atom of the alkoxyalkyl group has been replaced by a haloalkylaryl group. In a particularly preferred embodiment, haloalkylaryl-alkoxyalkyl is 2-[[3-(trifluoromethyl)phenyl]methoxy]ethyl.

The term "haloalkylheteroaryl" refers to a heteroaryl group, wherein at least one of the hydrogen atoms of the heteroaryl group has been replaced by a haloalkyl group. In a preferred embodiment, "haloalkylheteroaryl" refers to a heteroaryl group wherein 1 hydrogen atom of the heteroaryl group has been replaced by a haloalkyl group. In a particularly preferred embodiment haloalkylheteroaryl is selected from the group consisting of 5-(trifluoromethyl)-1,2,4-oxadiazol-3-yl, 5-(2,2,2-trifluoroethyl)-1,2,4-oxadiazol-3-yl, 5-(trifluoromethyl)-3-pyridyl, 4-(trifluoromethyl)pyrazol-1-yl, 3-(trifluoromethyl)pyrazol-1-yl, 5-(trifluoromethyl)imidazo[1,2-a]pyridin-2-yl, 4-(trifluoromethyl)-1,3-benzoxazol-6-yl, and 3-(2,2,2-trifluoroethyl)-1,2,4-oxadiazol-5-yl. The term "haloalkylheterocyclyl" refers to a heterocyclyl group, wherein at least one of the hydrogen atoms of the heterocyclyl group has been replaced by a haloalkyl group. In a preferred embodiment, "haloalkylheterocyclyl" refers to a heterocyclyl group wherein 1 hydrogen atom of the heterocyclyl group has been replaced by a haloalkyl group. The term "alkylheteroaryl" refers to a heteroaryl group, wherein at least one of the hydrogen atoms of the heteroaryl group has been replaced by an alkyl group. In a preferred embodiment, "alkylheteroaryl" refers to a heteroaryl group wherein 1 hydrogen atom of the heteroaryl group has been replaced by an alkyl group. In a particularly preferred embodiment alkylheteroaryl is selected from the group consisting of 2-methylthiazol-4-yl, 5-ethyl-1,2,4-oxadiazol-3-yl, 5-(2,2-dimethylpropyl)-1,2,4-oxadiazol-3-yl, 5-tert-butyl-1,2,4-oxadiazol-3-yl, 3-methylpyrazol-1-yl, 4-methylpyrazol-1-yl, 5-methyl-1,2,4-oxadiazol-3-yl, 5-isopropyl-1,2,4-oxadiazol-3-yl, 2-methyl-1H-benzimidazol-5-yl, 1-methylpyrrol-3-yl and 2,5-dimethyl-3H-pyrrol-1-yl.

The term "arylcycloalkyl" refers to a cycloalkyl group, wherein at least one of the hydrogen atoms of the cycloalkyl group has been replaced by an aryl group. In a preferred embodiment, "arylcycloalkyl" refers to a cycloalkyl group wherein 1 hydrogen atom of the cycloalkyl group has been replaced by an aryl group. In a particularly preferred embodiment arylcycloalkyl is 2-phenylcyclopropyl.

The term "cycloalkylheteroaryl" refers to a heteroaryl group, wherein at least one of the hydrogen atoms of the heteroaryl group has been replaced by a cycloalkyl group. In a preferred embodiment, "cycloalkylheteroaryl" refers to a heteroaryl group wherein 1 hydrogen atom of the heteroaryl group has been replaced by a cycloalkyl group. In a particularly preferred embodiment, cycloalkylheteroaryl is selected from the group consisting of (5-cyclopropyl-1,2,4-oxadiazol-3-yl), (3-cyclopropyl-1H-1,2,4-triazol-5-yl) and (3-cyclopropyl-1,2,4-oxadiazol-5-yl).

The term "alkylcycloalkylheteroaryl" refers to a cycloalkylheteroaryl group, wherein at least one of the hydrogen atoms of the cycloalkyl group comprised by said cycloalkylheteroaryl group has been replaced by an alkyl group. In a preferred embodiment, "alkylcycloalkylheteroaryl" refers to a cycloalkylheteroaryl group, wherein 1 of the hydrogen atoms of the cycloalkyl group comprised by said cycloalkylheteroaryl group has been replaced by an alkyl group. In a particularly preferred embodiment, alkylcycloalkylheteroaryl is 3-(1-methylcyclopropyl)-1,2,4-oxadiazole.

The term "haloalkylcycloalkylheteroaryl" refers to a cycloalkylheteroaryl group, wherein at least one of the hydrogen atoms of the cycloalkyl group comprised by said cycloalkylheteroaryl group has been replaced by a haloalkyl group. In a preferred embodiment, "haloalkylcycloalkylheteroaryl" refers to a cycloalkylheteroaryl group, wherein 1 of the hydrogen atoms of the cycloalkyl group comprised by said cycloalkylheteroaryl group has been replaced by a haloalkyl group. In a particularly preferred embodiment, haloalkylcycloalkylheteroaryl is [5-[1-(trifluoromethyl)cyclopropyl]-1,2,4-oxadiazol-3-yl] or [5-[1-(fluoromethyl)cyclopropyl]-1,2,4-oxadiazol-3-yl].

The term "cycloalkylaryl" refers to an aryl group, wherein at least one of the hydrogen atoms of the aryl group has been replaced by a cycloalkyl group. In a preferred embodiment, "cycloalkylaryl" refers to an aryl group wherein 1 hydrogen atom of the aryl group has been replaced by a cycloalkyl group.

The term "cycloalkylalkoxy" refers to an alkoxy group, wherein at least one of the hydrogen atoms of the alkoxy group has been replaced by a cycloalkyl group. In a preferred embodiment, "cycloalkylalkoxy" refers to an alkoxy group wherein 1 hydrogen atom of the alkoxy group has been replaced by a cycloalkyl group. In a particularly preferred embodiment, cycloalkylalkoxy is cyclopentylmethoxy.

The term "cyanoaryl" refers to an aryl group, wherein at least one of the hydrogen atoms of the aryl group has been replaced by a cyano group (—CN). In one embodiment, "cyanoaryl" refers to an aryl group wherein 1, 2 or 3 hydrogen atoms, preferably 1 hydrogen atom of the aryl group have been replaced by a cyano group. In a preferred embodiment, cyanoaryl is 2-cyanophenyl.

The term "cyanoheteroaryl" refers to a heteroaryl group, wherein at least one of the hydrogen atoms of the heteroaryl group has been replaced by a cyano group (—CN). In one embodiment, "cyanoheteroaryl" refers to a heteroaryl group wherein 1, 2 or 3 hydrogen atoms, preferably 1 hydrogen atom of the heteroaryl group have been replaced by a cyano group.

The term "cyanoalkylaryl" refers to an aryl group, wherein at least one of the hydrogen atoms of the aryl group has been replaced by a cyanoalkyl group. In one embodiment, "cyanoalkylaryl" refers to an aryl group wherein 1, 2 or 3 hydrogen atoms, preferably 1 hydrogen atom of the aryl group have been replaced by a cyanoalkyl group. In a preferred embodiment, cyanoalkylaryl is 3-(cyanomethyl)phenyl.

The term "cyanocycloalkyl" refers to a cycloalkyl group, wherein at least one of the hydrogen atoms of the cycloalkyl group has been replaced by a cyano group (—CN). In one embodiment, "cyanocycloalkyl" refers to a cycloalkyl group wherein 1, 2 or 3 hydrogen atoms, preferably 1 hydrogen atom of the cycloalkyl group have been replaced by a cyano group. In a preferred embodiment, cyanocycloalkyl is 1-cyanocyclopentyl.

The term "arylalkoxy" refers to an alkoxy group, wherein at least one of the hydrogen atoms of the alkoxy group has been replaced by an aryl group. In a preferred embodiment, "arylalkoxy" refers to an alkoxy group wherein 1 hydrogen atom of the alkoxy group has been replaced by an aryl group. In a particularly preferred embodiment, arylalkoxy is benzyloxy.

The term "arylalkoxyalkyl" refers to an alkyl group, wherein at least one of the hydrogen atoms of the alkyl group has been replaced by an arylalkoxy group. In a preferred embodiment, "arylalkoxyalkyl" refers to an alkyl group wherein 1 hydrogen atom of the alkyl group has been replaced by an arylalkoxy group. In a particularly preferred embodiment, arylalkoxyalkyl is 2-benzyloxy-1,1-dimethyl-ethyl.

The term "arylalkoxyalkylheteroaryl" refers to a heteroaryl group, wherein at least one of the hydrogen atoms of the heteroaryl group has been replaced by an arylalkoxyalkyl group. In a preferred embodiment, "arylalkoxyalkylheteroaryl" refers to a heteroaryl group wherein 1 hydrogen atom of the heteroaryl group has been replaced by an arylalkoxyalkyl group. In a particularly preferred embodiment, arylalkoxyalkylheteroaryl is 5-(2-benzyloxy-1,1-dimethyl-ethyl)-1,2,4-oxadiazol-3-yl.

The term "heteroarylalkoxy" refers to an alkoxy group, wherein at least one of the hydrogen atoms of the alkoxy group has been replaced by a heteroaryl group. In a preferred embodiment, "heteroarylalkoxy" refers to an alkoxy group wherein 1 hydrogen atom of the alkoxy group has been replaced by a heteroaryl group.

The term "haloheteroarylalkoxy" refers to an alkoxy group, wherein at least one of the hydrogen atoms of the alkoxy group has been replaced by a haloheteroaryl group. In a preferred embodiment, "haloheteroarylalkoxy" refers to an alkoxy group wherein 1 hydrogen atom of the alkoxy group has been replaced by a haloheteroaryl group. In a particularly preferred embodiment, "haloheteroarylalkoxy" is (2-chloro-4-pyridyl)methoxy or (6-chloro-2-pyridyl)methoxy.

The term "haloarylalkoxy" refers to an alkoxy group, wherein at least one of the hydrogen atoms of the alkoxy group has been replaced by a haloaryl group. In a preferred embodiment, "haloarylalkoxy" refers to an alkoxy group wherein 1 hydrogen atom of the alkoxy group has been replaced by a haloaryl group. In a particularly preferred embodiment, haloarylalkoxy is (3-chlorophenyl)methoxy or (2-chlorophenyl)methoxy. The term "aryloxy" refers to an aryl group, as previously defined, attached to the parent molecular moiety via an oxygen atom. In a preferred embodiment, aryloxy is phenoxy.

The term "haloaryloxy" refers to a haloaryl group, as previously defined, attached to the parent molecular moiety via an oxygen atom. In a preferred embodiment, haloaryloxy is 2-chlorophenoxy.

The term "haloalkylaryloxy" refers to a haloalkylaryl group, as previously defined, attached to the parent molecular moiety via an oxygen atom. In a preferred embodiment, haloalkylaryloxy is 3-(trifluoromethyl)phenoxy.

The term "aryloxyalkyl" refers to an alkyl group, wherein at least one of the hydrogen atoms of the alkyl group has been replaced by an aryloxy group. In a preferred embodiment, "aryloxyalkyl" refers to an alkyl group wherein 1 hydrogen atom of the alkyl group has been replaced by an aryloxy group. In a particularly preferred embodiment, aryloxyalkyl is indan-5-yloxymethyl.

The term "haloaryloxyalkyl" refers to an alkyl group, wherein at least one of the hydrogen atoms of the alkyl group has been replaced by a haloaryloxy group. In a preferred embodiment, "haloaryloxyalkyl" refers to an alkyl group wherein 1 hydrogen atom of the alkyl group has been replaced by a haloaryloxy group. In a particularly preferred embodiment, haloaryloxyalkyl is (3-chlorophenoxy)methyl.

The term "aryloxyaryl" refers to an aryl group, wherein at least one of the hydrogen atoms of the aryl group has been replaced by an aryloxy group. In a preferred embodiment, "aryloxyaryl" refers to an aryl group wherein 1 hydrogen atom of the aryl group has been replaced by an aryloxy group.

The term "aryloxyheteroaryl" refers to a heteroaryl group, wherein at least one of the hydrogen atoms of the heteroaryl group has been replaced by an aryloxy group. In a preferred embodiment, "aryloxyheteroaryl" refers to a heteroaryl group wherein 1 hydrogen atom of the heteroaryl group has been replaced by an aryloxy group.

The term "heterocyclylalkyl" refers to an alkyl group, wherein at least one of the hydrogen atoms of the alkyl group has been replaced by a heterocyclyl group. In a preferred embodiment, "heterocyclylalkyl" refers to an alkyl group wherein 1 hydrogen atom of the alkyl group has been replaced by a heterocyclyl group. In a particularly preferred embodiment, "heterocyclylalkyl" is selected from the group consisting of azetidin-1-ylmethyl, pyrrolidin-1-ylmethyl and 1-piperidylmethyl.

The term "arylheterocyclyl" refers to a heterocyclyl group, wherein at least one of the hydrogen atoms of the heterocyclyl group has been replaced by an aryl group. In a preferred embodiment, "arylheterocyclyl" refers to a heterocyclyl group wherein 1 hydrogen atom of the heterocyclyl group has been replaced by an aryl group. In a particularly preferred embodiment, "arylheterocyclyl" is 2-phenylpyrrolidin-1-yl.

The term "alkylheterocyclyl" refers to a heterocyclyl group, wherein at least one of the hydrogen atoms of the heterocyclyl group has been replaced by an alkyl group. In a preferred embodiment, "alkylheterocyclyl" refers to a heterocyclyl group wherein 1 or 2 hydrogen atom of the heterocyclyl group have been replaced by an alkyl group. In a particularly preferred embodiment, "alkylheterocyclyl" is 4,4-dimethyl-1-piperidyl or 4,4-diethyl-1-piperidyl.

The term "alkoxy-(haloalkyl)aryl" refers to an aryl group, wherein at least a first of the hydrogen atoms of the aryl group has been replaced by an alkoxy group and wherein at least a second of the hydrogen atoms of the aryl group has been replaced by a haloalkyl group. In a preferred embodiment, "alkoxy-(haloalkyl)aryl" refers to an aryl group wherein a first of the hydrogen atoms of the aryl group has been replaced by an alkoxy group and wherein a second of the hydrogen atoms of the aryl group has been replaced by a haloalkyl group. In a particularly preferred embodiment, "alkoxy-(haloalkyl)aryl" is 4-methoxy-3-(trifluoromethyl)phenyl.

The term "arylalkoxy-(alkyl)aryl" refers to an alkylaryl group, wherein at least one of the hydrogen atoms of the alkylaryl group has been replaced by an arylalkoxy group. In a preferred embodiment, "arylalkoxy-(alkyl)aryl" refers to an alkylaryl group wherein 1 hydrogen atom of the alkylaryl group has been replaced by an arylalkoxy group. In a particularly preferred embodiment, "arylalkoxy-(alkyl)aryl" is 2-benzyloxy-6-methyl-phenyl.

The term "hydroxyalkylaryl" refers to an aryl group, wherein at least one of the hydrogen atoms of the aryl group has been replaced by a hydroxyalkyl group. In a preferred embodiment, "hydroxyalkylaryl" refers to an aryl group wherein 1 hydrogen atom of the aryl group has been replaced by a hydroxyalkyl group. In a particularly preferred embodiment, "hydroxyalkylaryl" is 4-(hydroxymethyl)phenyl or 2-(hydroxymethyl)phenyl.

The term "hydroxyalkylheteroaryl" refers to a heteroaryl group, wherein at least one of the hydrogen atoms of the heteroaryl group has been replaced by a hydroxyalkyl group. In a preferred embodiment, "hydroxyalkylheteroaryl" refers to a heteroaryl group wherein 1 hydrogen atom of the heteroaryl group has been replaced by a hydroxyalkyl group. In a particularly preferred embodiment, "hydroxyalkylheteroaryl" is 5-(hydroxyalkyl)-1,2,4-oxadiazol-3-yl, such as 5-(2-hydroxy-1,1-dimethyl-ethyl)-1,2,4-oxadiazol-3-yl.

The term "hydroxyalkylheterocyclyl" refers to a heterocyclyl group, wherein at least one of the hydrogen atoms of the heterocyclyl group has been replaced by a hydroxyalkyl group. In a preferred embodiment, "hydroxyalkylheterocyclyl" refers to a heterocyclyl group wherein 1 hydrogen atom of the heterocyclyl group has been replaced by a hydroxyalkyl group. In a particularly preferred embodiment, "hydroxyalkylheterocyclyl" is 3-(1-hydroxyethyl)pyrrolidin-1-yl or 3-(1-hydroxy-1-methyl-ethyl)pyrrolidin-1-yl.

The term "alkoxyaryl" refers to an aryl group, wherein at least one of the hydrogen atoms of the aryl group has been replaced by an alkoxy group. In a preferred embodiment, "alkoxyaryl" refers to an aryl group wherein 1 hydrogen atom of the aryl group has been replaced by an alkoxy group. In a particularly preferred embodiment, "alkoxyaryl" is 3-ethoxy phenyl.

The term "alkoxyheteroaryl" refers to a heteroaryl group, wherein at least one of the hydrogen atoms of the heteroaryl group has been replaced by an alkoxy group. In a preferred embodiment, "alkoxyheteroaryl" refers to a heteroaryl group wherein 1 hydrogen atom of the heteroaryl group has been replaced by an alkoxy group.

The term "heteroarylalkyl" refers to an alkyl group, wherein at least one of the hydrogen atoms of the alkyl group has been replaced by a heteroaryl group. In a preferred embodiment, "heteroarylalkyl" refers to an alkyl group wherein 1 hydrogen atom of the alkyl group has been replaced by a heteroaryl group. In a particularly preferred embodiment, "heteroarylalkyl" is benzimidazol-1-ylmethyl.

The term "arylalkyl" refers to an alkyl group, wherein at least one of the hydrogen atoms of the alkyl group has been replaced by an aryl group. In a preferred embodiment, "arylalkyl" refers to an alkyl group wherein 1 hydrogen atom of the alkyl group has been replaced by an aryl group. In a particularly preferred embodiment, "arylalkyl" is benzyl.

The term "haloalkylarylalkyl" refers to an alkyl group, wherein at least one of the hydrogen atoms of the alkyl group has been replaced by a haloalkylaryl group. In a preferred embodiment, "haloalkylarylalkyl" refers to an alkyl group wherein 1 hydrogen atom of the alkyl group has been replaced by a haloalkylaryl group. In a particularly preferred embodiment, haloalkylarylalkyl is [3-(trifluoromethyl)phenyl]methyl.

The term "(arylalkoxy)aryl" refers to an aryl group, wherein at least one of the hydrogen atoms of the aryl group has been replaced by an arylalkoxy group. In a preferred embodiment, "(arylalkoxy)aryl" refers to an aryl group wherein 1 hydrogen atom of the aryl group has been replaced by an arylalkoxy group. In a particularly preferred embodiment, "(arylalkoxy)aryl" is 3-benzyloxyphenyl.

The term "(arylalkoxy)heteroaryl" refers to a heteroaryl group, wherein at least one of the hydrogen atoms of the heteroaryl group has been replaced by an arylalkoxy group. In a preferred embodiment, "(arylalkoxy)heteroaryl" refers to a heteroaryl group wherein 1 hydrogen atom of the heteroaryl group has been replaced by an arylalkoxy group.

The term "carbamoyl" refers to a group —C(O)—NR'R", wherein R' and R" are independently selected from the group consisting of H and alkyl. In a preferred embodiment, R' and R" are each alkyl. In a particularly preferred embodiment, R' and R" are both methyl (i.e., "carbamoyl" is dimethylcarbamoyl).

The term "carbamoylaryl" refers to an aryl group, wherein at least one of the hydrogen atoms of the aryl group has been replaced by a carbamoyl group. In a preferred embodiment, "carbamoylaryl" refers to an aryl group wherein 1 hydrogen atom of the aryl group has been replaced by a carbamoyl group. In a particularly preferred embodiment, "carbamoylaryl" is 4-(dimethylcarbamoyl)phenyl.

The term "alkanoyl" refers to a group alkyl-C(O)—.

The term "alkyl-(alkoxy)aryl" refers to an aryl group, wherein at least a first of the hydrogen atoms of the aryl group has been replaced by an alkoxy group and wherein at least a second of the hydrogen atoms of the aryl group has been replaced by an alkyl group. In a preferred embodiment, "alkyl-(alkoxy)aryl" refers to an aryl group wherein a first of the hydrogen atoms of the aryl group has been replaced by an alkoxy group and wherein a second of the hydrogen atoms of the aryl group has been replaced by an alkyl group. In a particularly preferred embodiment, "alkyl-(alkoxy)aryl" is 2-methoxy-5-methyl-phenyl.

The term "haloalkoxyaryl" refers to an aryl group, wherein at least one of the hydrogen atoms of the aryl group has been replaced by a haloalkoxy group. In a preferred embodiment, "haloalkoxyaryl" refers to an aryl group wherein 1 hydrogen atom of the aryl group has been replaced by a haloalkoxy group. In a particularly preferred embodiment, "haloalkoxyaryl" is selected from the group consisting of 2-(trifluoromethoxy)phenyl, 3-(trifluoromethoxy)phenyl and 4-(trifluoromethoxy)phenyl.

The term "haloalkoxyheteroaryl" refers to a heteroaryl group, wherein at least one of the hydrogen atoms of the heteroaryl group has been replaced by a haloalkoxy group. In a preferred embodiment, "haloalkoxyheteroaryl" refers to a heteroaryl group wherein 1 hydrogen atom of the heteroaryl group has been replaced by a haloalkoxy group.

The term "alkylhaloaryl" refers to a haloaryl group, wherein at least one of the hydrogen atoms of the haloaryl group has been replaced by an alkyl group. In a preferred embodiment, "alkylhaloaryl" refers to a haloaryl group wherein 1 hydrogen atom of the haloaryl group has been replaced by an alkyl group. In a particularly preferred embodiment, "alkylhaloaryl" is 3-tert-butyl-5-chloro-phenyl.

The term "haloalkylhaloaryl" refers to a haloaryl group, wherein at least one of the hydrogen atoms of the haloaryl group has been replaced by a haloalkyl group. In a preferred embodiment, "haloalkylhaloaryl" refers to a haloaryl group wherein 1 hydrogen atom of the haloaryl group has been replaced by a haloalkyl group. In a particularly preferred embodiment, "haloalkylhaloaryl" is 3-fluoro-4-(trifluoromethyl)phenyl.

The term "haloarylalkyl" refers to an alkyl group, wherein at least one of the hydrogen atoms of the alkyl group has been replaced by a haloaryl group. In a preferred embodiment, "haloarylalkyl" refers to an alkyl group wherein 1 hydrogen atom of the alkyl group has been replaced by a haloaryl group. In a particularly preferred embodiment, "haloarylalkyl" is (2-iodophenyl)methyl or (3-chlorophenyl)methyl.

The term "haloalkoxyarylalkyl" refers to an alkyl group, wherein at least one of the hydrogen atoms of the alkyl group has been replaced by a haloalkoxyaryl group. In a preferred embodiment, "haloalkoxyarylalkyl" refers to an alkyl group wherein 1 hydrogen atom of the alkyl group has been replaced by a haloalkoxyaryl group. In a particularly preferred embodiment, "haloalkoxyarylalkyl" is [2-(trifluoromethoxy)phenyl]methyl.

The term "hydroxy" refers to an —OH group.

The term "pentafluoro-lambda6-sulfanyl", also known as "pentafluorosulfanyl", refers to a group —SF$_5$.

The term "alkylsulfanyl" refers to an alkyl group bonded to the parent molecule via a sulfur atom, i.e. to a group alkyl-S—. A non-limiting example of an alkylsulfanyl group is methylsulfanyl, CH$_3$S—.

The term "haloarylsulfonyl" refers to a haloaryl group bonded to the parent molecule via a sulfonyl group, i.e. to a group haloaryl-SO$_2$—. Preferred, yet non-limiting examples of haloarylsulfonyl are (3-chlorophenyl)sulfonyl and (4-chlorophenyl)sulfonyl.

The term "one or more substituents" as used herein preferably refers to 1-6 substituents, such as 1, 2, 3, 4, 5 or 6 substituents. More preferably, the term "one or more substituents" as used herein refers to 1-3 substituents. Most preferably, the term "one or more substituents" as used herein refers to 1-2 substituents, in particular to 1 substituent.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic to base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethyl amine, tripropylamine, ethanolamine, lysine, arginine, N-ethylpiperidine, piperidine, polyimine resins and the like. Particular pharmaceutically acceptable salts of compounds of Formula (I) are the hydrochloride salts, methanesulfonic acid salts and citric acid salts.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxy carbonyl (Boc). Exemplary protecting groups and their application in organic synthesis are described, for example, in "Protective Groups in Organic Chemistry" by T. W. Greene and P. G. M. Wutts, 5th Ed., 2014, John Wiley & Sons, N.Y.

The compounds of Formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

The abbreviation "MAGL" refers to the enzyme monoacylglycerol lipase. The terms "MAGL" and "monoacylglycerol lipase" are used herein interchangeably.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e. causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human, that may be afflicted with or predisposed to the state, disorder or condition but does not yet experience or display clinical or subclinical symptoms of the state, disorder or condition.

The term "neuroinflammation" as used herein relates to acute and chronic inflammation of the nervous tissue, which is the main tissue component of the two parts of the nervous system; the brain and spinal cord of the central nervous system (CNS), and the branching peripheral nerves of the peripheral nervous system (PNS). Chronic neuroinflammation is associated with neurodegenerative diseases such as Alzheimer's disease, Parkinson's disease and multiple sclerosis. Acute neuroinflammation usually follows injury to the central nervous system immediately, e.g., as a result of traumatic brain injury (TBI).

The term "traumatic brain injury" ("TBI", also known as "intracranial injury"), relates to damage to the brain resulting from external mechanical force, such as rapid acceleration or deceleration, impact, blast waves, or penetration by a projectile.

The term "neurodegenerative diseases" relates to diseases that are related to the progressive loss of structure or function of neurons, including death of neurons. Examples of neurodegenerative diseases include, but are not limited to, multiple sclerosis, Alzheimer's disease, Parkinson's disease and amyotrophic lateral sclerosis.

The term "mental disorders" (also called mental illnesses or psychiatric disorders) relates to behavioral or mental patterns that may cause suffering or a poor ability to function in life. Such features may be persistent, relapsing and remitting, or occur as a single episode. Examples of mental disorders include, but are not limited to, anxiety and depression.

The term "pain" relates to an unpleasant sensory and emotional experience associated with actual or potential tissue damage. Examples of pain include, but are not limited to, nociceptive pain, chronic pain (including idiopathic pain), neuropathic pain, phantom pain and psychogenic pain. A particular example of pain is neuropathic pain, which is caused by damage or disease affecting any part of the nervous system involved in bodily feelings (i.e., the somatosensory system). In one embodiment, "pain" is neuropathic pain resulting from amputation or thoracotomy.

The term "neurotoxicity" relates to toxicity in the nervous system. It occurs when exposure to natural or artificial toxic substances (neurotoxins) alter the normal activity of the nervous system in such a way as to cause damage to nervous tissue. Examples of neurotoxicity include, but are not limited to, neurotoxicity resulting from exposure to substances used in chemotherapy, radiation treatment, drug therapies, drug abuse, and organ transplants, as well as exposure to heavy metals, certain foods and food additives, pesticides, industrial and/or cleaning solvents, cosmetics, and some naturally occurring substances.

The term "mammal" as used herein includes both humans and non-humans and includes but is not limited to humans, non-human primates, canines, felines, murines, bovines, equines, and porcines. In a particularly preferred embodiment, the term "mammal" refers to humans.

Compounds of the Invention

In a first aspect, the present invention provides compounds of Formula (I)

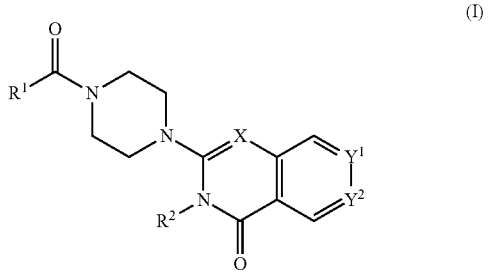

wherein:
X is C—H or N;
$Y^1$ is selected from the group consisting of C—H, C—F, C-alkyl, C-haloalkyl and N;
$Y^2$ is selected from the group consisting of C—H, C-halogen, C-alkyl and C-haloalkyl;
$R^1$ is selected from the group consisting of:
  i. aryl,
  ii. substituted aryl,
  iii. heteroaryl,
  iv. substituted heteroaryl,
  v. heterocyclyl,
  vi. substituted heterocyclyl,
  vii. cycloalkyl and
  viii. substituted cycloalkyl, wherein:
    each of said substituted aryl, substituted heteroaryl, substituted heterocyclyl and substituted cycloalkyl is independently substituted with one or more substituents selected from the group consisting of aminoalkyl, amino, haloalkylaryl, cycloalkyl, cycloalkylaryl, aryl-alkenyl, haloaryl-alkenyl, cyano(haloaryl), haloarylsulfonyl, alkyl(hydroxyheterocyclyl), alkyl(haloheterocyclyl), arylalkoxyalkylheteroaryl, hydroxyalkynyl, haloalkylaryl-alkoxyalkyl, haloalkylheteroaryl, haloalkylheterocyclyl, alkylheteroaryl, arylcycloalkyl, hydroxyalkylheterocyclyl, alkylsulfanyl, alkoxyheterocyclyl, cycloalkylheteroaryl, alkylcycloalkylheteroaryl, haloalkylcycloalkylheteroaryl, alkoxyalkylheteroaryl, alkoxyalkylheterocyclyl, alkoxyalkylaryl, cycloalkylalkoxy, arylalkoxy, aryloxyalkyl, haloaryloxyalkyl, aryloxyaryl, aryloxyheteroaryl, aryloxy, haloalkylaryloxy, halogen, heterocyclyl, hydroxyheterocyclyl, heterocyclylalkyl, heteroaryl, aryl, aryl-C(O)—, haloaryl, haloheteroaryl, halocycloalkyl, haloalkoxy, hydroxyalkoxy, alkoxyalkoxy, hydroxyalkoxyaryl, hydroxyalkoxyheteroaryl, alkoxy, alkyl, haloalkyl, cyano, cyanoaryl, cyanoheteroaryl, cyanocycloalkyl, cyanoalkylaryl, arylheterocyclyl, alkoxy-(haloalkyl)aryl, alkylaryl, arylalkoxy-(alkyl)aryl, haloaryloxy, hydroxyalkylaryl, hydroxyalkylheteroaryl, alkenyloxy, pentafluoro-lambda6-sulfanyl, heteroarylalkyl, heteroarylalkoxy, haloheteroarylalkoxy, alkoxyaryl, alkoxyheteroaryl, (arylalkoxy)aryl, (arylalkoxy)heteroaryl, carbamoylaryl, alkyl-(alkoxy)aryl, haloalkoxyaryl, haloalkoxyheteroaryl, alkylheterocyclyl, haloheterocyclyl, alkylhaloaryl, haloalkylhaloaryl and haloarylalkoxy, wherein:
    said aminoalkyl is substituted on the nitrogen atom with one or two substituents independently selected from the group consisting of H, alkyl, cycloalkyl, alkanoyl, arylalkyl and haloalkylarylalkyl; and
    said amino is substituted on the nitrogen atom with one or two substituents independently selected from the group consisting of H, alkyl, haloalkyl, cycloalkyl, hydroxyalkyl, alkoxyalkyl, haloarylalkyl, haloalkoxyarylalkyl, benzyl and benzyl substituted with a substituent selected from the group consisting of halogen, alkyl and haloalkyl; and
  $R^2$ is selected from the group consisting of hydrogen and alkyl; or a pharmaceutically acceptable salt thereof.

In one embodiment, the present invention provides compounds of Formula (I) as described herein, wherein:
X is C—H or N;
$Y^1$ is selected from the group consisting of C—H, C—F, C-alkyl, C-haloalkyl and N;
$Y^2$ is selected from the group consisting of C—H, C-halogen, C-alkyl and C-haloalkyl;
$R^1$ is selected from the group consisting of:
  i. aryl,
  ii. substituted aryl,
  iii. heteroaryl,
  iv. substituted heteroaryl,
  v. heterocyclyl,
  vi. substituted heterocyclyl,
  vii. cycloalkyl and
  viii. substituted cycloalkyl, wherein:
    each of said substituted aryl, substituted heteroaryl, substituted heterocyclyl and substituted cycloalkyl is independently substituted with one or more substituents selected from the group consisting of aminoalkyl, amino, haloalkylaryl, cycloalkyl, cycloalkylaryl, aryl-alkenyl, haloalkylarylalkoxyalkyl, haloalkylheteroaryl, haloalkylheterocyclyl, alkylheteroaryl, arylcycloalkyl, hydroxyalkylheterocyclyl, alkylsulfanyl, alkoxyheterocyclyl, cycloalkylheteroaryl, alkylcycloalkylheteroaryl, haloalkylcycloalkylheteroaryl, alkoxyalkylheteroaryl, alkoxyalkylheterocyclyl, alkoxyalkylaryl, cycloalkylalkoxy, arylalkoxy, aryloxyalkyl, haloaryloxyalkyl, aryloxyaryl, aryloxyheteroaryl, aryloxy, haloalkylaryloxy, halogen, heterocyclyl, hydroxyheterocyclyl, heterocyclylalkyl, heteroaryl, aryl, aryl-C(O)—, haloaryl, haloheteroaryl, halocycloalkyl, haloalkoxy, hydroxyalkoxy, alkoxyalkoxy, hydroxyalkoxyaryl, hydroxyalkoxyheteroaryl, alkoxy, alkyl, haloalkyl, cyano, cyanoaryl, cyanoheteroaryl, cyanocycloalkyl, cyanoalkylaryl, arylheterocyclyl, alkoxy-(haloalkyl)aryl, alkylaryl, arylalkoxy-(alkyl)aryl, haloaryloxy, hydroxyalkylaryl, hydroxyalkylheteroaryl, alkenyloxy, pentafluorosulfanyl, heteroarylalkyl, heteroarylalkoxy, haloheteroarylalkoxy, alkoxyaryl, alkoxyheteroaryl, (arylalkoxy)aryl, (arylalkoxy)heteroaryl, carbamoylaryl, alkyl-(alkoxy)aryl, haloalkoxyaryl, haloalkoxyheteroaryl, alkylheterocyclyl, haloheterocyclyl, alkylhaloaryl, haloalkylhaloaryl and haloarylalkoxy, wherein:

said aminoalkyl is substituted on the nitrogen atom with one or two substituents independently selected from the group consisting of H, alkyl, cycloalkyl, alkanoyl, arylalkyl and haloalkylarylalkyl; and said amino is substituted on the nitrogen atom with one or two substituents independently selected from the group consisting of H, alkyl, haloalkyl, cycloalkyl, hydroxyalkyl, alkoxyalkyl, haloarylalkyl, haloalkoxyarylalkyl, benzyl and benzyl substituted with a substituent selected from the group consisting of halogen, alkyl and haloalkyl; and $R^2$ is selected from the group consisting of hydrogen and alkyl; or a pharmaceutically acceptable salt thereof.

In one embodiment, the compound of Formula (I) is a compound of Formula (IA), wherein $R^2$, X, $Y^1$ and $Y^2$ are as described herein, $R^3$ is selected from the group consisting of alkyl, cyano and halogen, and $R^4$ is selected from the group consisting of hydrogen, alkyl, cycloalkyl, alkoxyalkyl, haloalkyl and hydroxyalkyl.

IA

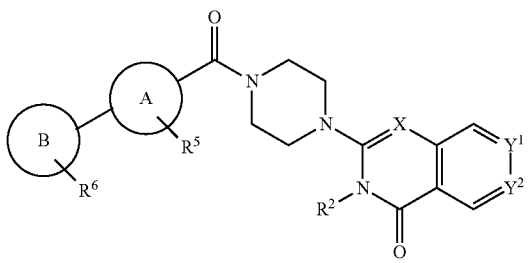

In one embodiment, the compound of Formula (I) is a compound of Formula (IB), wherein $R^2$, X, $Y^1$ and $Y^2$ are as described herein, A and B each independently represent aryl or heteroaryl, $R^5$ is selected from the group consisting of hydrogen, alkyl, cycloalkyl, haloalkyl and cyano, and $R^6$ is selected from the group consisting of hydrogen, alkyl, cycloalkyl, alkoxy, aryloxy, arylalkoxy, haloalkyl, haloalkoxy, hydroxyalkyl, hydroxyalkoxy and cyano.

IB

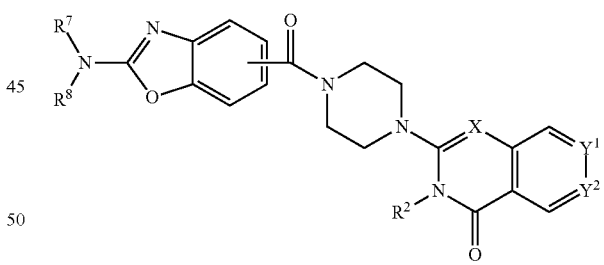

In one embodiment, the compound of Formula (I) is a compound of Formula (IC), wherein $R^2$, X, $Y^1$ and $Y^2$ are as described herein and wherein $R^7$ and $R^8$ are each independently selected from the group consisting of hydrogen, alkyl, cycloalkyl and haloalkyl; or $R^7$ and $R^8$, together with the nitrogen atom to which they are attached, form a monocyclic, 5-, 6- or 7-membered heterocyclic ring, optionally substituted with 1-2 substituents selected from the group consisting of fluorine and alkyl; or optionally substituted with 1 substituent selected from the group consisting of hydroxyl and alkoxy; or $R^7$ and $R^8$, together with the nitrogen atom to which they are attached, form an optionally substituted spirocyclic system selected from the group consisting of 2-azaspiro[3.3]heptan-2-yl, 1-azaspiro[3.3]heptan-1-yl, 1-azaspiro[3.4]octan-1-yl, 2-azaspiro[3.4]octan-2-yl, 1-azaspiro[3.5]nonan-1-yl, 2-azaspiro[3.5]nonan-2-yl, 4-azaspiro[2.4]heptan-4-yl, 5-azaspiro[2.4]heptan-5-yl, 6-azaspiro[3.4]octan-6-yl, 5-azaspiro[3.4]octan-5-yl, 1-azaspiro[4.4]nonane-1-yl, 2-azaspiro[4.4]nonane-2-yl, 5-azaspiro[2.5]octane-5-yl, 6-azaspiro[2.5]octane-6-yl, 6-azaspiro[3.5]nonane-6-yl, and 7-azaspiro[3.5]nonane-7-yl, wherein when said spirocyclic system is substituted, it is substituted with 1-4 fluorine substituents or with 1-2 hydroxy substituents.

IC

In one embodiment, the compound of Formula (I) is a compound of Formula (ID), wherein $R^2$, X, $Y^1$ and $Y^2$ are as described herein and $R^9$ is selected from the group consisting of hydrogen, cyano, alkyl, haloalkyl, —N($R^{10}R^{11}$), hydroxy, alkoxy, hydroxyalkoxy, and alkoxyalkoxy, wherein $R^{10}$ and $R^{11}$ are each independently selected from the group consisting of hydrogen, alkyl, haloalkyl, hydroxyalkyl and alkoxyalkyl; or $R^{10}$ and $R^{11}$, together with the nitrogen atom to which they are attached, form a heterocyclic ring, preferably a monocyclic heterocyclic ring, most preferably a heterocyclic ring selected from the group consisting of morpholine, piperazine and 1-methyl-piperazine. In a preferred embodiment, $R^9$ is selected from the group consisting of hydrogen, cyano, trifluoromethyl and morpholinyl.

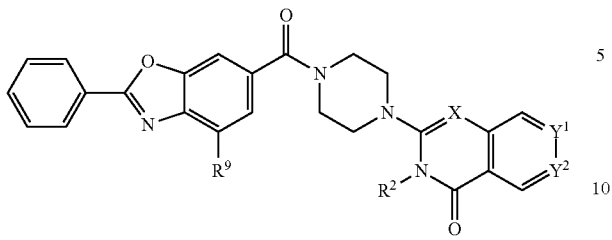

ID

In one embodiment, the compound of Formula (I) is a compound of Formula (IE) wherein $R^2$, X, $Y^1$ and $Y^2$ are as described herein, and $R^{12}$ is selected from the group consisting of hydrogen, alkyl, haloalkyl, cyano and halogen.

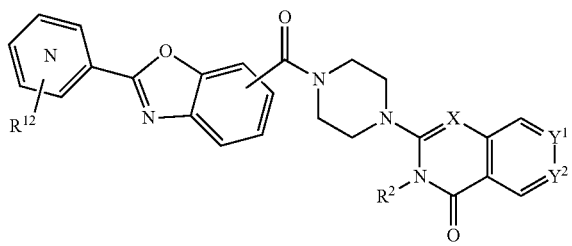

IE

In one embodiment, the compound of Formula (I) is a compound of Formula (IF), wherein $R^2$, X, $Y^1$ and $Y^2$ are as described herein, $R^{13}$ is selected from the group consisting of hydrogen, alkyl and haloalkyl and $R^{14}$ is selected from the group consisting of hydrogen, alkyl, haloalkyl, benzyl and benzyl substituted with a substituent selected from the group consisting of halogen, alkyl and haloalkyl; or $R^{13}$ and $R^{14}$, together with the nitrogen atom to which they are attached, form a monocyclic, 4-, 5-, 6- or 7-membered heterocyclic ring, optionally substituted with 1 substituent selected from the group consisting of haloalkyl and phenyl, or with 1 to 2 substituents selected from the group consisting of alkyl and halogen (in particular fluorine); or $R^{13}$ and $R^{14}$, together with the nitrogen atom to which they are attached, form a heterocyclic ring selected from the group consisting of 2-azabicyclo[2.2.1]heptanyl, indolinyl and 2,3-dihydro-1H-pyrrolo[2,3-b]pyridinyl; or $R^{13}$ and $R^{14}$, together with the nitrogen atom to which they are attached, form a spirocyclic system selected from the group consisting of 1-azaspiro[3.3]heptane-1-yl, 2-azaspiro[3.3]heptane-2-yl, 1-azaspiro[3.4]octane-1-yl, 2-azaspiro[3.4]octane-2-yl, 1-azaspiro[3.5]nonane-1-yl, 2-azaspiro[3.5]nonane-2-yl, 4-azaspiro[2.4]heptane-4-yl, 5-azaspiro[2.4]heptane-5-yl, 5-azaspiro[3.4]octane-5-yl, 6-azaspiro[3.4]octane-6-yl, 1-azaspiro[4.4]nonane-1-yl, 2-azaspiro[4.4]nonane-2-yl, 5-azaspiro[2.5]octane-5-yl, 6-azaspiro[2.5]octane-6-yl, 6-azaspiro[3.5]nonane-6-yl, 7-azaspiro[3.5]nonane-7-yl, wherein said spirocyclic system is optionally substituted with 1-4 halogen substituents (in particular fluorine) or with 1-2 hydroxy substituents.

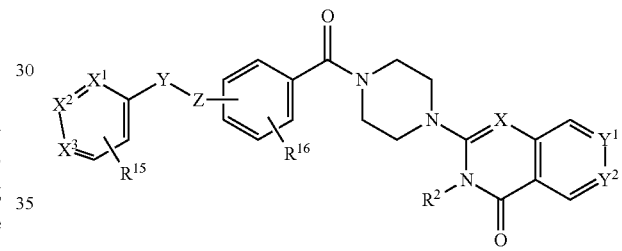

IF

In one embodiment, the compound of Formula (I) is a compound of Formula (IG), wherein $R^2$, X, $Y^1$ and $Y^2$ are as described herein; Y is $CH_2$ and Z is O; $X^1$, $X^2$ and $X^3$ are each selected from the group consisting of CH and N, wherein at most one of $X^1$, $X^2$ and $X^3$ is N; $R^{15}$ is selected from the group consisting of hydrogen, halogen, alkyl and haloalkyl; and $R^{16}$ is selected from the group consisting of hydrogen, halogen, alkyl, haloalkyl, cyano and imidazole-2-yl.

IG

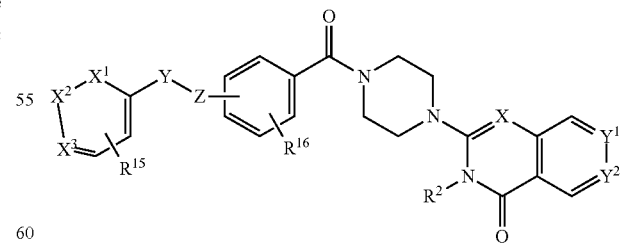

In one embodiment, the compound of Formula (I) is a compound of Formula (IH), wherein $R^2$, X, $Y^1$ and $Y^2$ are as described herein; Y is O and Z is $CH_2$; $X^1$, $X^2$ and $X^3$ are each selected from the group consisting of CH and N, wherein at most one of $X^1$, $X^2$ and $X^3$ is N; $R^{15}$ is selected from the group consisting of hydrogen, halogen, alkyl and haloalkyl; and $R^{16}$ is selected from the group consisting of hydrogen, halogen, alkyl, haloalkyl, cyano and imidazole-2-yl.

IH

In one embodiment, the compound of Formula (I) is a compound of Formula (IJ), wherein $R^2$, $Y^1$ and $Y^2$ are as described herein and B represents an optionally substituted mono-, bi- or spirocyclic heterocycle connected via a nitrogen atom.

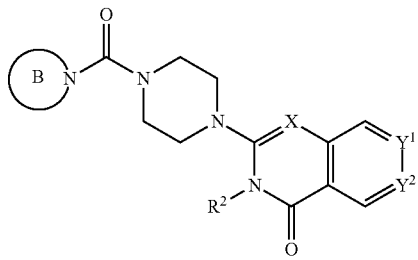

IJ

In one embodiment, the compound of Formula (I) is a compound of Formula (IK), wherein $R^2$, $Y^1$ and $Y^2$ are as described herein and C represents an optionally substituted mono-, bi- or spirocyclic heterocycle connected via a nitrogen atom and containing a second nitrogen substituted with a group $R^{17}SO_2$, wherein $R^{17}$ equals to $R^1$ as defined herein.

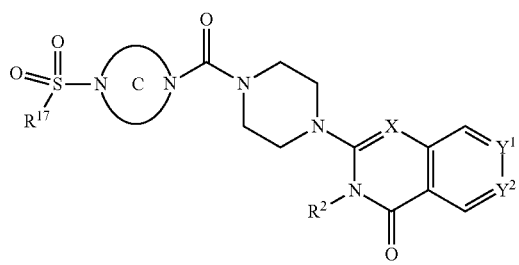

IK

In one embodiment, the compound of Formula (I) is a compound of Formula (IL), wherein $R^2$, $Y^1$ and $Y^2$ are as described herein and C represents an optionally substituted mono-, bi- or spirocyclic heterocycle connected via a nitrogen atom and containing a second nitrogen substituted with a group $R^{17}CH_2$, wherein $R^{17}$ equals to $R^1$ as defined herein.

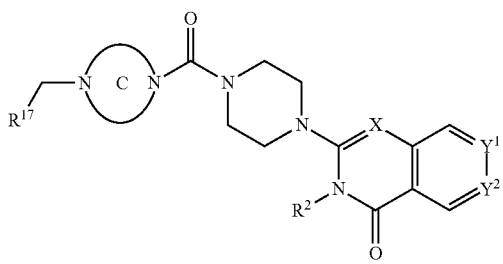

IL

In a particularly preferred embodiment, the present invention provides compounds of Formula (I) as described herein, wherein X is N.

In one embodiment, the present invention provides compounds of Formula (I) as described herein, wherein X is C—H.

In a preferred embodiment, the present invention provides compounds of Formula (I) as described herein, wherein $Y^1$ is selected from the group consisting of C—H, C—F and N.

In a particularly preferred embodiment, the present invention provides compounds of Formula (I) as described herein, wherein $Y^1$ is C—H.

In one embodiment, the present invention provides compounds of Formula (I) as described herein, wherein $Y^2$ is selected from the group consisting of C—H and C-halogen.

In a preferred embodiment, the present invention provides compounds of Formula (I) as described herein, wherein $Y^2$ is selected from the group consisting of C—H, C—F and C—Cl.

In a particularly preferred embodiment, the present invention provides compounds of Formula (I) as described herein, wherein $Y^2$ is C—H.

In a further particularly preferred embodiment, the present invention provides compounds of Formula (I) as described herein, wherein X is N and $Y^1$ and $Y^2$ are both C—H.

In one embodiment, the present invention provides compounds of Formula (I) as described herein, wherein $R^1$ is selected from the group consisting of:
i. aryl substituted with one or more substituents selected from the group consisting of:
aminoalkyl, amino, haloalkylaryl, cycloalkyl, aryl-alkenyl, haloalkylaryl-alkoxyalkyl, haloalkylaryloxy, haloalkylheteroaryl, alkylheteroaryl, arylcycloalkyl, cycloalkylheteroaryl, cycloalkylalkoxy, arylalkoxy, aryloxy, halogen, heterocyclyl, haloheterocyclyl, hydroxyalkylheterocyclyl, haloalkylheterocyclyl, haloaryloxyalkyl, alkoxyalkylheterocyclyl, heteroaryl, haloheteroarylalkoxy, aryl, haloaryl, haloalkoxy, alkoxy, alkyl, haloalkyl, cyano, cyanoaryl, cyanocycloalkyl, cyanoalkylaryl, arylheterocyclyl, alkoxy-(haloalkyl)aryl, arylalkoxy-(alkyl)aryl, haloaryloxy, hydroxyalkylaryl, alkenyloxy, pentafluorosulfanyl, heteroarylalkyl, alkoxyaryl, (arylalkoxy)aryl, carbamoylaryl, alkyl-(alkoxy)aryl, haloalkoxyaryl, alkylheterocyclyl and haloarylalkoxy, wherein:
said aminoalkyl is substituted on the nitrogen atom with one or two substituents independently selected from the group consisting of alkanoyl, arylalkyl and haloalkylarylalkyl; and
said amino is substituted on the nitrogen atom with two substituents independently selected from the group consisting of alkyl, haloarylalkyl and haloalkoxy arylalkyl;
ii. heteroaryl substituted with one or more substituents selected from the group consisting of:
alkylsulfanyl, heteroaryl, cycloalkyl, haloaryl, heterocyclyl, alkoxyheterocyclyl, hydroxyheterocyclyl, alkylheterocyclyl, aryl, alkyl, haloalkyl, cyano, cyanoaryl, halogen, arylalkoxy, alkoxy, dialkylamino, haloheterocyclyl, haloalkylhaloaryl, aryloxyalkyl, alkylaryl and haloalkylaryl; and
iii. heteroaryl.

In one embodiment, the present invention provides compounds of Formula (I) as described herein, wherein $R^1$ is selected from the group consisting of:
i. heteroaryl substituted with one or more substituents selected from the group consisting of:
aryl, alkylaryl, haloaryl, heterocyclyl, alkylheterocyclyl, cycloalkyl, cyano, alkyl and haloalkyl; and
ii. aryl substituted with one or more substituents selected from the group consisting of:
heterocyclyl, hydroxyalkylheterocyclyl, haloalkylaryl, haloalkylheteroaryl, haloheteroarylalkoxy, haloaryloxyalkyl, arylheterocyclyl, alkylheterocyclyl, haloarylalkoxy, halogen, haloalkyl, alkyl, heteroaryl, haloalkoxy, haloalkoxyaryl, hydroxyalkylaryl, alkoxy-(haloalkyl)aryl, alkylheterocyclyl, cycloalkylheteroaryl and aminoalkyl; wherein:

said aminoalkyl is substituted on the nitrogen atom with two substituents independently selected from the group consisting of alkanoyl and haloalkylarylalkyl.

In one embodiment, the present invention provides compounds of Formula (I) as described herein, wherein $R^1$ is selected from the group consisting of:
i. monocyclic heteroaryl substituted with one or more alkylaryl substituents;
ii. bicyclic heteroaryl substituted with one or more substituents selected from the group consisting of:
aryl, haloaryl, heterocyclyl, alkylheterocyclyl, cycloalkyl, cyano, alkyl and haloalkyl; and
iii. monocyclic aryl substituted with one or more substituents selected from the group consisting of:
heterocyclyl, hydroxyalkylheterocyclyl, haloalkylaryl, haloalkylheteroaryl, haloheteroarylalkoxy, haloaryloxyalkyl, arylheterocyclyl, alkylheteroaryl, haloarylalkoxy, halogen, haloalkyl, alkyl, heteroaryl, haloalkoxy, haloalkoxyaryl, hydroxyalkylaryl, alkoxy-substituted haloalkylaryl, alkylheterocyclyl, cycloalkylheteroaryl and aminoalkyl; wherein:
said aminoalkyl is substituted on the nitrogen atom with two substituents independently selected from the group consisting of alkanoyl and haloalkylarylalkyl.

In a preferred embodiment, the present invention provides compounds of Formula (I) as described herein, wherein $R^1$ is selected from the group consisting of:
i. benzoxazolyl substituted with 1 to 2 substituents selected from the group consisting of:
methyl, $CF_3$, phenyl, chlorophenyl, fluorophenyl, piperidinyl, cyclohexyl, methylpyrrolidinyl and CN;
ii. indolyl substituted once with phenyl or fluorophenyl;
iii. indazolyl substituted once with fluorophenyl;
iv. phenyl substituted with 1 to 2 substituents selected from the group of:
Cl, F, methyl, $CF_3$, pyrrolidinyl, hydroxyethylpyrrolidinyl, imidazolyl, dimethylpiperidinyl, trifluoromethylpyridyl, substituted phenyl, phenylcyclopropyl, substituted oxadiazolyl, chlorophenylmethoxy, 2,3-dihydroindolyl, 2-azaspiro[3.3]heptanyl, 5-azaspiro[2.4]heptanyl, (chloropyridyl)methoxy, (chlorophenoxy)methyl, azepanyl, 2,3-dihydropyrrolo[2,3-b]pyridin-1-yl, 2,3-dihydro-1H-pyrrolo[2,3-b]pyridin-4-yl and aminoethyl; wherein:
said substituted phenyl is substituted with 1-2 substituents independently selected from the group consisting of $CF_3$, methoxy, trifluoromethoxy and hydroxymethyl;
said substituted oxadiazolyl is substituted once with propan-2-yl, trifluoroethyl or cyclopropyl; and
said aminoethyl is substituted on the nitrogen atom with acetyl and trifluoromethylbenzyl; and
v. pyridyl substituted once with tert-butylphenyl.

In a particularly preferred embodiment, the present invention provides compounds of Formula (I) as described herein, wherein $R^1$ is selected from the group consisting of:

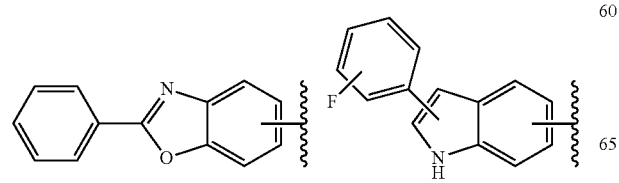

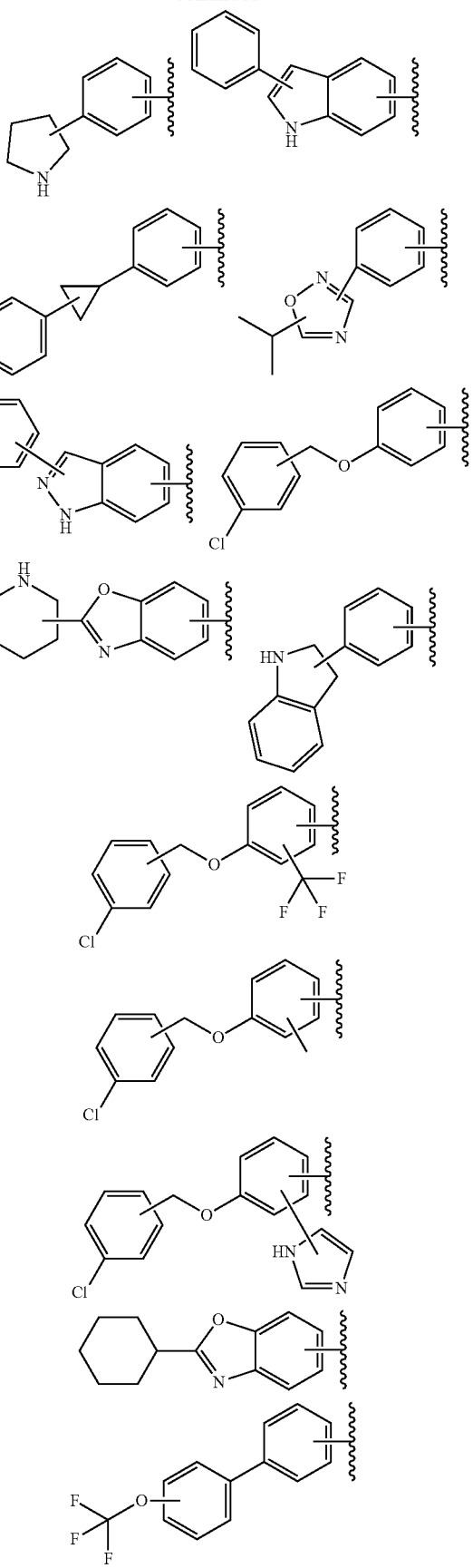

-continued

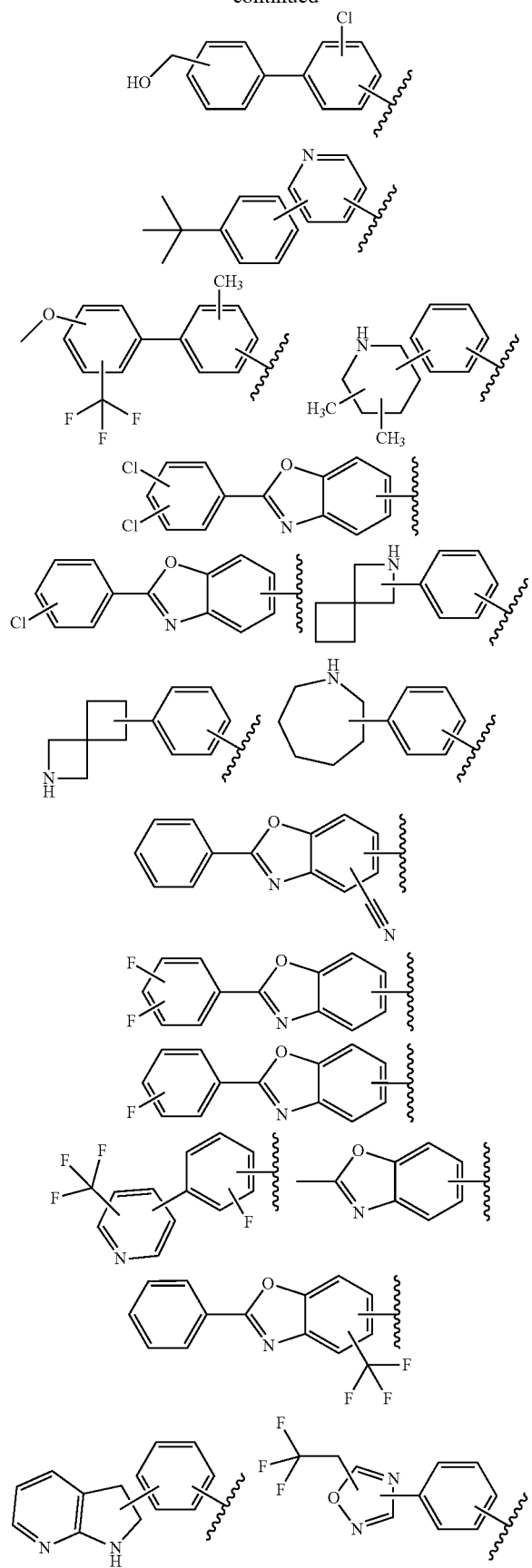

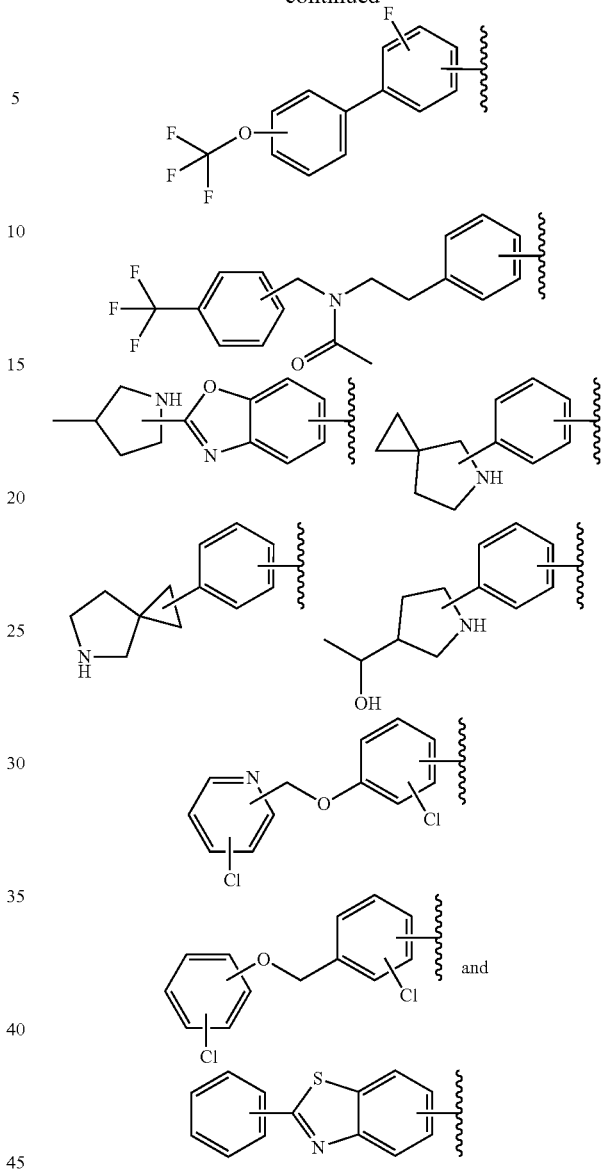

and wherein a wavy line indicates the point of attachment of $R^1$ to the rest of Formula (I).

In one embodiment, the present invention provides compounds of Formula (I) as described herein, wherein $R^1$ is selected from the group consisting of:
i. heteroaryl substituted with one or more substituents selected from the group consisting of:
aryl, haloaryl, haloalkylaryl, heterocyclyl, haloheterocyclyl and dialkylamino; and
ii. aryl substituted with one or more substituents selected from the group consisting of:
alkylheteroaryl and heterocyclyl.

In one embodiment, the present invention provides compounds of Formula (I) as described herein, wherein $R^1$ is selected from the group consisting of:
i. bicyclic heteroaryl substituted with one or more substituents selected from the group consisting of:
aryl, haloaryl, haloalkylaryl, heterocyclyl, haloheterocyclyl and dialkylamino; and
ii. monocyclic aryl substituted with one or more substituents selected from the group consisting of:
alkylheteroaryl and heterocyclyl.

In a preferred embodiment, the present invention provides compounds of Formula (I) as described herein, wherein $R^1$ is selected from the group consisting of:

i. benzoxazolyl substituted with 1 to 2 substituents selected from the group consisting of:

phenyl, chlorophenyl, trifluoromethylphenyl, morpholinyl, 2-azaspiro[3.4]octanyl, difluoro-2-azaspiro[3.3]heptanyl and methyl(propyl)amino; and ii. phenyl substituted with 1 substituent selected from the group consisting of substituted oxadiazolyl, 2-azaspiro[3.4]octanyl and 6-azaspiro[3.4]octan-yl, wherein:

said substituted oxadiazolyl is substituted once with 2,2-dimethylpropyl or tert-butyl.

In a particularly preferred embodiment, the present invention provides compounds of Formula (I) as described herein, wherein $R^1$ is selected from the group consisting of:

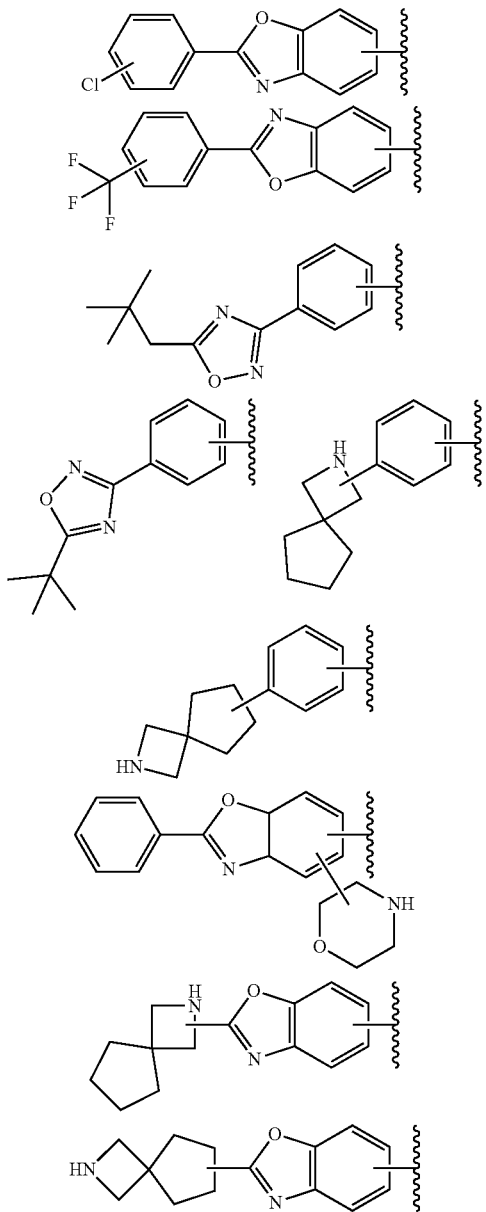
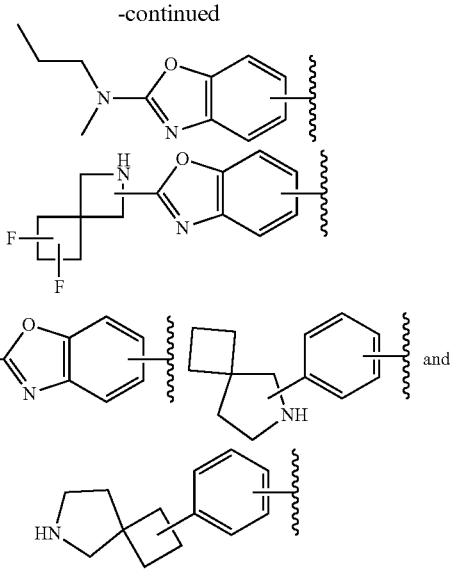

wherein a wavy line indicates the point of attachment of $R^1$ to the rest of Formula (I).

In a particularly preferred embodiment, the present invention provides compounds of Formula (I) as described herein, wherein $R^2$ is H.

In one embodiment, the present invention provides compounds of Formula (I) as described herein, wherein:

X is C—H or N;

$Y^1$ is selected from the group consisting of C—H, C—F and N;

$Y^2$ is selected from the group consisting of C—H and C-halogen;

$R^1$ is selected from the group consisting of:

i. aryl substituted with one or more substituents selected from the group consisting of:

aminoalkyl, amino, haloalkylaryl, cycloalkyl, aryl-alkenyl, haloalkylaryl-alkoxyalkyl, haloalkylaryloxy, haloalkylheteroaryl, alkylheteroaryl, arylcycloalkyl, cycloalkylheteroaryl, cycloalkylalkoxy, arylalkoxy, aryloxy, halogen, heterocyclyl, haloheterocyclyl, hydroxyalkylheterocyclyl, haloalkylheterocyclyl, haloaryloxyalkyl, alkoxyalkylheterocyclyl, heteroaryl, haloheteroarylalkoxy, aryl, haloaryl, haloalkoxy, alkoxy, alkyl, haloalkyl, cyano, cyanoaryl, cyanocycloalkyl, cyanoalkylaryl, arylheterocyclyl, alkoxy-(haloalkyl)aryl, arylalkoxy-(alkyl)aryl, haloaryloxy, hydroxyalkylaryl, alkenyloxy, pentafluorosulfanyl, heteroarylalkyl, alkoxyaryl, (arylalkoxy)aryl, carbamoylaryl, alkyl-(alkoxy)aryl, haloalkoxyaryl, alkylheterocyclyl and haloarylalkoxy, wherein:

said aminoalkyl is substituted on the nitrogen atom with one or two substituents independently selected from the group consisting of alkanoyl, arylalkyl and haloalkylarylalkyl; and said amino is substituted on the nitrogen atom with two substituents independently selected from the group consisting of alkyl, haloarylalkyl and haloalkoxyarylalkyl;

i. heteroaryl substituted with one or more substituents selected from the group consisting of:

alkylsulfanyl, heteroaryl, cycloalkyl, haloaryl, heterocyclyl, alkoxyheterocyclyl, hydroxyheterocyclyl, alkylheterocyclyl, aryl, alkyl, haloalkyl, cyano, cyanoaryl, halogen, arylalkoxy, alkoxy, dialkylamino, haloheterocyclyl, haloalkylhaloaryl, aryloxyalkyl, alkylaryl and haloalkylaryl; and
ii. heteroaryl; and
$R^2$ is selected from the group consisting of hydrogen and alkyl;
or a pharmaceutically acceptable salt thereof.

In one embodiment, the present invention provides compounds of Formula (I) as described herein, wherein:
X is C—H or N;
$Y^1$ is selected from the group consisting of C—H and C—F;
$Y^2$ is selected from the group consisting of C—H and C-halogen;
$R^1$ is selected from the group consisting of:
i. heteroaryl substituted with one or more substituents selected from the group consisting of:
aryl, alkylaryl, haloaryl, heterocyclyl, alkylheterocyclyl, cycloalkyl, cyano, alkyl and haloalkyl; and
ii. aryl substituted with one or more substituents selected from the group consisting of:
heterocyclyl, hydroxyalkylheterocyclyl, haloalkylaryl, haloalkylheteroaryl, haloheteroarylalkoxy, haloaryloxyalkyl, arylheterocyclyl, alkylheteroaryl, haloarylalkoxy, halogen, haloalkyl, alkyl, heteroaryl, haloalkoxy, haloalkoxyaryl, hydroxyalkylaryl, alkoxy-(haloalkyl)aryl, alkylheterocyclyl, cycloalkylheteroaryl and aminoalkyl; wherein:
said aminoalkyl is substituted on the nitrogen atom with two substituents independently selected from the group consisting of alkanoyl and haloalkylarylalkyl; and
$R^2$ is selected from the group consisting of hydrogen and alkyl;
or a pharmaceutically acceptable salt thereof.

In one embodiment, the present invention provides compounds of Formula (I) as described herein, wherein:
X, $Y^1$ and $Y^2$ are each C—H;
$R^1$ is selected from the group consisting of:
i. heteroaryl substituted with one or more substituents selected from the group consisting of:
aryl, haloaryl, haloalkylaryl, heterocyclyl, haloheterocyclyl and dialkylamino; and
ii. aryl substituted with one or more substituents selected from the group consisting of:
alkylheteroaryl and heterocyclyl; and
$R^2$ is hydrogen;
or a pharmaceutically acceptable salt thereof.

In a preferred embodiment, the present invention provides compounds of Formula (I) as described herein, wherein:
X is C—H or N;
$Y^1$ is selected from the group consisting of C—H and C—F;
$Y^2$ is selected from the group consisting of C—H, C—Cl and C—F;
$R^1$ is selected from the group consisting of:
i. benzoxazolyl substituted with 1 to 2 substituents selected from the group consisting of:
methyl, $CF_3$, phenyl, chlorophenyl, fluorophenyl, piperidinyl, cyclohexyl, methylpyrrolidinyl and CN; and
ii. indolyl substituted once with phenyl or fluorophenyl;
iii. indazolyl substituted once with fluorophenyl;
iv. phenyl substituted with 1 to 2 substituents selected from the group consisting of:
Cl, F, methyl, $CF_3$, pyrrolidinyl, hydroxyethylpyrrolidinyl, imidazolyl, dimethylpiperidinyl, trifluoromethylpyridyl, substituted phenyl, phenylcyclopropyl, substituted oxadiazolyl, chlorophenylmethoxy, 2,3-dihydroindolyl, 2-azaspiro[3.3]heptanyl, 5-azaspiro[2.4]heptanyl, (chloropyridyl)methoxy, (chlorophenoxy)methyl, azepanyl, 2,3-dihydropyrrolo[2,3-b]pyridin-1-yl, 2,3-dihydro-1H-pyrrolo[2,3-b]pyridin-4-yl and aminoethyl, wherein:
said substituted phenyl is substituted with 1-2 substituents independently selected from the group consisting of $CF_3$, methoxy, trifluoromethoxy and hydroxymethyl;
said substituted oxadiazolyl is substituted once with propan-2-yl, trifluoroethyl or cyclopropyl; and
said aminoethyl is substituted on the nitrogen atom with acetyl and trifluoromethylbenzyl; and
v. pyridyl substituted once with tert-butylphenyl; and
$R^2$ is selected from the group consisting of hydrogen and alkyl;
or a pharmaceutically acceptable salt thereof.

In a further preferred embodiment, the present invention provides compounds of Formula (I) as described herein, wherein:
X, $Y^1$ and $Y^2$ are each C—H;
$R^1$ is selected from the group consisting of:
i. benzoxazolyl substituted with 1 to 2 substituents selected from the group consisting of:
phenyl, chlorophenyl, trifluoromethylphenyl, morpholinyl, 2-azaspiro[3.4]octanyl, difluoro-2-azaspiro[3.3]heptanyl and methyl(propyl)amino; and
ii. phenyl substituted with 1 substituent selected from the group consisting of substituted oxadiazolyl, 2-azaspiro[3.4]octanyl and 6-azaspiro[3.4]octan-yl, wherein:
said substituted oxadiazolyl is substituted once with 2,2-dimethylpropyl or tert-butyl; and
$R^2$ is hydrogen;
or a pharmaceutically acceptable salt thereof.

In a particularly preferred embodiment, the present invention provides compounds of Formula (I) as described herein, wherein:
X is C—H or N;
$Y^1$ is selected from the group consisting of C—H and C—F;
$Y^2$ is selected from the group consisting of C—H, C—Cl and C—F;
$R^1$ is selected from the group consisting of:

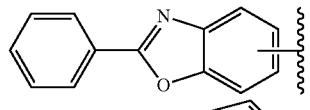

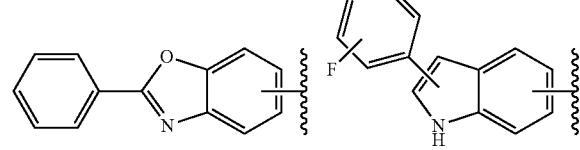

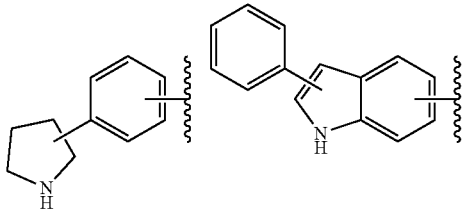

-continued
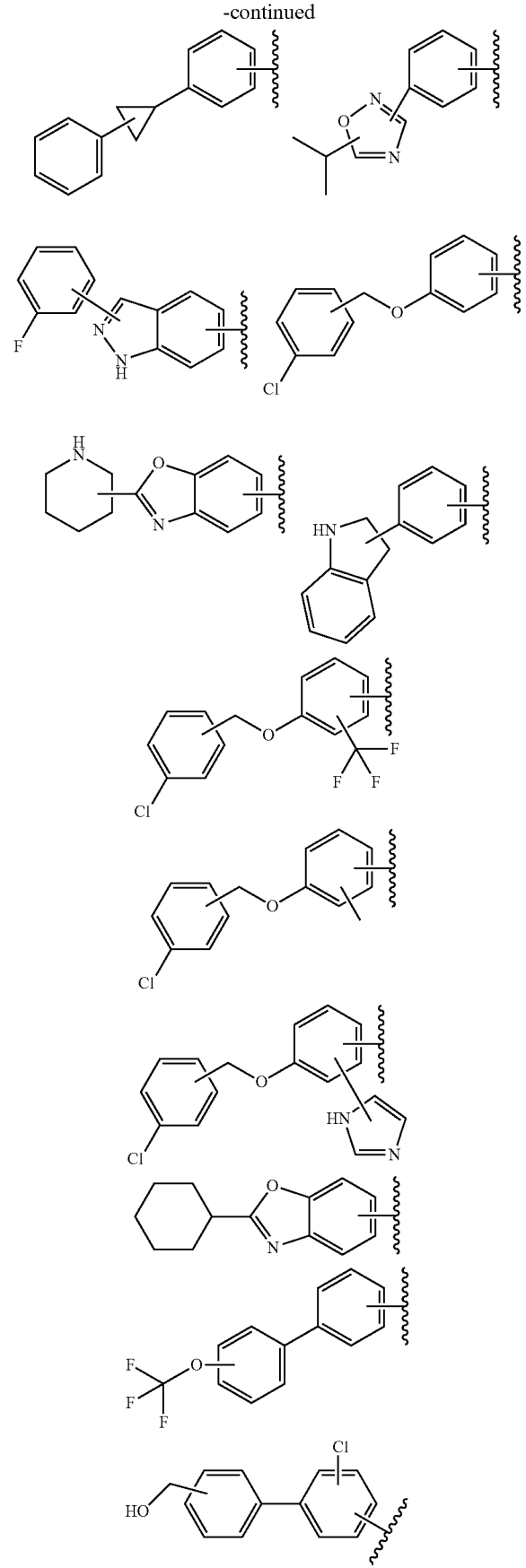
-continued
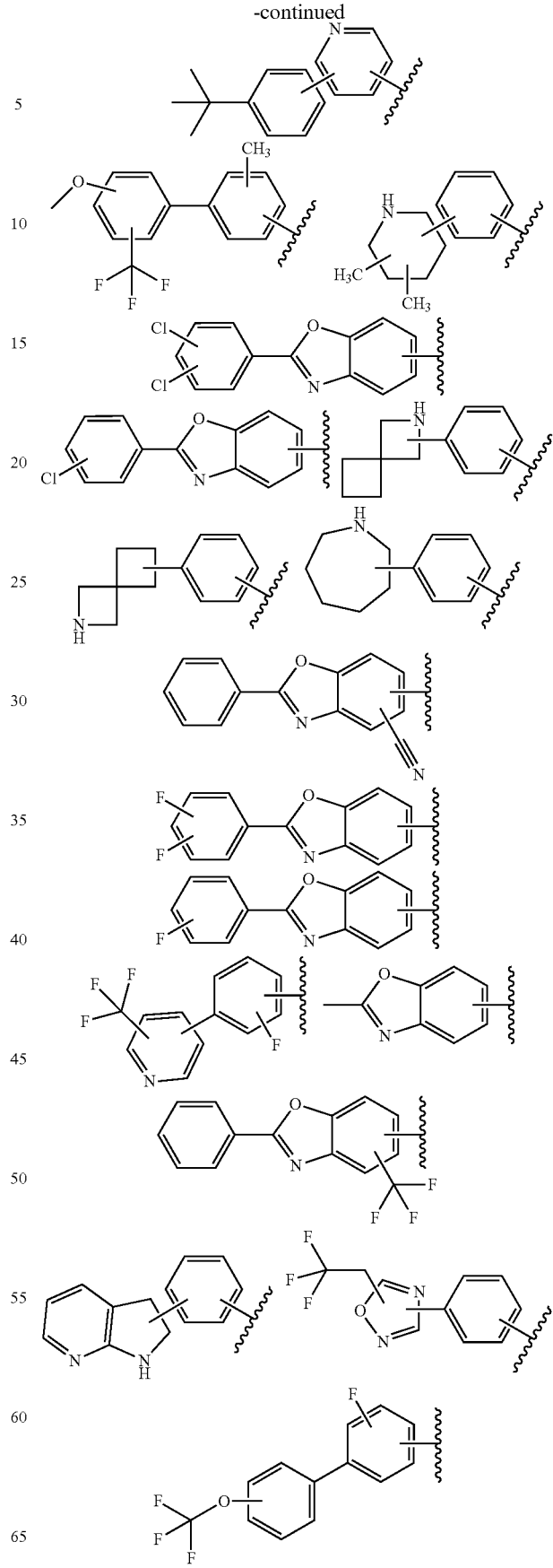

39
-continued

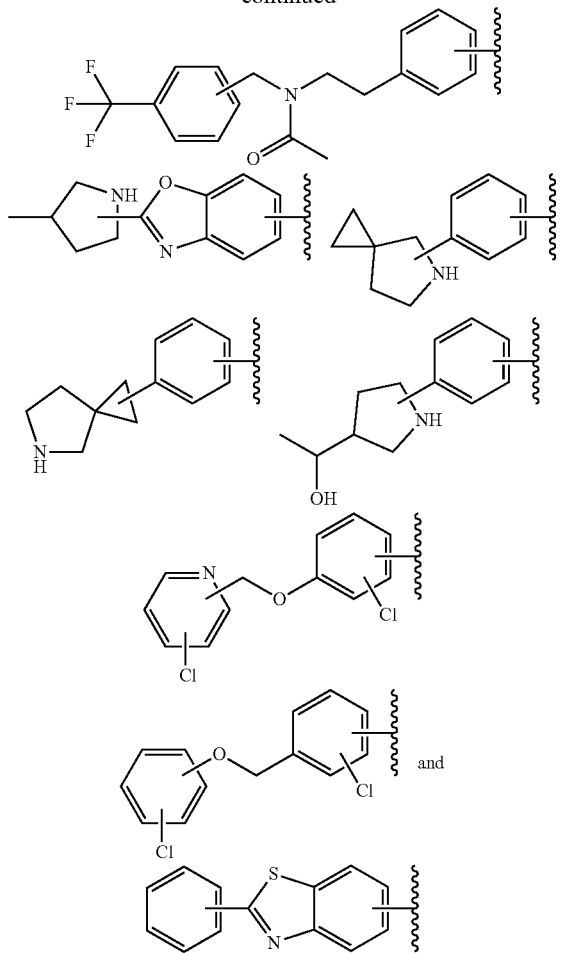

wherein a wavy line indicates the point of attachment of R¹ to the rest of Formula (I); and R² is selected from the group consisting of hydrogen and alkyl;

or a pharmaceutically acceptable salt thereof.

In a further particularly preferred embodiment, the present invention provides compounds of Formula (I) as described herein, wherein:

X, Y¹ and Y² are each C—H;

R¹ is selected from the group consisting of:

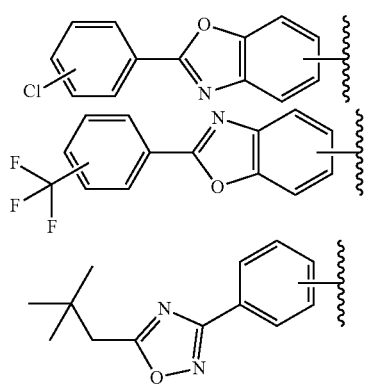

40
-continued wherein a wavy line indicates the point of attachment of R¹ to the rest of Formula (I); and R² is hydrogen;

to or a pharmaceutically acceptable salt thereof.

In one embodiment, the present invention provides compounds of Formula (I) as described herein, wherein R¹ is selected from the group consisting of:
  i. aryl substituted with one or more substituents selected from the group consisting of:
    aminoalkyl, amino, haloalkylaryl, cycloalkyl, haloaryl-alkenyl, hydroxyalkynyl, haloalkylaryl-alkoxyalkyl, haloalkylaryloxy, haloalkylheteroaryl, alkylheteroaryl, arylcycloalkyl, cycloalkylheteroaryl, cycloalkylalkoxy, arylalkoxy, aryloxy, halogen, heterocyclyl, haloheterocyclyl, hydroxyalkylheterocyclyl, hydroxyalkylheteroaryl, arylalkoxyalkylheteroaryl, haloalkylheterocyclyl, haloaryloxyalkyl, alkoxyalkylheterocyclyl, heteroaryl, haloheteroarylalkoxy, aryl, haloaryl, haloalkoxy, alkoxy, alkyl, haloalkyl, cyano, cyanoaryl, cyanocycloalkyl, cyanoalkylaryl, arylheterocyclyl, alkoxy-(haloalkyl)aryl, arylalkoxy-(alkyl)aryl, haloaryloxy, hydroxyalkylaryl, alkenyloxy, pentafluoro-lambda6-sulfanyl, heteroarylalkyl, alkoxyaryl, (arylalkoxy)aryl, carbamoylaryl, alkyl-(alkoxy)aryl, haloalkoxyaryl, alkylheterocyclyl, alkylcycloalkylheteroaryl and haloarylalkoxy, wherein:
  said aminoalkyl is substituted on the nitrogen atom with one or two substituents independently selected from the group consisting of alkanoyl, arylalkyl and haloalkylarylalkyl; and
  said amino is substituted on the nitrogen atom with one or two substituents independently selected from the group consisting of alkyl, haloarylalkyl and haloalkoxyarylalkyl;
ii. heteroaryl substituted with one or more (1,2) substituents selected from the group consisting of:
  alkylsulfanyl, heteroaryl, cycloalkyl, haloaryl, cyano(haloaryl), heterocyclyl, alkoxyheterocyclyl, hydroxyheterocyclyl, alkylheterocyclyl, alkyl(hydroxyheterocyclyl), alkyl(haloheterocyclyl), alkylheteroaryl, hydroxyalkylheterocyclyl, aryl, alkyl, haloalkyl, cyano, cyanoaryl, halogen, arylalkoxy, alkoxy, dialkylamino, haloheterocyclyl, haloalkylhaloaryl, aryloxyalkyl, alkylaryl, heteroaryl alkoxy and haloalkylaryl;
iii. heteroaryl;
iv. cycloalkyl, substituted once with alkylheteroaryl; and
v. heterocyclyl, substituted once with haloarylsulfonyl or haloarylalkyl.

In a preferred embodiment, the present invention provides compounds of Formula (I) as described herein, wherein $R^1$ is selected from the group consisting of:
i. heteroaryl substituted with one or more substituents selected from the group consisting of:
  aryl, alkylaryl, haloaryl, cyano(haloaryl), heterocyclyl, haloheterocyclyl, alkyl(haloheterocyclyl), alkylheterocyclyl, hydroxyalkylheterocyclyl, cycloalkyl, cyano, alkyl and haloalkyl; and
ii. aryl substituted with one or more substituents selected from the group consisting of:
  heterocyclyl, hydroxyalkylheterocyclyl, haloalkylaryl, haloalkylheteroaryl, haloheteroarylalkoxy, haloaryloxyalkyl, arylheterocyclyl, alkylheteroaryl, haloarylalkoxy, halogen, haloalkyl, alkyl, heteroaryl, haloalkoxy, haloalkoxyaryl, hydroxyalkylaryl, alkoxy-(haloalkyl)aryl, alkylheterocyclyl, cycloalkylheteroaryl, alkylcycloalkylheteroaryl and aminoalkyl; wherein:
    said aminoalkyl is substituted on the nitrogen atom with two substituents independently selected from the group consisting of alkanoyl and haloalkylarylalkyl.

In a further preferred embodiment, the present invention provides compounds of Formula (I) as described herein, wherein $R^1$ is selected from the group consisting of:
i. monocyclic heteroaryl substituted with one or more alkylaryl substituents;
ii. bicyclic heteroaryl substituted with one or more substituents selected from the group consisting of:
  aryl, haloaryl, cyano(haloaryl), heterocyclyl, haloheterocyclyl, alkyl(haloheterocyclyl), alkylheterocyclyl, hydroxyalkylheterocyclyl, cycloalkyl, cyano, alkyl and haloalkyl; and
iii. monocyclic aryl substituted with one or more substituents selected from the group consisting of:
  heterocyclyl, hydroxyalkylheterocyclyl, haloalkylaryl, haloalkylheteroaryl, haloheteroarylalkoxy, haloaryloxyalkyl, arylheterocyclyl, alkylheteroaryl, haloarylalkoxy, halogen, haloalkyl, alkyl, heteroaryl, haloalkoxy, haloalkoxyaryl, hydroxyalkylaryl, alkoxy-(haloalkyl)aryl, alkylheterocyclyl, cycloalkylheteroaryl, alkylcycloalkylheteroaryl and aminoalkyl; wherein:
    said aminoalkyl is substituted on the nitrogen atom with two substituents independently selected from the group consisting of alkanoyl and haloalkylarylalkyl.

In a particularly preferred embodiment, the present invention provides compounds of Formula (I) as described herein, wherein $R^1$ is selected from the group consisting of:
i. benzoxazolyl substituted with 1 to 2 substituents selected from the group consisting of:
  methyl, $CF_3$, phenyl, chlorophenyl, cyano-chlorophenyl, 2-azaspiro[3.3]heptanyl, 6-azaspiro[3.4]octanyl, difluoro-2-azaspiro[3.3]heptanyl, 3-fluoro-3-methyl-pyrrolidinyl, 3-(1-hydroxy-1-methyl-ethyl)pyrrolidinyl, fluorophenyl, piperidinyl, cyclohexyl, methylpyrrolidinyl and CN;
ii. indolyl substituted once with phenyl or fluorophenyl;
iii. indazolyl substituted once with fluorophenyl;
iv. phenyl substituted with 1 to 2 substituents selected from the group consisting of:
  Cl, F, methyl, $CF_3$, pyrrolidinyl, hydroxyethylpyrrolidinyl, dimethylpyrrolidinyl, diethylpyrrolidinyl, imidazolyl, dimethylpiperidinyl, trifluoromethylpyridyl, substituted phenyl, phenylcyclopropyl, substituted oxadiazolyl, chlorophenylmethoxy, 2,3-dihydroindolyl, 2-azaspiro[3.3]heptanyl, 5-azaspiro[2.4]heptanyl, (chloropyridyl)methoxy, (chlorophenoxy)methyl, azepanyl, 2,3-dihydropyrrolo[2,3-b]pyridin-1-yl, 2,3-dihydro-1H-pyrrolo[2,3-b]pyridin-4-yl and aminoethyl; wherein:
    said substituted phenyl is substituted with 1-2 substituents independently selected from the group consisting of $CF_3$, methoxy, trifluoromethoxy and hydroxymethyl;
    said substituted oxadiazolyl is substituted once with propan-2-yl, trifluoroethyl, 2-fluoro-1,1-dimethylethyl, tert-butyl, cyclopropyl or 1-methylcyclopropyl; and
    said aminoethyl is substituted on the nitrogen atom with acetyl and trifluoromethylbenzyl; and
v. pyridyl substituted once with tert-butylphenyl.

In another particularly preferred embodiment, the present invention provides compounds of Formula (I) as described herein, wherein $R^1$ is selected from the group consisting of:

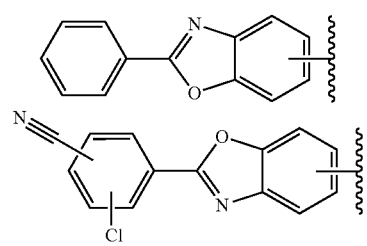

-continued
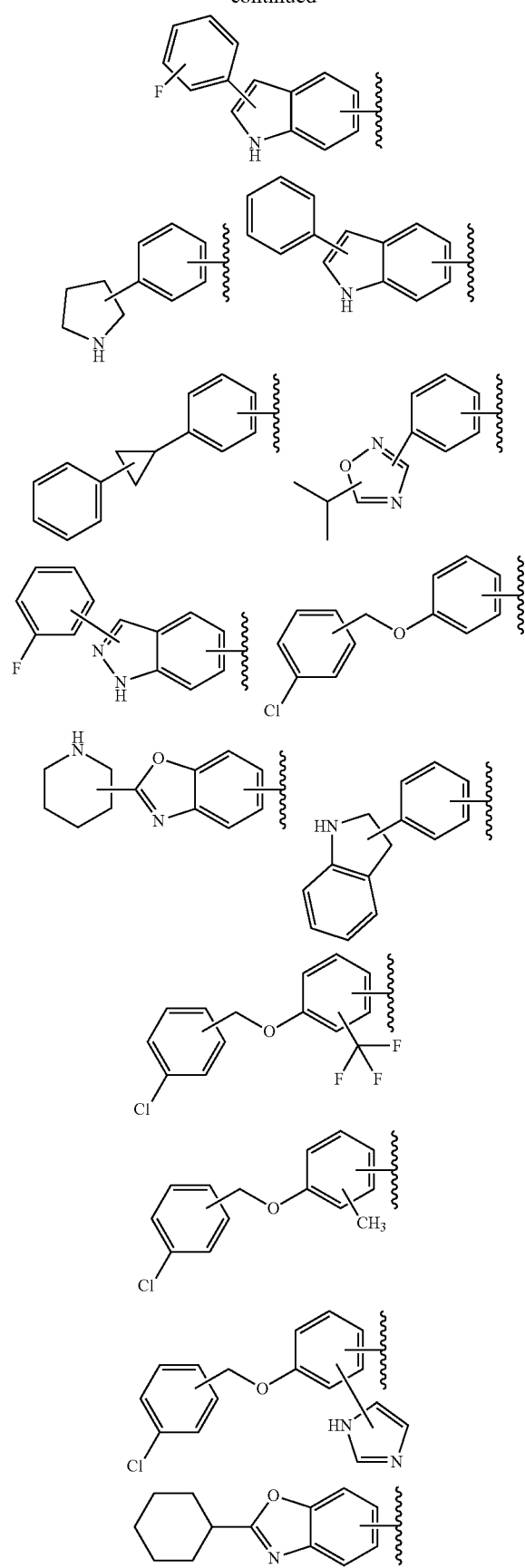
-continued
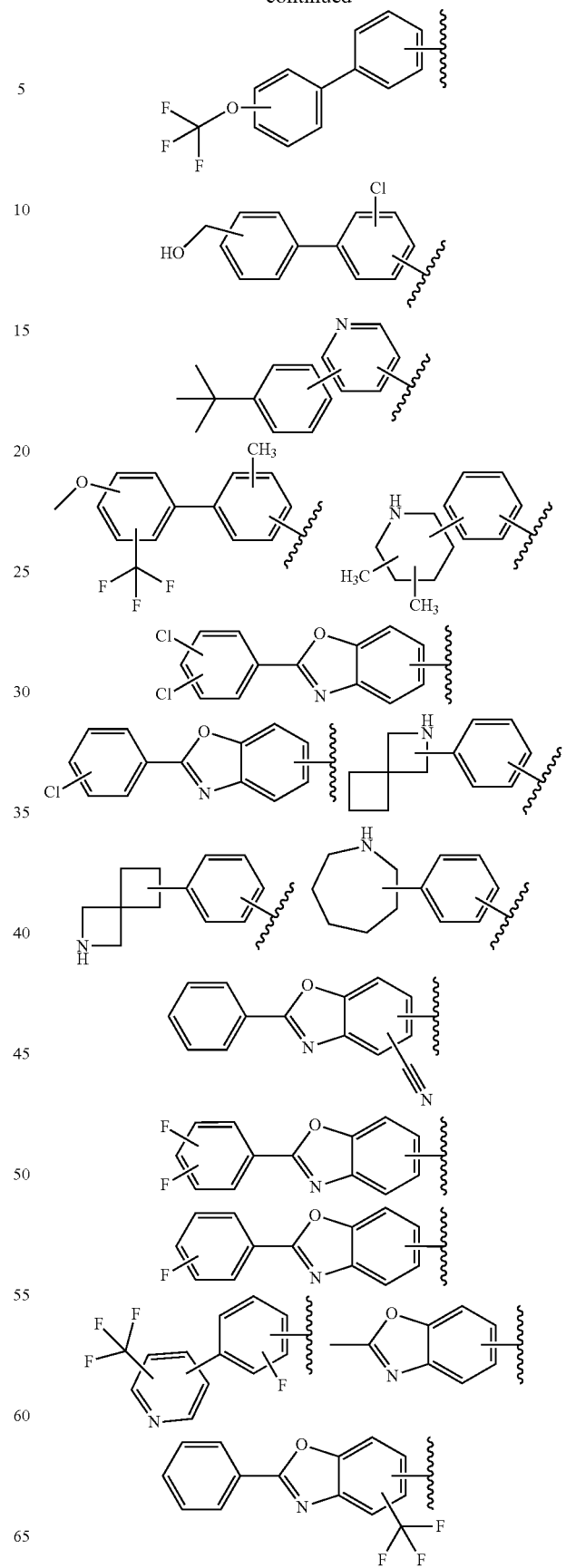

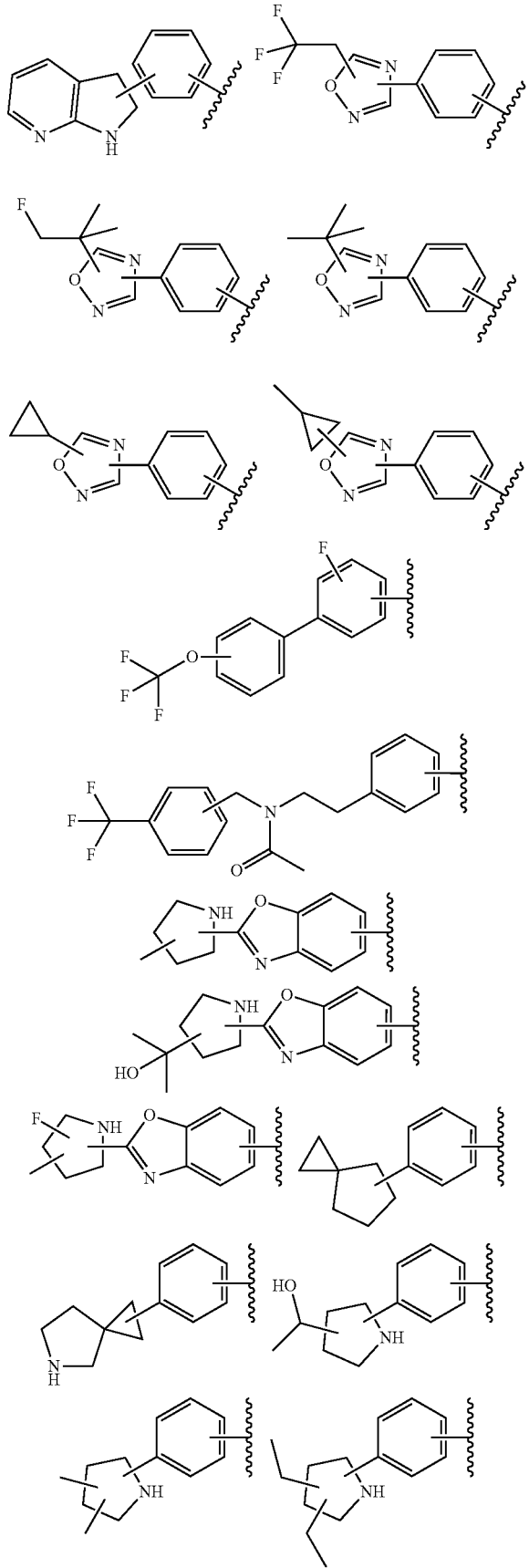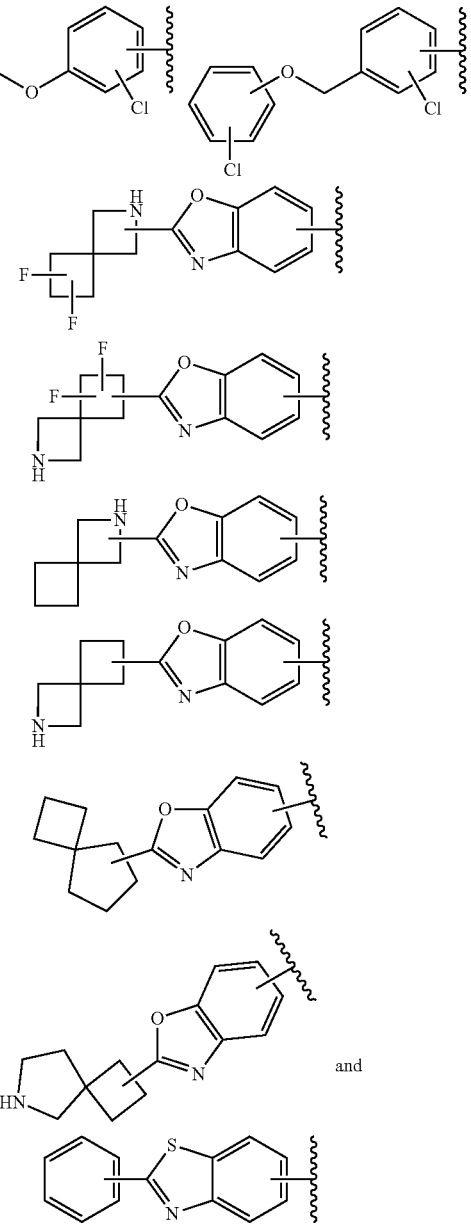
wherein a wavy line indicates the point of attachment of R¹ to the rest of Formula (I).
In yet another particularly preferred embodiment, the present invention provides compounds of Formula (I) as described herein, wherein R¹ is selected from the group consisting of:
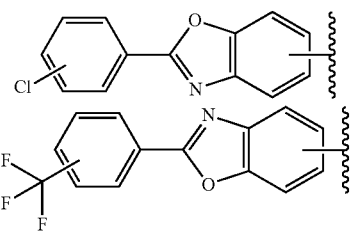

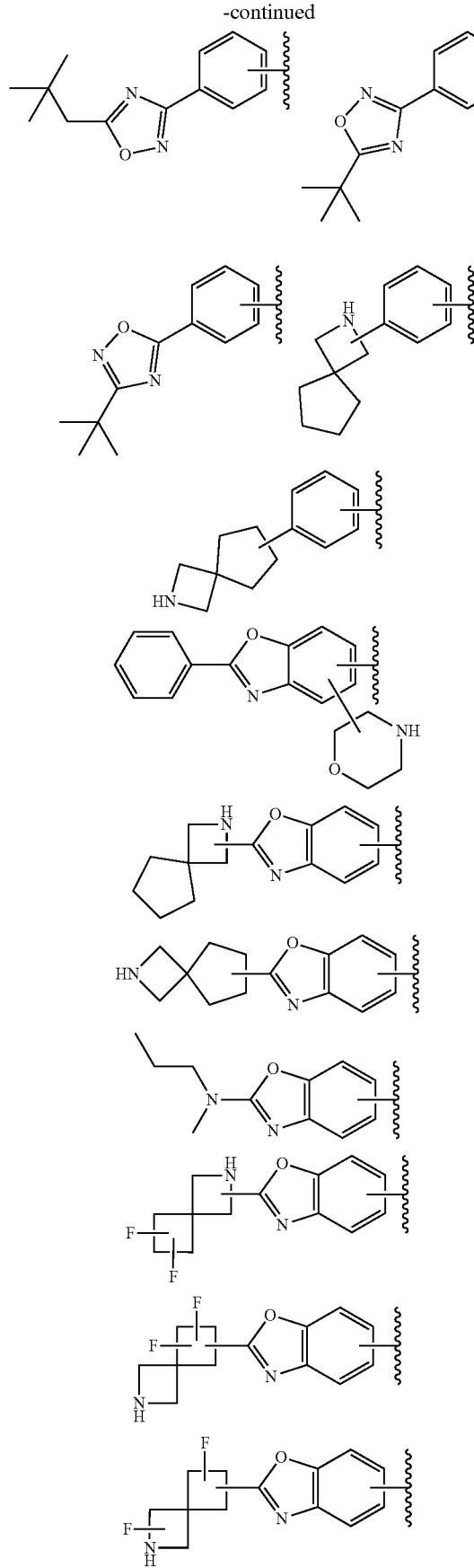
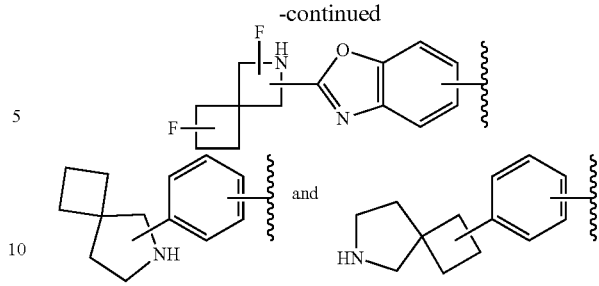

wherein a wavy line indicates the point of attachment of $R^1$ to the rest of Formula (I).

In one embodiment, the present invention provides compounds of Formula (I) as described herein, wherein:

X is C—H or N;

$Y^1$ is selected from the group consisting of C—H, C—F and N;

$Y^2$ is selected from the group consisting of C—H and C-halogen;

$R^1$ is selected from the group consisting of:
i. aryl substituted with one or more substituents selected from the group consisting of:
aminoalkyl, amino, haloalkylaryl, cycloalkyl, haloarylalkenyl, alkylcycloalkylheteroaryl, hydroxyalkynyl, haloalkylaryl-alkoxyalkyl, haloalkylaryloxy, haloalkylheteroaryl, alkylheteroaryl, arylcycloalkyl, cycloalkylheteroaryl, cycloalkylalkoxy, arylalkoxy, aryloxy, halogen, heterocyclyl, haloheterocyclyl, hydroxyalkylheterocyclyl, hydroxyalkylheteroaryl, arylalkoxyalkylheteroaryl, haloalkylheterocyclyl, haloaryloxyalkyl, alkoxyalkylheterocyclyl, heteroaryl, haloheteroarylalkoxy, aryl, haloaryl, haloalkoxy, alkoxy, alkyl, haloalkyl, cyano, cyanoaryl, cyanocycloalkyl, cyanoalkylaryl, arylheterocyclyl, alkoxy-(haloalkyl)aryl, arylalkoxy-(alkyl)aryl, haloaryloxy, hydroxyalkylaryl, alkenyloxy, pentafluoro-lambda6-sulfanyl, heteroarylalkyl, alkoxyaryl, (arylalkoxy)aryl, carbamoylaryl, alkyl-(alkoxy)aryl, haloalkoxyaryl, alkylheterocyclyl and haloarylalkoxy, wherein:
said aminoalkyl is substituted on the nitrogen atom with one or two substituents independently selected from the group consisting of alkanoyl, arylalkyl and haloalkylarylalkyl; and
said amino is substituted on the nitrogen atom with one or two substituents independently selected from the group consisting of alkyl, haloarylalkyl and haloalkoxyarylalkyl;
ii. heteroaryl substituted with one or more substituents selected from the group consisting of:
alkylsulfanyl, heteroaryl, cycloalkyl, haloaryl, cyano (haloaryl), heterocyclyl, alkoxyheterocyclyl, hydroxyheterocyclyl, alkylheterocyclyl, alkyl(hydroxyheterocyclyl), alkyl(haloheterocyclyl), alkylheteroaryl, hydroxyalkylheterocyclyl, aryl, alkyl, haloalkyl, cyano, cyanoaryl, halogen, arylalkoxy, alkoxy, dialkylamino, haloheterocyclyl, haloalkylhaloaryl, aryloxyalkyl, alkylaryl, heteroarylalkoxy and haloalkylaryl;
iii. heteroaryl;
iv. cycloalkyl, substituted once with alkylheteroaryl; and
v. heterocyclyl, substituted once with haloarylsulfonyl or haloarylalkyl; and R² is selected from the group consisting of hydrogen and alkyl;

or a pharmaceutically acceptable salt thereof.

In a preferred embodiment, the present invention provides compounds of Formula (I) as described herein, wherein:

X is C—H or N;

Y¹ is selected from the group consisting of C—H and C—F;

Y² is selected from the group consisting of C—H and C-halogen;

R¹ is selected from the group consisting of:
i. heteroaryl substituted with one or more substituents selected from the group consisting of:
aryl, alkylaryl, haloaryl, cyano(haloaryl), heterocyclyl, haloheterocyclyl, hydroxyalkylheterocyclyl, alkylheterocyclyl, alkyl(haloheterocyclyl), cycloalkyl, cyano, alkyl and haloalkyl; and
ii. aryl substituted with one or more substituents selected from the group consisting of:
heterocyclyl, hydroxyalkylheterocyclyl, haloalkylaryl, haloalkylheteroaryl, haloheteroarylalkoxy, haloaryloxyalkyl, arylheterocyclyl, alkylheteroaryl, haloarylalkoxy, halogen, haloalkyl, alkyl, heteroaryl, haloalkoxy, haloalkoxyaryl, hydroxyalkylaryl, alkoxy-(haloalkyl)aryl, alkylheterocyclyl, cycloalkylheterocyclyl, alkylcycloalkylheteroaryl and aminoalkyl; wherein:
said aminoalkyl is substituted on the nitrogen atom with two substituents independently selected from the group consisting of alkanoyl and haloalkylarylalkyl; and R² is selected from the group consisting of hydrogen and alkyl;

or a pharmaceutically acceptable salt thereof.

In a particularly preferred embodiment, the present invention provides compounds of Formula (I) as described herein, wherein:

X is N;

Y¹ and Y² are each C—H;

R¹ is selected from the group consisting of:
i. heteroaryl substituted with one or more substituents selected from the group consisting of:
aryl, haloaryl, haloalkylaryl, heterocyclyl, haloheterocyclyl and dialkylamino; and
ii. aryl substituted with one or more substituents selected from the group consisting of:
alkylheteroaryl and heterocyclyl; and R² is hydrogen;

or a pharmaceutically acceptable salt thereof.

In a further particularly preferred embodiment, the present invention provides compounds of Formula (I) as described herein, wherein:

X is C—H or N;

Y¹ is selected from the group consisting of C—H and C—F;

Y² is selected from the group consisting of C—H, C—Cl and C—F;

R¹ is selected from the group consisting of:
i. benzoxazolyl substituted with 1 to 2 substituents selected from the group consisting of:
methyl, CF₃, phenyl, chlorophenyl, cyano-chlorophenyl, 2-azaspiro[3.3]heptanyl, difluoro-2-azaspiro[3.3]heptanyl, 6-azaspiro[3.4]octanyl, 3-fluoro-3-methyl-pyrrolidinyl, 3-(1-hydroxy-1-methyl-ethyl) pyrrolidinyl, fluorophenyl, piperidinyl, cyclohexyl, methylpyrrolidinyl and CN; and
ii. indolyl substituted once with phenyl or fluorophenyl;
iii. indazolyl substituted once with fluorophenyl;
iv. phenyl substituted with 1 to 2 substituents selected from the group consisting of:
Cl, F, methyl, CF₃, pyrrolidinyl, hydroxyethylpyrrolidinyl, dimethylpyrrolidinyl, diethylpyrrolidinyl, imidazolyl, dimethylpiperidinyl, trifluoromethylpyridyl, substituted phenyl, phenylcyclopropyl, substituted oxadiazolyl, chlorophenylmethoxy, 2,3-dihydroindolyl, 2-azaspiro[3.3]heptanyl, 5-azaspiro[2.4]heptanyl, (chloropyridyl)methoxy, (chlorophenoxy)methyl, azepanyl, 2,3-dihydropyrrolo[2,3-b]pyridin-1-yl, 2,3-dihydro-1H-pyrrolo[2,3-b]pyridin-4-yl and aminoethyl, wherein:
said substituted phenyl is substituted with 1-2 substituents independently selected from the group consisting of CF₃, methoxy, trifluoromethoxy and hydroxymethyl;
said substituted oxadiazolyl is substituted once with propan-2-yl, trifluoroethyl, 2-fluoro-1,1-dimethylethyl, tert-butyl, cyclopropyl or 1-methylcyclopropyl; and
said aminoethyl is substituted on the nitrogen atom with acetyl and trifluoromethylbenzyl; and
v. pyridyl substituted once with tert-butylphenyl; and R² is selected from the group consisting of hydrogen and alkyl;

or a pharmaceutically acceptable salt thereof.

In yet a further particularly preferred embodiment, the present invention provides compounds of Formula (I) as described herein, wherein:

X is N;

Y¹ and Y² are both C—H;

R¹ is selected from the group consisting of:
i. benzoxazolyl substituted with 1 to 2 substituents selected from the group consisting of:
phenyl, chlorophenyl, trifluoromethylphenyl, morpholinyl, 2-azaspiro[3.4]octanyl, difluoro-2-azaspiro[3.3]heptanyl and methyl(propyl)amino; and
ii. phenyl substituted with 1 substituent selected from the group consisting of substituted oxadiazolyl, 2-azaspiro[3.4]octanyl and 6-azaspiro[3.4]octan-yl, wherein:
said substituted oxadiazolyl is substituted once with 2,2-dimethylpropyl or tert-butyl; and R² is hydrogen;

or a pharmaceutically acceptable salt thereof.

In a preferred embodiment, compounds of Formula (I) as described herein are selected from the group consisting of:

N-[2-[4-[4-(4-oxo-3H-quinazolin-2-yl)piperazine-1-carbonyl]phenyl]ethyl]-N-[[3-(trifluoromethyl)phenyl]methyl]acetamide;

2-[4-[4-[(E)-2-(3-fluorophenyl)ethenyl]benzoyl]piperazin-1-yl]-3H-quinazolin-4-one;

2-[4-(4-Phenoxybenzoyl)piperazin-1-yl]-3H-quinazolin-4-one;

2-[4-(3-Phenoxybenzoyl)piperazin-1-yl]-3H-quinazolin-4-one;

2-[4-[4-(Trifluoromethoxy)benzoyl]piperazin-1-yl]-3H-quinazolin-4-one;

2-[4-[3-(Trifluoromethoxy)benzoyl]piperazin-1-yl]-3H-quinazolin-4-one;

2-[4-(2-Phenyl-1,3-benzoxazole-5-carbonyl)piperazin-1-yl]-3H-quinazolin-4-one;

2-[4-(2-Phenyl-1,3-benzoxazole-6-carbonyl)piperazin-1-yl]-3H-quinazolin-4-one;

2-[4-(1H-Indole-5-carbonyl)piperazin-1-yl]-3H-quinazolin-4-one;

2-[4-[1-(4-Fluorophenyl)indole-5-carbonyl]piperazin-1-yl]-3H-quinazolin-4-one;
2-[4-(4-Pyrrolidin-1-ylbenzoyl)piperazin-1-yl]-3H-quinazolin-4-one;
2-[4-[4-[(2-Iodophenyl)methylamino]benzoyl]piperazin-1-yl]-3H-quinazolin-4-one;
2-[4-(3-Phenylmethoxybenzoyl)piperazin-1-yl]-3H-quinazolin-4-one;
2-[4-[4-[[2-(Trifluoromethoxy)phenyl]methylamino]benzoyl]piperazin-1-yl]-3H-quinazolin-4-one;
2-[4-[3-(Cyclopentylmethoxy)benzoyl]piperazin-1-yl]-3H-quinazolin-4-one;
2-[4-(4-Phenylbenzoyl)piperazin-1-yl]-3H-quinazolin-4-one;
2-[4-[4-[3-(Trifluoromethyl)phenyl]benzoyl]piperazin-1-yl]-3H-quinazolin-4-one;
2-[4-[4-(5-Methyl-1,2,4-oxadiazol-3-yl)benzoyl]piperazin-1-yl]-3H-quinazolin-4-one;
2-[4-(3-Phenyl-1,2-oxazole-5-carbonyl)piperazin-1-yl]-3H-quinazolin-4-one;
2-[4-(3-Chloro-4-pyrrolidin-1-ylbenzoyl)piperazin-1-yl]-3H-quinazolin-4-one;
N-benzyl-N-[2-[4-[4-(4-oxo-3H-quinazolin-2-yl)piperazine-1-carbonyl]phenyl]ethyl]acetamide;
2-[4-[3-(Trifluoromethyl)benzoyl]piperazin-1-yl]-3H-quinazolin-4-one;
2-[4-(2-Phenyl-1H-indole-5-carbonyl)piperazin-1-yl]-3H-quinazolin-4-one;
(Rac, cis)-2-[4-[4-[2-phenylcyclopropyl]benzoyl]piperazin-1-yl]-3H-quinazolin-4-one;
(Rac, trans)-2-[4-[4-[2-phenylcyclopropyl]benzoyl]piperazin-1-yl]-3H-quinazolin-4-one;
2-[4-[3-Bromo-5-(trifluoromethoxy)benzoyl]piperazin-1-yl]-3H-quinazolin-4-one;
2-[4-(3-Prop-2-enoxybenzoyl)piperazin-1-yl]-3H-quinazolin-4-one;
2-[4-[4-(2-Methylpropyl)benzoyl]piperazin-1-yl]-3H-quinazolin-4-one;
2-[4-[4-(5-Propan-2-yl-1,2,4-oxadiazol-3-yl)benzoyl]piperazin-1-yl]-3H-quinazolin-4-one;
2-[4-(2-Methyl-1-phenylbenzimidazole-5-carbonyl)piperazin-1-yl]-3H-quinazolin-4-one;
2-[4-[3,5-Bis(trifluoromethyl)benzoyl]piperazin-1-yl]-3H-quinazolin-4-one;
2-[4-[4-[2-[[3-(Trifluoromethyl)phenyl]methoxy]ethyl]benzoyl]piperazin-1-yl]-3H-quinazolin-4-one;
2-[4-(4-tert-Butyl-3-methoxybenzoyl)piperazin-1-yl]-3H-quinazolin-4-one;
2-[4-[4-(Pentafluoro-λ6-sulfanyl)benzoyl]piperazin-1-yl]-3H-quinazolin-4-one;
2-[4-[1-(4-Fluorophenyl)indazole-5-carbonyl]piperazin-1-yl]-3H-quinazolin-4-one;
2-[4-[4-(2,5-Dimethylpyrrol-1-yl)benzoyl]piperazin-1-yl]-3H-quinazolin-4-one;
2-[4-(Quinoline-7-carbonyl)piperazin-1-yl]-3H-quinazolin-4-one;
2-[4-[3-Bromo-4-(trifluoromethoxy)benzoyl]piperazin-1-yl]-3H-quinazolin-4-one;
2-[4-[4-(Benzimidazol-1-ylmethyl)benzoyl]piperazin-1-yl]-3H-quinazolin-4-one;
2-[4-[4-(1,3-Thiazol-2-yl)benzoyl]piperazin-1-yl]-3H-quinazolin-4-one:
2-[4-[4-(4-Methylpyrazol-1-yl)benzoyl]piperazin-1-yl]-3H-quinazolin-4-one;
2-[4-[4-(3-Methylpyrazol-1-yl)benzoyl]piperazin-1-yl]-3H-quinazolin-4-one;
2-[4-(6-Methoxy-1-benzofuran-2-carbonyl)piperazin-1-yl]-3H-quinazolin-4-one;
2-[4-[5-(2,3-Dihydro-1H-inden-5-yloxymethyl)furan-2-carbonyl]piperazin-1-yl]-3H-quinazolin-4-one;
2-[4-(1,5-Diphenylpyrazole-3-carbonyl)piperazin-1-yl]-3H-quinazolin-4-one;
2-[4-[4-[(3-Chlorophenyl)methoxy]benzoyl]piperazin-1-yl]-3H-quinazolin-4-one;
2-[4-(2-Phenyl-1H-benzimidazole-5-carbonyl)piperazin-1-yl]-3H-quinazolin-4-one;
2-[4-[2-(3-Fluorophenyl)-1H-indole-5-carbonyl]piperazin-1-yl]-3H-quinazolin-4-one;
2-[4-[4-[3-(Trifluoromethyl)phenyl]benzoyl]piperazin-1-yl]-3H-pyrido[3,4-d]pyrimidin-4-one;
2-[4-(2-Phenyl-1,3-benzoxazole-6-carbonyl)piperazin-1-yl]-3H-pyrido[3,4-d]pyrimidin-4-one;
2-[4-[1-(4-Fluorophenyl)pyrrolo[2,3-b]pyridine-5-carbonyl]piperazin-1-yl]-3H-quinazolin-4-one;
2-[4-(4-Piperidin-1-ylbenzoyl)piperazin-1-yl]-3H-quinazolin-4-one;
2-[4-[1-(4-Fluorophenyl)benzimidazole-5-carbonyl]piperazin-1-yl]-3H-quinazolin-4-one;
2-[4-(2-Piperidin-1-yl-1,3-benzoxazole-6-carbonyl)piperazin-1-yl]-3H-quinazolin-4-one;
3-Methyl-2-[4-(2-phenyl-1,3-benzoxazole-6-carbonyl)piperazin-1-yl]quinazolin-4-one;
2-[4-[4-[5-(Trifluoromethyl)-1,2,4-oxadiazol-3-yl]benzoyl]piperazin-1-yl]-3H-quinazolin-4-one;
2-[4-[4-[4-(Trifluoromethyl)pyrazol-1-yl]benzoyl]piperazin-1-yl]-3H-quinazolin-4-one;
2-[4-[4-[3-(Trifluoromethyl)pyrazol-1-yl]benzoyl]piperazin-1-yl]-3H-quinazolin-4-one;
2-[4-[4-(5-Cyclopropyl-1,2,4-oxadiazol-3-yl)benzoyl]piperazin-1-yl]-3H-quinazolin-4-one;
2-[4-[2-(3-Fluorophenyl)-1,3-benzoxazole-6-carbonyl]piperazin-1-yl]-3H-quinazolin-4-one;
2-[4-[2-(3-Chlorophenyl)-1,3-benzoxazole-6-carbonyl]piperazin-1-yl]-3H-quinazolin-4-one;
2-[4-[2-[3-(Trifluoromethyl)phenyl]-1,3-benzoxazole-6-carbonyl]piperazin-1-yl]-3H-quinazolin-4-one;
2-[4-(4-Phenylmethoxybenzoyl)piperazin-1-yl]-3H-quinazolin-4-one;
2-[4-[4-(Diethylamino)benzoyl]piperazin-1-yl]-3H-quinazolin-4-one;
2-[4-[3-[(3-Chlorophenyl)methoxy]benzoyl]piperazin-1-yl]-3H-quinazolin-4-one;
2-[4-[3-Chloro-4-[(3-chlorophenyl)methoxy]benzoyl]piperazin-1-yl]-3H-quinazolin-4-one;
2-[4-[4-[5-(2,2-Dimethylpropyl)-1,2,4-oxadiazol-3-yl]benzoyl]piperazin-1-yl]-3H-quinazolin-4-one;
2-[4-[4-[tert-Butyl(methyl)amino]benzoyl]piperazin-1-yl]-3H-quinazolin-4-one;
2-[4-[4-(2,3-Dihydroindol-1-yl)benzoyl]piperazin-1-yl]-3H-quinazolin-4-one;
2-[4-[4-(Azetidin-1-yl)benzoyl]piperazin-1-yl]-3H-quinazolin-4-one;
2-[4-(2-Chloro-4-pyrrolidin-1-ylbenzoyl)piperazin-1-yl]-3H-quinazolin-4-one;
2-[4-[4-[(3-Chlorophenyl)methoxy]-3-(trifluoromethyl)benzoyl]piperazin-1-yl]-3H-quinazolin-4-one;
2-[4-[4-[(3-Chlorophenyl)methoxy]-3-methylbenzoyl]piperazin-1-yl]-3H-quinazolin-4-one;
2-[4-(3-Pyrrolidin-1-ylbenzoyl)piperazin-1-yl]-3H-quinazolin-4-one;
2-[4-[4-(5-tert-Butyl-1,2,4-oxadiazol-3-yl)benzoyl]piperazin-1-yl]-3H-quinazolin-4-one;

2-[4-[4-[(3-Chlorophenyl)methoxy]-3-(1H-imidazol-2-yl)benzoyl]piperazin-1-yl]-3H-quinazolin-4-one;
2-[(3-Chlorophenyl)methoxy]-5-[4-(4-oxo-3H-quinazolin-2-yl)piperazine-1-carbonyl]benzonitrile;
2-[4-(4-Cyclohexylbenzoyl)piperazin-1-yl]-3H-quinazolin-4-one;
2-[4-(2-Cyclohexyl-1,3-benzoxazole-6-carbonyl)piperazin-1-yl]-3H-quinazolin-4-one;
2-[4-[4-(4-Oxo-3H-quinazolin-2-yl)piperazine-1-carbonyl]phenyl]benzonitrile;
2-[4-(1-Butyl-2-methylbenzimidazole-5-carbonyl)piperazin-1-yl]-3H-quinazolin-4-one;
2-[4-[4-[3,5-Bis(trifluoromethyl)phenyl]benzoyl]piperazin-1-yl]-3H-quinazolin-4-one;
2-[4-[4-[3-(Trifluoromethoxy)phenyl]benzoyl]piperazin-1-yl]-3H-quinazolin-4-one;
2-[4-[1-Propan-2-yl-2-(trifluoromethyl)benzimidazole-5-carbonyl]piperazin-1-yl]-3H-quinazolin-4-one;
2-[4-[5-[3-(Trifluoromethyl)phenyl]pyridine-3-carbonyl]piperazin-1-yl]-3H-quinazolin-4-one;
2-[4-[4-(3,4-Difluorophenyl)-2-fluorobenzoyl]piperazin-1-yl]-3H-quinazolin-4-one;
2-[4-[4-(2-Methoxy-5-methylphenyl)benzoyl]piperazin-1-yl]-3H-quinazolin-4-one;
2-[4-(3-Methyl-1-benzofuran-2-carbonyl)piperazin-1-yl]-3H-quinazolin-4-one;
2-[4-[3-[2-(Hydroxymethyl)phenyl]benzoyl]piperazin-1-yl]-3H-quinazolin-4-one;
2-[4-[4-[3-(Hydroxymethyl)phenyl]benzoyl]piperazin-1-yl]-3H-quinazolin-4-one;
2-[4-(3-Bromo-5-propan-2-yloxybenzoyl)piperazin-1-yl]-3H-quinazolin-4-one;
2-[4-[3-Chloro-5-[4-(hydroxymethyl)phenyl]benzoyl]piperazin-1-yl]-3H-quinazolin-4-one;
2-[4-[4-Chloro-3-(2-methylpropoxy)benzoyl]piperazin-1-yl]-3H-quinazolin-4-one;
2-[4-(3-Bromo-5-ethoxybenzoyl)piperazin-1-yl]-3H-quinazolin-4-one;
2-[4-[4-Fluoro-3-[2-(hydroxymethyl)phenyl]benzoyl]piperazin-1-yl]-3H-quinazolin-4-one;
2-[4-[3-Fluoro-4-[3-(trifluoromethyl)phenyl]benzoyl]piperazin-1-yl]-3H-quinazolin-4-one;
2-[4-[3-[2-(Trifluoromethoxy)phenyl]benzoyl]piperazin-1-yl]-3H-quinazolin-4-one;
2-[4-[6-(Trifluoromethyl)quinoline-3-carbonyl]piperazin-1-yl]-3H-quinazolin-4-one;
2-[4-(4,6-Dimethyl-TH-indole-2-carbonyl)piperazin-1-yl]-3H-quinazolin-4-one;
N,N-dimethyl-4-[2-methyl-4-[4-(4-oxo-3H-quinazolin-2-yl)piperazine-1-carbonyl]phenyl]benzamide;
2-[4-[2-(4-tert-Butylphenyl)pyridine-4-carbonyl]piperazin-1-yl]-3H-quinazolin-4-one;
2-[4-[4-(2-Chlorophenoxy)benzoyl]piperazin-1-yl]-3H-quinazolin-4-one;
2-[4-(3-tert-Butyl-5-chlorobenzoyl)piperazin-1-yl]-3H-quinazolin-4-one;
2-[4-[4-(3-Phenylmethoxyphenyl)benzoyl]piperazin-1-yl]-3H-quinazolin-4-one;
2-[4-[3-(2-Methyl-6-phenylmethoxyphenyl)benzoyl]piperazin-1-yl]-3H-quinazolin-4-one;
2-[4-[4-[4-Methoxy-3-(trifluoromethyl)phenyl]-3-methylbenzoyl]piperazin-1-yl]-3H-quinazolin-4-one;
2-[4-(7-Phenylmethoxy-TH-indole-3-carbonyl)piperazin-1-yl]-3H-quinazolin-4-one;
2-[4-[4-(2,6-Difluorophenyl)benzoyl]piperazin-1-yl]-3H-quinazolin-4-one;
2-[4-(1-Cyclopropylbenzimidazole-5-carbonyl)piperazin-1-yl]-3H-quinazolin-4-one;
2-[4-(6-tert-Butyl-1H-indole-2-carbonyl)piperazin-1-yl]-3H-quinazolin-4-one;
2-[4-(4-Chloro-3-ethoxybenzoyl)piperazin-1-yl]-3H-quinazolin-4-one;
2-[4-[4-(4,4-Dimethylpiperidin-1-yl)benzoyl]piperazin-1-yl]-3H-quinazolin-4-one;
2-[4-[5-(Trifluoromethyl)imidazo[1,2-a]pyridine-2-carbonyl]piperazin-1-yl]-3H-quinazolin-4-one;
4-[2-Fluoro-5-[4-(4-oxo-3H-quinazolin-2-yl)piperazine-1-carbonyl]phenyl]-N,N-dimethylbenzamide;
2-[4-[3-(3,5-Difluorophenyl)benzoyl]piperazin-1-yl]-3H-quinazolin-4-one;
2-[4-[2-(3,4-Dichlorophenyl)-1,3-benzoxazole-6-carbonyl]piperazin-1-yl]-3H-quinazolin-4-one;
2-[4-[2-(4-Chlorophenyl)-1,3-benzoxazole-6-carbonyl]piperazin-1-yl]-3H-quinazolin-4-one;
2-[4-[4-(3-Azabicyclo[2.2.1]heptan-3-yl)benzoyl]piperazin-1-yl]-3H-quinazolin-4-one;
2-[4-[4-(2-Azaspiro[3.3]heptan-2-yl)benzoyl]piperazin-1-yl]-3H-quinazolin-4-one;
2-[4-[4-(Azepan-1-yl)benzoyl]piperazin-1-yl]-3H-quinazolin-4-one;
2-[4-(2-Phenyl-[1,3]oxazolo[4,5-b]pyridine-6-carbonyl)piperazin-1-yl]-3H-quinazolin-4-one;
2-[4-[4-(3-Cyclopropyl-1H-1,2,4-triazol-5-yl)benzoyl]piperazin-1-yl]-3H-quinazolin-4-one;
2-[4-[4-(3-Cyclopropyl-1,2,4-oxadiazol-5-yl)benzoyl]piperazin-1-yl]-3H-quinazolin-4-one;
6-[4-(4-Oxo-3H-quinazolin-2-yl)piperazine-1-carbonyl]-2-phenyl-1,3-benzoxazole-4-carbonitrile;
2-[4-[4-(3,4-Dichlorophenyl)benzoyl]piperazin-1-yl]-3H-quinazolin-4-one;
2-[4-(6-Pyrrolidin-1-ylpyridine-3-carbonyl)piperazin-1-yl]-3H-quinazolin-4-one;
2-[4-[3-[5-(2,2-Dimethylpropyl)-1,2,4-oxadiazol-3-yl]benzoyl]piperazin-1-yl]-3H-quinazolin-4-one;
2-[4-[4-(2-Azaspiro[3.4]octan-2-yl)benzoyl]piperazin-1-yl]-3H-quinazolin-4-one;
2-[4-[4-(5-Ethyl-1,2,4-oxadiazol-3-yl)benzoyl]piperazin-1-yl]-3H-quinazolin-4-one;
2-[4-[4-(2-Methyl-1,3-thiazol-4-yl)benzoyl]piperazin-1-yl]-3H-quinazolin-4-one;
2-[4-[2-(3,4-Difluorophenyl)-1,3-benzoxazole-6-carbonyl]piperazin-1-yl]-3H-quinazolin-4-one;
2-[4-[2-[4-(Trifluoromethyl)phenyl]-1,3-benzoxazole-6-carbonyl]piperazin-1-yl]-3H-quinazolin-4-one;
2-[4-[2-[3-Fluoro-4-(trifluoromethyl)phenyl]-1,3-benzoxazole-6-carbonyl]piperazin-1-yl]-3H-quinazolin-4-one;
2-[4-[2-(4-Fluorophenyl)-1,3-benzoxazole-6-carbonyl]piperazin-1-yl]-3H-quinazolin-4-one;
6-Fluoro-2-[4-(2-phenyl-1,3-benzoxazole-6-carbonyl)piperazin-1-yl]-3H-quinazolin-4-one;
7-Fluoro-2-[4-(2-phenyl-1,3-benzoxazole-6-carbonyl)piperazin-1-yl]-3H-quinazolin-4-one;
2-[4-(4-Bromo-3-fluorobenzoyl)piperazin-1-yl]-3H-quinazolin-4-one;
2-[4-(5-Pyrrolidin-1-ylpyridine-2-carbonyl)piperazin-1-yl]-3H-quinazolin-4-one;
2-[4-[3-Fluoro-4-[5-(trifluoromethyl)pyridin-3-yl]benzoyl]piperazin-1-yl]-3H-quinazolin-4-one;
2-[4-(2-Methyl-1,3-benzoxazole-6-carbonyl)piperazin-1-yl]-3H-quinazolin-4-one;
2-[4-[2-Phenyl-4-(trifluoromethyl)-1,3-benzoxazole-6-carbonyl]piperazin-1-yl]-3H-quinazolin-4-one;

2-[4-(4-Bromo-3-methylbenzoyl)piperazin-1-yl]-3H-quinazolin-4-one;
2-[4-(2-Morpholin-4-yl-1,3-benzoxazole-6-carbonyl)piperazin-1-yl]-3H-quinazolin-4-one;
2-[4-[4-(2,3-Dihydropyrrolo[2,3-b]pyridin-1-yl)benzoyl]piperazin-1-yl]-3H-quinazolin-4-one;
2-[4-[4-(2-Phenylpyrrolidin-1-yl)benzoyl]piperazin-1-yl]-3H-quinazolin-4-one;
2-[4-(2-Pyridin-2-yl-1,3-benzoxazole-6-carbonyl)piperazin-1-yl]-3H-quinazolin-4-one;
2-[4-[4-[5-(2,2,2-Trifluoroethyl)-1,2,4-oxadiazol-3-yl]benzoyl]piperazin-1-yl]-3H-quinazolin-4-one;
2-[4-[4-(2-Oxa-6-azaspiro[3.3]heptan-6-yl)benzoyl]piperazin-1-yl]-3H-quinazolin-4-one;
2-[3-[4-[4-(4-oxo-3H-quinazolin-2-yl)piperazine-1-carbonyl]phenyl]phenyl]acetonitrile;
2-[4-[3-Fluoro-4-[3-(trifluoromethoxy)phenyl]benzoyl]piperazin-1-yl]-3H-quinazolin-4-one;
2-[4-[3-Methyl-4-[3-(trifluoromethoxy)phenyl]benzoyl]piperazin-1-yl]-3H-quinazolin-4-one;
2-[4-[4-(3-Ethoxyphenyl)benzoyl]piperazin-1-yl]-3H-quinazolin-4-one;
6-Chloro-2-[4-(2-phenyl-1,3-benzoxazole-6-carbonyl)piperazin-1-yl]-3H-quinazolin-4-one;
2-[4-[4-[2-[[3-(Trifluoromethyl)phenyl]methylamino]ethyl]benzoyl]piperazin-1-yl]-3H-quinazolin-4-one;
1-[4-[4-(4-Oxo-3H-quinazolin-2-yl)piperazine-1-carbonyl]phenyl]cyclopentane-1-carbonitrile;
2-[4-(4-Morpholin-4-yl-2-phenyl-1,3-benzoxazole-6-carbonyl)piperazin-1-yl]-3H-quinazolin-4-one;
2-[4-[2-(2-Azaspiro[3.4]octan-2-yl)-1,3-benzoxazole-6-carbonyl]piperazin-1-yl]-3H-quinazolin-4-one;
2-[4-[2-(7,7-Difluoro-2-azaspiro[3.3]heptan-2-yl)-1,3-benzoxazole-6-carbonyl]piperazin-1-yl]-3H-quinazolin-4-one;
2-[4-[2-[Methyl(propyl)amino]-1,3-benzoxazole-6-carbonyl]piperazin-1-yl]-3H-quinazolin-4-one;
N-[2-[4-[4-(1-oxo-2H-isoquinolin-3-yl)piperazine-1-carbonyl]phenyl]ethyl]-N-[[3-(trifluoromethyl)phenyl]methyl]acetamide;
2-[4-[2-(Oxan-4-yl)-1,3-benzoxazole-6-carbonyl]piperazin-1-yl]-3H-quinazolin-4-one;
2-[4-(2-Pyridin-4-yl-1,3-benzoxazole-6-carbonyl)piperazin-1-yl]-3H-quinazolin-4-one;
2-[4-(2-Pyridin-3-yl-1,3-benzoxazole-6-carbonyl)piperazin-1-yl]-3H-quinazolin-4-one;
3-[6-[4-(4-Oxo-3H-quinazolin-2-yl)piperazine-1-carbonyl]-1,3-benzoxazol-2-yl]benzonitrile;
2-[4-(2-Methylsulfanyl-1,3-benzoxazole-6-carbonyl)piperazin-1-yl]-3H-quinazolin-4-one;
2-[4-(2-Pyrrolidin-1-yl-1,3-benzoxazole-6-carbonyl)piperazin-1-yl]-3H-quinazolin-4-one;
2-[4-[2-(4-Methoxypiperidin-1-yl)-1,3-benzoxazole-6-carbonyl]piperazin-1-yl]-3H-quinazolin-4-one;
2-[4-[2-(4-Hydroxypiperidin-1-yl)-1,3-benzoxazole-6-carbonyl]piperazin-1-yl]-3H-quinazolin-4-one;
2-[4-[2-(3-Methylpyrrolidin-1-yl)-1,3-benzoxazole-6-carbonyl]piperazin-1-yl]-3H-quinazolin-4-one;
2-[4-[4-(6-Azaspiro[3.4]octan-6-yl)benzoyl]piperazin-1-yl]-3H-quinazolin-4-one;
2-[4-[4-(3,3-Difluoropyrrolidin-1-yl)benzoyl]piperazin-1-yl]-3H-quinazolin-4-one;
2-[4-[4-[3-(1-Hydroxyethyl)pyrrolidin-1-yl]benzoyl]piperazin-1-yl]-3H-quinazolin-4-one;
2-[4-[4-(Trifluoromethyl)piperidin-1-yl]benzoyl]piperazin-1-yl]-3H-quinazolin-4-one;
2-[4-[4-(5-Azaspiro[2.4]heptan-5-yl)benzoyl]piperazin-1-yl]-3H-quinazolin-4-one;
2-[4-[3-Chloro-4-[(4-chloropyridin-2-yl)methoxy]benzoyl]piperazin-1-yl]-3H-quinazolin-4-one;
2-[4-[3-Chloro-4-[(2-chloropyridin-4-yl)methoxy]benzoyl]piperazin-1-yl]-3H-quinazolin-4-one;
2-[4-(3-Phenylbenzoyl)piperazin-1-yl]-3H-quinazolin-4-one;
2-[4-[3-Chloro-4-[(6-chloropyridin-2-yl)methoxy]benzoyl]piperazin-1-yl]-3H-quinazolin-4-one;
2-[4-[3-[3-(Trifluoromethyl)phenyl]benzoyl]piperazin-1-yl]-3H-quinazolin-4-one;
2-[4-[4-[3-(Trifluoromethyl)phenoxy]benzoyl]piperazin-1-yl]-3H-quinazolin-4-one;
2-[4-[4-[3-(2,2,2-Trifluoroethyl)-1,2,4-oxadiazol-5-yl]benzoyl]piperazin-1-yl]-3H-quinazolin-4-one;
2-[4-[4-(2,5-Dimethylpyrrolidin-1-yl)benzoyl]piperazin-1-yl]-3H-quinazolin-4-one;
2-[4-[4-(4,4-Difluoropiperidin-1-yl)benzoyl]piperazin-1-yl]-3H-quinazolin-4-one;
2-[4-[3-Chloro-4-[(3-Chlorophenoxy)methyl]benzoyl]piperazin-1-yl]-3H-quinazolin-4-one;
2-[4-(2-Phenyl-1,3-benzothiazole-6-carbonyl)piperazin-1-yl]-3H-quinazolin-4-one;
2-[4-[2-(Oxolan-2-yl)-1,3-benzoxazole-6-carbonyl]piperazin-1-yl]-3H-quinazolin-4-one;
2-[4-[4-[3-(Methoxymethyl)pyrrolidin-1-yl]benzoyl]piperazin-1-yl]-3H-quinazolin-4-one;
2-[4-[2-(2,2,2-Trifluoroethyl)-1,3-benzoxazole-5-carbonyl]piperazin-1-yl]-3H-quinazolin-4-one;
2-[4-[4-[5-(1-methylcyclopropyl)-1,2,4-oxadiazol-3-yl]benzoyl]piperazin-1-yl]-3H-quinazolin-4-one;
2-[4-[4-[5-[1-(trifluoromethyl)cyclopropyl]-1,2,4-oxadiazol-3-yl]benzoyl]piperazin-1-yl]-3H-quinazolin-4-one;
2-[4-[4-[5-[1-(fluoromethyl)cyclopropyl]-1,2,4-oxadiazol-3-yl]benzoyl]piperazin-1-yl]-3H-quinazolin-4-one;
2-[4-[4-[5-(2-hydroxy-1,1-dimethyl-ethyl)-1,2,4-oxadiazol-3-yl]benzoyl]piperazin-1-yl]-3H-quinazolin-4-one;
2-[4-[2-Methyl-4-(1H-pyrazol-4-ylmethoxy)-1,3-benzoxazole-6-carbonyl]piperazin-1-yl]-3H-quinazolin-4-one;
2-[4-[4-[5-(1-Methylcyclopropyl)-1,2,4-oxadiazol-3-yl]benzoyl]piperazin-1-yl]-3H-quinazolin-4-one;
2-[4-[4-[5-(1-Fluoro-2-methylpropan-2-yl)-1,2,4-oxadiazol-3-yl]benzoyl]piperazin-1-yl]-3H-quinazolin-4-one;
2-Chloro-4-[6-[4-(4-oxo-3H-quinazolin-2-yl)piperazine-1-carbonyl]-1,3-benzoxazol-2-yl]benzonitrile;
2-[4-[4-(3-tert-Butyl-1,2,4-oxadiazol-5-yl)benzoyl]piperazin-1-yl]-3H-quinazolin-4-one;
2-[4-[3-(3-tert-Butyl-1,2,4-oxadiazol-5-yl)bicyclo[1.1.1]pentane-1-carbonyl]piperazin-1-yl]-3H-quinazolin-4-one;
2-[4-[3-(3-Chlorophenyl)sulfonyl-3,9-diazaspiro[5.5]undecane-9-carbonyl]piperazin-1-yl]-3H-quinazolin-4-one;
2-[4-[4-(5-tert-Butyl-1,2,4-oxadiazol-3-yl)benzoyl]piperazin-1-yl]-6-chloro-3H-quinazolin-4-one;
2-[4-[4-(3,3-Dimethylpyrrolidin-1-yl)benzoyl]piperazin-1-yl]-3H-quinazolin-4-one;
2-[4-[2-(1-Methylpyrrol-3-yl)-1,3-benzoxazole-6-carbonyl]piperazin-1-yl]-3H-quinazolin-4-one;
2-[4-[4-[5-(1-Hydroxy-2-methylpropan-2-yl)-1,2,4-oxadiazol-3-yl]benzoyl]piperazin-1-yl]-3H-quinazolin-4-one;
2-[4-[2-(8-Oxa-2-azaspiro[4.5]decan-2-yl)-1,3-benzoxazole-6-carbonyl]piperazin-1-yl]-3H-quinazolin-4-one;
2-[4-[2-(3-Methoxypyrrolidin-1-yl)-1,3-benzoxazole-6-carbonyl]piperazin-1-yl]-3H-quinazolin-4-one;

2-[4-[2-(6,6-Difluoro-2-azaspiro[3.3]heptan-2-yl)-1,3-benzoxazole-6-carbonyl]piperazin-1-yl]-3H-quinazolin-4-one;
2-[4-[2-(2-Azaspiro[3.4]octan-2-yl)-1,3-benzoxazole-6-carbonyl]piperazin-1-yl]-3-methylquinazolin-4-one;
2-[4-[2-(2-Azaspiro[3.3]heptan-2-yl)-1,3-benzoxazole-6-carbonyl]piperazin-1-yl]-3H-quinazolin-4-one;
2-[4-[2-(6-Hydroxy-2-azaspiro[3.3]heptan-2-yl)-1,3-benzoxazole-6-carbonyl]piperazin-1-yl]-3H-quinazolin-4-one;
2-[4-[2-(3-Hydroxy-3-methylpyrrolidin-1-yl)-1,3-benzoxazole-6-carbonyl]piperazin-1-yl]-3H-quinazolin-4-one;
2-[4-[2-(3-Fluoro-3-methylpyrrolidin-1-yl)-1,3-benzoxazole-6-carbonyl]piperazin-1-yl]-3H-quinazolin-4-one;
2-[4-[2-[3-(2-Hydroxypropan-2-yl)pyrrolidin-1-yl]-1,3-benzoxazole-6-carbonyl]piperazin-1-yl]-3H-quinazolin-4-one;
2-[4-[2-(6-Azaspiro[3.4]octan-6-yl)-1,3-benzoxazole-6-carbonyl]piperazin-1-yl]-3-methylquinazolin-4-one;
2-[4-[2-(6-Azaspiro[3.4]octan-6-yl)-1,3-benzoxazole-6-carbonyl]piperazin-1-yl]-3H-quinazolin-4-one;
2-[4-[4-[5-(2-Methyl-1-phenylmethoxypropan-2-yl)-1,2,4-oxadiazol-3-yl]benzoyl]piperazin-1-yl]-3H-quinazolin-4-one;
2-[4-[4-(3-Hydroxy-3-methylbut-1-ynyl)benzoyl]piperazin-1-yl]-3H-quinazolin-4-one;
2-[4-[4-(3,3-Diethylpyrrolidin-1-yl)benzoyl]piperazin-1-yl]-3H-quinazolin-4-one;
2-[4-[2-(4-Chlorophenyl)sulfonyl-2,7-diazaspiro[4.4]nonane-7-carbonyl]piperazin-1-yl]-3H-quinazolin-4-one;
2-[4-[2-(3-Chlorophenyl)sulfonyl-2,7-diazaspiro[4.4]nonane-7-carbonyl]piperazin-1-yl]-3H-quinazolin-4-one; and
2-[4-[7-[(3-Chlorophenyl)methyl]-2,7-diazaspiro[4.4]nonane-2-carbonyl]piperazin-1-yl]-3H-quinazolin-4-one or a pharmaceutically acceptable salt thereof.

In a further preferred embodiment, compounds of Formula (I) as described herein are selected from the group consisting of 2-[4-(2-Phenyl-1,3-benzoxazole-5-carbonyl)piperazin-1-yl]-3H-quinazolin-4-one;
2-[4-(2-Phenyl-1,3-benzoxazole-6-carbonyl)piperazin-1-yl]-3H-quinazolin-4-one;
2-[4-[1-(4-Fluorophenyl)indole-5-carbonyl]piperazin-1-yl]-3H-quinazolin-4-one;
2-[4-(4-Pyrrolidin-1-ylbenzoyl)piperazin-1-yl]-3H-quinazolin-4-one;
2-[4-[4-[3-(Trifluoromethyl)phenyl]benzoyl]piperazin-1-yl]-3H-quinazolin-4-one;
2-[4-(2-Phenyl-TH-indole-5-carbonyl)piperazin-1-yl]-3H-quinazolin-4-one;
(Rac, trans)-2-[4-[4-[2-phenylcyclopropyl]benzoyl]piperazin-1-yl]-3H-quinazolin-4-one;
2-[4-[4-(5-Propan-2-yl-1,2,4-oxadiazol-3-yl)benzoyl]piperazin-1-yl]-3H-quinazolin-4-one;
2-[4-[1-(4-Fluorophenyl)indazole-5-carbonyl]piperazin-1-yl]-3H-quinazolin-4-one;
2-[4-[4-[(3-Chlorophenyl)methoxy]benzoyl]piperazin-1-yl]-3H-quinazolin-4-one;
2-[4-[2-(3-Fluorophenyl)-1H-indole-5-carbonyl]piperazin-1-yl]-3H-quinazolin-4-one;
2-[4-(2-Piperidin-1-yl-1,3-benzoxazole-6-carbonyl)piperazin-1-yl]-3H-quinazolin-4-one;
3-Methyl-2-[4-(2-phenyl-1,3-benzoxazole-6-carbonyl)piperazin-1-yl]quinazolin-4-one;
2-[4-[3-Chloro-4-[(3-chlorophenyl)methoxy]benzoyl]piperazin-1-yl]-3H-quinazolin-4-one;
2-[4-[4-(2,3-Dihydroindol-1-yl)benzoyl]piperazin-1-yl]-3H-quinazolin-4-one;
2-[4-[4-[(3-Chlorophenyl)methoxy]-3-(trifluoromethyl)benzoyl]piperazin-1-yl]-3H-quinazolin-4-one;
2-[4-[4-[(3-Chlorophenyl)methoxy]-3-methylbenzoyl]piperazin-1-yl]-3H-quinazolin-4-one;
2-[4-[4-[(3-Chlorophenyl)methoxy]-3-(1H-imidazol-2-yl)benzoyl]piperazin-1-yl]-3H-quinazolin-4-one;
2-[4-(2-Cyclohexyl-1,3-benzoxazole-6-carbonyl)piperazin-1-yl]-3H-quinazolin-4-one;
2-[4-[4-[3-(Trifluoromethoxy)phenyl]benzoyl]piperazin-1-yl]-3H-quinazolin-4-one;
2-[4-[3-Chloro-5-[4-(hydroxymethyl)phenyl]benzoyl]piperazin-1-yl]-3H-quinazolin-4-one;
2-[4-[3-Fluoro-4-[3-(trifluoromethyl)phenyl]benzoyl]piperazin-1-yl]-3H-quinazolin-4-one;
2-[4-[2-(4-tert-Butylphenyl)pyridine-4-carbonyl]piperazin-1-yl]-3H-quinazolin-4-one;
2-[4-[4-[4-Methoxy-3-(trifluoromethyl)phenyl]-3-methylbenzoyl]piperazin-1-yl]-3H-quinazolin-4-one;
2-[4-[4-(4,4-Dimethylpiperidin-1-yl)benzoyl]piperazin-1-yl]-3H-quinazolin-4-one;
2-[4-[2-(3,4-Dichlorophenyl)-1,3-benzoxazole-6-carbonyl]piperazin-1-yl]-3H-quinazolin-4-one;
2-[4-[2-(4-Chlorophenyl)-1,3-benzoxazole-6-carbonyl]piperazin-1-yl]-3H-quinazolin-4-one;
2-[4-[4-(2-Azaspiro[3.3]heptan-2-yl)benzoyl]piperazin-1-yl]-3H-quinazolin-4-one;
2-[4-[4-(Azepan-1-yl)benzoyl]piperazin-1-yl]-3H-quinazolin-4-one;
2-[4-[4-(3-Cyclopropyl-1,2,4-oxadiazol-5-yl)benzoyl]piperazin-1-yl]-3H-quinazolin-4-one;
6-[4-(4-Oxo-3H-quinazolin-2-yl)piperazine-1-carbonyl]-2-phenyl-1,3-benzoxazole-4-carbonitrile;
2-[4-[2-(3,4-Difluorophenyl)-1,3-benzoxazole-6-carbonyl]piperazin-1-yl]-3H-quinazolin-4-one;
2-[4-[2-(4-Fluorophenyl)-1,3-benzoxazole-6-carbonyl]piperazin-1-yl]-3H-quinazolin-4-one;
6-Fluoro-2-[4-(2-phenyl-1,3-benzoxazole-6-carbonyl)piperazin-1-yl]-3H-quinazolin-4-one;
7-Fluoro-2-[4-(2-phenyl-1,3-benzoxazole-6-carbonyl)piperazin-1-yl]-3H-quinazolin-4-one;
2-[4-[3-Fluoro-4-[5-(trifluoromethyl)pyridin-3-yl]benzoyl]piperazin-1-yl]-3H-quinazolin-4-one;
2-[4-(2-Methyl-1,3-benzoxazole-6-carbonyl)piperazin-1-yl]-3H-quinazolin-4-one;
2-[4-[2-Phenyl-4-(trifluoromethyl)-1,3-benzoxazole-6-carbonyl]piperazin-1-yl]-3H-quinazolin-4-one;
2-[4-[4-(2,3-Dihydropyrrolo[2,3-b]pyridin-1-yl)benzoyl]piperazin-1-yl]-3H-quinazolin-4-one;
2-[4-[4-[5-(2,2,2-Trifluoroethyl)-1,2,4-oxadiazol-3-yl]benzoyl]piperazin-1-yl]-3H-quinazolin-4-one;
2-[4-[3-Fluoro-4-[3-(trifluoromethoxy)phenyl]benzoyl]piperazin-1-yl]-3H-quinazolin-4-one;
6-Chloro-2-[4-(2-phenyl-1,3-benzoxazole-6-carbonyl)piperazin-1-yl]-3H-quinazolin-4-one; and
N-[2-[4-[4-(1-oxo-2H-isoquinolin-3-yl)piperazine-1-carbonyl]phenyl]ethyl]-N-[[3-(trifluoromethyl)phenyl]methyl]acetamide;
2-[4-[2-(3-Methylpyrrolidin-1-yl)-1,3-benzoxazole-6-carbonyl]piperazin-1-yl]-3H-quinazolin-4-one;
2-[4-[4-[3-(1-Hydroxyethyl)pyrrolidin-1-yl]benzoyl]piperazin-1-yl]-3H-quinazolin-4-one;
2-[4-[4-(5-Azaspiro[2.4]heptan-5-yl)benzoyl]piperazin-1-yl]-3H-quinazolin-4-one;
2-[4-[3-Chloro-4-[(4-chloropyridin-2-yl)methoxy]benzoyl]piperazin-1-yl]-3H-quinazolin-4-one;

2-[4-[3-Chloro-4-[(3-Chlorophenoxy)methyl]benzoyl]piperazin-1-yl]-3H-quinazolin-4-one;
2-[4-(2-Phenyl-1,3-benzothiazole-6-carbonyl)piperazin-1-yl]-3H-quinazolin-4-one;
2-[4-[4-[5-(1-Methylcyclopropyl)-1,2,4-oxadiazol-3-yl]benzoyl]piperazin-1-yl]-3H-quinazolin-4-one;
2-[4-[4-[5-(1-Fluoro-2-methylpropan-2-yl)-1,2,4-oxadiazol-3-yl]benzoyl]piperazin-1-yl]-3H-quinazolin-4-one;
2-Chloro-4-[6-[4-(4-oxo-3H-quinazolin-2-yl)piperazine-1-carbonyl]-1,3-benzoxazol-2-yl]benzonitrile;
2-[4-[4-(5-tert-Butyl-1,2,4-oxadiazol-3-yl)benzoyl]piperazin-1-yl]-6-chloro-3H-quinazolin-4-one;
2-[4-[4-(3,3-Dimethylpyrrolidin-1-yl)benzoyl]piperazin-1-yl]-3H-quinazolin-4-one;
2-[4-[2-(2-Azaspiro[3.3]heptan-2-yl)-1,3-benzoxazole-6-carbonyl]piperazin-1-yl]-3H-quinazolin-4-one;
2-[4-[2-(3-Fluoro-3-methylpyrrolidin-1-yl)-1,3-benzoxazole-6-carbonyl]piperazin-1-yl]-3H-quinazolin-4-one;
2-[4-[2-[3-(2-Hydroxypropan-2-yl)pyrrolidin-1-yl]-1,3-benzoxazole-6-carbonyl]piperazin-1-yl]-3H-quinazolin-4-one;
2-[4-[2-(6-Azaspiro[3.4]octan-6-yl)-1,3-benzoxazole-6-carbonyl]piperazin-1-yl]-3H-quinazolin-4-one;
2-[4-[4-(3,3-Diethylpyrrolidin-1-yl)benzoyl]piperazin-1-yl]-3H-quinazolin-4-one;
2-[4-[4-(3-tert-Butyl-1,2,4-oxadiazol-5-yl)benzoyl]piperazin-1-yl]-3H-quinazolin-4-one; and
2-[4-[2-(6,6-Difluoro-2-azaspiro[3.3]heptan-2-yl)-1,3-benzoxazole-6-carbonyl]piperazin-1-yl]-3H-quinazolin-4-one;
or a pharmaceutically acceptable salt thereof.

In a particularly preferred embodiment, compounds of Formula (I) as described herein are selected from the group consisting of
2-[4-[2-(3-Chlorophenyl)-1,3-benzoxazole-6-carbonyl]piperazin-1-yl]-3H-quinazolin-4-one;
2-[4-[2-[3-(Trifluoromethyl)phenyl]-1,3-benzoxazole-6-carbonyl]piperazin-1-yl]-3H-quinazolin-4-one;
2-[4-[4-[5-(2,2-Dimethylpropyl)-1,2,4-oxadiazol-3-yl]benzoyl]piperazin-1-yl]-3H-quinazolin-4-one;
2-[4-[4-(5-tert-Butyl-1,2,4-oxadiazol-3-yl)benzoyl]piperazin-1-yl]-3H-quinazolin-4-one;
2-[4-[3-[5-(2,2-Dimethylpropyl)-1,2,4-oxadiazol-3-yl]benzoyl]piperazin-1-yl]-3H-quinazolin-4-one;
2-[4-[4-(2-Azaspiro[3.4]octan-2-yl)benzoyl]piperazin-1-yl]-3H-quinazolin-4-one;
2-[4-[4-(4-Morpholin-4-yl-2-phenyl-1,3-benzoxazole-6-carbonyl)piperazin-1-yl]-3H-quinazolin-4-one;
2-[4-[2-(2-Azaspiro[3.4]octan-2-yl)-1,3-benzoxazole-6-carbonyl]piperazin-1-yl]-3H-quinazolin-4-one;
2-[4-[2-(7,7-Difluoro-2-azaspiro[3.3]heptan-2-yl)-1,3-benzoxazole-6-carbonyl]piperazin-1-yl]-3H-quinazolin-4-one;
2-[4-[2-[Methyl(propyl)amino]-1,3-benzoxazole-6-carbonyl]piperazin-1-yl]-3H-quinazolin-4-one;
2-[4-[4-(6-Azaspiro[3.4]octan-6-yl)benzoyl]piperazin-1-yl]-3H-quinazolin-4-one;
2-[4-[4-(3-tert-Butyl-1,2,4-oxadiazol-5-yl)benzoyl]piperazin-1-yl]-3H-quinazolin-4-one; and
2-[4-[2-(6,6-Difluoro-2-azaspiro[3.3]heptan-2-yl)-1,3-benzoxazole-6-carbonyl]piperazin-1-yl]-3H-quinazolin-4-one;
or a pharmaceutically acceptable salt thereof.

In one embodiment, the present invention provides pharmaceutically acceptable salts of the compounds of Formula (I) as described herein. In a further particular embodiment, the present invention provides compounds according to Formula (I) as described herein (i.e., as free bases or acids, respectively).

Processes of Manufacturing

The preparation of compounds of Formula (I) of the present invention may be carried out in sequential or convergent synthetic routes. Syntheses of the invention are shown in the following general schemes. The skills required for carrying out the reaction and purification of the resulting products are known to those persons skilled in the art. The substituents and indices used in the following description of the processes have the significance given herein.

If one of the starting materials, intermediates or compounds of formula (I) contain one or more functional groups which are not stable or are reactive under the reaction conditions of one or more reaction steps, appropriate protecting groups (as described e.g., in "Protective Groups in Organic Chemistry" by T. W. Greene and P. G. M. Wutts, 5th Ed., 2014, John Wiley & Sons, N.Y.) can be introduced before the critical step applying methods well known in the art. Such protecting groups can be removed at a later stage of the synthesis using standard methods described in the literature.

If starting materials or intermediates contain stereogenic centers, compounds of formula (I) can be obtained as mixtures of diastereomers or enantiomers, which can be separated by methods well known in the art e.g., (chiral) HPLC or crystallization. Racemic compounds can e.g., be separated into their antipodes via diastereomeric salts by crystallization with optically pure acids or by separation of the antipodes by specific chromatographic methods using either a chiral adsorbent or a chiral eluent.

A person skilled in the art will acknowledge that in the synthesis of compounds of formula (I)—insofar not desired otherwise—an "orthogonal protection group strategy" will be applied, allowing the cleavage of several protective groups one at a time each without affecting other protecting groups in the molecule. The principle of orthogonal protection is well known in the art and has also been described in literature (e.g. Barany and R. B. Merrifield, *J. Am. Chem. Soc.* 1977, 99, 7363; H. Waldmann et al., *Angew. Chem. Int. Ed. Engl.* 1996, 35, 2056).

A person skilled in the art will acknowledge that the sequence of reactions may be varied depending on reactivity and nature of the intermediates.

If starting materials or intermediates are not commercially available or their synthesis not described in literature, they can be prepared in analogy to existing procedures for close analogues or as outlined in the experimental section.

The following abbreviations are used in the present text: AcOH=acetic acid, ACN=acetonitrile, CAS RN=chemical abstracts registration number, CDI=1,1'-carbonyldiimidazole, $Cs_2CO_3$=cesium carbonate, CO=carbon monoxide, CuCl=copper(I) chloride, CuCN=copper(I) cyanide, CuI=copper(I) iodide, DMAP=4-dimethylaminopyridine, DME=dimethoxyethane, DMEDA=N,N'-dimethylethylenediamine, DMF=N,N-dimethylformamide, DMA=dimethylacetamide, DCM=dichloromethane, DIPEA=N,N-diisopropylethylamine, dppf=1,1 bis(diphenylphosphino)ferrocene, EDC.HCl=N-(3-dimethylaminopropyl)-N'-ethylcarbodiimide hydrochloride, DCC=N,N'-Dicyclohexylcarbodiimide, TBTU=O-(Benzotriazol-1-yl)-N,N,N',N'-tetramethyluronium tetrafluoroborate, EI=electron impact, ESI=electrospray ionization, EtOAc=ethyl acetate, EtOH=ethanol, h=hour(s), $H_2O$=water, $H_2SO_4$=sulfuric acid, HATU=1-[bis(dimethylamino)methylene]-1H-1,2,3-triazolo[4,5-b]pyridinium-3-oxide hexafluorophosphate, HBTU=O-benzotriazole-N,N,N',N'-tetramethyl-uronium-hexafluoro-phosphate, HCl=hydrogen chloride, HOBt=1-hydroxy-1H-benzotriazole; HPLC=high performance liquid chromatography, iPrMgCl=isopropylmagnesium chloride, $I_2$=iodine, IPA=2-propanol, ISP=ion spray positive (mode), ISN=ion spray negative (mode), $K_2CO_3$=potassium carbonate, $KHCO_3$=potassium bicarbonate, KI=potassium iodide, KOH=potassium hydroxide, $K_3PO_4$=potassium phosphate tribasic, $LiAlH_4$ or LAH=lithium aluminium hydride, LiHMDS=lithium bis(trimethylsilyl)amide, LiOH=lithium hydroxide, $MgSO_4$=magnesium sulfate, min=minute(s), mL=milliliter, MPLC=medium pressure liquid chromatography, MS=mass spectrum, NaH=sodium hydride, $NaHCO_3$=sodium hydrogen carbonate, $NaNO_2$=sodium nitrite, NaOH=sodium hydroxide, $Na_2CO_3$=sodium carbonate, $Na_2SO_4$=sodium sulfate, $Na_2S_2O_3$=sodium thiosulfate, NBS=N-bromosuccinimide, nBuLi=n-butyllithium, $NEt_3$=triethylamine (TEA), $NH_4Cl$=ammonium chloride, NMP=N-methyl-2-pyrrolidone, $T_3P$=propylphosphonic anhydride, PE=petroleum ether, PG=protecting group, Pd—C=palladium on activated carbon, $PdCl_2(dppf)$-$CH_2Cl_2$=1,1'-bis(diphenylphosphino)ferrocene-palladium (II)dichloride dichloromethane complex, $Pd_2(dba)_3$=tris(dibenzylideneacetone)dipalladium(O), $Pd(OAc)_2$=palladium(II) acetate, $Pd(OH)_2$=palladium hydroxide, $Pd(PPh_3)_4$=tetrakis(triphenylphosphine)palladium(O), PTSA=p-toluenesulfonic acid, R=any group, RT=room temperature, S-PHOS=2-dicyclohexylphosphino-2',6'-dimethoxybiphenyl, TBAI=tetra butyl ammonium iodine, TEA=triethylamine, TFA=trifluroacetic acid, THF=tetrahydrofuran, TMEDA=N,N,N',N'-tetramethylethylenediamine, $ZnCl_2$=zinc chloride, Hal=halogen.

Compounds of Formula (I) wherein $R^1$, $R^2$, X, $Y^1$ and $Y^2$ are as described herein may be synthesized according to the general procedure outlined in Scheme 1.

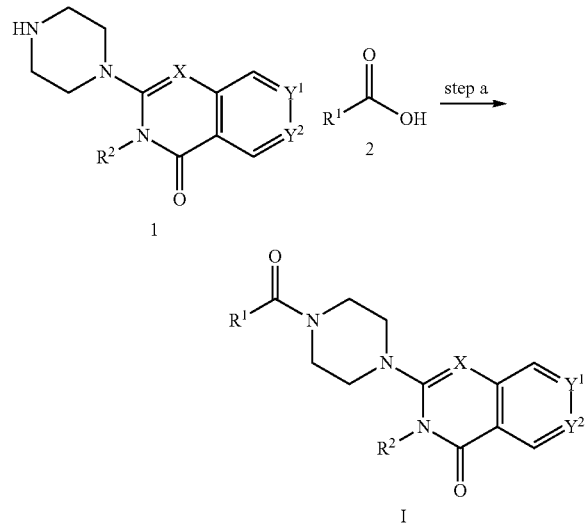

Reaction of intermediates 1 (either commercially available or prepared by methods described in literature, for example in V. J. Ram et al., *Bioorg. Med. Chem.* 2003, 11 (11), 2439-2444; A. Caruso et al., *J. Het. Chem.* 2014, 51(S1), E282-E293) with carboxylic acids 2 of the type $R^1COOH$, furnishes compounds of Formula (I) (step a). Amide couplings of this type are widely described in the literature and can be accomplished by the usage of coupling reagents such as CDI, DCC, HATU, HBTU, HOBT, TBTU, T3P or Mukaiyama reagent (Mukaiyama T. *Angew. Chem., Int. Ed. Engl.* 1979, 18, 707) in a suitable solvent e.g., DMF, DMA, DCM or dioxane, optionally in the presence of a base (e.g., $NEt_3$, DIPEA (Huenig's base) or DMAP).

Alternatively, the optionally protected carboxylic acids $R^1COOH$ 2 can be converted into their acid chlorides by treatment with, e.g. thionyl chloride or oxalyl chloride, neat or optionally in a solvent such as DCM. Reaction of the acid chloride with intermediates 1 in an appropriate solvent such as DCM or DMF and a base, e.g. $NEt_3$, Huenig's base, pyridine, DMAP or lithium bis(trimethylsilyl)amide at temperatures ranging from 0° C. to the reflux temperature of the solvent or solvent mixture yields compounds of Formula (I) (step a).

Alternatively, compounds of Formula (I) wherein $R^1$, $R^2$, X, $Y^1$ and $Y^2$ are as described herein can be synthesized as outlined in Scheme 2.

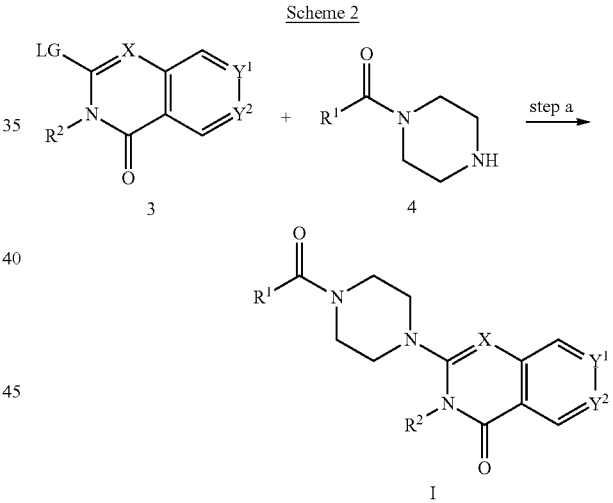

Reaction of intermediates 3 (either commercially available or prepared by methods described in literature, for example in V. J. Ram et al., *Bioorg. Med. Chem.* 2003, 11 (11), 2439-2444; A. Caruso et al., *J. Het. Chem.* 2014, 51(S1), E282-E293) in which LG signifies a suitable leaving group such as chlorine with piperazine derivatives 4 (either commercially available or prepared by literature methods) using a suitable solvent and base such as, e.g. DIPEA in EtOH, or $K_2CO_3$ in NMP, optionally at elevated temperatures up to the boiling point of the solvent or applying microwave heating, furnishes compounds of Formula (I) (step a).

In case intermediates 1 in which $R^2$, $Y^1$ and $Y^2$ are as described herein and X signifies nitrogen are commercially not available or their synthesis is not described in literature, they can be prepared, for example, as outlined in Scheme 3.

Scheme 3

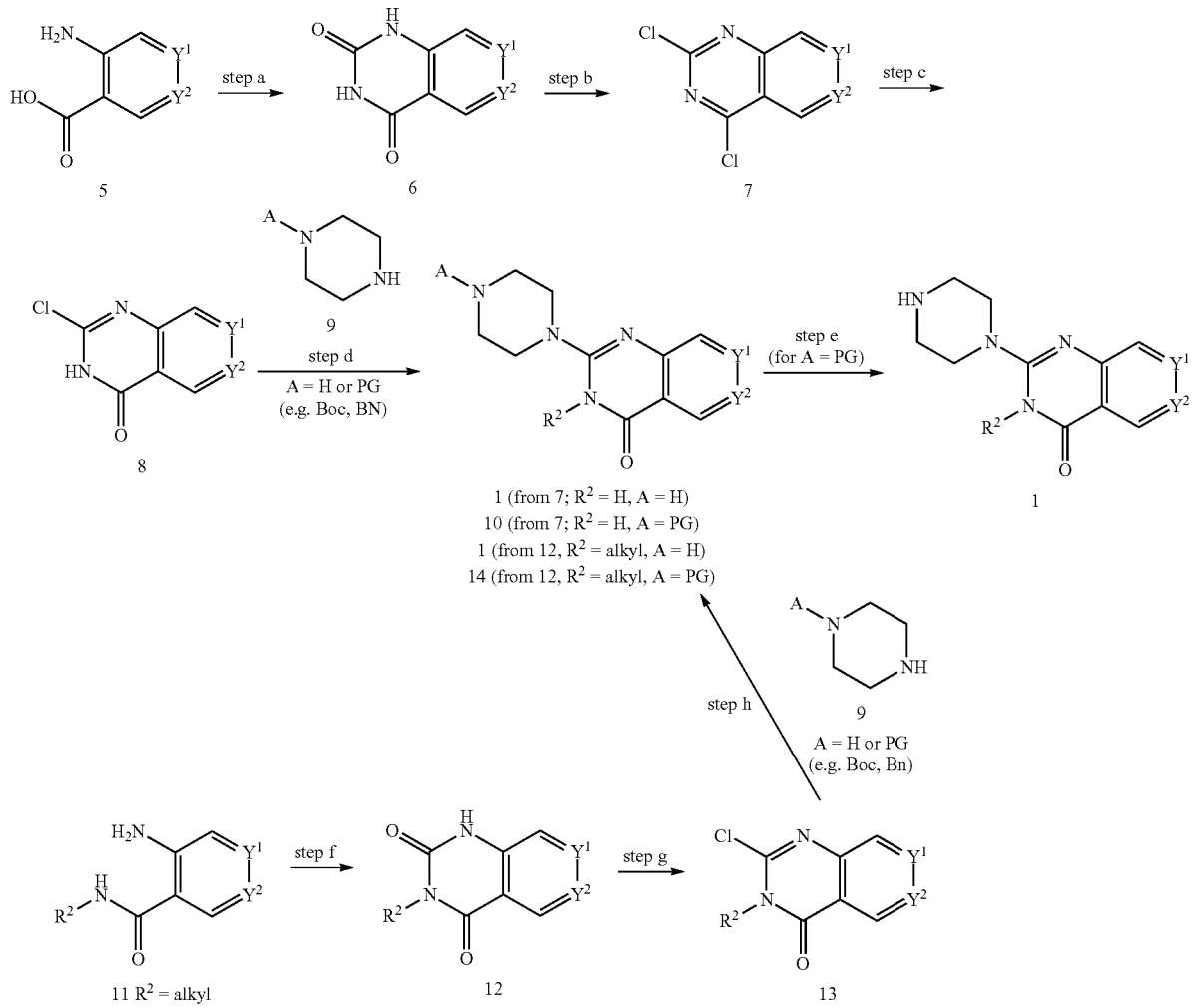

Reaction of intermediates 5, either commercially available or prepared by methods known by a person skilled in the art, with urea, preferable at elevated temperatures, gives intermediates 6 (step a). Reactions of this type are also described in literature (e.g., V. Prabhakar, et al., *Het. Lett.* 2016, 6(4), 775-793; F. Samrin et al., *J Het. Chem.* 2012, 49(6), 1391-1397).

Treatment of intermediates 6 with $POCl_3$ in analogy to literature procedures (e.g., V. Prabhakar, et al., *Het. Lett.* 2016, 6(4), 775-793), optionally in the presence of N,N-dimethylaniline or DIPEA, yields intermediates 7 (step b).

Intermediates 7 can be converted into intermediates 8 for example by reaction with aqueous NaOH and a suitable solvent such as THF (step c). Reactions of this type are broadly described in literature (e.g. F. Samrin et al., *J. Het. Chem.* 2012, 49(6), 1391-1397).

Reaction of intermediates 8 (either commercially available or be prepared by methods described in literature, for example in V. J. Ram et al., *Bioorg. Med. Chem.* 2003, 11 (11), 2439-2444; A. Caruso et al., *J Het. Chem.* 2014, 51(S1), E282-E293) with piperazine (9, A=H) or piperazine derivatives (9, A=PG) in which PG denotes a protecting group such as, e.g. a Boc protecting group (commercially available or prepared by methods well known in the art), applying the conditions described under Scheme 2, step a, provides intermediates 1 (A=H, $R^2$=H) and 10 (A=PG, e.g. Boc, $R^2$=H), respectively (step d).

Removal of the protective group in intermediates 10, applying methods know in the art (e.g., a Boc group using TFA in $CH_2Cl_2$ at temperatures between 0° C. and room temperature and as described for example in "Protective Groups in Organic Chemistry" by T. W. Greene and P. G. M. Wuts, 4th Ed., 2006, Wiley N.Y.), furnishes intermediates 1 ($R^2$=H) (step e).

Intermediates 1 in which $R^2$ signifies an alkyl group, X signifies nitrogen and $Y^1$ and $Y^2$ are as described herein and that are commercially not available or their synthesis is not described in literature, can be synthesized from intermediates 11 as outlined in Scheme 3.

Cyclization of intermediates 11 (either commercially available or prepared in analogy to literature methods), using for example CDI and a suitable base and solvent such as DBU and THF gives intermediates 12 (step f). Cyclization reactions of that type have been also described in literature (e.g., R. L. Jacobs, *J. Het. Chem.* 1970, 7(6), 1337-45; C. Couturier et al., *Bioorg. Med. Chem. Lett.* 2016, 26(21), 5290-5299).

Treatment of intermediates 12 for example with POCl₃, in analogy to published procedures (e.g., C. Couturier et al., *Bioorg. Med. Chem. Lett.* 2016, 26(21), 5290-5299), optionally in the presence of a base such as DIPEA or TEA furnishes intermediates 13 (step g).

Intermediates 13 can then be reacted with piperazine (9, A=H) or piperazine derivatives (9, A=PG) as described before under Scheme 3, step d, to provide intermediates 1 ($R^2$=alkyl) and 14 (A=PG, e.g. Boc), respectively (step h).

Removal of the protective group in intermediates 14 applying the methods described under Scheme 3, step e, furnishes intermediates 1 in which $R^2$ signifies an alkyl group (step e).

If intermediates 1, in which $R^2$, $Y^1$ and $Y^2$ are as described herein and X signifies C—H, are commercially not available they can be prepared for example as outlined in Scheme 4.

mercially available or prepared in analogy to literature procedures (e.g. WO2013132253; WO2016094730; R. Wang et al., *Org. Biomol. Chem.* 2011, 9(16), 5802-5808;), by treatment with a suitable alkylating agent such as $R^2$LG in which LG is a suitable leaving group such as chlorine, bromine, iodine, —OSO₂alkyl (e.g. mesylate (methanesulfonate), —OSO₂fluoroalkyl (e.g. triflate (trifluoromethanesulfonate) or —OSO₂aryl (e.g. tosylate (p-toluenesulfonate)), using a suitable base in an appropriate solvent (e.g. sodium hydride in DMF) at temperatures between 0° C. and the boiling temperature of the solvent (step d).

In one embodiment, the compound of Formula (I) is a compound of Formula (IA), wherein $R^2$, X, $Y^1$ and $Y^2$ are as described herein, $R^3$ is selected from the group consisting of alkyl, cyano and halogen, and $R^4$ is selected from the group consisting of hydrogen, alkyl, cycloalkyl, alkylcycloalkyl,

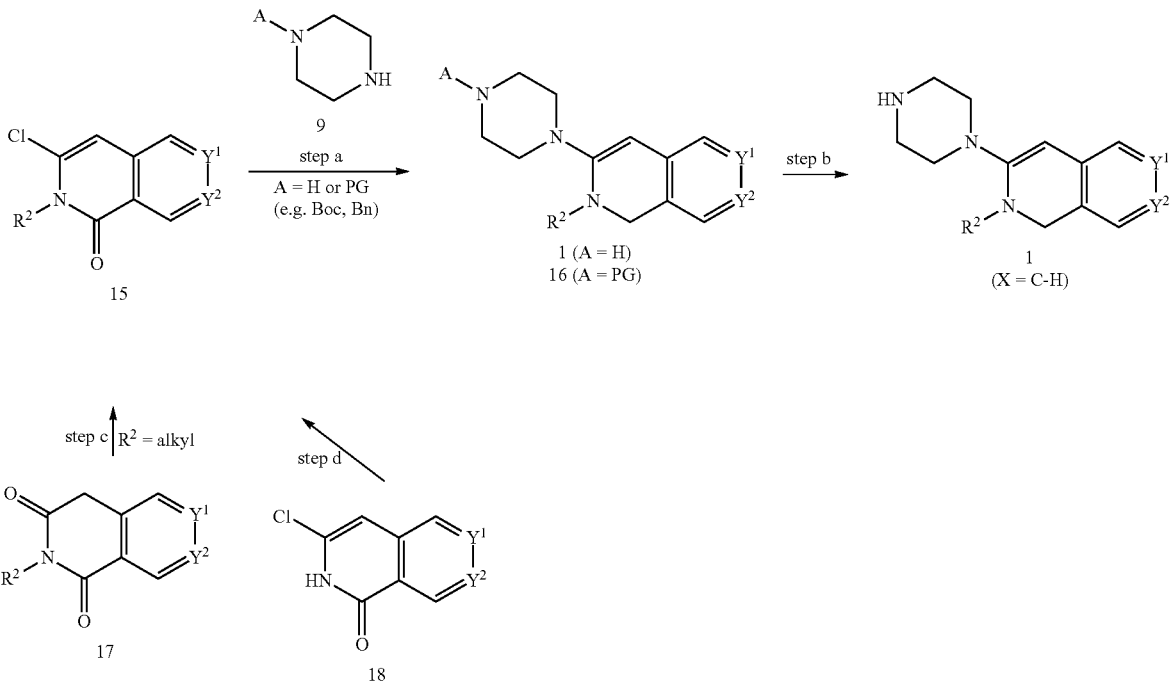

Intermediates 15, either commercially available or synthesized according to literature procedures, can be reacted with piperazine (9, A=H) or piperazine derivatives (9, A=PG) in which PG denotes a protecting group such as, e.g. a Boc protecting group (commercially available or prepared by methods well known in the art), applying the conditions described under Scheme 2, step a, to provide intermediates 1 (A=H) and 16 (A=PG, e.g. Boc), respectively (step a).

Removal of the protective group in intermediates 16 applying for example the methods described under Scheme 2, step e, furnishes intermediates 1 (X=C—H; step b).

Intermediates 15 in which $R^2$ signifies an alkyl group can be prepared for example from intermediates 17 by reaction with POCl₃, preferably at elevated temperatures up to the boiling point of the solvent. Reactions of this type have been described in literature, e.g. B. Li et al., *Tetrahedron Lett.* 2010, 51(29), 3748-3751 (step c).

Intermediates 15 in which $R^2$ signifies an alkyl group can be alternatively prepared from intermediates 18, either comhaloalkylcycloalkyl, alkoxyalkyl, haloalkyl and hydroxyalkyl. Compounds of Formula (IA) can be prepared by methods known in the art and for example as depicted in Scheme 5.

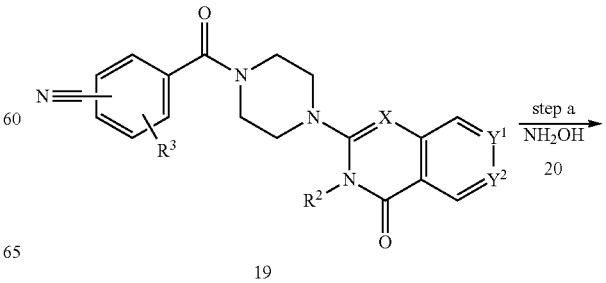

-continued

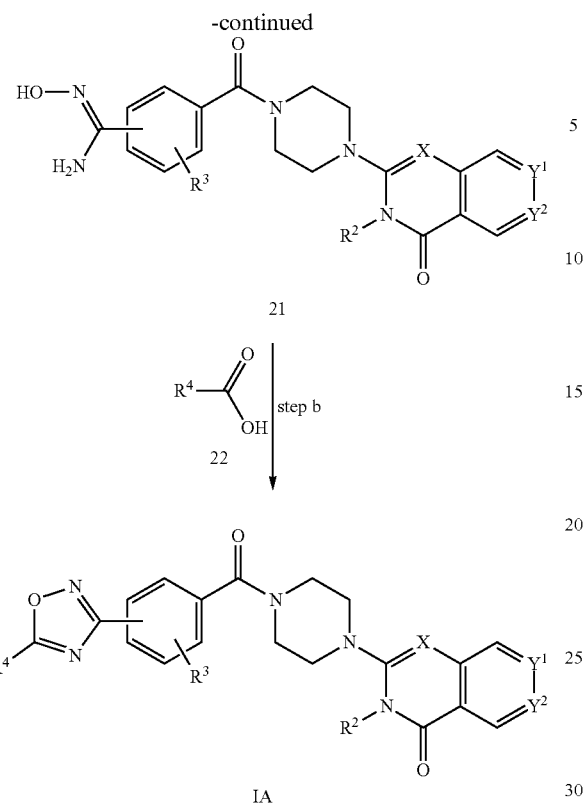

21

22

IA

Reaction of intermediates 19, synthesized according to methodologies described under Schemes 1 or 2, with hydroxylamine 20 in the presence of an appropriate solvent and base such as $Na_2CO_3$ in EtOH provides amidoxime intermediates 21 (step a).

Reacting 21 with suitably activated acids $R^4COOH$ 22, for example in form of their acid chlorides (prepared by methods well known in the art), in the presence of a suitable base and solvent such as DIPEA in DME at temperatures ranging from room temperature to the boiling point of the solvent, furnishes compounds IA (step b).

In one embodiment, the compound of Formula (I) is a compound of Formula (IB), wherein $R^2$, X, $Y^1$ and $Y^2$ are as described herein, A and B each independently represent aryl or heteroaryl, $R^5$ is selected from the group consisting of hydrogen, alkyl, cycloalkyl, haloalkyl and cyano, and $R^6$ is selected from the group consisting of hydrogen, alkyl, cycloalkyl, alkoxy, aryloxy, arylalkoxy, haloalkyl, haloalkoxy, hydroxyalkyl, hydroxyalkoxy and cyano. Compounds of Formula (IB) can be prepared for example from intermediates 23 (synthesized according to methods outlined under Schemes 1 and 2) by applying cross-coupling reactions such as Negishi, Heck, Stille, Suzuki, Sonogashira or Buchwald-Hartwig reaction (Scheme 6).

Scheme 6

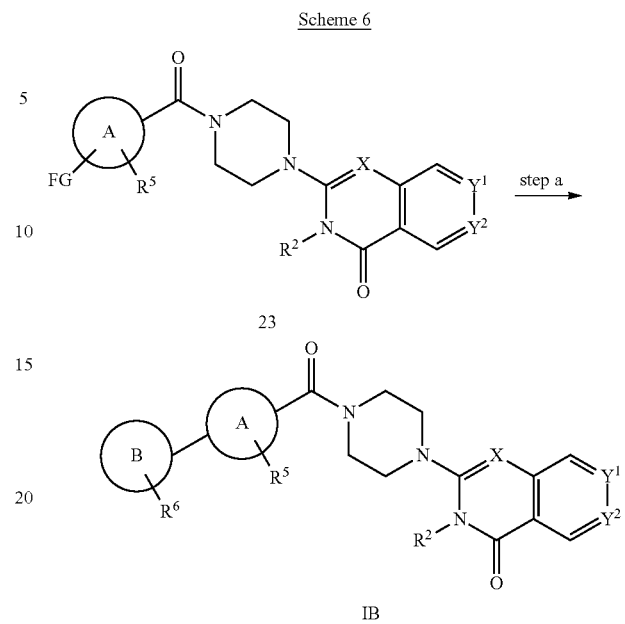

23

IB

Reactions of this type are broadly described in literature and well known to persons skilled in the art. For example, reaction of intermediates 23 (prepared for example in analogy to methods described in Schemes 1 and 2) in which FG signifies a suitable functional group such as, e.g. chloro, bromo, iodo, —$OSO_2$alkyl (e.g. mesylate (methanesulfonate), —$OSO_2$fluoroalkyl (e.g. triflate (trifluoromethanesulfonate) or —$OSO_2$aryl (e.g. tosylate (p-toluenesulfonate) with $R^6$-substituted aryl or heteroaryl boronic acids or boronic esters (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1st Ed., 2005, John Wiley & Sons, New York) using a suitable catalyst (e.g. dichloro[1,1'-bis(diphenylphosphino)-ferrocene]palladium (II) dichloromethane adduct, tetrakis(triphenylphosphine)palladium(0) or palladium(II)acetate with triphenylphosphine) in an appropriate solvent (e.g. dioxane, dimethoxyethane, water, toluene, DMF or mixtures thereof) and a suitable base (e.g. $Na_2CO_3$, $NaHCO_3$, KF, $K_2CO_3$ or $NEt_3$) at temperatures between room temperature and the boiling point of the solvent or solvent mixture, yields compounds of Formula (IB) (step a). Suzuki reactions of this type are broadly described in literature (e.g. A. Suzuki, *Pure Appl. Chem.* 1991, 63, 419-422; A. Suzuki, N. Miyaura, *Chem. Rev.* 1995, 95, 2457-2483; A. Suzuki, *J. Organomet. Chem.* 1999, 576, 147-168; V. Polshettiwar et al., *Chem. Sus. Chem.* 2010, 3, 502-522) and are well known to those skilled in the art. Alternatively, aryl- or heteroaryl-trifluoroborates can be used in the cross-coupling reaction applying a palladium catalyst such as, e.g. tetrakis(triphenylphosphine)-palladium(0), palladium(II) acetate or dichloro[1,1'-bis(diphenylphosphino)ferrocene]-palladium(II) dichloromethane adduct in the presence of a suitable base such as cesium carbonate or potassium phosphate in solvents such as toluene, THF, dioxane, water or mixtures thereof, at temperatures between room temperature and the boiling point of the solvent or solvent mixture.

In one embodiment, the compound of Formula (I) is a compound of Formula (IC), wherein $R^2$, X, $Y^1$ and $Y^2$ are as described herein and wherein $R^7$ and $R^8$ are each independently selected from the group consisting of hydrogen, alkyl, cycloalkyl and haloalkyl; or $R^7$ and $R^8$, together with the nitrogen atom to which they are attached, form a monocyclic, 5-, 6- or 7-membered heterocyclic ring, optionally substituted with 1-2 substituents selected from the group consisting of halogen and alkyl; or optionally substituted with 1 substituent selected from the group consisting of hydroxyl and alkoxy; or $R^7$ and $R^8$, together with the nitrogen atom to which they are attached, form an optionally substituted spirocyclic system selected from the group consisting of 2-azaspiro[3.3]heptan-2-yl, 1-azaspiro[3.3]heptan-1-yl, 1-azaspiro[3.4]octan-1-yl, 2-azaspiro[3.4]octan-2-yl, 1-azaspiro[3.5]nonan-1-yl, 2-azaspiro[3.5]nonan-2-yl, 4-azaspiro[2.4]heptan-4-yl, 5-azaspiro[2.4]heptan-5-yl, 6-azaspiro[3.4]octan-6-yl, 5-azaspiro[3.4]octan-5-yl, 1-azaspiro[4.4]nonane-1-yl, 2-azaspiro[4.4]nonane-2-yl, 5-azaspiro[2.5]octane-5-yl, 6-azaspiro[2.5]octane-6-yl, 6-azaspiro[3.5]nonane-6-yl, and 7-azaspiro[3.5]nonane-7-yl, wherein when said spirocyclic system is substituted, it is substituted with 1-4 fluorine substituents or with 1-2 hydroxy substituents. Compounds of Formula (IC) can be prepared, for example, as outlined in Scheme 7.

Intermediates 26 can be used for acylation of intermediates 1 as described in Scheme 1 to provide compounds of Formula (IC) (step c).

Intermediates 24 in which LG signifies a chlorine can be prepared in analogy to literature procedures (e.g. WO2007025897A2), for example by treatment of commercially available intermediates 27 with oxalyl or thionyl chloride in a suitable solvent such as, e.g. DMF (step d).

In one embodiment, the compound of Formula (I) is a compound of Formula (ID), wherein $R^2$, X, $Y^1$ and $Y^2$ are as described herein and $R^9$ is selected from the group consisting of hydrogen, cyano, alkyl, haloalkyl, —N($R^{10}R^{11}$), hydroxy, alkoxy, hydroxyalkoxy, and alkoxyalkoxy, wherein $R^{10}$ and $R^{11}$ are each independently selected from the group consisting of hydrogen, alkyl, haloalkyl, hydroxyalkyl and alkoxyalkyl; or $R^{10}$ and $R^{11}$, together with the nitrogen atom to which they are attached, form a heterocyclic ring, preferably a monocyclic heterocyclic ring, most preferably a heterocyclic ring selected from the group consisting of morpholine, piperazine and 1-methyl-piperazine. In a preferred embodiment, $R^9$ is selected from the group consisting of hydrogen, cyano, trifluoromethyl and morpholinyl. Compounds of Formula (ID) can be synthesized, for example,

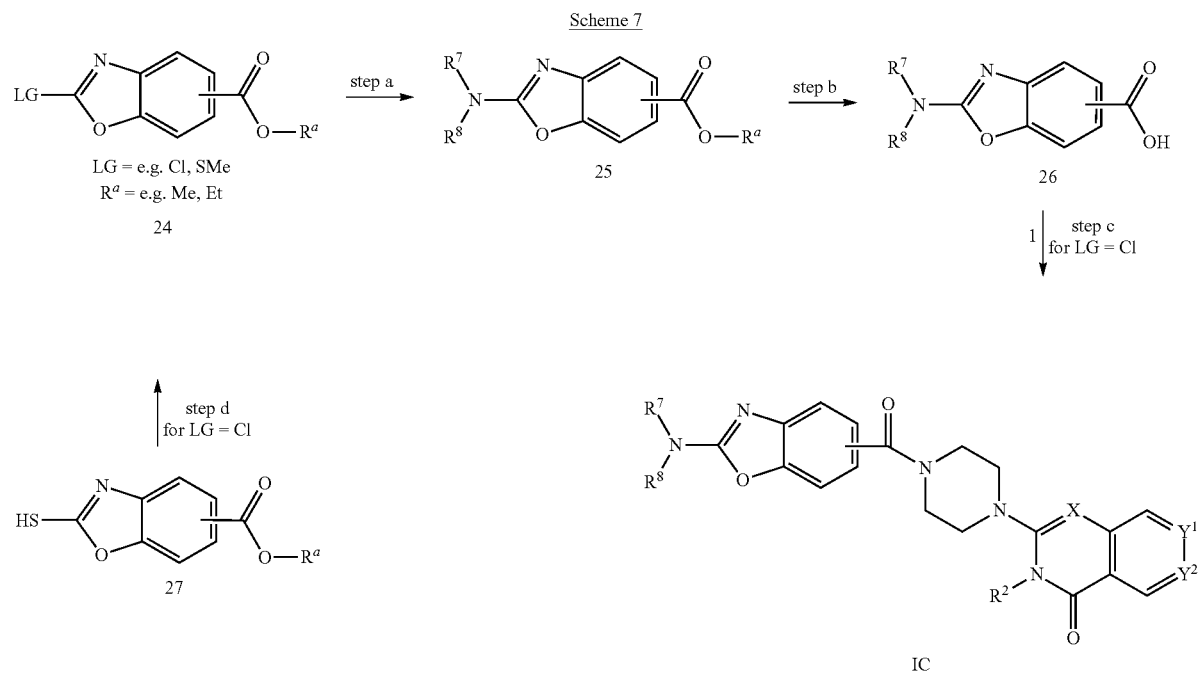

Intermediates 24, either commercially available or prepared in analogy to literature methods, in which LG denotes a leaving group such as, e.g. a chloro or methylthio group (e.g. LG=SMe group: T. H. M. Jonckers et al., *Bioorg. Med. Chem. Lett.* 2012, 22, 4998-5002; WO2009071650), can be reacted with amines of the type ($R^7R^8$)NH in an appropriate solvent such as THF or DMF to give intermediates 25 (step a).

Cleavage of the ester group in intermediates 25, using methods known to a person skilled in the art (e.g., a methyl or ethyl ester under basic conditions with LiOH or NaOH in polar solvents such as, e.g. MeOH, $H_2O$ or THF or mixtures of said solvents) furnishes intermediates 26 (step b).

according to Scheme 8 by acylation of intermediates 1 with intermediates 39 (step i) applying the methods described in Scheme 1.

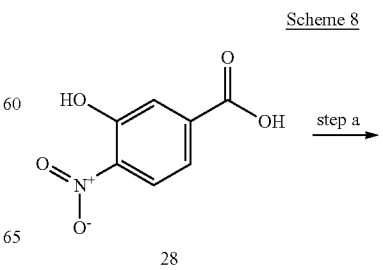

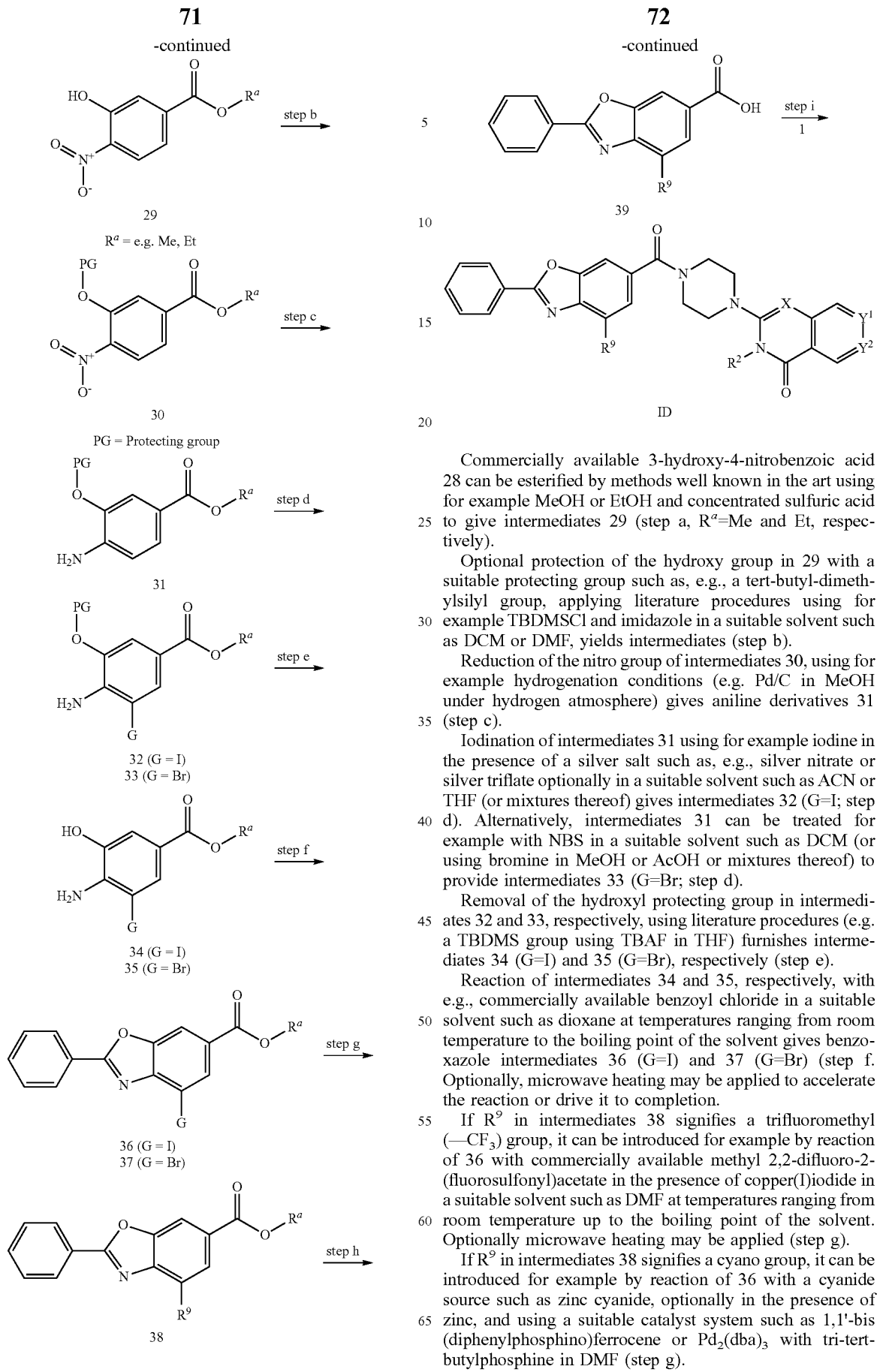

Commercially available 3-hydroxy-4-nitrobenzoic acid 28 can be esterified by methods well known in the art using for example MeOH or EtOH and concentrated sulfuric acid to give intermediates 29 (step a, $R^a$=Me and Et, respectively).

Optional protection of the hydroxy group in 29 with a suitable protecting group such as, e.g., a tert-butyl-dimethylsilyl group, applying literature procedures using for example TBDMSCl and imidazole in a suitable solvent such as DCM or DMF, yields intermediates (step b).

Reduction of the nitro group of intermediates 30, using for example hydrogenation conditions (e.g. Pd/C in MeOH under hydrogen atmosphere) gives aniline derivatives 31 (step c).

Iodination of intermediates 31 using for example iodine in the presence of a silver salt such as, e.g., silver nitrate or silver triflate optionally in a suitable solvent such as ACN or THF (or mixtures thereof) gives intermediates 32 (G=I; step d). Alternatively, intermediates 31 can be treated for example with NBS in a suitable solvent such as DCM (or using bromine in MeOH or AcOH or mixtures thereof) to provide intermediates 33 (G=Br; step d).

Removal of the hydroxyl protecting group in intermediates 32 and 33, respectively, using literature procedures (e.g. a TBDMS group using TBAF in THF) furnishes intermediates 34 (G=I) and 35 (G=Br), respectively (step e).

Reaction of intermediates 34 and 35, respectively, with e.g., commercially available benzoyl chloride in a suitable solvent such as dioxane at temperatures ranging from room temperature to the boiling point of the solvent gives benzoxazole intermediates 36 (G=I) and 37 (G=Br) (step f. Optionally, microwave heating may be applied to accelerate the reaction or drive it to completion.

If $R^9$ in intermediates 38 signifies a trifluoromethyl (—$CF_3$) group, it can be introduced for example by reaction of 36 with commercially available methyl 2,2-difluoro-2-(fluorosulfonyl)acetate in the presence of copper(I)iodide in a suitable solvent such as DMF at temperatures ranging from room temperature up to the boiling point of the solvent. Optionally microwave heating may be applied (step g).

If $R^9$ in intermediates 38 signifies a cyano group, it can be introduced for example by reaction of 36 with a cyanide source such as zinc cyanide, optionally in the presence of zinc, and using a suitable catalyst system such as 1,1'-bis (diphenylphosphino)ferrocene or $Pd_2(dba)_3$ with tri-tert-butylphosphine in DMF (step g).

If R$^9$ in intermediates 38 signifies —N(R$^{10}$R$^{11}$), such as morpholinyl, it can be introduced by reaction of intermediates 37 with primary or secondary amines of the type HN(R$^{10}$R$^{11}$), using a suitable catalyst system (e.g. palladium (II) acetate with RuPhos), base (e.g. sodium or potassium tert-butoxide) and solvent (e.g. toluene) at temperatures ranging from room temperature up to the boiling point of the solvent, optionally applying microwave heating (step g).

If R$^9$ in intermediates 38 signifies a hydroxyalkoxy or alkoxyalkoxy group it can be introduced for example by reaction of intermediates 36 or 37 with alcohols of the type Intermediates 39 can be used for acylation of intermediates 1 applying the methods described under Scheme 1 to furnish compounds of Formula (ID) (step i).

In one embodiment, the compound of Formula (I) is a compound of Formula (IE) wherein R$^2$, X, Y$^1$ and Y$^2$ are as described herein, and R$^{12}$ is selected from the group consisting of hydrogen, alkyl, haloalkyl, cyano and halogen. Compounds of Formula (IE) can be prepared, for example, as described in Scheme 9.

Scheme 9

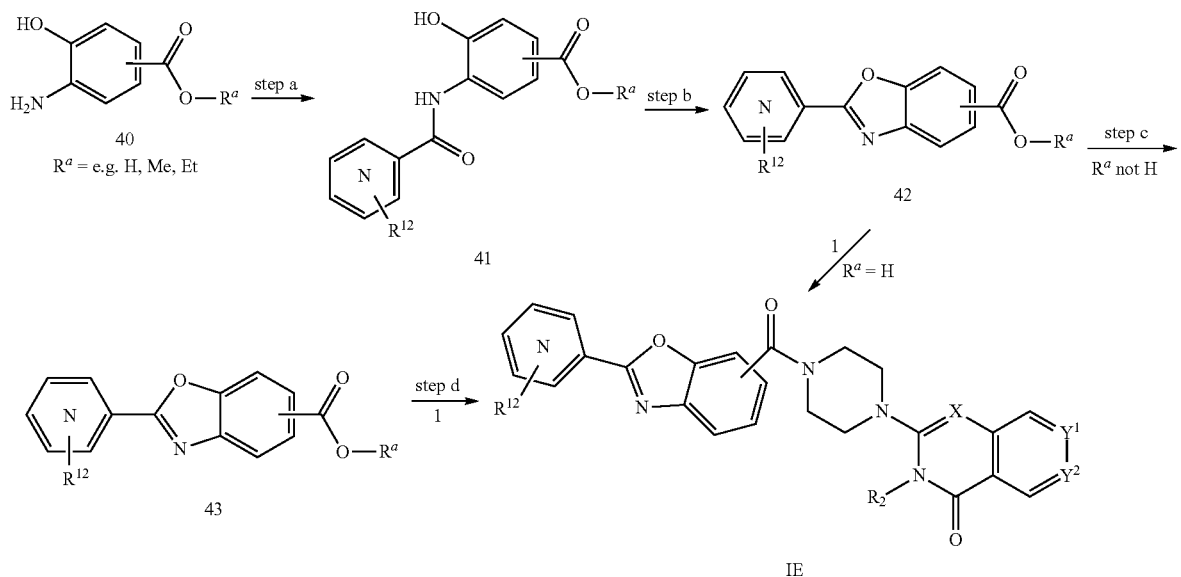

hydroxyalkyl-OH or alkoxyalkyl-OH in the presence of a suitable catalyst and solvent system such as, e.g. Pd$_2$(dba)$_3$, Tol-BINAP in toluene, optionally in the presence of an appropriate base to furnish intermediates 38 (step g). Alternatively, intermediates 36 or 37 can be first converted into intermediates 38 in which R$^9$ signifies a hydroxyl group, for example by first converting the halogen group in 36 or 37 into a boronate ester, for example by cross-coupling with bis(pinacolato)boron in the presence of a suitable catalyst such as PdCl$_2$(dppf) using an appropriate base and solvent such KOAc in dioxane or DMSO, and oxidizing the boronic acid ester with, e.g. H$_2$O$_2$ in a suitable solvent or solvent mixture such as AcOH and MeOH to provide 38 (R$^9$=OH). The resulting alcohol function in intermediates 38 can then be alkylated with a suitable alkylating agent such as alkyl-LG in which LG is a suitable leaving group such as chlorine, bromine, iodine, —OSO$_2$alkyl (e.g. mesylate (methanesulfonate), —OSO$_2$fluoroalkyl (e.g. triflate (trifluoromethanesulfonate) or —OSO$_2$aryl (e.g. tosylate (p-toluenesulfonate)) applying the methods described unter Scheme 4, step d, to furnish intermediates 38 (step g). Transformations of this type have been widely described in literature and are well known in the art.

Cleavage of the ester group in intermediates 38 as described under Scheme 6, step b, provides intermediates 39 (step h).

Amidation of commercially available intermediates 40 with pyridine-2-, 3- or 4-carboxylic acids (R$^a$=H) applying for example the amide coupling conditions as described under Scheme 1, step a, yields intermediates 41 (step a).

Intermediates 41 can be cyclized to the benzoxazole intermediates 42 by applying literature conditions such as pTsOH in a suitable solvent such as toluene, DMSO or xylene at temperatures ranging from room temperature up to the boiling point of the solvent. Microwave heating may be applied to accelerate the reaction (step b). Depending on the reaction conditions and type of ester group a concomitant cyclization to the benzoxazole and ester cleavage may occur (e.g. using PPA at elevated temperatures for methyl or ethyl ester) to furnish intermediates 43.

Ester hydrolysis in intermediates 42 by methods well known in the art and as mentioned for example under Scheme 6, step b, furnishes intermediates 43 (step c). Intermediates 43 with pyridine-3- or 4-yl substituent have also been described in literature, e.g. WO2005113523.

Amide coupling of intermediates 43 with intermediates 1 using for example the conditions described under Scheme 1, step a, furnishes Compounds of Formula (IE) (step d).

In case R$^a$ in intermediates 42 signifies a hydrogen, they can be used directly for acylation of intermediates 1 applying the reaction conditions described before (step e).

In one embodiment, the compound of Formula (I) is a compound of Formula (IF), wherein R$^2$, X, Y$^1$ and Y$^2$ are as described herein, R$^{13}$ is selected from the group consisting of hydrogen, alkyl and haloalkyl and R$^{14}$ is selected from the group consisting of hydrogen, alkyl, haloalkyl, benzyl and benzyl substituted with a substituent selected from the group consisting of halogen, alkyl and haloalkyl; or $R^{13}$ and $R^{14}$, together with the nitrogen atom to which they are attached, form a monocyclic, 4-, 5-, 6- or 7-membered heterocyclic ring, optionally substituted with 1 substituent selected from the group consisting of haloalkyl and phenyl, or with 1 to 2 substituents selected from the group consisting of alkyl and halogen (in particular fluorine); or $R^{13}$ and $R^{14}$, together with the nitrogen atom to which they are attached, form a heterocyclic ring selected from the group consisting of 2-azabicyclo[2.2.1]heptanyl, indolinyl and 2,3-dihydro-IH-pyrrolo[2,3-b]pyridinyl; or $R^{13}$ and $R^{14}$, together with the nitrogen atom to which they are attached, form a spirocyclic system selected from the group consisting of 1-azaspiro[3.3]heptane-1-yl, 2-azaspiro[3.3]heptane-2-yl, 1-azaspiro[3.4]octane-1-yl, 2-azaspiro[3.4]octane-2-yl, 1-azaspiro[3.5]nonane-1-yl, 2-azaspiro[3.5]nonane-2-yl, 4-azaspiro[2.4]heptane-4-yl, 5-azaspiro[2.4]heptane-5-yl, 5-azaspiro[3.4]octane-5-yl, 6-azaspiro[3.4]octane-6-yl, 1-azaspiro[4.4]nonane-1-yl, 2-azaspiro[4.4]nonane-2-yl, 5-azaspiro[2.5]octane-5-yl, 6-azaspiro[2.5]octane-6-yl, 6-azaspiro[3.5]nonane-6-yl, 7-azaspiro[3.5]nonane-7-yl, wherein said spirocyclic system is optionally substituted with 1-4 halogen substituents (in particular fluorine) or with 1-2 hydroxy substituents. In a preferred embodiment, the substituent —N($R^{13}R^{14}$) is in the 3- or 4-position of the phenyl ring to which it is attached. Compounds of Formula (IF) can be prepared for example as described in Scheme 10.

tuted benzoic acid esters with primary or secondary amines of the type $R^{13}R^{14}$NH using a suitable base and solvent such as $CsCO_3$ in DMF, or bromo- or iodo-substituted benzoic acid esters using a suitable catalyst system such as $Pd_2(dba)_3$ and Xantphos in the presence of a base such as $K_3PO_4$ in an appropriate solvent such as dioxane. The reaction can be carried out at temperatures ranging from room temperature up to the boiling point of the solvent. Microwave heating may be applied to accelerate the reaction.

In case $R^a$ in intermediates 45 signifies a methyl or ethyl group, the ester can be hydrolyzed by methods well known in the art and as mentioned for example under Scheme 6, step b, to provide intermediates 46 (step b).

Amidation of intermediates 1 with intermediates 46 applying for example the conditions described under Scheme 1, step a, furnishes compounds of Formula (IF) (ep c).

In case $R^a$ in intermediates 45 signifies a hydrogen they can be used directly for acylation of intermediates 1 applying the reaction conditions described under Scheme 1, step a, to furnish compounds of Formula (IF) (step d).

Several intermediates of type 45 and 46 are also commercially available or their synthesis has been described in literature (e.g. *J Am. Chem. Soc.* 2008, 130(20), 6586; *Chem. Biol. Drug Design* 2015, 86(2), 223).

In one embodiment, the compound of Formula (I) is a compound of Formula (IG) or (IH), respectively, wherein $R^2$, X, $Y^1$ and $Y^2$ are as described herein; Y is $CH_2$ and Z is O; or Y is O and Z is $CH_2$; $X^1$, $X^2$ and $X^3$ are each selected Scheme 10

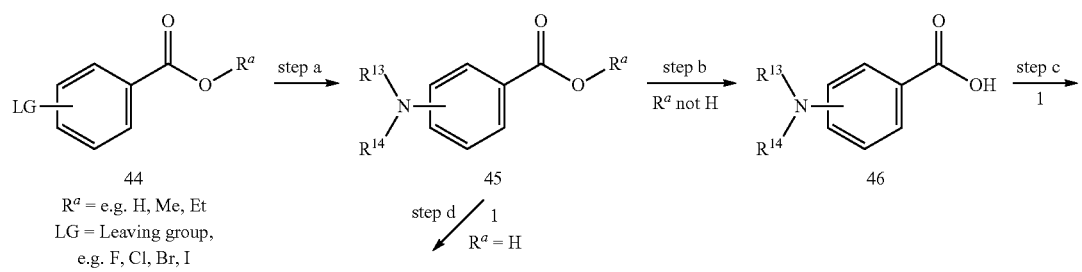

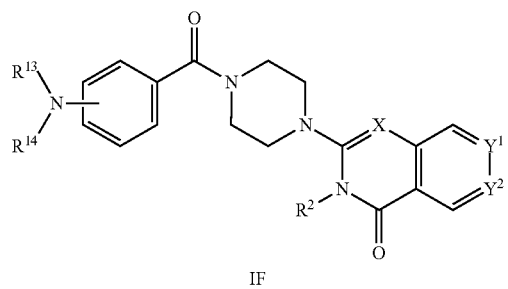

IF

Intermediates 44, either commercially available or synthesized by methods known in the art, in which LG signifies a suitable leaving group such as fluoro, chloro, bromo or iodo and $R^a$ signifies either hydrogen or an alkyl group like for example a methyl or ethyl group, can be reacted with primary or secondary amines of the type HN$R^{13}R^{14}$ to give intermediates 45 (step a). Reactions of that type are widely described in literature, for example reacting fluoro-substifrom the group consisting of CH and N, wherein at most one of $X^1$, $X^2$ and $X^3$ is N; $R^{15}$ is selected from the group consisting of hydrogen, halogen, alkyl and haloalkyl; and $R^{16}$ is selected from the group consisting of hydrogen, halogen, alkyl, haloalkyl, cyano and imidazole-2-yl. Compounds of Formula (IG) can be prepared, for example, as described in Scheme 11.

Scheme 11

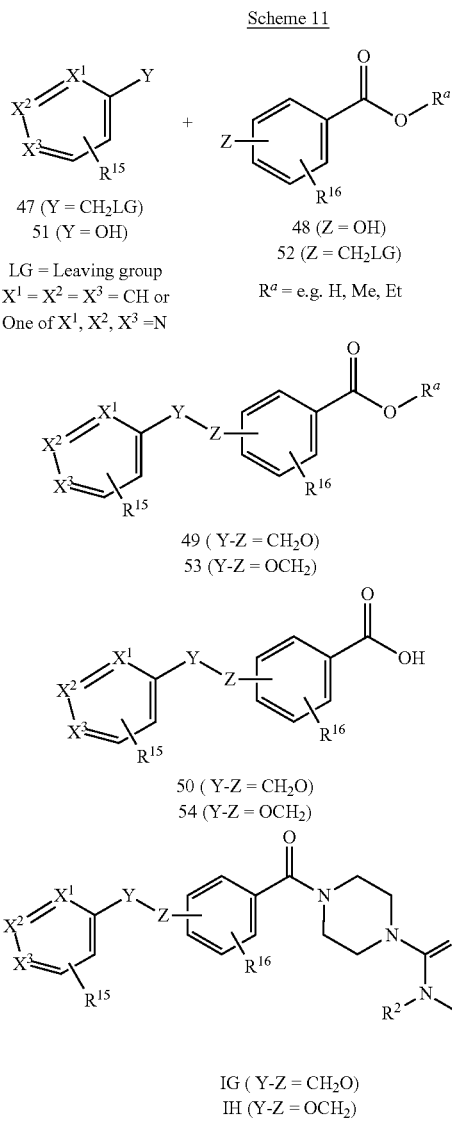

47 (Y = CH₂LG)
51 (Y = OH)

LG = Leaving group
X¹ = X² = X³ = CH or
One of X¹, X², X³ = N 48 (Z = OH)
52 (Z = CH₂LG)

Rᵃ = e.g. H, Me, Et 49 (Y-Z = CH₂O)
53 (Y-Z = OCH₂)

50 (Y-Z = CH₂O)
54 (Y-Z = OCH₂)

IG (Y-Z = CH₂O)
IH (Y-Z = OCH₂)

Alkylation of intermediates 48 with intermediates 47 and of intermediates 51 with intermediates 52, respectively, all either commercially available or prepared by methods well known in the art, in which LG signifies a leaving group such as chlorine, bromine, iodine, —OSO₂alkyl (e.g. mesylate (methanesulfonate), —OSO₂fluoroalkyl (e.g. triflate (trifluoromethanesulfonate) or —OSO₂aryl (e.g. tosylate (p-toluenesulfonate)), using a suitable base in an appropriate solvent (e.g. sodium hydride in DMF) at temperatures between 0° C. and the boiling temperature of the solvent, yields intermediates 49 and 53, respectively (step a).

Ester hydrolysis in intermediates 49 and 53 by methods well known in the art and as described for example under Scheme 6, step b, provides intermediates 50 and 54 (step b), respectively. Several of intermediates of type 50 and 54 are also commercially available or can be prepared in analogy to methods described in literature.

Amidation of intermediates 1 with intermediates 50 or 54 applying the reaction conditions described under Scheme 1, step a, furnishes compounds IG or IH, respectively (step c).

Alternatively, compounds IG and IH may be prepared according to Scheme 12.

Scheme 12

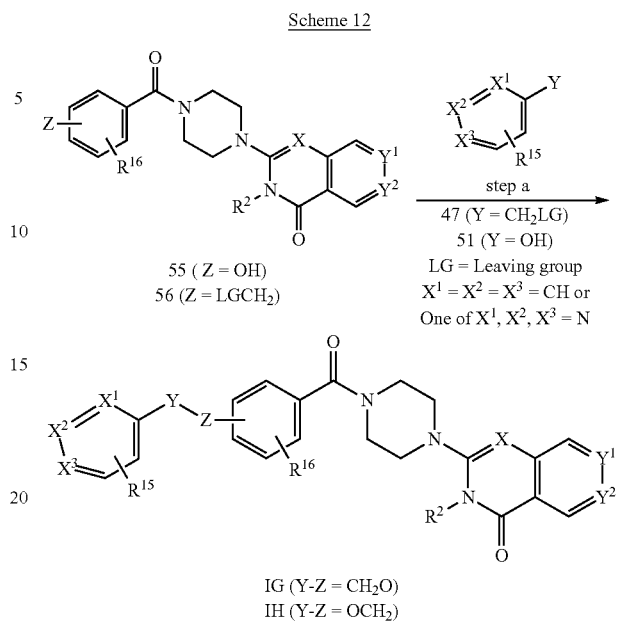

55 (Z = OH)
56 (Z = LGCH₂)

47 (Y = CH₂LG)
51 (Y = OH)

LG = Leaving group
X¹ = X² = X³ = CH or
One of X¹, X², X³ = N

IG (Y-Z = CH₂O)
IH (Y-Z = OCH₂)

Compounds 55, which can be prepared by methods know by a person skilled in the art, can be alkylated with compounds 47, for example according to the methods described in Scheme 11, step a, to give compounds IG (step a).

Alternatively, compounds 56 which can be prepared by literature methods can be reacted with compounds 47 applying the conditions for example described in Scheme 11, step a, to provide compounds IH (step a).

In one embodiment, the compound of Formula (I) is a compound of Formula (IJ), wherein R², Y¹ and Y² are as described herein and B represents an optionally substituted mono-, bi- or spirocyclic heterocycle connected via a nitrogen atom. Compounds of Formula (IJ) can be prepared, for example, as described in Scheme 13.

Scheme 13

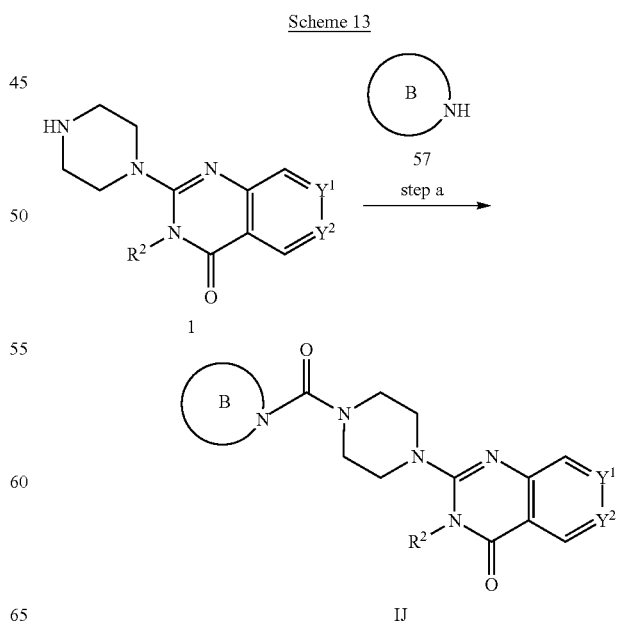

IJ

Compounds 1 are reacted with heterocycles 57 in the presence of a urea forming reagent such as bis(trichloromethyl) carbonate using a suitable base and solvent such as, e.g. sodium bicarbonate in DCM, to give compounds of formula IJ (step a). Further urea forming reagents include but are not limited to phosgene, trichloromethyl chloroformate, (4-nitrophenyl)carbonate, 1,1'-carbonyldiimidazole or 1,1'-carbonyl-di-(1,2,4-triazole). Reactions of this type and the use of these reagents are widely described in literature (e.g. G. Sartori et al., *Green Chemistry* 2000, 2, 140). A person skilled in the art will acknowledge that the order of the addition of the reagents can be important in this type of reactions due to the reactivity and stability of the intermediary formed carbamoyl intermediates, as well as for avoiding formation of undesired symmetrical urea by-products.

In one embodiment, the compound of Formula (I) is a compound of Formula (IK) or (IL), wherein $R^2$, $Y^1$ and $Y^2$ are as described herein and C represents an optionally substituted mono-, bi- or spirocyclic heterocycle connected via a nitrogen atom and containing a second nitrogen substituted with a group $R^{17}SO_2$ or $R^{17}CH_2$, respectively, wherein $R^{17}$ equals to $R^t$ as defined herein. Compounds of Formula (IK) and (IL) can be prepared, for example, as described in Scheme 14.

Compounds 1 are reacted with optionally substituted and optionally mono-protected mono-, bi- or spirocyclic heterocycles 58 applying the conditions described for example under Scheme 13, step a, to give intermediates 59 (step a).

Removal of the protective group in intermediates 59 applying the methods described for example under Scheme 3, step e, provides intermediates 60 (step b).

Acylation of intermediates 59 with, e.g. sulfonylchlorides of type $R^{17}SO_2Cl$, either commercially available or prepared by methods known in the art, using a suitable base and solvent, e.g. DIPEA in DCM, furnishes compounds IK (step c). Reactions of that type are broadly described in literature (e.g. CHEMIK 2014, 68, 620).

Alternatively, intermediates 60 can be subjected to a reductive amination reaction with aldehydes of type $R^{17}$CHO using a suitable reducing agent and solvent such as NaBH$_3$CN in MeOH, AcOH or mixtures thereof to give compounds IL (step d).

In one aspect, the present invention provides a process of manufacturing the compounds of Formula (I) as described herein, comprising the steps of:

a) reacting an amine 1, wherein $R^2$, X, $Y^1$ and $Y^2$ are as described herein,

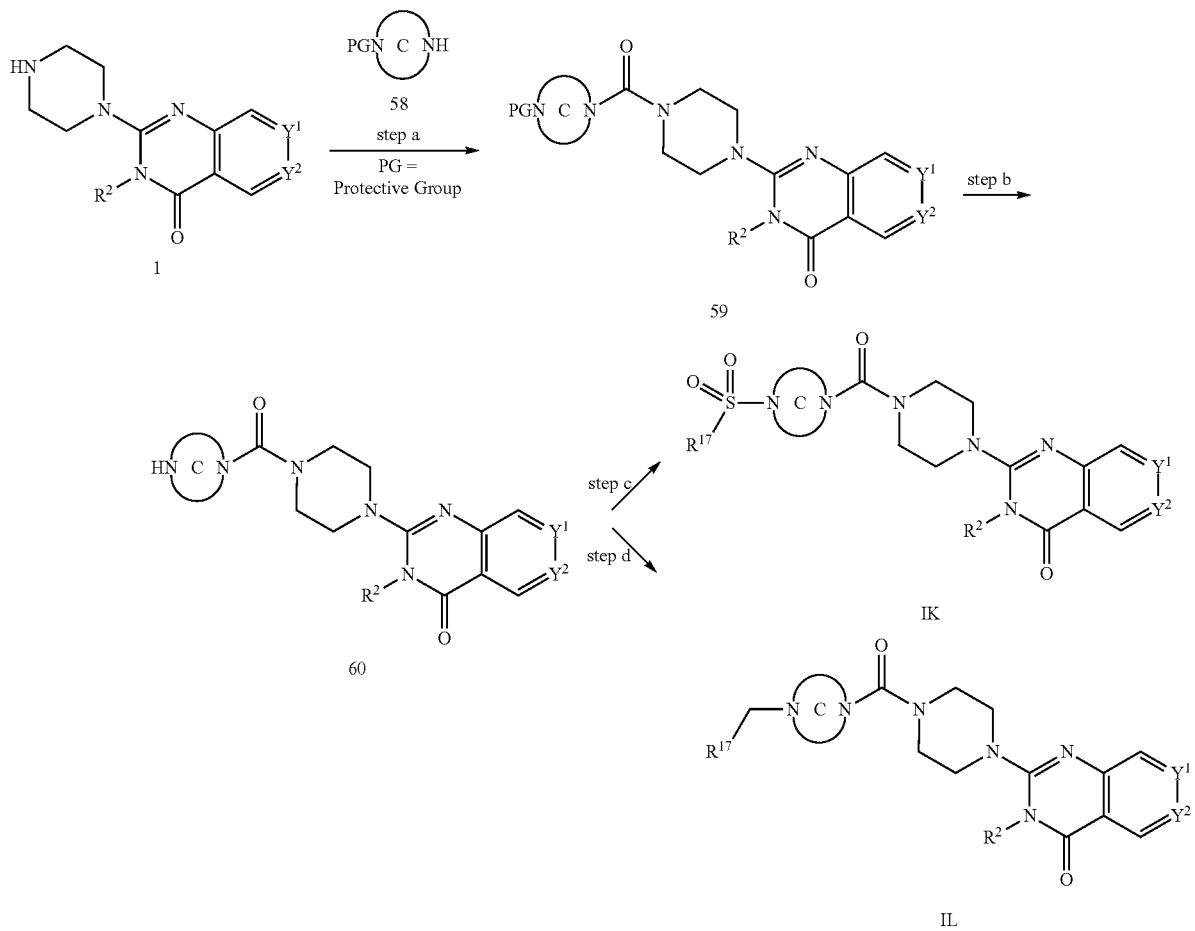

Scheme 14

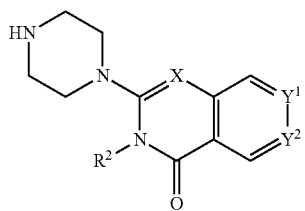

with an acid 2, wherein R¹ is as described herein

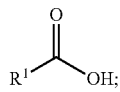

or b) reacting an amine 1, wherein R², X, Y¹ and Y² are as described herein,

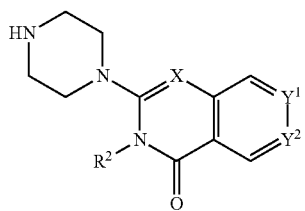

with an acid chloride 2a, wherein R¹ is as described herein

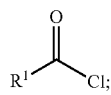

or c) reacting a compound of formula 3, wherein R², X, Y¹ and Y² are as described herein

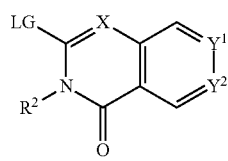

with a piperazine derivative 4, wherein R¹ is as described herein

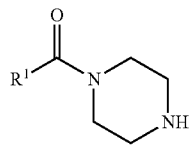

to form said compound of Formula (I).

In a further aspect, the present invention provides a compound according to Formula (I) as described herein, when manufactured according to any one of the described processes.

In one embodiment, there is provided a process of manufacturing compounds of Formula (I) as described herein, comprising reacting an amine 1, wherein R², X, Y¹ and Y² are as described herein,

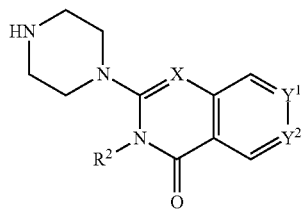

with an acid 2, wherein R¹ is as described herein,

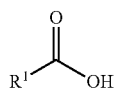

to form said compound of Formula (I).

In one embodiment, said amine 1 is reacted with said acid 2 in the presence of a coupling reagent, preferably in the presence of a coupling reagent selected from the group consisting of CDI, DCC, HATU, HBTU, HOBT, TBTU, T3P and Mukaiyama reagent.

In one embodiment, said amine 1 is reacted with said acid 2 in a solvent, preferably in a solvent selected from the group consisting of DMF, DMA, DCM and dioxane.

In one embodiment, said amine 1 is reacted with said acid 2 in the presence of a base, preferably in the presence of a base selected from the group consisting of NEt₃, DIPEA (Huenig's base) and DMAP.

In a preferred embodiment, said amine 1 is reacted with said acid 2 in a solvent and in the presence of a coupling reagent and a base, preferably in a solvent selected from the group consisting of DMF, DMA, DCM and dioxane, in the presence of a coupling reagent selected from the group consisting of CDI, DCC, HATU, HBTU, HOBT, TBTU, T3P and Mukaiyama reagent and in the presence of a base selected from the group consisting of NEt₃, DIPEA (Huenig's base) and DMAP.

In one embodiment, there is provided a process of manufacturing compounds of Formula (I) as described herein, comprising s reacting an amine 1, wherein R², X, Y¹ and Y² are as described herein,

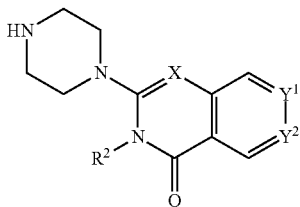

with an acid chloride 2a, wherein $R^1$ is as described herein,

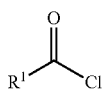

to form said compound of Formula (I).

In one embodiment, the process according to the invention comprises reacting an amine 1 with an acid chloride 2a to form a compound of Formula (I), wherein the acid chloride 2a is obtained by reacting a carboxylic acid 2 with thionyl chloride or oxalyl chloride.

In one embodiment, said amine 1 is reacted with said acid chloride 2a in a solvent, preferably in a solvent selected from the group consisting of DCM and DMF, or a mixture thereof.

In one embodiment, said amine 1 is reacted with said acid chloride 2a in the presence of a base, preferably in the presence of a base selected from the group consisting of $NEt_3$, Huenig's base, pyridine, DMAP and lithium bis(trimethylsilyl)amide.

In a preferred embodiment, said amine 1 is reacted with said acid chloride 2a in a solvent and in the presence of a base, preferably in a solvent selected from the group consisting of DCM and DMF, or a mixture thereof, and in the presence of a base selected from the group consisting of $NEt_3$, Huenig's base, pyridine, DMAP and lithium bis(trimethylsilyl)amide.

In one embodiment, there is provided a process of manufacturing compounds of Formula (I) as described herein, comprising reacting a compound of formula 3, wherein $R^2$, X, $Y^1$ and $Y^2$ are as described herein, and wherein LG is a leaving group, such as chlorine,

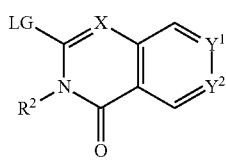

with a piperazine derivative 4, wherein $R^1$ is as described herein

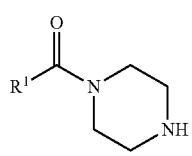

to form said compound of Formula (I).

In one embodiment, said compound of formula 3 is reacted with said piperazine derivative 4 in a solvent, preferably in a solvent selected from the group consisting of NMP and EtOH.

In one embodiment, said compound of formula 3 is reacted with said piperazine derivative 4 in the presence of a base, preferably in the presence of a base selected from the group consisting of DIPEA and $K_2CO_3$.

In a preferred embodiment, said compound of formula 3 is reacted with said piperazine derivative 4 in a solvent and in the presence of a base, preferably in a solvent selected from the group consisting of NMP and EtOH and in the presence of a base selected from the group consisting of DIPEA and $K_2CO_3$.

MAGL Inhibitory Activity

Compounds of the present invention are MAGL inhibitors. Thus, in one aspect, the present invention provides the use of compounds of Formula (I) or a pharmaceutically acceptable salt thereof as described herein for inhibiting MAGL in a mammal.

In a further aspect, the present invention provides compounds of Formula (I) or a pharmaceutically acceptable salt thereof as described herein for use in a method of inhibiting MAGL in a mammal.

In a further aspect, the present invention provides the use of compounds of Formula (I) or a pharmaceutically acceptable salt thereof as described herein for the preparation of a medicament for inhibiting MAGL in a mammal.

In a further aspect, the present invention provides a method for inhibiting MAGL in a mammal, which method comprises administering an effective amount of a compound or a pharmaceutically acceptable salt thereof of Formula (I) as described herein to the mammal.

Compounds were profiled for MAGL inhibitory activity by measuring the enzymatic activity of MAGL by following the hydrolysis of 4-nitorphenylacetate resulting in 4-nitrophenol, which absorbs at 405-412 nm (G. G. Muccioli, G. Labar, D. M. Lambert, Chem. Bio. Chem. 2008, 9, 2704-2710).

The assay was carried out in 384 well assay plates (black with clear bottom, non-binding surface treated, Corning Ref. 3655) in a total volume of 40 µL. Compound dilutions were made in 100% DMSO (VWR Chemicals 23500.297) in a polypropylene plate in 3-fold dilution steps to give a final concentration range in the assay from 25 µM to 1.7 nM. 1 µL compound dilutions (100% DMSO) were added to 19 µL MAGL (recombinant wild-type) in assay buffer (50 mM TRIS (GIBCO, 15567-027), 1 mM EDTA (Fluka, 03690-100 ml)). The plate was shaked for 1 min at 2000 rpm (Variomag Teleshake) and then incubated for 15 min at RT. To start the reaction, 20 µL 4-Nitrophenlyacetate (Sigma N-8130) in assay buffer with 6% EtOH was added. The final concentrations in the assay were 1 nM MAGL and 300 µM 4-Nitrophenylacetate. After shaking (1 min, 2000 rpm) and 5 min incubation at RT, the absorbance at 405 nm was measured for a fist time (Molecular Devices, SpectraMax Paradigm). A second measurement was then done after incubation for 80 min at RT. From the two measurements, the slope was calculated by subtracting the first from the second measurement.

| Example | $IC_{50}$ MAGL [µM] |
|---|---|
| 1 | 0.020 |
| 2 | 0.050 |

| Example | IC$_{50}$ MAGL [μM] |
|---|---|
| 3 | 0.600 |
| 4 | 1.1 |
| 5 | 6.2 |
| 6 | 6.0 |
| 7 | 0.144 |
| 8 | 0.073 |
| 9 | 9.5 |
| 10 | 0.049 |
| 11 | 0.244 |
| 12 | 0.037 |
| 13 | 0.51 |
| 14 | 0.086 |
| 15 | 0.510 |
| 16 | 0.760 |
| 17 | 0.036 |
| 18 | 5.2 |
| 19 | 7.1 |
| 20 | 0.650 |
| 21 | 0.120 |
| 22 | 6.4 |
| 23 | 0.072 |
| 24 | 0.340 |
| 25 | 0.070 |
| 26 | 1.3 |
| 27 | 6.7 |
| 28 | 1.7 |
| 29 | 0.240 |
| 30 | 0.910 |
| 31 | 4.3 |
| 32 | 0.120 |
| 33 | 4.2 |
| 34 | 9.9 |
| 35 | 0.091 |
| 36 | 9.5 |
| 37 | 6.9 |
| 38 | 2.1 |
| 39 | 9.9 |
| 40 | 5.1 |
| 41 | 3.5 |
| 42 | 6.7 |
| 43 | 8.7 |
| 44 | 5.2 |
| 45 | 1.3 |
| 46 | 0.067 |
| 47 | 0.520 |
| 48 | 0.051 |
| 49 | 1.3 |
| 50 | 4.7 |
| 51 | 0.220 |
| 52 | 0.640 |
| 53 | 0.560 |
| 54 | 0.044 |
| 55 | 0.240 |
| 56 | 0.450 |
| 57 | 1.1 |
| 58 | 0.210 |
| 59 | 0.420 |
| 60 | 0.066 |
| 61 | 0.019 |
| 62 | 0.024 |
| 63 | 0.110 |
| 64 | 0.320 |
| 65 | 0.270 |
| 66 | 0.030 |
| 67 | 0.0044 |
| 68 | 9.9 |
| 69 | 0.042 |
| 70 | 4.5 |
| 71 | 0.400 |
| 72 | 0.032 |
| 73 | 0.020 |
| 74 | 3.9 |
| 75 | 0.019 |
| 76 | 0.033 |
| 77 | 0.170 |
| 78 | 0.140 |
| 79 | 0.055 |
| 80 | 1.6 |
| 81 | 1.3 |
| 82 | 0.130 |
| 83 | 0.020 |
| 84 | 1.2 |
| 85 | 1.6 |
| 86 | 0.590 |
| 87 | 0.250 |
| 88 | 7.6 |
| 89 | 3.6 |
| 90 | 1.4 |
| 91 | 1.8 |
| 92 | 0.140 |
| 93 | 1.1 |
| 94 | 1.0 |
| 95 | 1.8 |
| 96 | 0.022 |
| 97 | 0.390 |
| 98 | 0.960 |
| 99 | 0.390 |
| 100 | 2.8 |
| 101 | 0.250 |
| 102 | 0.320 |
| 103 | 0.230 |
| 104 | 0.041 |
| 105 | 1.6 |
| 106 | 0.041 |
| 107 | 0.570 |
| 108 | 0.780 |
| 109 | 10.0 |
| 110 | 0.085 |
| 111 | 4.5 |
| 112 | 0.027 |
| 113 | 5.5 |
| 114 | 1.7 |
| 115 | 1.5 |
| 116 | 0.005 |
| 117 | 0.042 |
| 118 | 0.081 |
| 119 | 0.046 |
| 120 | 0.056 |
| 121 | 1.5 |
| 122 | 1.4 |
| 123 | 0.530 |
| 124 | 0.150 |
| 125 | 0.120 |
| 126 | 4.7 |
| 127 | 0.050 |
| 128 | 0.020 |
| 129 | 1.6 |
| 130 | 1.9 |
| 131 | 0.036 |
| 132 | 0.160 |
| 133 | 0.091 |
| 134 | 0.053 |
| 135 | 0.049 |
| 136 | 0.260 |
| 137 | 5.3 |
| 138 | 3.5 |
| 139 | 0.160 |
| 140 | 0.140 |
| 141 | 0.180 |
| 142 | 4.5 |
| 143 | 1.3 |
| 144 | 0.310 |
| 145 | 0.270 |
| 146 | 2.4 |
| 147 | 0.190 |
| 148 | 3.6 |
| 149 | 0.780 |
| 150 | 0.042 |
| 151 | 0.190 |
| 152 | 0.140 |
| 153 | 0.099 |

-continued

| Example | IC$_{50}$ MAGL [μM] |
|---|---|
| 154 | 1.8 |
| 155 | 6.3 |
| 156 | 0.032 |
| 157 | 0.010 |
| 158 | 0.039 |
| 159 | 0.087 |
| 160 | 0.049 |
| 161 | 0.880 |
| 162 | 0.770 |
| 163 | 1.9 |
| 164 | 0.260 |
| 165 | 1.3 |
| 166 | 0.300 |
| 167 | 0.250 |
| 168 | 0.970 |
| 169 | 0.052 |
| 170 | 0.007 |
| 171 | 0.572 |
| 172 | 0.440 |
| 173 | 0.190 |
| 174 | 0.045 |
| 175 | 0.048 |
| 176 | 0.223 |
| 177 | 1.5 |
| 178 | 0.292 |
| 179 | 0.598 |
| 180 | 0.088 |
| 181 | 0.259 |
| 182 | 0.084 |
| 183 | 1.4 |
| 184 | 0.005 |
| 185 | 0.052 |
| 186 | 2.6 |
| 187 | 0.206 |
| 188 | 2.4 |
| 189 | 1.2 |
| 190 | 0.063 |
| 191 | 0.023 |
| 192 | 0.014 |
| 193 | 0.025 |
| 194 | 8.5 |
| 195 | 0.034 |
| 196 | 0.007 |
| 197 | 0.012 |
| 198 | 0.207 |
| 199 | 0.112 |
| 200 | 0.118 |
| 201 | 0.121 |
| 202 | 0.022 |
| 203 | 0.265 |
| 204 | 0.016 |
| 205 | 1.0 |
| 206 | 0.297 |
| 207 | 0.090 |
| 208 | 0.053 |
| 209 | 0.172 |
| 210 | 0.006 |
| 211 | 0.011 |
| 212 | 1.5 |
| 213 | 0.003 |
| 214 | 7.2 |
| 215 | 1.6 |
| 216 | 5.7 |

In one aspect, the present invention provides compounds of Formula (I) and their pharmaceutically acceptable salts as described herein, wherein said compounds of Formula (I) and their pharmaceutically acceptable salts have IC$_{50}$'s for MAGL inhibition below 25 μM, preferably below 10 μM, more preferably below 5 μM as measured in the MAGL assay described herein.

In one embodiment, compounds of Formula (I) and their pharmaceutically acceptable salts as described herein have IC$_{50}$ (MAGL inhibition) values between 0.000001 μM and 25 μM, particular compounds have IC$_{50}$ values between 0.000005 μM and 10 μM, further particular compounds have IC$_{50}$ values between 0.00005 μM and 5 μM, as measured in the MAGL assay described herein.

In one embodiment, the present invention provides compounds of Formula (I) and their pharmaceutically acceptable salts as described herein, wherein said compounds of Formula (I) and their pharmaceutically acceptable salts have an IC$_{50}$ for MAGL below 25 μM, preferably below 10 μM, more preferably below 5 μM as measured in an assay comprising the steps of:
  a) providing a solution of a compound Formula (I), or a pharmaceutically acceptable salt thereof, in DMSO;
  b) providing a solution of MAGL (recombinant wild-type) in assay buffer (50 mM tris(hydroxymethyl)aminomethane; 1 mM ethylenediaminetetraacetic acid);
  c) adding 1 μL of compound solution from step a) to 19 μL of MAGL solution from step b);
  d) shaking the mixture for 1 min at 2000 rpm;
  e) incubating for 15 min at RT;
  f) adding 20 μL of a solution of 4-nitrophenlyacetate in assay buffer (50 mM tris(hydroxymethyl)aminomethane; 1 mM ethylenediaminetetraacetic acid, 6% EtOH);
  g) shaking the mixture for 1 min at 2000 rpm;
  h) incubating for 5 min at RT;
  i) measuring the absorbance of the mixture at 405 nm a first time;
  j) incubating a further 80 min at RT;
  k) measuring the absorbance of the mixture at 405 nm a second time;
  l) subtracting the absorbance measured under i) from the absorbance measured under k) and calculating the slope of absorbance;
wherein:
  i) the concentration of the compound of Formula (I), or the pharmaceutically acceptable salt thereof in the assay after step f) is in the range of 25 μM to 1.7 nM;
  ii) the concentration of MAGL in the assay after step f) is 1 nM;
  iii) the concentration of 4-nitrophenylacetate in the assay after step f) is 300 μM; and
  iv) steps a) to l) are repeated for at least 3 times, each time with a different concentration of the compound of Formula (I), or the pharmaceutically acceptable salt thereof.

Using the Compounds of the Invention

In one aspect, the present invention provides compounds of Formula (I) or a pharmaceutically acceptable salt thereof as described herein for use as therapeutically active substance.

In a further aspect, the present invention provides the use of compounds or a pharmaceutically acceptable salt thereof of Formula (I) as described herein for the treatment or prophylaxis of neuroinflammation, neurodegenerative diseases, pain, cancer or mental disorders, or any combination thereof, in a mammal.

In one embodiment, the present invention provides the use of compounds or a pharmaceutically acceptable salt thereof of Formula (I) as described herein for the treatment or prophylaxis of neuroinflammation or neurodegenerative diseases, or any combination thereof, in a mammal.

In one embodiment, the present invention provides the use of compounds or a pharmaceutically acceptable salt thereof of Formula (I) as described herein for the treatment or prophylaxis of neurodegenerative diseases in a mammal.

In one embodiment, the present invention provides the use of compounds or a pharmaceutically acceptable salt thereof of Formula (I) as described herein for the treatment or prophylaxis of cancer in a mammal.

In one aspect, the present invention provides the use of compounds or a pharmaceutically acceptable salt thereof of Formula (I) as described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer or pain, or any combination thereof, in a mammal.

In a preferred embodiment, the present invention provides the use of compounds or a pharmaceutically acceptable salt thereof of Formula (I) as described herein for the treatment or prophylaxis of multiple sclerosis, Alzheimer's disease or Parkinson's disease, or any combination thereof, in a mammal.

In a particularly preferred embodiment, the present invention provides the use of compounds or a pharmaceutically acceptable salt thereof of Formula (I) as described herein for the treatment or prophylaxis of multiple sclerosis in a mammal.

In one aspect, the present invention provides compounds or a pharmaceutically acceptable salt thereof of Formula (I) as described herein for use in the treatment or prophylaxis of neuroinflammation, neurodegenerative diseases, pain, cancer or mental disorders, or any combination thereof, in a mammal.

In one embodiment, the present invention provides compounds or a pharmaceutically acceptable salt thereof of Formula (I) as described herein for use in the treatment or prophylaxis of neuroinflammation or neurodegenerative diseases, or any combination thereof, in a mammal.

In one embodiment, the present invention provides compounds or a pharmaceutically acceptable salt thereof of Formula (I) as described herein for use in the treatment or prophylaxis of cancer in a mammal.

In one embodiment, the present invention provides compounds or a pharmaceutically acceptable salt thereof of Formula (I) as described herein for use in the treatment or prophylaxis of neurodegenerative diseases in a mammal.

In one aspect, the present invention provides compounds or a pharmaceutically acceptable salt thereof of Formula (I) as described herein for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer or pain, or any combination thereof, in a mammal.

In a preferred embodiment, the present invention provides compounds or a pharmaceutically acceptable salt thereof of Formula (I) as described herein for use in the treatment or prophylaxis of multiple sclerosis, Alzheimer's disease or Parkinson's disease, or any combination thereof, in a mammal.

In a particularly preferred embodiment, the present invention provides compounds or a pharmaceutically acceptable salt thereof of Formula (I) as described herein for use in the treatment or prophylaxis of multiple sclerosis in a mammal.

In one aspect, the present invention provides the use of compounds or a pharmaceutically acceptable salt thereof of Formula (I) as described herein for the preparation of a medicament for the treatment or prophylaxis of neuroinflammation, neurodegenerative diseases, pain, cancer or mental disorders, or any combination thereof, in a mammal.

In one embodiment, the present invention provides the use of compounds or a pharmaceutically acceptable salt thereof of Formula (I) as described herein for the preparation of a medicament for the treatment or prophylaxis of neuroinflammation or neurodegenerative diseases, or any combination thereof, in a mammal.

In one embodiment, the present invention provides the use of compounds or a pharmaceutically acceptable salt thereof of Formula (I) as described herein for the preparation of a medicament for the treatment or prophylaxis of neurodegenerative diseases in a mammal.

In one embodiment, the present invention provides the use of compounds or a pharmaceutically acceptable salt thereof of Formula (I) as described herein for the preparation of a medicament for the treatment or prophylaxis of cancer in a mammal.

In a further aspect, the present invention provides the use of compounds or a pharmaceutically acceptable salt thereof of Formula (I) as described herein for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer or pain, or any combination thereof, in a mammal.

In a preferred embodiment, the present invention provides the use of compounds or a pharmaceutically acceptable salt thereof of Formula (I) as described herein for the preparation of a medicament for the treatment or prophylaxis of multiple sclerosis, Alzheimer's disease or Parkinson's disease, or any combination thereof, in a mammal.

In a particularly preferred embodiment, the present invention provides the use of compounds or a pharmaceutically acceptable salt thereof of Formula (I) as described herein for the preparation of a medicament for the treatment or prophylaxis of multiple sclerosis in a mammal.

In one aspect, the present invention provides a method for the treatment or prophylaxis of neuroinflammation, neurodegenerative diseases, pain, cancer or mental disorders, or any combination thereof, in a mammal, which method comprises administering an effective amount of a compound or a pharmaceutically acceptable salt thereof of Formula (I) as described herein to the mammal.

In one embodiment, the present invention provides a method for the treatment or prophylaxis of neuroinflammation or neurodegenerative diseases, or any combination thereof, in a mammal, which method comprises administering an effective amount of a compound or a pharmaceutically acceptable salt thereof of Formula (I) as described herein to the mammal.

In one embodiment, the present invention provides a method for the treatment or prophylaxis of neurodegenerative diseases in a mammal, which method comprises administering an effective amount of a compound or a pharmaceutically acceptable salt thereof of Formula (I) as described herein to the mammal.

In one aspect, the present invention provides a method for the treatment or prophylaxis of multiple sclerosis, Alzheimer's disease, Parkinson's disease, amyotrophic lateral sclerosis, traumatic brain injury, neurotoxicity, stroke, amyloid lateral sclerosis, epilepsy, anxiety, migraine, depression or pain, or any combination thereof, in a mammal, which method comprises administering an effective amount of a compound or a pharmaceutically acceptable salt thereof of Formula (I) as described herein to the mammal.

In a preferred embodiment, the present invention provides a method for the treatment or prophylaxis of multiple sclerosis, Alzheimer's disease or Parkinson's disease, or any combination thereof, in a mammal, which method comprises administering an effective amount of a compound or a pharmaceutically acceptable salt thereof of Formula (I) as described herein to the mammal.

In a particularly preferred embodiment, the present invention provides a method for the treatment or prophylaxis of multiple sclerosis in a mammal, which method comprises administering an effective amount of a compound or a pharmaceutically acceptable salt thereof of Formula (I) as described herein to the mammal.

Pharmaceutical Compositions and Administration

In one aspect, the present invention provides a pharmaceutical composition comprising a compound or a pharmaceutically acceptable salt thereof of Formula (I) as described herein and a pharmaceutically acceptable excipient.

The compounds of Formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of Formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography or crystallization.

All reaction examples and intermediates were prepared under an argon atmosphere if not specified otherwise.

Method A1

Example 3

2-[4-(4-Phenoxybenzoyl)piperazin-1-yl]-3H-quinazolin-4-one

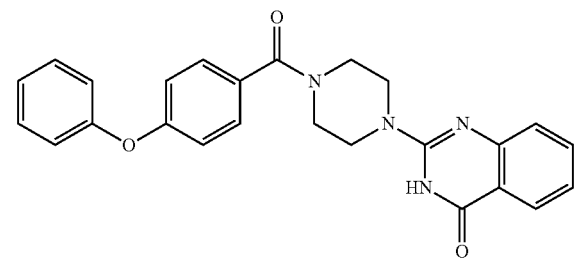 [SMILES: O=C(c1ccc(Oc2ccccc2)cc1)N1CCN(c2nc3ccccc3c(=O)[nH]2)CC1]

4-Phenoxybenzoic acid (36.9 mg, 172 µmol, CAS RN 2215-77-2) was dissolved in DCM (1.2 mL) at RT, whereupon HATU (131 mg, 344 µmol, CAS RN 148893-10-1) and TEA (87.1 mg, 120 µL, 861 µmol) were added. The resulting mixture was allowed to stir for 30 min before the addition of 2-piperazino-4(3H)-quinazolinone monoacetate (50 mg, 172 µmol, CAS RN 22587-29-7). The resulting solution was then stirred at RT for 18 h. The reaction mixture was concentrated in vacuo and the yellow residue was purified on a preparative HPLC (Gemini NX column) using a gradient of ACN:H$_2$O (containing 0.1% HCOOH) (20:80 to 98:2) to furnish the product as a white solid (25 mg, 33%). $^1$H NMR (600 MHz, DMSO-d$_6$) δ ppm 11.48 (s, 1H), 7.92 (dd, J=7.9, 1.4 Hz, 1H), 7.58-7.63 (m, 1H), 7.46-7.50 (m, 1H), 7.42-7.45 (m, 2H), 7.29 (d, J=8.2 Hz, 1H), 7.22 (s, 1H), 7.18 (br d, J=0.9 Hz, 1H), 7.11 (dd, J=8.6, 0.9 Hz, 2H), 7.01-7.07 (m, 2H), 3.68 (br s, 8H). MS (ESI): m/z=427.2 [M+H]$^+$.

Method A2

Example 123

2-[4-[4-(3-Cyclopropyl-1,2,4-oxadiazol-5-yl)benzoyl]piperazin-1-yl]-3H-quinazolin-4-one

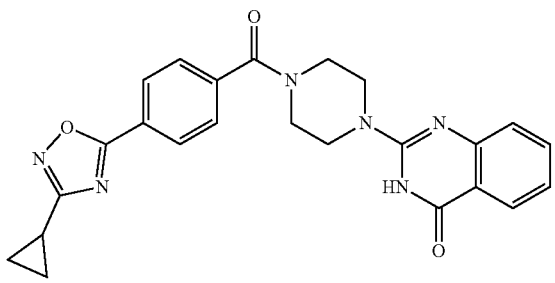 [SMILES: O=C(c1ccc(-c2nc(C3CC3)no2)cc1)N1CCN(c2nc3ccccc3c(=O)[nH]2)CC1]

4-(3-Cyclopropyl-1,2,4-oxadiazol-5-yl)benzoic acid (39.6 mg, 172 µmol, CAS RN 1165931-66-7) was dissolved in DMF (1 mL) at RT, whereupon HATU (72 mg, 189 µmol, CAS RN 148893-10-1) and TEA (87.1 mg, 120 µL, 861 µmol) were added. The reaction mixture was allowed to stir for 10 min before 2-piperazino-4(3H)-quinazolinone monoacetate (50 mg, 172 μmol, CAS RN 22587-29-7) was added. The reaction solution was stirred at RT for 72 h. The reaction solution was purified on a preparative HPLC (Gemini NX column) using a gradient of ACN:H$_2$O (containing 0.1% HCOOH) (20:80 to 98:2) to yield the product as a white solid (17 mg, 22%). MS (ESI): m/z=443.3 [M+H]$^+$.

Method A3

Example 71

2-[4-(2-Chloro-4-pyrrolidin-1-ylbenzoyl)piperazin-1-yl]-3H-quinazolin-4-one

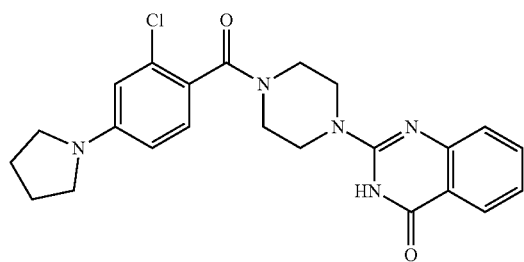 [SMILES: O=C(c1ccc(N2CCCC2)cc1Cl)N1CCN(c2nc3ccccc3c(=O)[nH]2)CC1]

To a solution of 2-chloro-4-pyrrolidin-1-yl-benzoic acid (31.1 mg, 138 μmol, CAS RN 192513-60-3), HATU (57.6 mg, 152 μmol, CAS RN 148893-10-1) and 2-piperazino-4(3H)-quinazolinone monoacetate (40 mg, 138 μmol, CAS RN 22587-29-7) in DMF (0.5 mL) was added DIPEA (71.2 mg, 96.3 μL, 551 μmol). The reaction mixture was stirred at RT for 66 h. To the light brown solution was added dropwise H$_2$O (1 mL). A precipitate formed which was subsequently collected by filtration. The filter cake was washed with plenty of H$_2$O and dried under high vacuum to afford an off-white solid (11 mg; 18%). MS (ESI): m/z=436.2 [M–H]$^-$.

Method B

Example 97

2-[4-[3-[2-(Trifluoromethoxy)phenyl]benzoyl]piperazin-1-yl]-3H-quinazolin-4-one

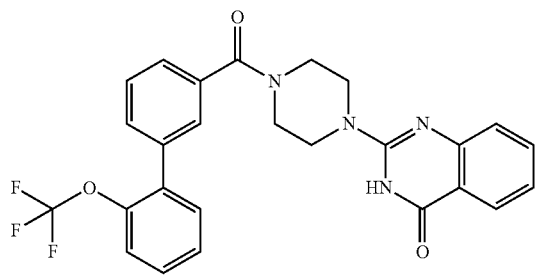 [SMILES: O=C(c1cccc(-c2ccccc2OC(F)(F)F)c1)N1CCN(c2nc3ccccc3c(=O)[nH]2)CC1]

To a stirred solution of 2-piperazino-4(3H)-quinazolinone hydrochloride (0.06 g, 0.22 mmol, CAS RN 591244-85-8) in DMF (1 mL) were added DIPEA (0.2 mL, 1.1 mmol), T$_3$P (0.15 g, 0.48 mmol, 50% solution in EtOAc) and 3-[2-(trifluoromethoxy)phenyl]benzoic acid (0.09 g, 0.33 mmol, CAS RN 765276-04-8) and the reaction mixture was stirred for 16 h. The reaction mixture was purified through preparative HPLC to afford an white solid (35 mg, 31%) MS (ESI): m/z=495.2 [M+H]$^+$.

Method C

Example 63

2-[4-(4-Phenylmethoxybenzoyl)piperazin-1-yl]-3H-quinazolin-4-one

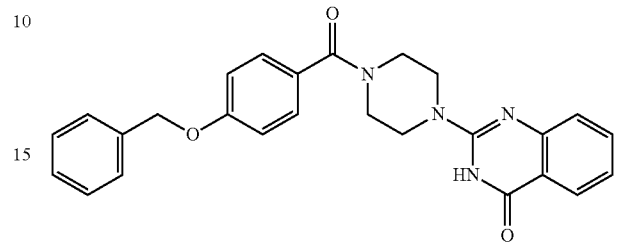

To a stirred solution of 2-piperazino-4(3H)-quinazolinone hydrochloride (300 mg, 1.12 mmol, CAS RN 591244-85-8) in DMF (5 mL) was added DIPEA (0.6 mL, 3.4 mmol), EDC.HCl (431.2 mg, 2.3 mmol, CAS RN 25952-53-8), HOBT (304 mg, 2.25 mmol, CAS RN 2592-95-2) at 25° C. After 30 min stirring, 4-benzyloxybenzoic acid (256 mg, 1.12 mmol, CAS RN 1486-51-7) was added and the reaction mixture was stirred at RT for 16 h. H$_2$O (20 mL) was added and the precipitate was collected by filtration and washed with H$_2$O (2×10 mL) followed by EtOAc (10 mL). The filter cake was dried under high vacuum to afford a white solid (362 mg, 72.5%). $^1$H NMR (DMSO-d$_6$, 400 MHz at 100° C.): δ ppm 3.61-3.70 (m, 8H), 5.17 (s, 2H), 6.94-7.17 (m, 3H), 7.29-7.47 (m, 8H), 7.57-7.60 (m, 1H), 7.92-7.94 (m, 1H), 11.17 (br s, 1H). MS (ESI): m/z=440.9 [M+H]$^+$.

Method D

Example 21

N-benzyl-N-[2-[4-[4-(4-oxo-3H-quinazolin-2-yl)piperazine-1-carbonyl]phenyl]ethyl]acetamide

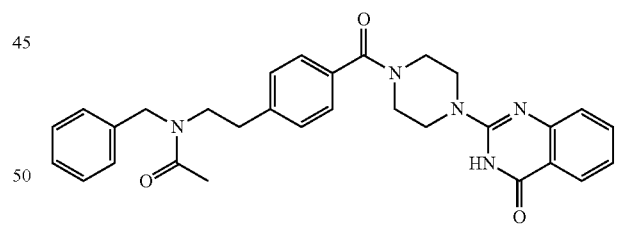

To a stirred solution of N-benzyl-N-[2-[4-(piperazine-1-carbonyl)phenyl]ethyl]acetamide (300 mg, 0.820 mmol, BB8) in EtOH (6 mL) was added DIPEA (0.71 mL, 4.1 mmol) and 2-chloro-3H-quinazolin-4-one (222 mg, 1.23 mmol, CAS RN 607-69-2). The reaction mixture was stirred at 100° C. in a sealed tube for 16 h. The reaction mixture was concentrated in vacuo. The residue was diluted with DCM and washed three times with H$_2$O. The organic layers were combined, dried over Na$_2$SO and filtered. The filtrate was concentrated under reduced pressure and the crude product purified by column chromatography to afford an off-white solid (160 mg, 36.5%). $^1$H NMR (DMSO-d$_6$, 400 MHz): δ ppm 2.01 (s, 3H), 2.79-2.86 (m, 2H), 3.42-3.70 (m, 10H), 4.54 (s, 2H), 7.15 (t, J=7.1 Hz, 1H), 7.24-7.37 (m, 10H), 7.58 (t, J=7.6 Hz, 1H), 7.93 (d, J=7.8 Hz, 1H), 11.13 (br s, 1H). MS (ESI): m/z=510.2 [M+H]⁺.
Method E Example 147

2-[4-[4-[5-(2,2,2-Trifluoroethyl)-1,2,4-oxadiazol-3-yl]benzoyl]piperazin-1-yl]-3H-quinazolin-4-one

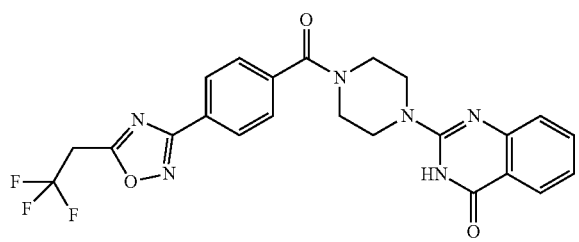 [SMILES: O=C(c1ccc(-c2noc(CC(F)(F)F)n2)cc1)N1CCN(c2nc3ccccc3c(=O)[nH]2)CC1]

To a solution of 3,3,3-trifluoropropanoic acid (783.2 mg, 6.12 mmol, CAS RN 2516-99-6) in DCM (5 mL) was added a catalytic amount of DMF (0.030 mmol) at 0° C. Oxalyl chloride (0.56 mL, 6.73 mmol, CAS RN 79-37-8) was added dropwise (gas formation) and the reaction mixture was allowed to slowly warm up to 25° C. within 1 h. After that, the mixture was concentrated in vacuum. The residue was added to a stirred mixture of DIPEA (2.11 mL, 12.23 mmol) and N'-hydroxy-4-[4-(4-oxo-3H-quinazolin-2-yl)piperazine-1-carbonyl]benzamidine (400.0 mg, 1.02 mmol, BB45) in DME (10 mL). After the addition, the reaction mixture was heated to 80° C. for 15 h. The reaction was quenched with H₂O (20 mL) and concentrated under reduced pressure to remove DME. The remaining slurry was extracted with EtOAc (3×20 mL) and the combined organic layers were washed with brine (10 mL) and dried over Na₂SO₄ After the filtration the filtrate was concentrated in vacuum. The residue was purified with prep-TLC (PE:EtOAc=1:2) to obtain a light yellow powder (14.5 mg, 2.9%). MS (ESI): m/z=485.1 [M+H]⁺.
Method F Example 151

2-[4-[3-Methyl-4-[3-(trifluoromethoxy)phenyl]benzoyl]piperazin-1-yl]-3H-quinazolin-4-one

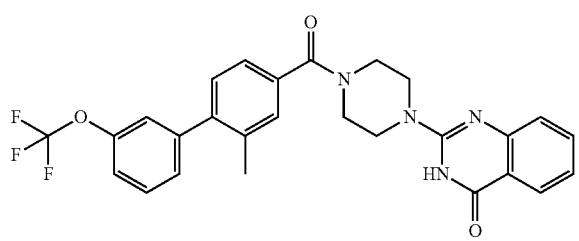 [SMILES: Cc1cc(C(=O)N2CCN(c3nc4ccccc4c(=O)[nH]3)CC2)ccc1-c1cccc(OC(F)(F)F)c1]

2-[4-(4-Bromo-3-methylbenzoyl)piperazin-1-yl]-3H-quinazolin-4-one (30 mg, 70.2 μmol, Example 142), (3-(trifluoromethoxy)phenyl)boronic acid (14.5 mg, 70.2 μmol, CAS RN 179113-90-7), Cs₂CO₃ (45.8 mg, 140 μmol,) and [1,1'-bis(diphenylphosphino)ferrocene]dichloropalladium (II) (15 mg, 20.5 μmol) were suspended in a mixture of dioxane (2 mL)/H₂O (0.5 mL). The reaction mixture was stirred at 80° C. for 15 h under an argon atmosphere and then filtered through a syringe filter. The filtrate was concentrated in vacuo. The crude product was purified by prep. HPLC to give an off-white solid (13 mg, 36.4%). MS (ESI): m/z=509.4 [M+H]⁺.
Method G Example 175

2-[4-[3-Chloro-4-[(4-chloropyridin-2-yl)methoxy]benzoyl]piperazin-1-yl]-3H-quinazolin-4-one

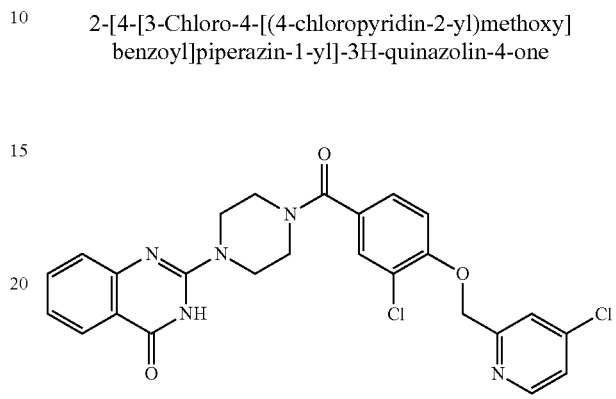

To a solution of 2-[4-(3-chloro-4-hydroxy-benzoyl)piperazin-1-yl]-3H-quinazolin-4-one (208.3 mg, 0.540 mmol, BB62) in DMF (5 mL) was added K₂CO₃ (187.1 mg, 1.35 mmol) and (4-chloro-2-pyridyl)methyl methanesulfonate (100.0 mg, 0.450 mmol, BB63) under inert gas atmosphere. The reaction was stirred at 25° C. for 12 h. The reaction was quenched with water (1 mL) and extracted three times with EtOAc (10 mL each). The combined organic layers were washed twice with H₂O (10 mL each) and brine (5 ml), dried over Na₂SO₄ and concentrated. The residue was purified by prep-HPLC to get the desired compound as a colorless solid (10.4 mg, 4.3%). MS (ESI): m/z=510 [M+H]⁺.
Method H Example 189

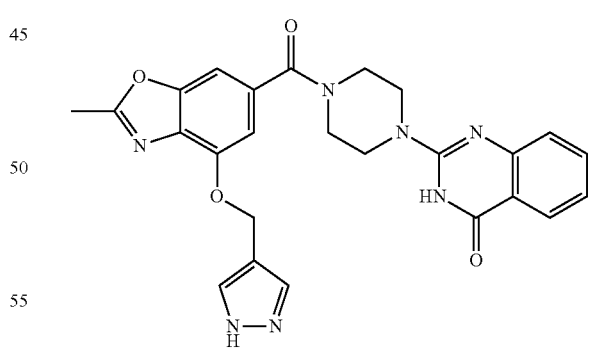

To a solution of 2-[4-[2-methyl-4-[(1-tritylpyrazol-4-yl)methoxy]-1,3-benzoxazole-6-carbonyl]piperazin-1-yl]-3H-quinazolin-4-one (300.0 mg, 0.410 mmol, BB66) in DCM (10 mL) was added TFA (0.81 mL, 10.46 mmol) and the mixture was stirred at 20° C. for 1 h. The mixture was concentrated under vacuum and the residue purified by reversed phase column to give the desired compound as a colorless solid (13.3 mg, 5.7%). MS (ESI): m/z=486.1 [M+H]⁺.

Method I

Example 190

2-[4-[4-[5-(1-Methylcyclopropyl)-1,2,4-oxadiazol-3-yl]benzoyl]piperazin-1-yl]-3H-quinazolin-4-one

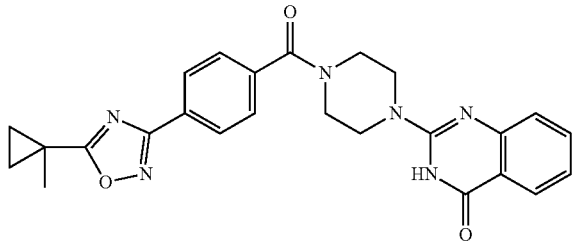 [SMILES: CC1(c2nc(-c3ccc(C(=O)N4CCN(c5nc6ccccc6c(=O)[nH]5)CC4)cc3)no2)CC1]

To a solution of 1-methylcyclopropane-1-carboxylic acid (10.4 mg, 104 µmol, CAS RN 6914-76-7) in dry DMF (943 µL) was added 1,1'-carbonyldiimidazole (16.8 mg, 104 µmol) and the reaction mixture was stirred for 15 min. Then, N'-hydroxy-4-[4-(4-oxo-3H-quinazolin-2-yl)piperazine-1-carbonyl]benzamidine (50 mg, 94.3 µmol, BB67) was added in one portion. The reaction mixture was stirred at 100° C. for 2 h. The reaction was allowed to reach RT. The crude residue was diluted with EtOAc and washed twice with $H_2O$. The organic phase was dried over sodium sulfate and evaporated. The crude product was purified by reverse-phase HPLC to give the desired compound as a colorless solid (15.1 mg, 35.1%). MS (ESI): m/z=457.4 $[M+H]^+$.

Method J

Example 195

2-[4-[3-(3-Chlorophenyl)sulfonyl-3,9-diazaspiro[5.5]undecane-9-carbonyl]piperazin-1-yl]-3H-quinazolin-4-one

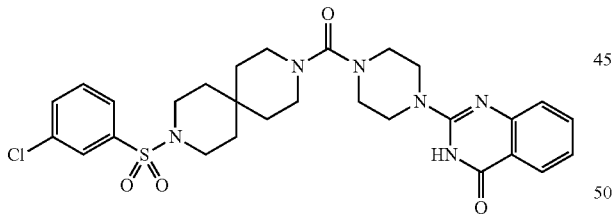

To an ice-cold suspension of bis(trichloromethyl) carbonate (34.1 mg, 115 µmol) and sodium bicarbonate (55.2 mg, 657 µmol) in DCM (2 mL) was added in one portion 3-((3-chlorophenyl)sulfonyl)-3,9-diazaspiro[5.5]undecane hydrochloride (60 mg, 164 µmol, BB71) and the mixture was stirred at RT overnight. The suspension was filtered over a syringe filter and the filtrate was evaporated. The residue was dissolved in DCM (2 mL) and added dropwise to an ice-cold solution of 2-(piperazin-1-yl)quinazolin-4(3H)-one dihydrochloride (49.8 mg, 164 µmol, BB53) and DIPEA (84.9 mg, 115 µL, 657 µmol) in DCM (2 mL). The suspension was stirred at RT overnight. The reaction mixture was poured on water and DCM and the layers were separated. The aqueous layer was extracted three times with DCM. The organic layers were washed twice with $H_2O$, dried over $MgSO_4$, filtered, treated with silica gel and evaporated. The compound was purified by silica gel chromatography on a 4 g column using an MPLC system eluting with a gradient of DCM:MeOH (100:0 to 90:10) to get the desired compound as a colorless solid (0.052 g; 54.1%). MS (ESI): m/z=585.2 $[M+H]^+$.

Method K

Example 214

2-[4-[2-(4-Chlorophenyl)sulfonyl-2,7-diazaspiro[4.4]nonane-7-carbonyl]piperazin-1-yl]-3H-quinazolin-4-one

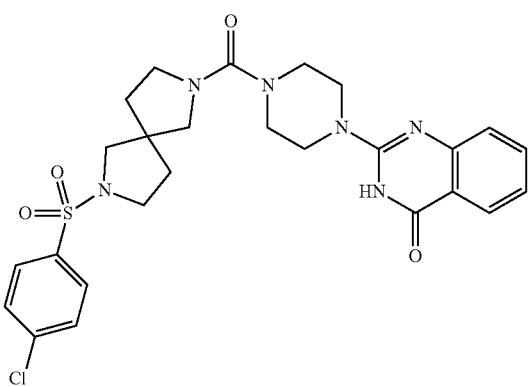 [SMILES: O=C(N1CCN(c2nc3ccccc3c(=O)[nH]2)CC1)N1CCC2(CCN(S(=O)(=O)c3ccc(Cl)cc3)C2)C1]

To a suspension of sodium hydride (60% in mineral oil, 44.7 mg, 1.12 mmol) in DMF (3 ml) at 0° C. was added dropwise a solution of 2-(4-(2,7-diazaspiro[4.4]nonane-2-carbonyl)piperazin-1-yl)quinazolin-4(3H)-one (150 mg, 149 µmol, BB84) in DMF (1 mL). After stirring at RT for 30 min., 4-chlorobenzenesulfonyl chloride (31.5 mg, 149 µmol, CAS RN 98-60-2) was added. The reaction mixture was stirred at RT for 3 days. Then the reaction mixture was poured on water and EtOAc and the layers were separated. The aqueous layer was extracted six times with EtOAc. The organic layers were dried over $MgSO_4$, filtered, treated with silica gel and evaporated. The compound was purified by silica gel chromatography on a 4 g column using an MPLC system eluting with a gradient of DCM:MeOH (100:0 to 90:10) to provide the desired compound as a colorless solid (46 mg, 55.4%). MS (ESI): m/z=557.2 $[M+H]^+$.

Method L

Example 216

2-[4-[7-[(3-Chlorophenyl)methyl]-2,7-diazaspiro[4.4]nonane-2-carbonyl]piperazin-1-yl]-3H-quinazolin-4-one

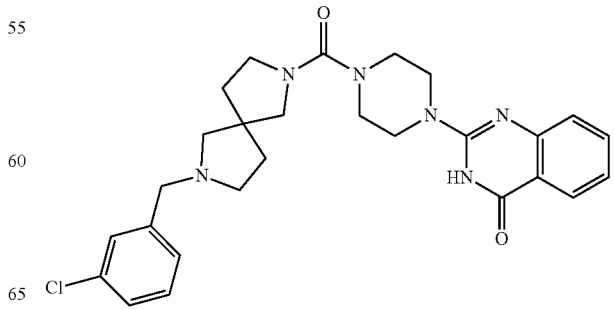

To a solution of 2-(4-(2,7-diazaspiro[4.4]nonane-2-carbonyl)piperazin-1-yl)quinazolin-4(3H)-one (24 mg, 62.8 µmol, BB84) and 4-chlorobenzaldehyde (17.6 mg, 126 µmol, CAS RN 104-88-1) in DCM (0.5 mL) was added sodium triacetoxyborohydride (66.5 mg, 314 µmol) and the reaction mixture was stirred at RT for 3 h. To the reaction mixture was added saturated aqueous NaHCO$_3$ solution and the layers were separated. The aqueous layer was washed twice with DCM. The organic layers were dried over MgSO$_4$, filtered, treated with silica gel and evaporated. The compound was purified by silica gel chromatography on a 4 g column using an MPLC system eluting with a gradient of DCM:MeOH (100:0 to 80:20). The product was purified on a preparative HPLC (Gemini NX column) using a gradient of ACN:H$_2$n (containing 0.1 TEA) (20:80 to 98:2) to get the desired compound as a colorless solid (15 mg, 47.1%). MS (ESI): m/z=505.6 [M−H]$^-$.

The following examples were synthesized from the suitable building blocks in analogy to reaction methods herein described.

| Ex. | Systematic Name/Structure | Building block(s) | MS, m/z | Method |
| --- | --- | --- | --- | --- |
| 1 | N-[2-[4-[4-(4-oxo-3H-quinazolin-2-yl)piperazine-1-carbonyl]phenyl]ethyl]-N-[[3-(trifluoromethyl)phenyl]methyl]acetamide | BB1 | 578.2 [M + H]$^+$ | A1 |
| 2 | 2-[4-[4-[(E)-2-(3-fluorophenyl)ethenyl]benzoyl]piperazin-1-yl]-3H-quinazolin-4-one | BB2 | 455.2 [M + H]$^+$ | A3 |
| 3 | 2-[4-(4-Phenoxybenzoyl)piperazin-1-yl]-3H-quinazolin-4-one | 4-Phenoxybenzoic acid CAS RN 2215-77-2 | 427.2 [M + H]$^+$ | A1 |

-continued

| Ex. | Systematic Name/Structure | Building block(s) | MS, m/z | Method |
|---|---|---|---|---|
| 4 | 2-[4-(3-Phenoxybenzoyl)piperazin-1-yl]-3H-quinazolin-4-one | 3-Phenoxybenzoic acid CAS RN 3739-38-6 | 427.2 [M + H]+ | A1 |
| 5 | 2-[4-[4-(Trifluoromethoxy)benzoyl]piperazin-1-yl]-3H-quinazolin-4-one | 4-(Trifluoromethoxy) benzoic acid CAS RN 330-12-1 | 419.2 [M + H]+ | A1 |
| 6 | 2-[4-[3-(Trifluoromethoxy)benzoyl]piperazin-1-yl]-3H-quinazolin-4-one | 3-(Trifluoromethoxy) benzoic acid CAS RN 1014-81-9 | 419.2 [M + H]+ | A1 |
| 7 | 2-[4-(2-Phenyl-1,3-benzoxazole-5-carbonyl)piperazin-1-yl]-3H-quinazolin-4-one | 2-Phenyl-1,3-benzoxazole-5-carboxylic acid CAS RN 21095-64-7 | 452.2 [M + H]+ | A1 |

-continued

| Ex. | Systematic Name/Structure | Building block(s) | MS, m/z | Method |
|---|---|---|---|---|
| 8 | 2-[4-(2-Phenyl-1,3-benzoxazole-6-carbonyl)piperazin-1-yl]-3H-quinazolin-4-one 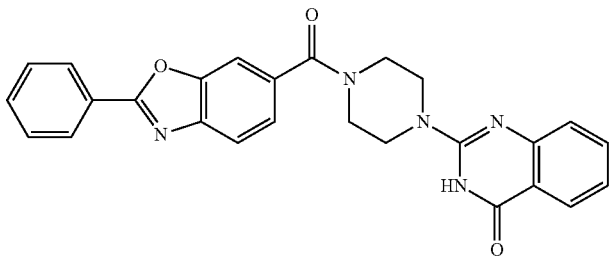 [SMILES: O=C(c1ccc2nc(-c3ccccc3)oc2c1)N1CCN(c2nc3ccccc3c(=O)[nH]2)CC1] | 2-Phenyl-1,3-benzoxazole-6-carboxylic acid CAS RN 594839-90-4 | 452.2 [M + H]$^+$ | A1 |
| 9 | 2-[4-(1H-indole-5-carbonyl)piperazin-1-yl]-3H-quinazolin-4-one 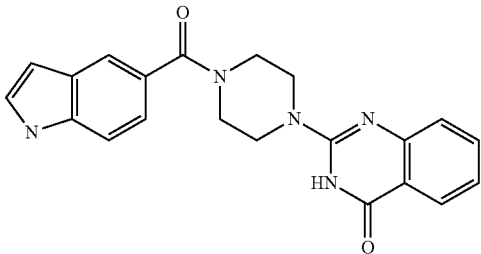 [SMILES: O=C(c1ccc2[nH]ccc2c1)N1CCN(c2nc3ccccc3c(=O)[nH]2)CC1] | 1H-indole-5-carboxylic acid CAS RN 1670-81-1 | 374.2 [M + H]$^+$ | A1 |
| 10 | 2-[4-[1-(4-Fluorophenyl)indole-5-carbonyl]piperazin-1-yl]-3H-quinazolin-4-one 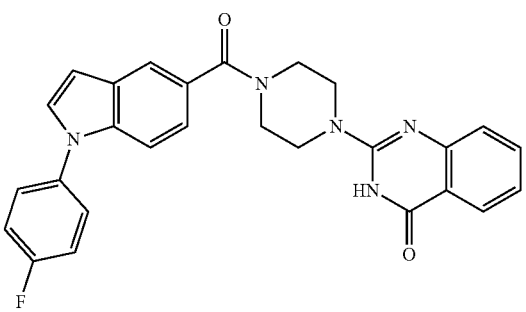 [SMILES: O=C(c1ccc2c(ccn2-c2ccc(F)cc2)c1)N1CCN(c2nc3ccccc3c(=O)[nH]2)CC1] | BB3 | 468.2 [M + H]$^+$ | A1 |
| 11 | 2-[4-(4-Pyrrolidin-1-ylbenzoyl)piperazin-1-yl]-3H-quinazolin-4-one 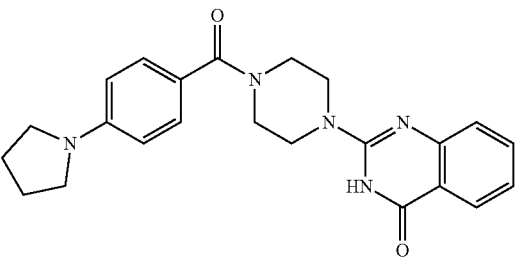 [SMILES: O=C(c1ccc(N2CCCC2)cc1)N1CCN(c2nc3ccccc3c(=O)[nH]2)CC1] | 4-(Pyrrolidin-1-yl)benzoic acid CAS RN 22090-27-3 | 402.3 [M − H]$^-$ | A1 |

-continued

| Ex. | Systematic Name/Structure | Building block(s) | MS, m/z | Method |
|---|---|---|---|---|
| 12 | 2-[4-[4-[(2-Iodophenyl)methylamino]benzoyl]piperazin-1-yl]-3H-quinazolin-4-one 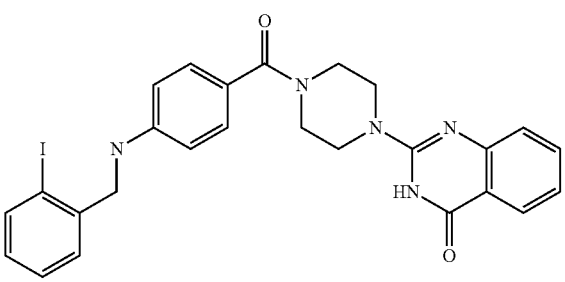 [SMILES: O=C(c1ccc(NCc2ccccc2I)cc1)N1CCN(c2nc3ccccc3c(=O)[nH]2)CC1] | BB4 | 564.1 [M − H]− | A1 |
| 13 | 2-[4-(3-Phenylmethoxybenzoyl)piperazin-1-yl]-3H-quinazolin-4-one 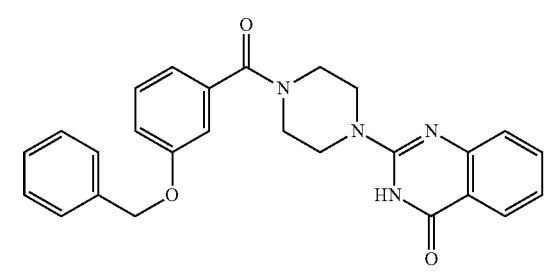 [SMILES: O=C(c1cccc(OCc2ccccc2)c1)N1CCN(c2nc3ccccc3c(=O)[nH]2)CC1] | BB5 | 441.2 [M + H]+ | A1 |
| 14 | 2-[4-[4-[(2-(Trifluoromethoxy)phenyl]methylamino]benzoyl]piperazin-1-yl]-3H-quinazolin-4-one 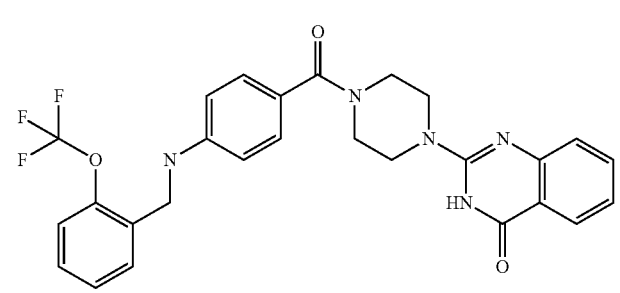 [SMILES: O=C(c1ccc(NCc2ccccc2OC(F)(F)F)cc1)N1CCN(c2nc3ccccc3c(=O)[nH]2)CC1] | BB6 | 524.2 [M + H]+ | A1 |
| 15 | 2-[4-[3-(Cyclopentylmethoxy)benzoyl]piperazin-1-yl]-3H-quinazolin-4-one 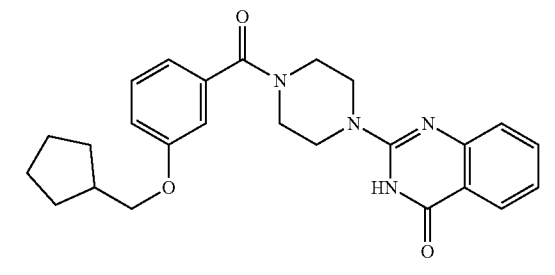 [SMILES: O=C(c1cccc(OCC2CCCC2)c1)N1CCN(c2nc3ccccc3c(=O)[nH]2)CC1] | BB7 | 433.3 [M + H]+ | A1 |

-continued

| Ex. | Systematic Name/Structure | Building block(s) | MS, m/z | Method |
|---|---|---|---|---|
| 16 | 2-[4-(4-Phenylbenzoyl)piperazin-1-yl]-3H-quinazolin-4-one | [1,1'-Biphenyl]-4-carboxylic acid CAS RN 92-92-2 | 411.2 $[M + H]^+$ | A1 |
| 17 | 2-[4-[4-[3-(Trifluoromethyl)phenyl]benzoyl]piperazin-1-yl]-3H-quinazolin-4-one | 3'-(Trifluoromethyl)-[1,1'-biphenyl]-4-carboxylic acid CAS RN 195457-70-6 | 479.2 $[M + H]^+$ | A1 |
| 18 | 2-[4-[4-(5-Methyl-1,2,4-oxadiazol-3-yl)benzoyl]piperazin-1-yl]-3H-quinazolin-4-one | 4-(5-Methyl-1,2,4-oxadiazol-3-yl)benzoic acid CAS RN 9 5124-68-2 | 417.2 $[M + H]^+$ | A1 |
| 19 | 2-[4-(3-Phenyl-1,2-oxazole-5-carbonyl)piperazin-1-yl]-3H-quinazolin-4-one | 3-Phenyl-1,2-oxazole-5-carboxylic acid CAS RN 14442-12-7 | 402.2 $[M + H]^+$ | A1 |

-continued

| Ex. | Systematic Name/Structure | Building block(s) | MS, m/z | Method |
|---|---|---|---|---|
| 20 | 2-[4-(3-Chloro-4-pyrrolidin-1-ylbenzoyl)piperazin-1-yl]-3H-quinazolin-4-one | 3-Chloro-4-pyrrolidin-1-ylbenzoic acid CAS RN 585517-09-5 | 438.2 [M + H]+ | A3 |
| 21 | N-benzyl-N-[2-[4-[4-(4-oxo-3H-quinazolin-2-yl)piperazine-1-carbonyl]phenyl]ethyl]acetamide | BB8 | 510.2 [M + H]+ | D |
| 22 | 2-[4-[3-(Trifluoromethyl)benzoyl]piperazin-1-yl]-3H-quinazolin-4-one | 3-(Trifluoromethyl)benzoic acid CAS RN 454-92-2 | 403.2 [M + H]+ | A1 |
| 23 | 2-[4-(2-Phenyl-1H-indole-5-carbonyl)piperazin-1-yl]-3H-quinazolin-4-one | 2-Phenyl-1H-indole-5-carboxylic acid CAS RN 110073-82-0 | 450.3 [M + H]+ | A2 |

| Ex. | Systematic Name/Structure | Building block(s) | MS, m/z | Method |
|---|---|---|---|---|
| 24 | (Rac, cis)-2-[4-[4-[2-Phenylcyclopropyl]benzoyl]piperazin-1-yl]-3H-quinazolin-4-one | BB9 | 451.3 [M + H]+ | A2 |
| 25 | (Rac, trans)-2-[4-[4-[2-Phenylcyclopropyl]benzoyl]piperazin-1-yl]-3H-quinazolin-4-one | BB10 | 451.3 [M + H]+ | A2 |
| 26 | 2-[4-[3-Bromo-5-(trifluoromethoxy)benzoyl]piperazin-1-yl]-3H-quinazolin-4-one | 3-Bromo-5-(trifluoromethoxy) benzoic acid CAS RN 453565-90-7 | 498.2 [M + H]+ | A2 |
| 27 | 2-[4-(3-Allyloxybenzoyl)piperazin-1-yl]-3H-quinazolin-4-one | 3-Allyloxybenzoic acid CAS RN 103203-83-4 | 391.2 [M + H]+ | A3 |

-continued

| Ex. | Systematic Name/Structure | Building block(s) | MS, m/z | Method |
|---|---|---|---|---|
| 28 | 2-[4-(4-Isobutylbenzoyl)piperazin-1-yl]-3H-quinazolin-4-one | 4-Isobutylbenzoic acid CAS RN 38861-88-0 | 391.2 [M + H]⁺ | A3 |
| 29 | 2-[4-[4-(5-Isopropyl-1,2,4-oxadiazol-3-yl)benzoyl]piperazin-1-yl]-3H-quinazolin-4-one | 4-(5-Isopropyl-1,2,4-oxadiazol-3-yl)benzoic acid CAS RN 915920-28-4 | 445.2 [M + H]⁺ | A3 |
| 30 | 2-[4-(2-Methyl-1-phenylbenzimidazole-5-carbonyl)piperazin-1-yl]-3H-quinazolin-4-one | 2-Methyl-1-phenyl-benzimidazole-5-carboxylic acid CAS RN 92437-43-9 | 465.2 [M + H]⁺ | A3 |
| 31 | 2-[4-[3,5-Bis(trifluoromethyl)benzoyl]piperazin-1-yl]-3H-quinazolin-4-one | 3,5-Bis(trifluoromethyl)benzoic acid CAS RN 72-89-3 | 471.1 [M + H]⁺ | A3 |

-continued

| Ex. | Systematic Name/Structure | Building block(s) | MS, m/z | Method |
|---|---|---|---|---|
| 32 | 2-[4-[4-[2-[[3-(Trifluoromethyl)phenyl]methoxy]ethyl]benzoyl]piperazin-1-yl]-3H-quinazolin-4-one | BB11 | 537.3 [M + H]⁺ | A2 |
| 33 | 2-[4-(4-tert-Butyl-3-methoxybenzoyl)piperazin-1-yl]-3H-quinazolin-4-one | 4-(tert-Butyl)-3-methoxybenzoic acid CAS RN 79822-46-1 | 421.3 [M + H]⁺ | A2 |
| 34 | 2-[4-[4-(Pentafluoro-λ6-sulfanyl)benzoyl]piperazin-1-yl]-3H-quinazolin-4-one | 4-(Pentafluoro-λ6-sulfanyl)benzoic acid CAS RN 832-32-6 | 461.2 [M + H]⁺ | A1 |
| 35 | 2-[4-[1-(4-Fluorophenyl)indazole-5-carbonyl]piperazin-1-yl]-3H-quinazolin-4-one | BB12 | 469.1 [M + H]⁺ | C |

-continued

| Ex. | Systematic Name/Structure | Building block(s) | MS, m/z | Method |
|---|---|---|---|---|
| 36 | 2-[4-[4-(2,5-Dimethylpyrrol-1-yl)benzoyl]piperazin-1-yl]-3H-quinazolin-4-one<br>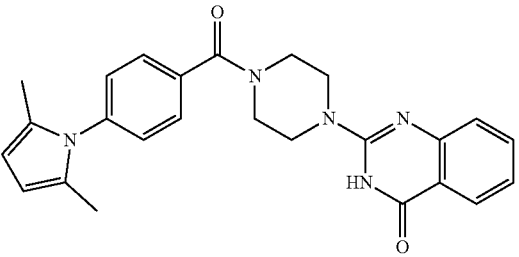 [SMILES: Cc1ccc(C)n1-c1ccc(C(=O)N2CCN(c3nc4ccccc4c(=O)[nH]3)CC2)cc1] | 4-(2,5-Dimethyl-1H-pyrrol-1-yl)benzoic acid<br>CAS RN 15898-26-7 | 428.3<br>[M + H]⁺ | A2 |
| 37 | 2-[4-(Quinoline-7-carbonyl)piperazin-1-yl]-3H-quinazolin-4-one<br>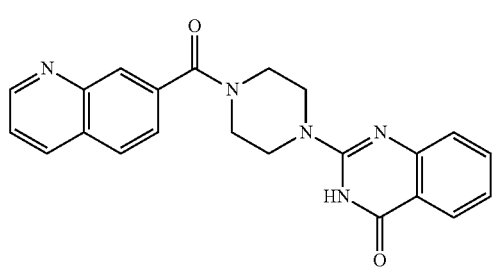 [SMILES: O=C(c1ccc2cccnc2c1)N1CCN(c2nc3ccccc3c(=O)[nH]2)CC1] | Quinoline-7-carboxylic acid<br>CAS RN 1078-30-4 | 384.3<br>[M − H]⁻ | A2 |
| 38 | 2-[4-[3-Bromo-4-(trifluoromethoxy)benzoyl]piperazin-1-yl]-3H-quinazolin-4-one<br>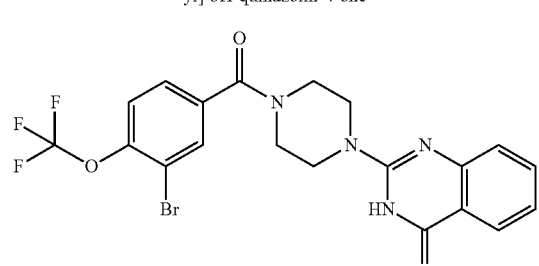 | 3-Bromo-4-(trifluoromethoxy)benzoic acid<br>CAS RN 85373-96-2 | 498.1<br>[M + H]⁺ | A2 |
| 39 | 2-[4-[4-(Benzimidazol-1-ylmethyl)benzoyl]piperazin-1-yl]-3H-quinazolin-4-one<br>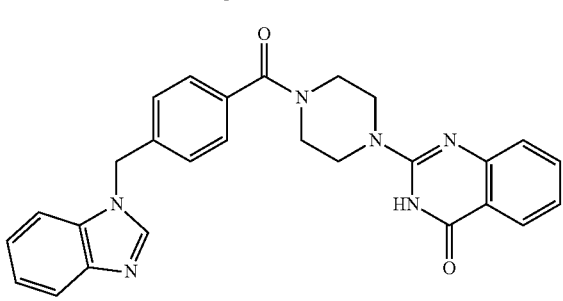 [SMILES: O=C(c1ccc(Cn2cnc3ccccc32)cc1)N1CCN(c2nc3ccccc3c(=O)[nH]2)CC1] | 4-(Benzimidazol-1-ylmethyl)benzoic acid<br>CAS RN 139742-50-0 | 463.3<br>[M − H]⁻ | A2 |

-continued

| Ex. | Systematic Name/Structure | Building block(s) | MS, m/z | Method |
|---|---|---|---|---|
| 40 | 2-[4-[4-(1,3-Thiazol-2-yl)benzoyl]piperazin-1-yl]-3H-quinazolin-4-one<br>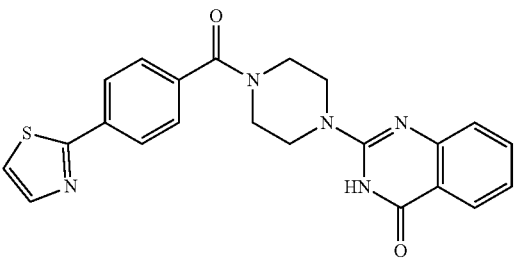 [SMILES: O=C(c1ccc(-c2nccs2)cc1)N1CCN(c2nc3ccccc3c(=O)[nH]2)CC1] | 4-(Thiazol-2-yl)benzoic acid<br>CAS RN 266369-49-7 | 418.2<br>[M + H]$^+$ | A2 |
| 41 | 2-[4-[4-(4-Methylpyrazol-1-yl)benzoyl]piperazin-1-yl]-3H-quinazolin-4-one<br>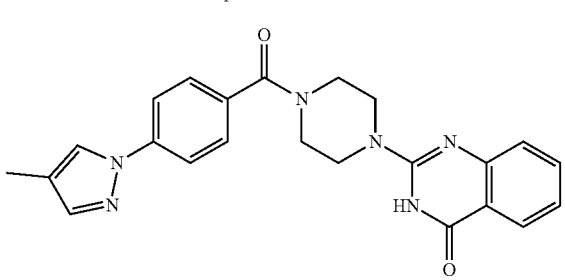 | 4-(4-Methylpyrazol-1-yl)benzoic acid<br>CAS RN 220462-24-8 | 413.3<br>[M − H]$^-$ | A2 |
| 42 | 2-[4-[4-(3-Methylpyrazol-1-yl)benzoyl]piperazin-1-yl]-3H-quinazolin-4-one<br>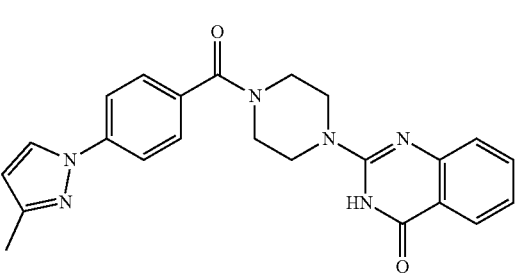 [SMILES: Cc1ccn(-c2ccc(C(=O)N3CCN(c4nc5ccccc5c(=O)[nH]4)CC3)cc2)n1] | 4-(3-Methyl-1H-pyrazol-1-yl)benzoic acid<br>CAS RN 72899-91-3 | 413.3<br>[M − H]$^-$ | A2 |
| 43 | 2-[4-(6-Methoxy-1-benzofuran-2-carbonyl)piperazin-1-yl]-3H-quinazolin-4-one<br>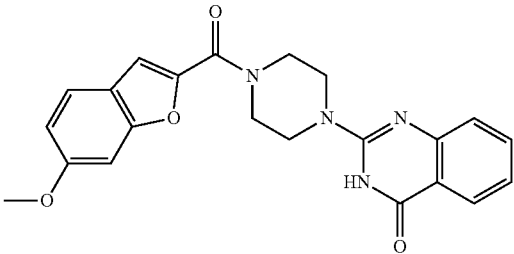 [SMILES: COc1ccc2cc(C(=O)N3CCN(c4nc5ccccc5c(=O)[nH]4)CC3)oc2c1] | 6-Methoxybenzofuran-2-carboxylic acid<br>CAS RN 50551-61-6 | 405.2<br>[M + H]$^+$ | A2 |

| Ex. | Systematic Name/Structure | Building block(s) | MS, m/z | Method |
|---|---|---|---|---|
| 44 | 2-[4-[5-(Indan-5-yloxymethyl)furan-2-carbonyl]piperazin-1-yl]-3H-quinazolin-4-one 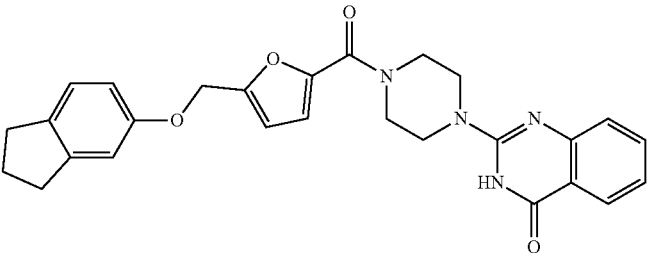 [SMILES: O=C(c1ccc(COc2ccc3c(c2)CCC3)o1)N1CCN(c2nc3ccccc3c(=O)[nH]2)CC1] | 5-(Indan-5-yloxymethyl)-furan-2-carboxylic acid CAS RN 375351-99-8 | 471.3 [M + H]+ | A2 |
| 45 | 2-[4-(1,5-Diphenylpyrazole-3-carbonyl)piperazin-1-yl]-3H-quinazolin-4-one 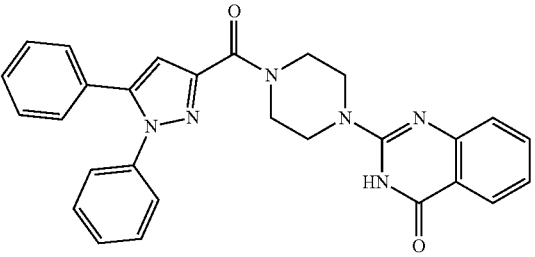 [SMILES: O=C(c1cc(-c2ccccc2)n(-c2ccccc2)n1)N1CCN(c2nc3ccccc3c(=O)[nH]2)CC1] | 1,5-Diphenylpyrazole-3-carboxylic acid CAS RN 13599-22-9 | 477.3 [M + H]+ | A2 |
| 46 | 2-[4-[4-[(3-Chlorophenyl)methoxy]benzoyl]piperazin-1-yl]-3H-quinazolin-4-one 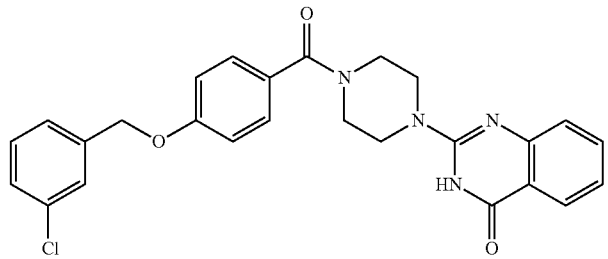 [SMILES: O=C(c1ccc(OCc2cccc(Cl)c2)cc1)N1CCN(c2nc3ccccc3c(=O)[nH]2)CC1] | 4-((3-Chlorophenyl)methoxy)benzoic acid CAS RN 84403-70-3 | 475.2 [M + H]+ | A2 |
| 47 | 2-[4-(2-Phenyl-1H-benzimidazole-5-carbonyl)piperazin-1-yl]-3H-quinazolin-4-one 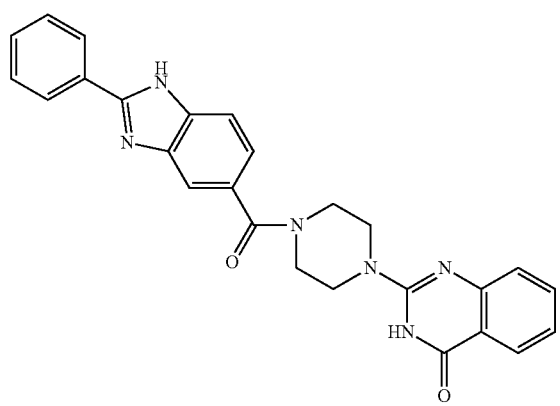 [SMILES: O=C(c1ccc2[nH]c(-c3ccccc3)nc2c1)N1CCN(c2nc3ccccc3c(=O)[nH]2)CC1] | BB13 | 451.3 [M + H]+ | C |

-continued

| Ex. | Systematic Name/Structure | Building block(s) | MS, m/z | Method |
|---|---|---|---|---|
| 48 | 2-[4-[2-(3-Fluorophenyl)-1H-indole-5-carbonyl]piperazin-1-yl]-3H-quinazolin-4-one | BB14 | 468.0 [M + H]+ | C |
| 49 | 2-[4-[4-[3-(Trifluoromethyl)phenyl]benzoyl]piperazin-1-yl]-3H-pyrido[3,4-d]pyrimidin-4-one | 1) 3'-(Trifluoromethyl)-[1,1'-biphenyl]-4-carboxylic acid CAS RN 195457-70-6<br>2) BB15 | 480.2 [M + H]+ | A2 |
| 50 | 2-[4-(2-Phenyl-1,3-benzoxazole-6-carbonyl)piperazin-1-yl]-3H-pyrido[3,4-d]pyrimidin-4-one | 1) 2-Phenyl-1,3-benzooxazole-6-carboxylic acid CAS RN 594839-90-4<br>2) BB15 | 453.2 [M + H]+ | A3 |
| 51 | 2-[4-[1-(4-Fluorophenyl)pyrrolo[2,3-b]pyridine-5-carbonyl]piperazin-1-yl]-3H-quinazolin-4-one | BB16 | 469.1 [M + H]+ | C |

-continued

| Ex. | Systematic Name/Structure | Building block(s) | MS, m/z | Method |
|---|---|---|---|---|
| 52 | 2-[4-(4-Piperidin-1-ylbenzoyl)piperazin-1-yl]-3H-quinazolin-4-one | 4-(1-Piperidyl)benzoic acid CAS RN 22090-24-0 | 418.2 [M + H]$^+$ | A3 |
| 53 | 2-[4-[1-(4-Fluorophenyl)benzimidazole-5-carbonyl]piperazin-1-yl]-3H-quinazolin-4-one | BB17 | 469.1 [M + H]$^+$ | C |
| 54 | 2-[4-(2-Piperidin-1-yl-1,3-benzoxazole-6-carbonyl)piperazin-1-yl]-3H-quinazolin-4-one | 2-(1-Piperidyl)-1,3-benzoxazole-6-carboxylic acid Preparation described in Bioorg. Med. Chem. Lett. 2012, 22, 4998-5002 | 459.2 [M + H]$^+$ | A3 |
| 55 | 3-Methyl-2-[4-(2-phenyl-1,3-benzoxazole-6-carbonyl)piperazin-1-yl]quinazolin-4-one | 1) 2-Phenyl-1,3-benzoxazole-6-carboxylic acid (CAS RN 594839-90-4) 2) 3-Methyl-2-piperazin-1-yl-3H-quinazolin-4-one (Princeton RBK_069842) | 466.1 [M + H]$^+$ | A3 |

-continued

| Ex. | Systematic Name/Structure | Building block(s) | MS, m/z | Method |
|---|---|---|---|---|
| 56 | 2-[4-[4-[5-(Trifluoromethyl)-1,2,4-oxadiazol-3-yl]benzoyl]piperazin-1-yl]-3H-quinazolin-4-one | 4-[5-(Trifluoromethyl)-1,2,4-oxadiazol-3-yl]benzoic acid CAS RN 340736-76-7 | 471.1 [M + H]$^+$ | A3 |
| 57 | 2-[4-[4-[4-(Trifluoromethyl)pyrazol-1-yl]benzoyl]piperazin-1-yl]-3H-quinazolin-4-one | 4-[4-(Trifluoromethyl) pyrazol-1-yl]benzoic acid CAS RN 340736-76-7 | 469.2 [M + H]$^+$ | A3 |
| 58 | 2-[4-[4-[3-(Trifluoromethyl)pyrazol-1-yl]benzoyl]piperazin-1-yl]-3H-quinazolin-4-one | 4-[3-(Trifluoromethyl) pyrazol-1-yl]benzoic acid CAS RN 220462-27-1 | 469.2 [M + H]$^+$ | A3 |
| 59 | 2-[4-[4-(5-Cyclopropyl-1,2,4-oxadiazol-3-yl)benzoyl]piperazin-1-yl]-3H-quinazolin-4-one | 4-(5-Cyclopropyl-1,2,4-oxadiazol-3-yl)benzoic acid CAS RN 915920-27-3 | 443.2 [M + H]$^+$ | A3 |

-continued

| Ex. | Systematic Name/Structure | Building block(s) | MS, m/z | Method |
|---|---|---|---|---|
| 60 | 2-[4-[2-(3-Fluorophenyl)-1,3-benzoxazole-6-carbonyl]piperazin-1-yl]-3H-quinazolin-4-one | BB18 | 470.2 [M + H]⁺ | A3 |
| 61 | 2-[4-[2-(3-Chlorophenyl)-1,3-benzoxazole-6-carbonyl]piperazin-1-yl]-3H-quinazolin-4-one | BB19 | 486.1 [M + H]⁺ | A3 |
| 62 | 2-[4-[2-[3-(Trifluoromethyl)phenyl]-1,3-benzoxazole-6-carbonyl]piperazin-1-yl]-3H-quinazolin-4-one | BB20 | 520.2 [M + H]⁺ | A3 |
| 63 | 2-[4-(4-Phenylmethoxybenzoyl)piperazin-1-yl]-3H-quinazolin-4-one | 4-Benzyloxybenzoic acid CAS RN 1486-51-7 | 440.9 [M + H]⁺ | C |

| Ex. | Systematic Name/Structure | Building block(s) | MS, m/z | Method |
|---|---|---|---|---|
| 64 | 2-[4-[4-(Diethylamino)benzoyl]piperazin-1-yl]-3H-quinazolin-4-one | 4-(Diethylamino)benzoic acid CAS RN 5429-28-7 | 406.2 [M + H]+ | A3 |
| 65 | 2-[4-[3-[(3-Chlorophenyl)methoxy]benzoyl]piperazin-1-yl]-3H-quinazolin-4-one | 3-[(3-Chlorophenyl)methoxy]benzoic acid CAS RN 302569-44-4 | 475.3 [M + H]+ | C |
| 66 | 2-[4-[3-Chloro-4-[(3-chlorophenyl)methoxy]benzoyl]piperazin-1-yl]-3H-quinazolin-4-one | BB21 | 509.3 [M + H]+ | C |
| 67 | 2-[4-[4-[5-(2,2-Dimethylpropyl)-1,2,4-oxadiazol-3-yl]benzoyl]piperazin-1-yl]-3H-quinazolin-4-one | 4-[5-(2,2-Dimethylpropyl)-1,2,4-oxadiazol-3-yl]benzoic acid CAS RN 1305938-51-5 | 473.2 [M + H]+ | A3 |

-continued

| Ex. | Systematic Name/Structure | Building block(s) | MS, m/z | Method |
|---|---|---|---|---|
| 68 | 2-[4-[4-[tert-Butyl(methyl)amino]benzoyl]piperazin-1-yl]-3H-quinazolin-4-one | 4-[tert-Butyl(methyl)amino]benzoic acid CAS RN 67688-78-2 | 420.2 [M + H]⁺ | A3 |
| 69 | 2-[4-[4-(2,3-Dihydroindol-1-yl)benzoyl]piperazin-1-yl]-3H-quinazolin-4-one | 4-(2,3-Dihydro-indol-1-yl)-benzoic acid CAS RN 1020933-45-2 | 452.4 [M + H]⁺ | A2 |
| 70 | 2-[4-[4-(Azetidin-1-yl)benzoyl]piperazin-1-yl]-3H-quinazolin-4-one | BB22 | 390.3 [M + H]⁺ | A2 |
| 71 | 2-[4-(2-Chloro-4-pyrrolidin-1-ylbenzoyl)piperazin-1-yl]-3H-quinazolin-4-one | 2-Chloro-4-pyrrolidin-1-yl-benzoic acid CAS RN 192513-60-3 | 436.2 [M + H]⁺ | A3 |

-continued

| Ex. | Systematic Name/Structure | Building block(s) | MS, m/z | Method |
|---|---|---|---|---|
| 72 | 2-[4-[4-[(3-Chlorophenyl)methoxy]-3-(trifluoromethyl)benzoyl]piperazin-1-yl]-3H-quinazolin-4-one | BB23 | 543.1 [M + H]⁺ | C |
| 73 | 2-[4-[4-[(3-Chlorophenyl)methoxy]-3-methylbenzoyl]piperazin-1-yl]-3H-quinazolin-4-one | BB24 | 489.3 [M + H]⁺ | C |
| 74 | 2-[4-(3-Pyrrolidin-1-ylbenzoyl)piperazin-1-yl]-3H-quinazolin-4-one | 3-Pyrrolidin-1-ylbenzoic acid CAS RN 72548-79-9 | 404.2 [M + H]⁺ | A3 |
| 75 | 2-[4-[4-(5-tert-Butyl-1,2,4-oxadiazol-3-yl)benzoyl]piperazin-1-yl]-3H-quinazolin-4-one | 4-(5-tert-Butyl-1,2,4-oxadiazol-3-yl)benzoic acid CAS RN 1119452-72-0 | 459.2 [M + H]⁺ | A3 |

-continued

| Ex. | Systematic Name/Structure | Building block(s) | MS, m/z | Method |
|---|---|---|---|---|
| 76 | 2-[4-[4-[(3-Chlorophenyl)methoxy]-3-(1H-imidazol-2-yl)benzoyl]piperazin-1-yl]-3H-quinazolin-4-one | BB25 | 541.3 [M + H]+ | C |
| 77 | 2-[(3-Chlorophenyl)methoxy]-5-[4-(4-oxo-3H-quinazolin-2-yl)piperazine-1-carbonyl]benzonitrile | BB26 | 500.2 [M + H]+ | C |
| 78 | 2-[4-(4-Cyclohexylbenzoyl)piperazin-1-yl]-3H-quinazolin-4-one | 4-Cyclohexylbenzoic acid CAS RN 20029-52-1 | 417.5 [M + H]+ | A2 |
| 79 | 2-[4-(2-Cyclohexyl-1,3-benzoxazole-6-carbonyl)piperazin-1-yl]-3H-quinazolin-4-one | 2-Cyclohexyl-1,3-benzoxazole-6-carboxylic acid CAS RN 1181353-33-2 | 458.2 [M + H]+ | A3 |

| Ex. | Systematic Name/Structure | Building block(s) | MS, m/z | Method |
|---|---|---|---|---|
| 80 | 2-[4-[4-(4-Oxo-3H-quinazolin-2-yl)piperazine-1-carbonyl]phenyl]benzonitrile | 2'-Cyano[1,1'-biphenyl]-4-carboxylic acid CAS RN 5728-44-9 | 436.3 [M + H]+ | B |
| 81 | 2-[4-(1-Butyl-2-methylbenzimidazole-5-carbonyl)piperazin-1-yl]-3H-quinazolin-4-one | 1-Butyl-2-methyl-1,3-benzimidazole-5-carboxylic acid CAS RN 1152495-95-8 | 445.3 [M + H]+ | B |
| 82 | 2-[4-[4-[3,5-Bis(trifluoromethyl)phenyl]benzoyl]piperazin-1-yl]-3H-quinazolin-4-one | 3',5'-Bis(trifluoromethyl)biphenyl-4-carboxylic acid CAS RN 195457-74-0 | 547.3 [M + H]+ | B |
| 83 | 2-[4-[4-[3-(Trifluoromethoxy)phenyl]benzoyl]piperazin-1-yl]-3H-quinazolin-4-one | 4-(3-Trifluoromethoxyphenyl)benzoic acid CAS RN 1093758-81-6 | 495.3 [M + H]+ | B |

-continued

| Ex. | Systematic Name/Structure | Building block(s) | MS, m/z | Method |
|---|---|---|---|---|
| 84 | 2-[4-[1-Isopropyl-2-(trifluoromethyl)benzimidazole-5-carbonyl]piperazin-1-yl]-3H-quinazolin-4-one | 1-Isopropyl-2-(trifluoromethyl)-1H-benzimidazole-5-carboxylic acid CAS RN 306935-42-2 | 485.3 [M + H]$^+$ | B |
| 85 | 2-[4-[5-[3-(Trifluoromethyl)phenyl]pyridine-3-carbonyl]piperazin-1-yl]-3H-quinazolin-4-one | 5-(3-Trifluoromethyl-phenyl) nicotinic acid CAS RN 893740-46-0 | 480.2 [M + H]$^+$ | B |
| 86 | 2-[4-[4-(3,4-Difluorophenyl)-2-fluorobenzoyl]piperazin-1-yl]-3H-quinazolin-4-one | 3.3',4'-Trifluoro-[1,1'-biphenyl]-4-carboxylic acid CAS RN 1179174-66-3 | 465.2 [M + H]$^+$ | B |
| 87 | 2-[4-[4-(2-Methoxy-5-methylphenyl)benzoyl]piperazin-1-yl]-3H-quinazolin-4-one | 2'-Methoxy-5'-methyl-[1,1'-biphenyl]-4-carboxylic acid CAS RN 1181269-37-3 | 453.2 [M − H]$^−$ | B |

-continued

| Ex. | Systematic Name/Structure | Building block(s) | MS, m/z | Method |
|---|---|---|---|---|
| 88 | 2-[4-(3-Methylbenzofuran-2-carbonyl)piperazin-1-yl]-3H-quinazolin-4-one | 3-Methylbenzofuran-2-carboxylic acid CAS RN 24673-56-1 | 389.2 [M + H]⁺ | B |
| 89 | 2-[4-[3-[2-(Hydroxymethyl)phenyl]benzoyl]piperazin-1-yl]-3H-quinazolin-4-one | 2'-(Hydroxymethyl)biphenyl-3-carboxylic acid CAS RN 773872-29-0 | 439.2 [M + H]⁺ | B |
| 90 | 2-[4-[4-[3-(Hydroxymethyl)phenyl]benzoyl]piperazin-1-yl]-3H-quinazolin-4-one | 3'-(Hydroxymethyl)[1,1'-biphenyl]-4-carboxylic acid CAS RN 773872-85-8 | 441.3 [M + H]⁺ | B |
| 91 | 2-[4-(3-Bromo-5-isopropyloxybenzoyl)piperazin-1-yl]-3H-quinazolin-4-one | 3-Bromo-5-isopropoxy-benzoic acid CAS RN 1119779-04-2 | 471.1 [M − H]⁻ | B |

| Ex. | Systematic Name/Structure | Building block(s) | MS, m/z | Method |
|---|---|---|---|---|
| 92 | 2-[4-[3-Chloro-5-[4-(hydroxymethyl)phenyl]benzoyl]piperazin-1-yl]-3H-quinazolin-4-one | 5-Chloro-4'-(hydroxymethyl)-[1,1'-biphenyl]-3-carboxylic acid CAS RN 1262005-64-0 | 475.2 [M + H]+ | B |
| 93 | 2-[4-[4-Chloro-3-(2-methylpropoxy)benzoyl]piperazin-1-yl]-3H-quinazolin-4-one | 4-Chloro-3-isobutoxybenzoic acid CAS RN 1280786-73-3 | 439.2 [M − H]− | B |
| 94 | 2-[4-(3-Bromo-5-ethoxybenzoyl)piperazin-1-yl]-3H-quinazolin-4-one | 3-Bromo-5-ethoxybenzoic acid CAS RN 855198-27-5 | 457.1 [M − H]− | B |
| 95 | 2-[4-[4-Fluoro-3-[2-(hydroxymethyl)phenyl]benzoyl]piperazin-1-yl]-3H-quinazolin-4-one | 4-Fluoro-3-(2-hydroxymethyl-phenyl)benzoic acid CAS RN 1262011-07-3 | 457.2 [M − H]− | B |

| Ex. | Systematic Name/Structure | Building block(s) | MS, m/z | Method |
|---|---|---|---|---|
| 96 | 2-[4-[3-Fluoro-4-[3-(trifluoromethyl)phenyl]benzoyl]piperazin-1-yl]-3H-quinazolin-4-one | 2-Fluoro-3'-(trifluoromethyl)-[1,1'-biphenyl]-4-carboxylic acid CAS RN 1261750-12-2 | 497.2 [M + H]⁺ | B |
| 97 | 2-[4-[3-[2-(Trifluoromethoxy)phenyl]benzoyl]piperazin-1-yl]-3H-quinazolin-4-one | 3-[2-(Trifluoromethoxy)phenyl]benzoic acid CAS RN 765276-04-8 | 495.2 [M + H]⁺ | B |
| 98 | 2-[4-[6-(Trifluoromethyl)quinoline-3-carbonyl]piperazin-1-yl]-3H-quinazolin-4-one | 6-(Trifluoromethyl)quinoline-3-carboxylic acid CAS RN 71082-45-6 | 454.2 [M + H]⁺ | B |
| 99 | 2-[4-(4,6-Dimethyl-1H-indole-2-carbonyl)piperazin-1-yl]-3H-quinazolin-4-one | 4,6-Dimethyl-1H-indole-2-carboxylic acid CAS RN 383132-27-2 | 402.3 [M + H]⁺ | B |

| Ex. | Systematic Name/Structure | Building block(s) | MS, m/z | Method |
|---|---|---|---|---|
| 100 | N,N-dimethyl-4-[2-methyl-4-[4-(4-oxo-3H-quinazolin-2-yl)piperazine-1-carbonyl]phenyl]benzamide | 4'-(Dimethylcarbamoyl)-2-methyl-[1,1'-biphenyl]-4-carboxylic acid CAS RN 1261915-37-0 | 494.3 [M − H]⁻ | B |
| 101 | 2-[4-[2-(4-tert-Butylphenyl)pyridine-4-carbonyl]piperazin-1-yl]-3H-quinazolin-4-one | 2-(4-tert-Butylphenyl) pyridine-4-carboxylic acid CAS RN 1226273-21-7 | 468.4 [M + H]⁺ | B |
| 102 | 2-[4-[4-(2-Chlorophenoxy)benzoyl]piperazin-1-yl]-3H-quinazolin-4-one | 4-(2-Chlorophenoxy) benzoic acid CAS RN 613656-16-9 | 461.3 [M + H]⁺ | B |
| 103 | 2-[4-(3-tert-Butyl-5-chlorobenzoyl)piperazin-1-yl]-3H-quinazolin-4-one | 3-(tert-Butyl)-5-chlorobenzoic acid CAS RN 1000341-32-1 | 423.3 [M − H]⁻ | B |

-continued

| Ex. | Systematic Name/Structure | Building block(s) | MS, m/z | Method |
|---|---|---|---|---|
| 104 | 2-[4-[4-(3-Phenylmethoxyphenyl)benzoyl]piperazin-1-yl]-3H-quinazolin-4-one | 3'-(Benzyloxy)[1,1'-biphenyl]-4-carboxylic acid CAS RN 122294-08-0 | 517.4 [M + H]+ | B |
| 105 | 2-[4-[3-(2-Methyl-6-phenylmethoxyphenyl)benzoyl]piperazin-1-yl]-3H-quinazolin-4-one | 2-Benzyloxy-6-methylbiphenyl-3'-carboxylic acid CAS RN 1420800-42-5 | 531.4 [M + H]+ | B |
| 106 | 2-[4-[4-[4-Methoxy-3-(trifluoromethyl)phenyl]-3-methylbenzoyl]piperazin-1-yl]-3H-quinazolin-4-one | 4'-Methoxy-2-methyl-3'-(trifluoromethyl)-[1,1'-biphenyl]-4-carboxylic acid CAS RN 1262006-62-1 | 523.3 [M + H]+ | B |
| 107 | 2-[4-(7-Benzyloxy-1H-indole-3-carbonyl)piperazin-1-yl]-3H-quinazolin-4-one | 7-Benzyloxy-1H-indole-3-carboxylic acid CAS RN 24370-75-0 | 480.3 [M + H]+ | B |

-continued

| Ex. | Systematic Name/Structure | Building block(s) | MS, m/z | Method |
|---|---|---|---|---|
| 108 | 2-[4-[4-(2,6-Difluorophenyl)benzoyl]piperazin-1-yl]-3H-quinazolin-4-one | 2',6'-Difluoro-[1,1'-biphenyl]-4-carboxylic acid CAS RN 505082-79-1 | 445.3 [M − H]⁻ | B |
| 109 | 2-[4-(1-Cyclopropylbenzimidazole-5-carbonyl)piperazin-1-yl]-3H-quinazolin-4-one | 1-Cyclopropyl-benzimidazole-5-carboxylic acid CAS RN 887350-88-1 | 415.3 [M + H]⁺ | B |
| 110 | 2-[4-(6-tert-Butyl-1H-indole-2-carbonyl)piperazin-1-yl]-3H-quinazolin-4-one | 6-tert-Butyl-1H-indole-2-carboxylic acid CAS RN 383133-22-0 | 430.3 [M + H]⁺ | B |
| 111 | 2-[4-(4-Chloro-3-ethoxybenzoyl)piperazin-1-yl]-3H-quinazolin-4-one | 4-Chloro-3-ethoxybenzoic acid CAS RN 97209-05-7 | 413.2 [M + H]⁺ | B |

-continued

| Ex. | Systematic Name/Structure | Building block(s) | MS, m/z | Method |
|---|---|---|---|---|
| 112 | 2-[4-[4-(4,4-Dimethylpiperidin-1-yl)benzoyl]piperazin-1-yl]-3H-quinazolin-4-one | 4-(4,4-Dimethylpiperidin-1-yl)benzoic acid CAS RN 406233-26-9 | 444.5 [M − H]⁻ | B |
| 113 | 2-[4-[5-(Trifluoromethyl)imidazo[1,2-a]pyridine-2-carbonyl]piperazin-1-yl]-3H-quinazolin-4-one | 5-(Trifluoromethyl)imidazo[1,2-a]pyridine-2-carboxylic acid CAS RN 1260798-62-6 | 443.2 [M + H]⁺ | B |
| 114 | 4-[2-Fluoro-5-[4-(4-oxo-3H-quinazolin-2-yl)piperazine-1-carbonyl]phenyl]-N,N-dimethylbenzamide | 3-[4-(N,N-Dimethylamino-carbonyl)phenyl]-4-fluorobenzoic acid CAS RN 1262010-01-4 | 500.3 [M + H]⁺ | B |
| 115 | 2-[4-[3-(3,5-Difluorophenyl)benzoyl]piperazin-1-yl]-3H-quinazolin-4-one | 3-Biphenyl-3',5'-difluorocarboxylic acid CAS RN 177734-83-7 | 447.3 [M + H]⁺ | B |

-continued

| Ex. | Systematic Name/Structure | Building block(s) | MS, m/z | Method |
| --- | --- | --- | --- | --- |
| 116 | 2-[4-[2-(3,4-Dichlorophenyl)-1,3-benzoxazole-6-carbonyl]piperazin-1-yl]-3H-quinazolin-4-one | BB27 | 520.1 [M + H]$^+$ | A3 |
| 117 | 2-[4-[2-(4-Chlorophenyl)-1,3-benzoxazole-6-carbonyl]piperazin-1-yl]-3H-quinazolin-4-one | B28 | 486.1 [M + H]$^+$ | A3 |
| 118 | 2-[4-[4-(3-Azabicyclo[2.2.1]heptan-3-yl)benzoyl]piperazin-1-yl]-3H-quinazolin-4-one | BB29 | 428.5 [M − H]$^−$ | A2 |
| 119 | 2-[4-[4-(2-Azaspiro[3.3]heptan-2-yl)benzoyl]piperazin-1-yl]-3H-quinazolin-4-one | BB30 | 428.5 [M − H]$^−$ | A2 |

-continued

| Ex. | Systematic Name/Structure | Building block(s) | MS, m/z | Method |
|---|---|---|---|---|
| 120 | 2-[4-[4-(Azepan-1-yl)benzoyl]piperazin-1-yl]-3H-quinazolin-4-one | 4-(Azepan-1-yl)benzoic acid CAS RN 314248-55-0 | 430.5 [M − H]⁻ | A2 |
| 121 | 2-[4-(2-Phenyl-[1,3]oxazolo[4,5-b]pyridine-6-carbonyl)piperazin-1-yl]-3H-quinazolin-4-one | BB31 | 453.2 [M + H]⁺ | A3 |
| 122 | 2-[4-[4-(3-Cyclopropyl-1H-1,2,4-triazol-5-yl)benzoyl]piperazin-1-yl]-3H-quinazolin-4-one | 4-(3-Cyclopropyl-1H-[1,2,4]triazol-5-yl)-benzoic acid CAS RN 1375474-58-0 | 440.3 [M − H]⁻ | A2 |
| 123 | 2-[4-[4-(3-Cyclopropyl-1,2,4-oxadiazol-5-yl)benzoyl]piperazin-1-yl]-3H-quinazolin-4-one | 4-(3-Cyclopropyl-1,2,4-oxadiazol-5-yl)benzoic acid CAS RN 1165931-66-7 | 443.3 [M + H]⁺ | A2 |

| Ex. | Systematic Name/Structure | Building block(s) | MS, m/z | Method |
|---|---|---|---|---|
| 124 | 6-[4-(4-Oxo-3H-quinazolin-2-yl)piperazine-1-carbonyl]-2-phenyl-1,3-benzoxazole-4-carbonitrile | BB32 | 477.2 [M + H]$^+$ | A3 |
| 125 | 2-[4-[4-(3,4-Dichlorophenyl)benzoyl]piperazin-1-yl]-3H-quinazolin-4-one | 4-(3,4-Dichlorophenyl) benzoic acid CAS RN 7111-64-0 | 479.2 [M + H]$^+$ | A2 |
| 126 | 2-[4-(6-Pyrrolidin-1-ylpyridine-3-carbonyl)piperazin-1-yl]-3H-quinazolin-4-one | 6-Pyrrolidin-1-yl-pyridine-3-carboxylic acid CAS RN 210963-95-4 | 403.5 [M − H]$^-$ | A2 |
| 127 | 2-[4-[3-[5-(2,2-Dimethylpropyl)-1,2,4-oxadiazol-3-yl]benzoyl]piperazin-1-yl]-3H-quinazolin-4-one | 3-[5-(2,2-Dimethylpropyl)-1,2,4-oxadiazol-3-yl]benzoic acid CAS RN 1292018-36-0 | 473.3 [M + H]$^+$ | A2 |

-continued

| Ex. | Systematic Name/Structure | Building block(s) | MS, m/z | Method |
|---|---|---|---|---|
| 128 | 2-[4-[4-(2-Azaspiro[3.4]octan-2-yl)benzoyl]piperazin-1-yl]-3H-quinazolin-4-one | BB33 | 442.5 [M − H]⁻ | A2 |
| 129 | 2-[4-[4-(5-Ethyl-1,2,4-oxadiazol-3-yl)benzoyl]piperazin-1-yl]-3H-quinazolin-4-one | 4-(5-Ethyl-1,2,4-oxadiazol-3-yl)benzoic acid CAS RN 769132-76-5 | 431.3 [M + H]⁺ | A2 |
| 130 | 2-[4-[4-(2-Methyl-1,3-thiazol-4-yl)benzoyl]piperazin-1-yl]-3H-quinazolin-4-one | 4-(2-Methyl-1,3-thiazol-4-yl)benzoic acid CAS RN 294620-60-3 | 430.3 [M − H]⁻ | A2 |
| 131 | 2-[4-[2-(3,4-Difluorophenyl)-1,3-benzoxazole-6-carbonyl]piperazin-1-yl]-3H-quinazolin-4-one | BB34 | 488.4 [M + H]⁺ | A3 |

-continued

| Ex. | Systematic Name/Structure | Building block(s) | MS, m/z | Method |
|---|---|---|---|---|
| 132 | 2-[4-[2-[4-(Trifluoromethyl)phenyl]-1,3-benzoxazole-6-carbonyl]piperazin-1-yl]-3H-quinazolin-4-one | BB35 | 520.4 [M + H]+ | A3 |
| 133 | 2-[4-[2-[3-Fluoro-4-(trifluoromethyl)phenyl]-1,3-benzoxazole-6-carbonyl]piperazin-1-yl]-3H-quinazolin-4-one | BB36 | 538.4 [M + H]+ | A3 |
| 134 | 2-[4-[2-(4-Fluorophenyl)-1,3-benzoxazole-6-carbonyl]piperazin-1-yl]-3H-quinazolin-4-one | B37 | 470.4 [M + H]+ | A3 |
| 135 | 6-Fluoro-2-[4-(2-phenyl-1,3-benzoxazole-6-carbonyl)piperazin-1-yl]-3H-quinazolin-4-one | 1) 2-Phenyl-1,3-benzoxazole-6-carboxylic acid CAS RN 594839-90-4 2) BB38 | 470.1 [M + H]+ | A3 |

-continued

| Ex. | Systematic Name/Structure | Building block(s) | MS, m/z | Method |
|---|---|---|---|---|
| 136 | 7-Fluoro-2-[4-(2-phenyl-1,3-benzoxazole-6-carbonyl)piperazin-1-yl]-3H-quinazolin-4-one | 1) 2-Phenyl-1,3-benzoxazole-6-carboxylic acid CAS RN 594839-90-4 2) BB39 | 468.1 [M − H]⁻ | A3 |
| 137 | 2-[4-(4-Bromo-3-fluorobenzoyl)piperazin-1-yl]-3H-quinazolin-4-one | 4-Bromo-3-fluorobenzoic acid CAS RN 153556-42-4 | 433.2 [M + H]⁺ | A2 |
| 138 | 2-[4-(5-Pyrrolidin-1-ylpyridine-2-carbonyl)piperazin-1-yl]-3H-quinazolin-4-one | 5-(1-Pyrrolidinyl)-2-pyridinecarboxylic acid CAS RN 950603-19-7 | 403.6 [M − H]⁻ | A2 |
| 139 | 2-[4-[3-Fluoro-4-[5-(trifluoromethyl)pyridin-3-yl]benzoyl]piperazin-1-yl]-3H-quinazolin-4-one | 1) Example 137 2) (5-(Trifluoromethyl)pyridin-3-yl)boronic acid CAS RN 947533-51-9 | 498.3 [M + H]⁺ | F |

| Ex. | Systematic Name/Structure | Building block(s) | MS, m/z | Method |
| --- | --- | --- | --- | --- |
| 140 | 2-[4-(2-Methyl-1,3-benzoxazole-6-carbonyl)piperazin-1-yl]-3H-quinazolin-4-one | 2-Methylbenzo-1,3-oxazole-6-carboxylic acid CAS RN 13452-14-7 | 390.3 [M + H]+ | A3 |
| 141 | 2-[4-[2-Phenyl-4-(trifluoromethyl)-1,3-benzoxazole-6-carbonyl]piperazin-1-yl]-3H-quinazolin-4-one | BB40 | 520.4 [M + H]+ | A3 |
| 142 | 2-[4-(4-Bromo-3-methylbenzoyl)piperazin-1-yl]-3H-quinazolin-4-one | 4-Bromo-3-methylbenzoic acid CAS RN 7697-28-1 | 429.3 [M + H]+ | A2 |
| 143 | 2-[4-(2-Morpholin-4-yl-1,3-benzoxazole-6-carbonyl)piperazin-1-yl]-3H-quinazolin-4-one | BB41 | 461.1 [M + H]+ | A2 |

| Ex. | Systematic Name/Structure | Building block(s) | MS, m/z | Method |
|---|---|---|---|---|
| 144 | 2-[4-[4-(2,3-Dihydropyrrolo[2,3-b]pyridin-1-yl)benzoyl]piperazin-1-yl]-3H-quinazolin-4-one 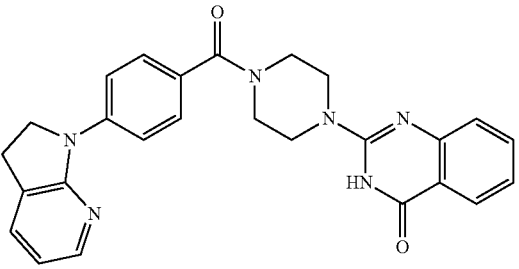 [SMILES: O=C(c1ccc(N2CCc3cccnc32)cc1)N1CCN(c2nc3ccccc3c(=O)[nH]2)CC1] | BB42 | 451.4 [M − H]− | A2 |
| 145 | 2-[4-[4-(2-Phenylpyrrolidin-1-yl)benzoyl]piperazin-1-yl]-3H-quinazolin-4-one 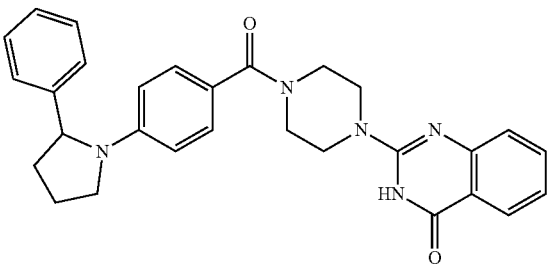 [SMILES: O=C(c1ccc(N2CCCC2c2ccccc2)cc1)N1CCN(c2nc3ccccc3c(=O)[nH]2)CC1] | BB43 | 478.5 [M − H]− | A2 |
| 146 | 2-[4-(2-Pyridin-2-yl-1,3-benzoxazole-6-carbonyl)piperazin-1-yl]-3H-quinazolin-4-one 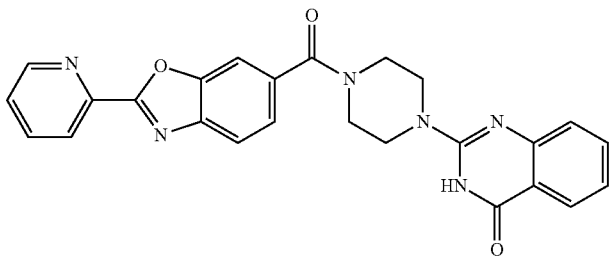 [SMILES: O=C(c1ccc2nc(-c3ccccn3)oc2c1)N1CCN(c2nc3ccccc3c(=O)[nH]2)CC1] | BB44 | 453.1 [M + H]+ | B |
| 147 | 2-[4-[4-[5-(2,2,2-Trifluoroethyl)-1,2,4-oxadiazol-3-yl]benzoyl]piperazin-1-yl]-3H-quinazolin-4-one 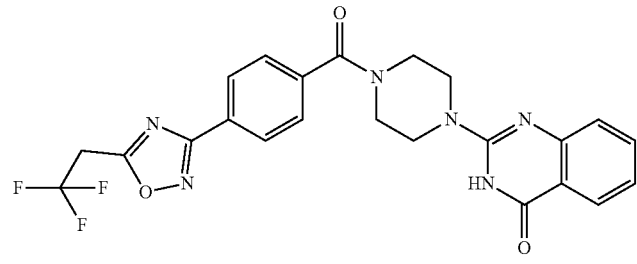 [SMILES: O=C(c1ccc(-c2noc(CC(F)(F)F)n2)cc1)N1CCN(c2nc3ccccc3c(=O)[nH]2)CC1] | BB45 | 485.1 [M + H]+ | E |

-continued

| Ex. | Systematic Name/Structure | Building block(s) | MS, m/z | Method |
|---|---|---|---|---|
| 148 | 2-[4-[4-(2-Oxa-6-azaspiro[3.3]heptan-6-yl)benzoyl]piperazin-1-yl]-3H-quinazolin-4-one | BB46 | 430.4 [M − H]− | A2 |
| 149 | 2-[3-[4-[4-(4-Oxo-3H-quinazolin-2-yl)piperazine-1-carbonyl]phenyl]phenyl]acetonitrile | 1) BB 47 2) 2-(3-(4,4,5,5-Tetramethyl-1,3,2-dioxaborolan-2-yl)phenyl)acetonitrile CAS RN 396131-82-1 | 450.3 [M + H]+ | F |
| 150 | 2-[4-[3-Fluoro-4-[3-(trifluoromethoxy)phenyl]benzoyl]piperazin-1-yl]-3H-quinazolin-4-one | 1) Example 137 2) (3-(Trifluoromethoxy)phenyl)boronic acid CAS RN 179113-90-7 | 513.3 [M + H]+ | F |
| 151 | 2-[4-[3-Methyl-4-[3-(trifluoromethoxy)phenyl]benzoyl]piperazin-1-yl]-3H-quinazolin-4-one | 1) Example 142 2) (3-(Trifluoromethoxy)phenyl)boronic acid CAS RN 179113-90-7 | 509.4 [M + H]+ | F |

-continued

| Ex. | Systematic Name/Structure | Building block(s) | MS, m/z | Method |
|---|---|---|---|---|
| 152 | 2-[4-[4-(3-Ethoxyphenyl)benzoyl]piperazin-1-yl]-3H-quinazolin-4-one | 1) BB 47<br>2) 2-(3-Ethoxyphenyl)-4,4,5,5-tetramethyl-1,3,2-dioxaborolane CAS RN 1400274-77-2 | 455.4 [M + H]+ | F |
| 153 | 6-Chloro-2-[4-(2-phenyl-1,3-benzoxazole-6-carbonyl)piperazin-1-yl]-3H-quinazolin-4-one | 1) 2-Phenyl-1,3-benzoxazole-6-carboxylic acid CAS RN 594839-90-4<br>2) BB48 | 486.1 [M + H]+ | A3 |
| 154 | 2-[4-[4-[2-[[3-(Trifluoromethyl)phenyl]methylamino]ethyl]benzoyl]piperazin-1-yl]-3H-quinazolin-4-one | BB49 | 534.4 [M − H]− | A3 |
| 155 | 1-[4-[4-(4-Oxo-3H-quinazolin-2-yl)piperazine-1-carbonyl]phenyl]cyclopentane-1-carbonitrile | BB50 | 428.3 [M + H]+ | A2 |

-continued

| Ex. | Systematic Name/Structure | Building block(s) | MS, m/z | Method |
|---|---|---|---|---|
| 156 | 2-[4-(4-Morpholin-4-yl-2-phenyl-1,3-benzoxazole-6-carbonyl)piperazin-1-yl]-3H-quinazolin-4-one 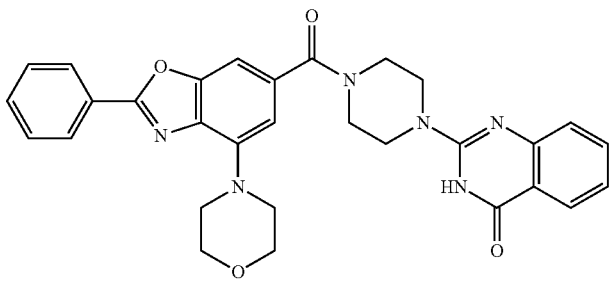 [SMILES: O=C(c1cc(N2CCOCC2)c2nc(-c3ccccc3)oc2c1)N1CCN(c2nc3ccccc3c(=O)[nH]2)CC1] | BB51 | 537.2 [M + H]⁺ | A2 |
| 157 | 2-[4-[2-(2-Azaspiro[3.4]octan-2-yl)-1,3-benzoxazole-6-carbonyl]piperazin-1-yl]-3H-quinazolin-4-one 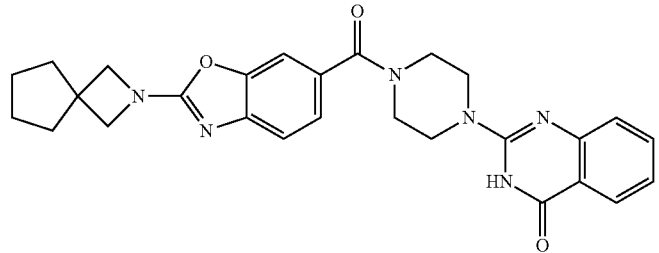 [SMILES: O=C(c1ccc2nc(N3CC4(CCCC4)C3)oc2c1)N1CCN(c2nc3ccccc3c(=O)[nH]2)CC1] | BB52 | 485.2 [M + H]⁺ | A3 |
| 158 | 2-[4-[2-(7,7-Difluoro-2-azaspiro[3.3]heptan-2-yl)-1,3-benzoxazole-6-carbonyl[piperazin-1-yl]-3H-quinazolin-4-one 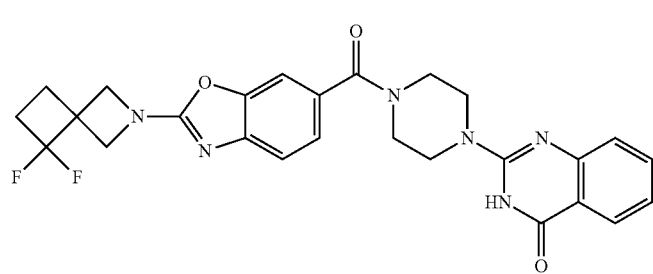 [SMILES: O=C(c1ccc2nc(N3CC4(CCC4(F)F)C3)oc2c1)N1CCN(c2nc3ccccc3c(=O)[nH]2)CC1] | BB158 | 507.2 [M + H]⁺ | A3 |
| 159 | 2-[4-[2-[Methyl(propyl)amino]-1,3-benzoxazole-6-carbonyl]piperazin-1-yl]-3H-quinazolin-4-one 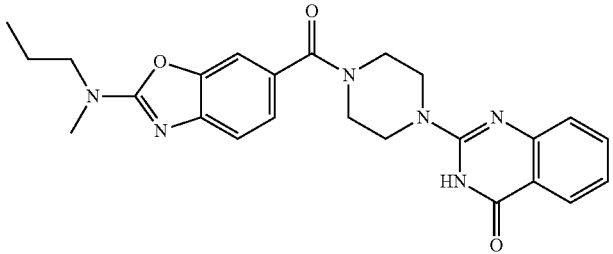 [SMILES: CCCN(C)c1nc2ccc(C(=O)N3CCN(c4nc5ccccc5c(=O)[nH]4)CC3)cc2o1] | BB159 | 447.2 [M + H]⁺ | A3 |

-continued

| Ex. | Systematic Name/Structure | Building block(s) | MS, m/z | Method |
|---|---|---|---|---|
| 160 | N-[2-[4-[4-(1-oxo-2H-isoquinolin-3-yl)piperazine-1-carbonyl]phenyl]ethyl]-N-[[3-(trifluoromethyl)phenyl]methyl]acetamide | 1) BB8<br>2) 3-Chloro-2H-isoquinolin-1-one (CAS RN 7742-74-7) | 577.3 [M + H]⁺ | D, using NMP, K2CO3 at 140° C. |

The following examples were prepared in analogy to examples 1-160, using the methods herein described.

| Ex. | Systematic Name/Structure | Building block(s) | MS, m/z | Method |
|---|---|---|---|---|
| 161 | 2-[4-[2-(Oxan-4-yl)-1,3-benzoxazole-6-carbonyl]piperazin-1-yl]-3H-quinazolin-4-one | 2-Tetrahydropyran-4-yl-1,3-benzoxazole-6-carboxylic acid (BB54) and 2-Piperazin-1-yl-3H-quinazolin-4-one hydrochloride (BB53a) | 460.1 [M + H]⁺ | B (50° C., 12 h) |
| 162 | 2-[4-[2-(Pyridin-4-yl-1,3-benzoxazole-6-carbonyl)piperazin-1-yl]-3H-quinazolin-4-one | 2-(4-Pyridyl)-1,3-benzoxazole-6-carboxylic acid (BB55) and 2-Piperazin-1-yl-3H-quinazolin-4-one hydrochloride (BB53a) | 453.1 [M + H]⁺ | B |
| 163 | 2-[4-[2-(Pyridin-3-yl-1,3-benzoxazole-6-carbonyl)piperazin-1-yl]-3H-quinazolin-4-one | 2-(3-Pyridyl)-1,3-benzoxazole-6-carboxylic acid (BB56) and 2-Piperazin-1-yl-3H-quinazolin-4-one hydrochloride (BB53a) | 453.1 [M + H]⁺ | B (TEA as base) |

-continued

| Ex. | Systematic Name/Structure | Building block(s) | MS, m/z | Method |
|---|---|---|---|---|
| 164 | 3-[6-[4-(4-Oxo-3H-quinazolin-2-yl)piperazine-1-carbonyl]-1,3-benzoxazol-2-yl]benzonitrile | 2-(3-Cyanophenyl)-1,3-benzoxazole-6-carboxylic acid (BB57) and 2-Piperazin-1-yl-3H-quinazolin-4-one hydrochloride (BB53a) | 477.3 [M + H]$^+$ | A2 |
| 165 | 2-[4-(2-Methylsufanyl-1,3-benzoxazole-6-carbonyl)piperazin-1-yl]-3H-quinazolin-4-one | 2-(Methylsulfanyl)-1,3-benzoxazole-6-carboxylic acid (CAS RN 929344-61-6) and BB53 | 422.1 [M + H]$^+$ | A3 |
| 166 | 2-[4-(2-Pyrrolidin-1-yl-1,3-benzoxazole-6-carbonyl)piperazin-1-yl]-3H-quinazolin-4-one | 2-Pyrrolidin-1-yl-1,3-benzoxazole-6-carboxylic acid (BB85) and BB53 | 445.2 [M + H]$^+$ | A2 (DIPEA as base) |
| 167 | 2-[4-[2(4-Methoxypiperidin-1-yl)-1,3-benzoxazole-6-carbonyl]piperazin-1-yl]-3H-quinazolin-4-one | 2-(4-Methoxy-1-piperidyl)-1,3-benzoxazole-6-carboxylic acid (BB86) and BB53 | 489.2 [M + H]$^+$ | A2 (DIPEA as base) |

-continued

| Ex. | Systematic Name/Structure | Building block(s) | MS, m/z | Method |
|---|---|---|---|---|
| 168 | 2-[4-[2(4-Hydroxypiperidin-1-yl)-1,3-benzoxazole-6-carbonyl]piperazin-1-yl]-3H-quinazolin-4-one | 2-(4-Hydroxy-1-piperidyl)-1,3-benzoxazole-6-carboxylic acid (BB87) and BB53 | 475.2 [M + H]$^+$ | A3 |
| 169 | 2-[4-[2(3-Methylpyrrolidin-1-yl)-1,3-benzoxazole-6-carbonyl]piperazin-1-yl]-3H-quinazolin-4-one | 2-(3-Methylpyrrolidin-1-yl)-1,3-benzoxazole-6-carboxylic acid (BB88) and BB53 | 459.2 [M + H]$^+$ | A3 |
| 170 | 2-[4-[4-(6-Azaspiro[3.4]octan-6-yl)benzoyl]piperazin-1-yl]-3H-quinazolin-4-one | 4-(6-Azaspiro[3.4]octan-6-yl)benzoic acid (BB58) and BB53 | 444.2 [M + H]$^+$ | A3 |
| 171 | 2-[4-[4-(3,3-Difluoropyrrolidin-1-yl)benzoyl]piperazin-1-yl]-3H-quinazolin-4-one | 4-(3,3-Difluoropyrrolidin-1-yl)benzoic acid (BB59) and BB53 | 440.2 [M + H]$^+$ | A3 |
| 172 | 2-[4-[4-[3-(1-Hydroxyethyl)pyrrolidin-1-yl]benzoyl]piperazin-1-yl]-3H-quinazolin-4-one | 4-[3-(1-Hydroxyethyl)pyrrolidin-1-yl]benzoic acid (CAS RN 1713773-59-1) and BB53 | 448.2 [M + H]$^+$ | A2 |

-continued

| Ex. | Systematic Name/Structure | Building block(s) | MS, m/z | Method |
|---|---|---|---|---|
| 173 | 2-[4-[4-[4-(Trifluoromethyl)piperidin-1-yl]benzoyl]piperazin-1-yl]-3H-quinazolin-4-one | 4-[4-(Trifluoromethyl)-1-piperidyl]benzoic acid (BB60) and BB53 | 486.2 [M + H]$^+$ | A3 |
| 174 | 2-[4-[4-(5-Azaspiro[2.4]heptan-5-yl)benzoyl]piperazin-1-yl]-3H-quinazolin-4-one | 4-(5-Azaspiro[2.4]heptan-5-yl)benzoic acid (BB61) and BB53 | 430.2 [M + H]$^+$ | A3 (followed by prep-HPLC) |
| 175 | 2-[4-[3-Chloro-4-[(4-chloropyridin-2-yl)methoxy]benzoyl]piperazin-1-yl]-3H-quinazolin-4-one | BB62 and BB63 | 510.0 [M + H]$^+$ | G |
| 176 | 2-[4-[3-Chloro-4-[(2-chloropyridin-4-yl)methoxy]benzoyl]piperazin-1-yl]-3H-quinazolin-4-one | BB53a and BB64 | 510.0 [M + H]$^+$ | C (TEA, followed by prep-HPLC) |

-continued

| Ex. | Systematic Name/Structure | Building block(s) | MS, m/z | Method |
|---|---|---|---|---|
| 177 | 2-[4-(3-Phenylbenzoyl)piperazin-1-yl]-3H-quinazolin-4-one | 3-Phenylbenzoic acid (CAS RN 716-76-7) and BB53 | 411.2 [M + H]$^+$ | A3 (followed by prep-HPLC) |
| 178 | 2-[4-[3-Chloro-4-[(6-chloropyridin-2-yl)methoxy]benzoyl]piperazin-1-yl]-3H-quinazolin-4-one | B62 and B65 | 510.0 [M + H]$^+$ | G |
| 179 | 2-[4-[3-[3-(Trifluoromethyl)phenyl]benzoyl]piperazin-1-yl]-3H-quinazolin-4-one | 3-[3-(Trifluoromethyl)phenyl]benzoic acid (CAS 168619-05-4) and BB53 | 479.2 [M + H]$^+$ | A3 |
| 180 | 2-[4-[4-[3-(Trifluoromeyhyl)phenoxy]benzoyl]piperazin-1-yl]-3H-quinazolin-4-one | 4-[3-(Trifluoromethyl)phenoxy]benzoic acid (CAS RN 632366-11-1) and BB53 | 495.5 [M + H]$^+$ | A3 |

-continued

| Ex. | Systematic Name/Structure | Building block(s) | MS, m/z | Method |
|---|---|---|---|---|
| 181 | 2-[4-[4-[3-(2,2,2-Trifluorethyl)-1,2,4-oxadiazol-5-yl]benzoyl]piperazin-1-yl]-3H-quinazolin-4-one | 4-[3-(2,2,2-Trifluorethyl)-1,2,4-oxadiazol-5-yl]benzoic acid (MDL No: MFCD17603897; Enamine Ltd.) and BB53 | 485.2 $[M + H]^+$ | A3 |
| 182 | 2-[4-[4-(2,5-Dimethylpyrrolidin-1-yl)benzoyl]piperazin-1-yl]-3H-quinazolin-4-one | 4-(2,5-Dimethyl-pyrrolidin-1-yl)benzoic acid (MDL No.: MFCD11557937; Zerenex Molecular Ltd.) and BB53 | 432.2 $[M + H]^+$ | A3 (followed by prpe-HPLC) |
| 183 | 2-[4-[4-(4,4-Difluoropiperidin-1-yl)benzoyl]piperazin-1-yl]-3H-quinazolin-4-one | 4-(4,4-Difluoro-1-piperidyl)benzoic acid (CAS RN 1292835-65-4) and BB53 | 454.2 $[M + H]^+$ | A3 (TEA as base) |
| 184 | 2-[4-[3-Chloro-4-[(3-Chlorophenoxy)methyl]benzoyl]piperazin-1-yl]-3H-quinazolin-4-one | BB89 and BB53a | 509.2 $[M + H]^+$ | C |
| 185 | 2-[4-(2-Phenyl-1,3-benzothiazole-6-carbonyl)piperazin-1-yl]-3H-quinazolin-4-one | 2-Phenyl-1,3-benzothiazole-6-carboxylic acid (CAS RN 19989-69-6) and BB53 | 468.1 $[M + H]^+$ | A2 (DIPEA as base) |

-continued

| Ex. | Systematic Name/Structure | Building block(s) | MS, m/z | Method |
|---|---|---|---|---|
| 186 | 2-[4-[2-(Oxolan-2-yl)-1,3-benzoxazole-6-carbonyl]piperazin-1-yl]-3H-quinazolin-4-one | 2-Tetrahydrofuran-2-yl-1,3-benzoxazole-6-carboxylic acid (CAS RN 1499713-88-0) and BB53 | 446.4 [M + H]$^+$ | A2 (DIPEA as base) |
| 187 | 2-[4-[4-[3-(Methoxymethyl)pyroolidin-1-yl]benzoyl]piperazin-1-yl]-3H-quinazolin-4-one | 4-[3-(Methoxymethyl)pyrrolidin-1-yl]benzoic acid (MDL No. MFCD20087746) and BB53 | 448.5 [M + H]$^+$ | A2 |
| 188 | 2-[4-[2-(2,2,2-Trifluorethyl)-1,3-benzoxazole-5-carbonyl]piperazin-1-yl]-3H-quinazolin-4-one | 2-(2,2,2-Trifluoroethyl)-1,3-benzoxazole-5-carboxylic acid (MDL No.: MFCD23556505; Enamine Ltd.) and BB53 | 458.1 [M + H]$^+$ | A2 |
| 189 | 2-[4-[2-Methyl-4-(1H-pyrazol-4-ylmethoxy)-1,3-benzoxazole-6-carbonyl]piperazin-1-yl]-3H-quinazolin-4-one | 2-[4-[2-Methyl-4-[(l-tritylpyrazol-4-yl)methoxy]-1,3-benzoxazole-6-carbonyl]piperazin-1-yl]-3H-quinazolin-4-one (BB66) | 486.1 [M + H]$^+$ | H |

-continued

| Ex. | Systematic Name/Structure | Building block(s) | MS, m/z | Method |
|---|---|---|---|---|
| 190 | 2-[4-[4-[5-(1-Methylcyclopropyl)-1,2,4-oxadiazol-3-yl]benzoyl]piperazin-1-yl]-3H-quinazolin-4-one | 1-Methyl-cyclopropane-1-carboxylic acid (CAS RN 6914-76-7) and N'-Hydroxy-4-[4-(4-oxo-3H-quinazolin-2-yl)piperazine-1-carbonyl]benzamidine (BB67) | 457.4 [M + H]+ | I |
| 191 | 2-[4-[4-[5-(1-Fluoro-2-methylpropan-2-yl)-1,2,4-oxadiazol-3-yl]benzoyl]piperazin-1-yl]-3H-quinazolin-4-one | 3-Fluoro-2,2-dimethylpropanoic acid (CAS RN 64241-77-6) and N'-Hydroxy-4-[4-(4-oxo-3H-quinazolin-2-yl)piperazine-1-carbonyl]benzamidine (BB67) | 477.4 [M + H]+ | I |
| 192 | 2-Chloro-4-[6-[4-(4-oxo-3H-quinazolin-2-yl)piperazin-1-carbonyl]-1,3-benzoxazol-2-yl]benzonitrile | 2-(3-Chloro-4-cyano-phenyl)-1,3-benzoxazole-6-carboxylic acid (BB68) and 2-Piperazin-1-yl-3H-quinazolin-4-one; hydrochloride salt (BB53a) | 511.1 [M + H]+ | C (followed by prep-HPLC; TEA as base) |
| 193 | 2-[4-[4-(3-tert-Butyl-1,2,4-oxadiazol-5-yl)benzoyl]piperazin-1-yl]-3H-quinazolin-4-one | (4-(3-(tert-Butyl)-1,2,4-oxadiazol-5-yl)phenyl)(piperazin-1-yl)methanone hydrochloride (BB69) and 2-Chloroqninazolin-4(3H)-one (CAS RN 607-69-2) | 459.4 [M + H]+ | D (microwave, 100° C., 1 h) |
| 194 | 2-[4-[3-(3-tert-Butyl-1,2,4-oxadiazol-5-yl)bicyclo[1.1.1]pentane-1-carbonyl]piperazin-1-yl]-3H-quinazolin-4-one | [3-(3-tert-Butyl-1,2,4-oxadiazol-5-yl)-1-bicyclo[1.1.1]pentanyl]-piperazin-1-yl-methanone hydrochloride (BB70) and 2-Chloroquirtazolin-4(3H)-one (CAS RN 607-69-2) | 449.4 [M + H]+ | D (microwave, 100 C°., 1 h) |

| Ex. | Systematic Name/Structure | Building block(s) | MS, m/z | Method |
|---|---|---|---|---|
| 195 | 2-[4-[3-(3-Chlorophenyl)sulfonyl-3,9-diazaspiro[5.5]undecane-9-carbonyl]piperazin-1-yl]-3H-quinazolin-4-one | 3-((3-Chlorophenyl)sulfonyl)-3,9-diazaspiro[5.5]undecane hydrochloride (BB71) and 2-(Piperazin-1yl)quinazolin-4(3H)-dihydrochloride (BB53) | 585.2 [M + H]$^+$ | J |
| 196 | 2-[4-[4-(5-tert-Butyl-1,2,4-oxadiazol-3-yl)benzoyl]piperazin-1-yl]-6-chloro-3H-quinazolin-4-one | 6-Chloro-2-(piperazin-1-yl)quinazolin-4(3H)-one hydrochloride (BB48) and 4-(5-tert-Butyl-1,2,4-oxadiazol-3-yl)benzoic acid (CAS RN 1119452-72-0) | 493.4 [M + H]$^+$ | A3 (followed by MPLC chromatography) |
| 197 | 2-[4-[4-(3,3-Dimethylpyrrolidin-1yl)-benzoyl]piperazin-1-yl]-3H-quinazolin-4-one | 4-(3,3-Dimethyl-pyrrolidin-1-yl)benzoic acid (CAS RN 406234-21-7) and BB53 | 432.2 [M + H]$^+$ | A2 (precipiation with H2O) |
| 198 | 2-[4-[2-(1-Methylpyrrol-3-yl)-1,3-benzoxazole-6-carbonyl]piperazin-1-yl]-3H-quinazolin-4-one | 2-(1-Methylpyrrol-3-yl)-1,3-benzoxazole-6-carboxylic acid (BB72) and BB53 | 455.2 [M + H]$^+$ | C (followed by prep-HPLC) |
| 199 | 2-[4-[4-[5-(1-Hydroxy-2-methylpropan-2-yl)-1,2,4-oxadiazol-3-yl]benzoyl]piperazin-1-yl]-3H-quinazolin-4-one | 4-[5-(2-Hydroxy-1,1-dimethyl-ethyl)-1,2,4-oxadiazol-3-yl]benzoic acid (BB73) and BB53 | 475.2 [M + H]$^+$ | A2 (DIPEA as base; MPLC purification) |

-continued

| Ex. | Systematic Name/Structure | Building block(s) | MS, m/z | Method |
|---|---|---|---|---|
| 200 | 2-[4-[2-(8-Oxa-2-azaspiro[4.5]decan-2-yl)-1,3-benzoxazole-6-carbonyl]piperazin-1-yl]-3H-quinazolin-4-one | 2-(8-Oxa-2-azaspiro[4.5]decan-2-yl)-1,3-benzoxazole-6-carboxylic acid (BB74) and BB53 | 515.2 [M + H]$^+$ | A3 |
| 201 | 2-[4-[2-(3-Methoxypyrrolidin-1-yl)-1,3-benzoxazole-6-carbonyl]piperazin-1-yl]-3H-quinazolin-4-one | 2-(3-Methoxy-pyrrolidin-1-yl)-1,3-benzoxazole-6-carboxylic acid (BB75) and BB53 | 475.2 [M + H]$^+$ | A3 |
| 202 | 2-[4-[2-(6,6-Difluoro-2-azaspiro[3.3]heptan-2-yl)-1,3-benzoxazole-6-carbonyl]piperazin-1-yl]-3H-quinazolin-4-one | 2-(6,6-Difluoro-2-azaspiro[3.3]heptan-2-yl)-1,3-benzoxazole-6-carboxylic acid (BB76) and BB53 | 507.2 [M + H]$^+$ | A3 |
| 203 | 2-[4-[2-(2-Azaspiro[3.4]octan-2-yl)-1,3-benzoxazole-6-carbonyl]piperazin-1-yl]-3-methylquinazolin-4-one | 3-Methyl-2-piperazin-1-yl-quinazolin-4-one (MDL No.: MFCD11107655; Princeton BioMolecular Research) and 2-(2-Azaspiro[3.4]octan-2-yl)-1,3-benzoxazole-6-carboxylic acid (BB52) | 499.2 [M + H]$^+$ | A3 (MPLC purification) |
| 204 | 2-[4-[2-(2-Azaspiro[3.3]heptan-2-yl)-1,3-benzoxazole-6-carbonyl]piperazin-1-yl]-3H-quinazolin-4-one | 2-(2-Azaspiro[3.3]heptan-2-yl)-1,3-benzoxazole-6-carboxylic acid (BB77) and BB53 | 471.2 [M + H]$^+$ | A3 |

-continued

| Ex. | Systematic Name/Structure | Building block(s) | MS, m/z | Method |
|---|---|---|---|---|
| 205 | 2-[4-[2(6-Hydroxy-2-azaspiro[3.3]heptan-2-yl)-1,3-benzoxazole-6-carbonyl]piperazin-1-yl]-3H-quinazolin-4-one | 2-(6-Hydroxy-2-azaspiro[3.3]heptan-2-yl)-1,3-benzoxazole-6-carboxylic acid (BB78) and BB53 | 487.2 [M + H]⁺ | A3 |
| 206 | 2[4-[2-(3-Hydroxy-3-methylpyrrolidin-1-yl)-1,3-benzoxazole-6-carbonyl]piperazin-1-yl]-3H-quinazolin-4-one | 2-(3-Hydroxy-3-methyl-pyrrolidin-1-yl)-1,3-benzoxazole-6-carboxylic acid (BB79) and BB53 | 475.2 [M + H]⁺ | A3 (MPLC purification) |
| 207 | 2-[4-[2-(3-Fluoro-3-methylpyrrolidin-1-yl)-1,3-benzoxazole-6-carbonyl]piperazin-1-yl]-3H-quinazolin-4-one | 2-(3-Fluoro-3-methyl-pyrrolidin-1,3-benzoxazole-6 carboxylic acid (BB80) and BB53 | 477.2 [M + H]⁺ | A3 (precipiation followed by MPLC purification) |
| 208 | 2-[4-[2-[3-(2-Hydroxypropan-2-yl)pyrrolidin-1-yl]-1,3-benzoxazole-6-carbonyl]piperazin-1-yl]-3H-quinazolin-4-one | 2-[3-(1-Hydroxy-1-methyl-ethyl)pyrrolidin-1-yl]-1,3-benzoxazole-6 carboxylic acid (BB81) and BB53 | 503.2 [M + H]⁺ | A3 |
| 209 | 2-[4-[2-(6-Azaspiro[3.4]octan-6-yl)-1,3-benzoxazole-6-carbonyl]piperazin-1-yl]-3-methylquinazolin-4-one | 2-(6-Azaspiro[3.4]octan-6-yl)-1,3-benzoxazole-6-carboxylic acid (BB82) and 3-Methyl-2-piperazin-1-yl-quinazolin-4-one (MDL No.: MFCD11107655; Princeton BioMolecular Research) | 499.2 [M + H]⁺ | A3 |

-continued

| Ex. | Systematic Name/Structure | Building block(s) | MS, m/z | Method |
|---|---|---|---|---|
| 210 | 2-[4-[2-(6-Azaspiro[3.4]octan-6-yl)-1,3-benzoxazole-6-carbonyl]piperazin-1-yl]-3H-quinazolin-4-one | BB 82 and BB53 | 485.2 [M + H]⁺ | A3 (followed by MPLC purification) |
| 211 | 2-[4-[4-[5-(2-Methyl-1-phenylmethoxypropan-2-yl)-1,2,4-oxadiazol-3-yl]benzoyl]piperazin-1-yl]-3H-quinazolin-4-one | 4-[5-(2-Benzyloxy-1,1-dimethyl-ethyl)-1,2,4-oxadiazol-3-yl]benzoic acid (BB83) and BB53 | 565.3 [M + H]⁺ | A3 |
| 212 | 2-[4-[4-(3-Hydroxy-3-methylbut-1-ynyl)benzoyl]piperazin-1-yl]-3H-quinazolin-4-one | 4-(3-Hydroxy-3-methyl-but-1-ynyl)benzoic acid (CAS RN: 63165-02-6) and BB53 | 417.4 [M + H]⁺ | A2 |
| 213 | 2-[4-[4-(3,3-Diethylpyrrolidin-1-yl)benzoyl]piperazin-1-yl]-3H-quinazolin-4-one | 4-(3,3-Diethyl-pyrrolidin-1-yl)benzoic acid (MDL No.: MFCD23395109; Enamine Ltd.) and BB53 | 460.3 [M + H]⁺ | A2 |

-continued

| Ex. | Systematic Name/Structure | Building block(s) | MS, m/z | Method |
|---|---|---|---|---|
| 214 | 2-[4-[2-(4-Chlorophenyl)sulfonyl-2,7-diazaspiro[4.4]nonane-7-carbonyl]piperazin-1-yl]-3H-quinazolin-4-one | 2-[4-(2,7-Diazaspiro[4.4]nonane-2-carbonyl)piperazin-1-yl]-3H-quinazolin-4-one (BB84) and 4-Chlorobenzenesulfonyl chloride (CAS RN 98-60-2) | 557.2 [M + H]$^+$ | K |
| 215 | 2-[4-[2-(3-Chlorophenyl)sulfonyl-2,7-diazaspiro[4.4]nonane-7-carbonyl]piperazin-1-yl]-3H-quinazolin-4-one | 2-[4-(2,7-Diazaspiro[4.4]nonane-2-carbonyl)piperazin-1-yl]-3H-quinazolin-4-one (BB84) and 3-Chlorobenzenesulfonyl chloride (CAS RN 2888-60-4) | 557.2 [M + H]$^+$ | K |
| 216 | 2-[4-[7-(3-Chlorophenyl)methyl]-2,7-diazaspiro[4.4]nonane-2-carbonyl]piperazin-1-yl]-3H-quinazolin-4-one | 2-[4-(2,7-Diazaspiro[4.4]nonane-2-carbonyl)piperazin-1-yl]-3H-quinazolin-4-one (BB84) and 3-Chlorobenzenzaldehyde (CAS RN 587-04-2) | 507.2 [M + H]$^+$ | L |

Synthesis of Building Blocks
BB1

4-[2-[[3-(Trifluoromethyl)phenyl]methylamino]ethyl]benzoic acid

To a stirred solution of methyl 4-[2-[acetyl-[[3-(trifluoromethyl) phenyl]methyl]amino]ethyl]benzoate (550.0 mg, 1.45 mmol) in THF (6 mL), MeOH (2 mL), H$_2$O (2 mL) was added LiOH. H$_2$O (182.5 mg, 4.35 mmol, CAS RN 1310-66-3) and was stirred at 25° C. for 16 h. After completion of the reaction (monitored by TLC), the reaction mixture was evaporated to dryness. The residue was diluted with H$_2$O and neutralised with a citric acid solution. The mixture was extracted with EtOAc. The organic layers were dried over Na$_2$SO$_4$ and concentrated under reduced pressure to afford a light brown gum. (520 mg, 1.42 mmol). $^1$H NMR (400 MHz, DMSO-d$_6$) δ 12.66 (s, 1H), 7.85 (t, J=7.6 Hz, 1H), 7.68-7.57 (m, 1H), 7.55 (s, 1H), 7.33 (dd, J=21.3, 8.0 Hz, 1H), 4.64 (d, J=11.8 Hz, 1H), 3.55-3.46 (m, 1H), 3.32 (s, 2H), 2.95-2.79 (m, 1H), 1.99 (d, J=4.6 Hz, 1H), 1.93 (d, J=17.1 Hz, 2H). MS (ESI): m/z=366.0 [M+H]$^+$.

Intermediates a) Methyl 4-[2-[acetyl-[[3-(trifluoromethyl) phenyl]methyl]amino]ethyl]benzoate To a stirred solution of methyl 4-[2-[[3-(trifluoromethyl) phenyl]methylamino]ethyl]benzoate (700.0 mg, 2.08 mmol) in DCM (10 mL) were added TEA (0.87 mL, 6.23 mmol, CAS RN 121-44-8) and acetic anhydride (0.25 mL, 2.7 mmol, CAS RN 108-24-7). The reaction mixture was stirred at 25° C. for 16 h. After completion of the reaction (monitored by TLC), it was diluted with DCM (20 mL) and washed with $H_2O$. The organic layer was dried over $Na_2SO_4$ and concentrated under reduced pressure. The crude product was purified under silica gel column chromatography by using 40-45% EtOAc in n-hexane to afford a light brown gum (550 mg, 1.45 mmol). $^1$H NMR (400 MHz, DMSO-$d_6$) δ 7.87 (t, J=7.7 Hz, 1H), 7.67-7.48 (m, 2H), 7.36 (dd, J=21.4, 7.7 Hz, 1H), 4.63 (d, J=11.5 Hz, 1H), 3.50 (q, J=9.6, 8.6 Hz, 1H), 3.32 (s, 1H), 2.96-2.81 (m, 1H), 1.97 (d, J=17.7 Hz, 1H). MS (ESI): m/z=380.2 [M+H]$^+$.

b) 4-[2-[[3-(Trifluoromethyl)phenyl]methylamino] ethyl]benzoate

To a stirred solution of methyl 4-(2-aminoethyl) benzoate (0.04 mL, 2.93 mmol, CAS RN 77265-67-9) in DCM (10 mL) was added 3-(trifluoromethyl) benzaldehyde (425.0 mg, 2.44 mmol, CAS RN 454-89-7) and the solution was stirred at 25° C. for 30 min. After that, one drop of acetic acid was added and stirring continued for 30 min. Sodium triacetoxyborohydride (1.29 g, 6.1 mmol, CAS RN 56553-60-7) was added and the reaction mixture was stirred at 25° C. for 6 h. After completion of the reaction, it was diluted with DCM, washed with aqueous solution of $NaHCO_3$ and $H_2O$, dried over $Na_2SO_4$ and concentrated under reduced pressure to afford a light brown semi solid (700 mg, 2.08 mmol). $^1$H NMR (400 MHz, DMSO-$d_6$) δ 7.84 (dd, J=17.9, 7.9 Hz, 2H), 7.66-7.45 (m, 4H), 7.35 (d, J=7.9 Hz, 2H), 7.23 (d, J=8.3 Hz, OH), 3.79 (s, 2H), 3.69 (s, 1H), 2.89 (s, OH), 2.83-2.70 (m, 4H), 1.87 (s, 6H), 1.26-1.13 (m, 1H). MS (ESI): m/z=337.8 [M+H]$^+$.

BB2

Ethyl 4-[(E)-2-(3-fluorophenyl)vinyl]benzoate

To a solution of ethyl 4-[(E)-2-(3-fluorophenyl)vinyl] benzoate (816 mg, 3 mmol) in THF (5 mL) was added aq. 1M NaOH solution (4.5 mL, 4.5 mmol) and the reaction mixture was stirred at RT for 5 h. The reaction mixture was acidified with aq. 1M HCl solution and resulting precipitate was filtered off. The filter cake was washed with $H_2O$ and heptane to give a white solid (0.515 g, 2.13 mmol). MS (ESI): m/z=241.1 [M–H]$^-$.

Intermediate: Ethyl 4-[(E)-2-(3-fluorophenyl)vinyl]benzoate

To an ice-cold suspension of NaH, 55% suspension in mineral oil (0.406 g) in DMF (10 mL) was added ethyl 4-diethoxyphosphorylbenzoate (6.16 g, 20.5 mmol, CAS RN 71441-08-2) in portions and the mixture was stirred at RT for 1.5 h. After cooling down to –10° C., a solution of 3-fluorobenzaldehyde (1.5 g, 12.1 mmol, CAS RN 456-48-4) in DMF (5 mL) was added dropwise. Stirring was continued for 30 min. at 0° C., then allowed to warm up to RT under stirring overnight. The reaction mixture was treated with ice-water and the resulting precipitate was filtered off to give an off-white solid (3.18 g, 11.76 mmol). The crude product was used for the next step without further purification.

BB3

(1-(4-Fluorophenyl)-1H-indole-5-carboxylic acid)

Methyl 1-(4-fluorophenyl)-1H-indole-5-carboxylate (330 mg, 1.23 mmol) was dissolved in THF (3.06 mL), whereupon $H_2O$ (3.06 mL) was added. To this solution, LiOH (117 mg, 4.9 mmol) was added and the reaction mixture was heated to 55° C. for 18 hrs. After this, the reaction mixture was adjusted to a pH of approx. 3, whereupon the formation of a white solid was noted. This white slurry was filtered off and washed with $H_2O$, before being dried in vacuo to remove excess $H_2O$, yielding a white powder (294.6 mg, 1.15 mmol). $^1$H NMR (300 MHz, DMSO-$d_6$) δ 12.61 (br s, 1H), 8.33 (d, J=1.21 Hz, 1H), 7.81 (dd, J=1.61, 8.86 Hz, 1H), 7.74 (d, J=3.43 Hz, 1H), 7.63-7.69 (m, 2H), 7.53 (d, J=8.86 Hz, 1H), 7.40-7.48 (m, 2H), 6.85 (dd, J=0.60, 3.43 Hz, 1H). MS (ESI): m/z=256.1 [M+H]$^+$.

Intermediate: Methyl 1-(4-fluorophenyl)-1H-indole-5-carboxylate

1-Fluoro-4-iodobenzene (1.32 mL, 11.4 mmol, CAS RN 352-34-1), (1R,2R)—N,N'-dimethyl-1,2-cyclohexanediamine (270 μL, 1.71 mmol, CAS RN 68737-65-5) and CuI (109 mg, 571 μmol, CAS RN 7681-65-4) were added to a suspension of methyl 1H-indole-5-carboxylate (1 g, 5.71 mmol, CAS RN 1011-65-0) in toluene (8 mL) at RT. The reaction mixture was heated at 85° C. for 21 hrs. The reaction was then diluted with DCM, filtered through a 40 μm silica pad before being concentrated in vacuo with silica and purified via flash column chromatography ($SiO_2$, 40 g, 100-200 mesh, Eluent: Hep:EtOAc 9:1, gradient over 13 min., total run time 25 min.) yielding a white solid (0.522 g, 1.94 mmol). $^1$H NMR (300 MHz, DMSO-$d_6$) δ 8.36 (d, J=1.21 Hz, 1H), 7.82 (dd, J=1.71, 8.76 Hz, 1H), 7.76 (d, J=3.22 Hz, 1H), 7.62-7.69 (m, 2H), 7.55 (d, J=8.87 Hz, 1H), 7.41-7.48 (m, 2H), 6.86-6.89 (m, 1H), 3.87 (s, 3H). MS (ESI): m/z=270.1 [M+H]$^+$.

BB4

4-((2-Iodobenzyl)amino)benzoic acid

4-Aminobenzoic acid (118 mg, 862 μmol, CAS RN 150-13-0) was suspended in DCM (6.9 mL) at RT, whereupon 2-iodobenzaldehyde (200 mg, 862 μmol, CAS RN 26260-02-6) and AcOH (49.3 μl, 862 μmol, CAS RN 64-19-7) were added. The reaction mixture was allowed to stir for 4 h before the addition of sodium triacetoxyborohydride (274 mg, 1.29 mmol, CAS RN 56553-60-7), after which the reaction mixture was stirred for an additional 18 h. The reaction mixture was diluted with EtOAc and poured into a 100 mL separating funnel containing EtOAc (50 mL) and $H_2O$ (25 mL) The aqueous layer was extracted with EtOAc (3×30 mL), before the combined organic layers were dried over $Na_2SO_4$, filtered and concentrated in vacuo. The crude product (358 mg) was purified via flash column chromatography ($SiO_2$, 12 g, 100-200 mesh, Eluent: DCM:MeOH, 100:0 to 9:1 gradient over 25 min.), and fractions containing the product were combined and concentrated in vacuo to yield a pale yellow solid (204.5 mg, 567 μmol). $^1$H NMR (600 MHz, DMSO-$d_6$) δ ppm 11.99 (br s, 2H), 7.88 (dd, J=7.8, 1.2 Hz, 1H), 7.66 (d, J=9.0 Hz, 2H), 7.33-7.40 (m, 1H), 7.28 (dd, J=7.7, 1.6 Hz, 1H), 7.01-7.08 (m, 2H), 6.51-6.58 (m, 3H), 5.86 (br s, 1H), 4.26 (d, J=5.7 Hz, 2H). MS (ESI): m/z=354.0 [M+H]$^+$.

BB5

3-(Benzyloxy)benzoic acid

Methyl 3-(benzyloxy)benzoate (101 mg, 417 μmol) was dissolved in THF (2.78 mL) at RT, whereupon LiOH (1.04 mL, 1.67 mmol, CAS RN 1310-65-2) was added. The reaction was stirred at RT for 20 h, acidified to approximately pH 3 and then poured into a 100 mL separating funnel containing EtOAc (50 mL). The aqueous layer was extracted (2×40 mL) and the solution concentrated in vacuo to yield a yellow solid (86.6 mg, 372 µmol). $^1$H NMR (300 MHz, DMSO-$d_6$) δ 7.50-7.57 (m, 2H), 7.23-7.49 (m, 7H), 5.15-5.18 (m, 2H). MS (ESI): m/z=227.1 [M−H]$^+$.

Intermediate: Methyl 3-(benzyloxy)benzoate

Methyl 3-hydroxybenzoate (225 mg, 1.48 mmol, CAS RN 19438-10-9) was dissolved in ACN (7.39 mL) at RT, whereupon NaH, 55% in mineral oil (71 mg, 1.77 mmol, CAS RN 7646-69-7) was added slowly. The reaction mixture was allowed to stir for 15 min. before the addition of benzyl bromide (253 mg, 176 µl, 1.48 mmol, 100-39-0). The reaction mixture was then stirred at RT for 1 h before another batch of benzyl bromide (52.7 µl, 444 µmol, CAS RN 100-39-0) was added and the reaction left stirring at RT overnight. After 18 h the reaction mixture was diluted with EtOAc, before being poured into a 100 mL separating funnel containing EtOAc (50 mL) and H$_2$O (20 mL). The aqueous layer was extracted with EtOAc (3×40 mL), before being dried over Na$_2$SO$_4$, filtered and concentrated in vacuo to yield a crude residue, which was then purified via flash column chromatography (SiO$_2$, 12 g, 100-200 mesh, Eluent: n-Hep:EtOAc, 100:0 to 1:1 gradient over 25 mins, total run time 30 mins.). to yield a white solid (248.7 mg, 1.01 mmol). $^1$H NMR (300 MHz, DMSO-$d_6$) δ 7.52-7.58 (m, 2H), 7.28-7.49 (m, 7H), 5.16-5.19 (m, 2H), 3.84-3.86 (m, 3H). MS (ESI): m/z=243.1 [M+H]$^+$.

BB6

4-((2-(Trifluoromethoxy)benzyl)amino)benzoic acid

The desired compound was obtained in analogy to BB4, using 4-aminobenzoic acid (118 mg, 862 µmol, CAS RN 150-13-0) and 2-(trifluoromethoxy)benzaldehyde (200 mg, 862 µmol, CAS RN 94651-33-9 as a white solid (192.4 mg, 0.40 mmol). $^1$H NMR (600 MHz, DMSO-$d_6$) δ ppm 7.66 (d, J=9.0 Hz, 2H), 7.31-7.47 (m, 4H), 7.02 (t, J=6.0 Hz, 1H), 6.56 (d, J=8.9 Hz, 2H), 4.40 (d, J=5.8 Hz, 2H). MS (ESI): m/z=320.0 [M+H]$^+$.

BB7

3-(Cyclopentylmethoxy)benzoic acid

The desired compound was obtained in analogy to BB5 (saponification), using (methyl 3-(cyclopentylmethoxy)benzoate (60.4 mg, 258 µmol) as a white solid (50.5 mg, 0.22 mmol)$^1$H NMR (300 MHz, DMSO-$d_6$) δ 12.77-13.17 (m, 1H), 7.49-7.54 (m, 1H), 7.36-7.44 (m, 2H), 7.15-7.20 (m, 1H), 3.86-3.92 (m, 2H), 2.25-2.37 (m, 1H), 1.71-1.85 (m, 2H), 1.48-1.67 (m, 4H), 1.27-1.40 (m, 2H). MS (ESI): m/z=221.1 [M+H]$^+$.

Intermediate: Methyl 3-(cyclopentylmethoxy)benzoate

Methyl 3-hydroxybenzoate (291.3 mg, 1.91 mmol, CAS RN 19438-10-9) was dissolved in ACN (7.66 mL) at RT, whereupon NaH, 55% in mineral oil (91.9 mg, 2.3 mmol, CAS RN 7646-69-7) was added slowly. The reaction mixture was allowed to stir for 15 mins before the addition of (iodomethyl)cyclopentane (280 µl, 2.11 mmol, CAS RN 27935-87-1). The reaction mixture was stirred at 60° C. for 3 days. After this time the reaction mixture was diluted with EtOAc and poured into a 100 mL separating funnel containing EtOAc (50 mL) and H$_2$O (20 mL). The aqueous layer was extracted with EtOAc (3×40 mL), before the combined organic phases were dried over Na$_2$SO$_4$, filtered and concentrated in vacuo to yield a crude residue, which was then purified via flash column chromatography (SiO$_2$, 100-200 mesh, 12 g, Eluent: n-Hep:EtOAc, 100:0 to 1:1 gradient over 25 mins, total run time 30 mins.). Fractions containing product were combined and concentrated in vacuo to yield a colourless viscous oil (71.3 mg, 0.31 mmol). $^1$H NMR (300 MHz, CHLOROFORM-d) δ 7.59-7.63 (m, 1H), 7.54-7.56 (m, 1H), 7.29-7.36 (m, 1H), 7.07-7.12 (m, 1H), 3.91 (s, 3H), 3.85-3.89 (m, 2H), 2.29-2.45 (m, 1H), 1.79-1.92 (m, 2H), 1.56-1.67 (m, 4H), 1.30-1.43 (m, 2H). MS (ESI): m/z=235.1 [M+H]$^+$.

BB8

N-Benzyl-N-[2-[4-(piperazine-1-carbonyl)phenyl]ethyl]acetamide hydrochloride

To a solution of tert-butyl 4-[4-[2-[acetyl(benzyl)amino]ethyl]benzoyl]piperazine-1-carboxylate (500.0 mg, 1.07 mmol) in dry DCM (5 mL) was added 4N HCl in dioxane (5.0 mL, 1.07 mmol, CAS RN 7647-01-0) and the reaction mixture was stirred at 25° C. for 16 h in a sealed tube. The reaction mixture was concentrated to dryness to get a light green solid (420 mg, 1.04 mmol). MS (ESI): m/z=366 [M+H]$^+$.

Intermediates a) tert-Butyl 4-[4-[2-[acetyl(benzyl)amino]ethyl]benzoyl]piperazine-1-carboxylate To a suspension of NaH (0.13 g, 5.33 mmol) in dry DMF (20 mL) was added benzyl bromide (0.48 mL, 4 mmol, CAS RN 100-39-0) in DMF (2 mL) and the mixture was stirred for 15 min. Then tert-butyl 4-[4-(2-acetamidoethyl)benzoyl]piperazine-1-carboxylate (1.0 g, 2.66 mmol) was added drop wise and the reaction stirred at 25° C. for 16 h. After completion of the reaction, it was quenched with saturated NH$_4$Cl solution and extracted with EtOAC (2×10 mL). The combined organic layer was washed with H$_2$O, brine, dried over Na$_2$SO$_4$ and concentrated to dryness to get a light brown solid (571 mg, 1.23 mmol). $^1$H NMR (DMSO-$d_6$, 400 MHz): 1.40 (s, 9H), 1.96-2.01 (m, 2H), 2.72-2.88 (m, 6H), 3.31-3.52 (m, 7H), 4.54 (s, 2H), 7.20-7.39 (m, 9H). MS (ESI): m/z=466 [M+H]$^+$.

b) tert-Butyl 4-[4-(2-acetamidoethyl)benzoyl]piperazine-1-carboxylate

To a stirred solution of 4-(2-acetamidoethyl)benzoic acid (2.0 g, 9.65 mmol) in dry DMF (40 mL) was added DIPEA (5.04 mL, 28.95 mmol) and HBTU (7.32 g, 19.3 mmol, CAS RN 94790-37-1) at 25° C. and was stirred for 30 min. After that 1-Boc-piperazine (1.98 g, 10.62 mmol, CAS RN 57260-71-6) was added in one portion and the reaction mixture was stirred at 25° C. for 16 h. The reaction mixture was diluted with EtOAc and washed with Na$_2$HCO$_3$ solution and H$_2$O. The organic layer was separated off, dried over Na$_2$SO$_4$ and concentrated under reduced pressure. The crude product was purified under column (100-200 mesh, silica gel) chromatography by using 80-85% EtOAc in n-hexane to afford a light brown gum (3.1 g, 8.26 mmol). $^1$H NMR (DMSO-$d_6$, 400 MHz): 1.41 (s, 9H), 2.68-2.91 (m, 8H), 3.12-3.62 (m, 7H), 7.27 (d, J=7.7 Hz, 2H), 7.33 (d, J=7.6 Hz, 2H). MS (ESI): m/z=376.1 [M+H]⁺.

c) 4-(2-Acetamidoethyl)benzoic acid

To a stirred solution of methyl 4-(2-acetamidoethyl)benzoate (3.9 g, 17.63 mmol) in THF (40 mL), MeOH (10 mL) H2O (4 mL) was added LiOH.H$_2$O (2.22 g, 52.88 mmol, CAS RN 1310-66-3) and was stirred at 25° C. for 16 h. After completion of reaction (as monitored by TLC), volatiles were evaporated to dryness, diluted with H2O and neutralized with citric acid solution and extracted with 10% MeOH/DCM (2×100 mL). The combined organic layers were dried over Na$_2$SO$_4$ and concentrated under reduced pressure to get 4-(2-acetamidoethyl) benzoic acid (3.2 g, 15.44 mmol) as a light brown gum. ¹H NMR (DMSO-d$_6$, 400 MHz): 1.77 (s, 3H), 2.76 (t, J=6.9 Hz, 2H), 3.25-3.34 (m, 2H), 7.31 (d, J=7.8 Hz, 2H), 7.86 (d, J=7.8 Hz, 2H), 12.8 (s, 1H). MS (ESI): m/z=208 [M+H]⁺.

d) Methyl 4-(2-acetamidoethyl)benzoate

To a stirred solution of methyl 4-(2-aminoethyl)benzoate (3.8 g, 21.2 mmol, CAS RN 77265-67-9) in DCM (40 mL) was added triethyl amine (4.43 mL, 31.8 mmol) and acetic anhydride (2.0 mL, 21.2 mmol, CAS RN 108-24-7), and was stirred at 25° C. for 16 h. After completion of reaction (monitored by TLC) it was diluted with DCM (50 mL) and washed with H$_2$O, dried over Na$_2$SO$_4$ and concentrated under reduced pressure to yield methyl 4-(2-acetamidoethyl) benzoate (4.1 g, 18.5 mmol, 77.8% yield) as a light brown gum which was directly used in next step without further purification. ¹H NMR (400 MHz, DMSO-d6) δ ¹H NMR (DMSO-d$_6$, 400 MHz): 1.76 (s, 2H), 2.77 (t, J=7.1 Hz, 2H), 3.25-3.30 (m, 2H), 3.83 (s, 3H), 7.34 (d, J=7.9 Hz, 2H), 7.88 (d, J=8.0 Hz, 2H). MS (ESI): m/z=222.0 [M+H]⁺.

BB9

(Rac, cis)-4-(2-phenylcyclopropyl)benzoic acid

The desired compound was obtained in analogy to BB5, using methyl 4-((rac, cis)-2-phenylcyclopropyl)benzoate (47.7 mg, 189 µmol), as an off-white solid (32.7 mg, 131 µmol). ¹H NMR (300 MHz, DMSO-d$_6$) δ 12.47-12.90 (m, 1H), 7.60-7.65 (m, 2H), 6.98-7.13 (m, 7H), 2.54-2.63 (m, 2H), 1.59-1.67 (m, 1H), 1.41-1.50 (m, 1H). MS (ESI): m/z=239.1 [M+H]⁺.

Intermediate: (Rac, cis)-4-(2-phenylcyclopropyl)benzoate

Methyl 4-formylbenzoate (400 mg, 2.44 mmol, CAS RN 1571-08-0) was dissolved in dry dioxane (8 mL) at RT, whereupon N-tosylhydrazine (454 mg, 2.44 mmol, CAS RN 1576-35-8) was added. The reaction was heated to 70° C. with a condenser attached for 1 h, after which complete formation of the hydrazone intermediate was noted. After this time, K$_2$CO$_3$ (505 mg, 3.66 mmol, CAS RN 584-08-7) and styrene (564 µl, 4.87 mmol, CAS RN 100-42-5) were added, along with additional dry dioxane (16 mL). The reaction mixture was then heated to 110° C. for an additional 6 h, after which the reaction mixture was allowed to cool to RT and concentrated in vacuo before being taken up in EtOAc, filtered through a celite pad and concentrated in vacuo to yield a crude yellow oil (745.2 mg). The crude residue was purified via flash column chromatography (SiO$_2$, 100-200 mesh, 40 g, Eluent: 0-66% EtOAc in n-heptane over 25 mins.) Fractions containing the product were combined and concentrated in vacuo to yield a clear viscous oil (153.9 mg) in a diastereoisomeric ratio of 3:1. The mixture was separated by SFC, which produced methyl 4-(rac, cis)-(2-phenylcyclopropyl)benzoate as a pale yellow il (50.4 mg, 0.19 mmol). ¹H NMR (600 MHz, CHLOROFORM-d) δ ppm 7.93-7.98 (m, 2H), 7.28-7.32 (m, 2H), 7.19-7.22 (m, 1H), 7.16-7.21 (m, 2H), 7.12-7.16 (m, 2H), 3.91 (s, 3H), 2.22-2.26 (m, 1H), 2.18-2.22 (m, 1H), 1.53-1.56 (m, 3H), 1.48-1.57 (m, 5H). MS (ESI): m/z=253.1 [M+H]⁺.

BB10

(Rac, trans)-4-(2-phenylcyclopropyl)benzoic acid

The desired compound was obtained in analogy to BB5, using methyl 4-((rac, trans)-2-phenylcyclopropyl)benzoate (34.7 mg, 138 µmol) as an off-white solid (37.5 mg, 134 µmol). ¹H NMR (300 MHz, DMSO-d$_6$) δ 12.73-12.83 (m, 1H), 7.82-7.88 (m, 2H), 7.25-7.32 (m, 4H), 7.13-7.21 (m, 3H), 2.25-2.32 (m, 2H), 1.50-1.59 (m, 2H). MS (ESI): m/z=239.1 [M+H]⁺.

Intermediate: (Rac, trans)-4-(2-phenylcyclopropyl)benzoate

The desired compound was obtained in analogy to intermediate BB9 as a pale yellow oil (36.0 mg, 0.15 mmol). ¹H NMR (600 MHz, CHLOROFORM-d) δ ppm 7.73-7.76 (m, 2H), 7.07-7.12 (m, 2H), 7.03-7.07 (m, 1H), 6.96-6.97 (m, 4H), 6.94-6.96 (m, 5H), 6.94-6.97 (m, 4H), 3.84 (s, 3H), 2.55-2.63 (m, 1H), 2.47-2.53 (m, 1H), 1.51-1.53 (m, 1H), 1.45 (q, J=6.3 Hz, 1H). MS (ESI): m/z=239.1 [M+H]⁺.

BB11

4-(2-((3-(Trifluoromethyl)benzyl)oxy)ethyl)benzoic acid

The desired compound was obtained in analogy to BB5, using 4-[2-[[3-(trifluoromethyl)phenyl]methoxy]ethyl]benzoate (86.5 mg, 268 µmol) as a white solid (79.0 mg, 249.2 µmol) ¹H NMR (300 MHz, DMSO-d$_6$) δ 12.47-13.21 (m, 1H), 12.87 (br s, 1H), 7.83-7.89 (m, 2H), 7.54-7.65 (m, 4H), 7.34-7.39 (m, 2H), 4.57-4.59 (m, 2H), 3.69-3.75 (m, 2H), 2.92-2.98 (m, 2H). MS (ESI): m/z=283.1 [M–H]⁻.

Intermediate: 4-[2-[[3-(Trifluoromethyl)phenyl] methoxy]ethyl]benzoate

Methyl 4-(2-hydroxyethyl)benzoate (284.8 mg, 1.58 mmol, CAS RN 46190-45-8) was dissolved in acetonitrile (6.32 mL) at RT, whereupon NaH, 60% dispersion in mineral oil (75.9 mg, 1.9 mmol, CAS RN 7646-69-7) was added slowly. The resulting solution was allowed to stir for 30 mins before the addition of 3-(trifluoromethyl)benzyl bromide (378 mg, 241 µl, 1.58 mmol, CAS RN 402-23-3), after which the reaction mixture was then stirred at 45° C. for 3 days. The reaction mixture was then poured into a 100 mL separating funnel containing EtOAc (50 mL) and H$_2$O (25 mL). The aqueous layer was extracted with EtOAc (3×50 mL), dried over Na$_2$SO$_4$, filtered and concentrated in vacuo. The crude residue (viscous yellow oil (483 mg)) was taken up in EtOAc and concentrated in vacuo with silica, before being purified via flash column chromatography (SiO$_2$, 40 g, 100-200 mesh, Eluent: Hep:EtOAc, 100:0 to 2:1 over 25 min.) fractions containing the product were combined and concentrated in vacuo to yield a colourless viscous oil (94 mg, 0.27 mmol). $^1$H NMR (300 MHz, CHLOROFORM-d) δ 7.95-8.00 (m, 2H), 7.49-7.56 (m, 2H), 7.41-7.47 (m, 2H), 7.28-7.33 (m, 2H), 4.53-4.57 (m, 2H), 3.91 (s, 3H), 3.70-3.77 (m, 2H), 2.96-3.03 (m, 2H). MS (ESI): m/z=339.1 [M+H]$^+$.

BB12

1-(4-Fluorophenyl)-1H-indazole-5-carboxylic acid

To a stirred solution of methyl 1-(4-fluorophenyl) indazole-5-carboxylate (350.0 mg, 1.3 mmol) in THF (6 mL), MeOH (2 mL), H$_2$O (2 mL) was added LiOH.H$_2$O (163 mg, 3.89 mmol, CAS RN 1310-66-3). The reaction mixture was stirred at 25° C. for 16 h. The reaction mixture was concentrated in vacuo, diluted with H$_2$O and neutralized with citric acid solution and then extracted with EtOAc (3×30 mL). The combined organic layers were dried over Na$_2$SO$_4$ and concentrated under reduced pressure to afford a light brown gum (330 mg, 1.29 mmol). MS: (ESI): m/z=255.1 [M–H]$^-$.

Intermediate: Methyl 1-(4-fluorophenyl)-1H-indazole-5-carboxylate

To a suspension of methyl 1H-indazole-5-carboxylate (100.0 mg, 0.570 mmol, CAS RN 473416-12-5) in toluene (10 mL) was added 4-fluoroiodobenzene (138.62 mg, 0.620 mmol, CAS RN 352-34-1), trans-N,N'-Dimethylcyclohexane-1,2-diamine (24.22 mg, 0.170 mmol, CAS RN 67579-81-1), K$_3$PO$_4$ (361.47 mg, 1.7 mmol, CAS RN 7778-53-2) and CuI, 99% (10.81 mg, 0.060 mmol, CAS RN 7681-65-4) successively. The reaction mixture was heated to 110° C. for 4 h. The reaction mixture was diluted with CH$_2$Cl$_2$ (20 mL), filtered through the bed of celite and concentrated to get crude residue which was purified via combiflash column (SiO$_2$, 100-200 mesh) using 10% EtOAc in n-hexane as eluent to get methyl 1-(4-fluorophenyl) indazole-5-carboxylate (60 mg, 0.220 mmol) as an off white solid $^1$H NMR (400 MHz, DMSO-d$_6$) δ 8.58 (d, J=13.4 Hz, 2H), 8.04 (d, J=8.9 Hz, 1H), 7.89-7.78 (m, 3H), 7.46 (t, J=8.6 Hz, 2H), 3.32 (s, 3H). MS: (ESI): m/z=271.1 [M+H]$^+$.

BB13

2-Phenyl-1H-1,3-benzimidazole-5-carboxylic acid

To a stirred solution of methyl 2-phenyl-1H-benzimidazole-5-carboxylate (1.0 g, 3.96 mmol) in THF (9 mL), MeOH (3 mL), H$_2$O (3 mL) was added LiOH. H$_2$O (0.5 g, 11.89 mmol, CAS RN 1310-66-3) and stirred at 25° C. for 16 h. The reaction mixture was concentrated in vacuo. The residue was diluted with H$_2$O and neutralized with citric acid solution. The precipitate was filtered off through a sintered funnel and the solids were washed with H$_2$O, dried under reduced pressure to afford an off-white solid (900 mg, 3.78 mmol). $^1$H NMR (400 MHz, DMSO-d$_6$) δ 13.20 (s, 1H), 8.26-8.17 (m, 3H), 7.89-7.82 (m, 1H), 7.64 (d, J=8.3 Hz, 1H), 7.56 (dt, J=13.2, 6.6 Hz, 3H). MS: (ESI): m/z=237.1 [M–H]$^-$.

Intermediate: Methyl 2-phenyl-1H-benzimidazole-5-carboxylate

To a stirred solution of benzaldehyde (0.73 mL, 7.22 mmol, CAS RN 100-52-7) and methyl 3,4-diaminobenzoate (1.0 g, 6.02 mmol, CAS RN 36692-49-6) in DMF (10 mL) was added sodium metabisulfite (1.93 mL, 15.04 mmol, CAS RN 7681-57-4) and the reaction was stirred at 110° C. for 16 h. Then the reaction mixture was poured onto ice-water. The precipitate was collected and washed with H$_2$O. The solids were dried under reduced pressure to afford a light brown solid (1.5 g, 5.95 mmol). $^1$H NMR (400 MHz, DMSO-d$_6$) δ 8.20 (dt, J=4.5, 1.6 Hz, 3H), 7.86 (dd, J=8.4, 1.7 Hz, 1H), 7.69 (d, J=8.5 Hz, 1H), 7.61-7.52 (m, 3H), 3.88 (s, 3H). MS: (ESI): m/z=252.8 [M+H]$^+$.

BB14

2-(3-Fluorophenyl)-1H-indole-5-carboxylic acid

To a stirred solution of methyl 2-(3-fluorophenyl)-1H-indole-5-carboxylate (450.0 mg, 1.67 mmol) in THF (6 mL), MeOH (2 mL), H$_2$O (2 mL) was added LiOH. H$_2$O (210.37 mg, 5.01 mmol, CAS RN 1310-66-3) and was stirred at 25° C. for 16 h. The reaction mixture was concentrated in vacuo. The residue was diluted with H$_2$O and neutralized with citric acid solution. The precipitate was filtered off through a sintered funnel and the solids were washed with H$_2$O, dried under reduced pressure to afford a light brown solid. (305 mg, 1.19 mmol). $^1$H NMR (400 MHz, DMSO-d$_6$) δ 12.47 (s, 1H), 11.95 (s, 1H), 8.23 (s, 1H), 7.75 (t, J=6.9 Hz, 2H), 7.67-7.59 (m, 1H), 7.54-7.51 (m, 2H), 4.47-7.45 (m, 1H), 7.15 (m, 2H). MS (EI): m/z=254.3 [M–H]$^-$.

Intermediates a) Methyl 2-(3-fluorophenyl)-1H-indole-5-carboxylate

To a stirred solution of methyl 4-amino-3-[2-(3-fluorophenyl)ethynyl]benzoate (1.3 g, 4.83 mmol) in toluene (40 mL) was added 18-crown-6 (1.28 g, 4.83 mmol, CAS RN 17455-13-9), potassium tert butoxide (1.08 g, 9.66 mmol) and was stirred at 90° C. for 16 h. H$_2$O was added and the mixture was extracted with EtOAc. The organic layers were combined, dried over Na$_2$SO$_4$ and concentrated under reduced pressure to get a brown semi solid (450 mg, 1.67 mmol) $^1$H NMR (400 MHz, DMSO-d$_6$) δ 11.96 (s, 1H), 8.22 (t, J=14.5 Hz, 1H), 7.75 (t, J=6.9 Hz, 2H), 7.62 (s, 1H), 7.54 (s, 2H), 7.16 (d, J=10.4 Hz, 2H), 3.5 (s, 3H). MS (EI): m/z=270.1 [M+H].

b) Methyl 4-amino-3-[2-(3-fluorophenyl) ethynyl]benzoate

To a stirred solution of methyl 4-amino-3-iodobenzoate (5.0 g, 18.05 mmol, CAS RN 19718-49-1) in THF (50 mL) was added 3-fluorophenylacetylene (6.5 g, 54.14 mmol, CAS RN 2561-17-3), TEA (10.06 mL, 72.19 mmol) and argon was purged for 20 min. Then bis(triphenylphosphine) palladium(II) dichloride (633.35 mg, 0.900 mmol, CAS RN 13965-03-2) and copper iodide (171.85 mg, 0.900 mmol, CAS RN 7681-65-4) were added and then continued degassing for another 10 min. The reaction mixture was stirred for 16 h at 25° C. The reaction mixture was concentrated under reduced pressure. The crude product was purified by silica gel column chromatography by using 5-10% EtOAc in n-hexane to afford a light brown solid (4.7 g, 17.45 mmol). $^1$H NMR (400 MHz, DMSO-d$_6$) δ 7.85 (d, J=2.1 Hz, 1H), 7.67 (dd, J=8.7, 2.1 Hz, 1H), 7.58 (d, J=10.0 Hz, 1H), 7.53-7.40 (m, 2H), 7.24 (td, J=8.9, 8.2, 2.5 Hz, 1H), 6.77 (d, J=8.7 Hz, 1H), 6.46 (s, 2H), 3.77 (s, 3H). MS (EI): m/z=270 [M+H]+.

BB15

2-Piperazin-1-yl-3H-pyrido[3,4-d]pyrimidin-4-one hydrochloride

To a stirred solution of tert-butyl 4-(4-oxo-3H-pyrido[3,4-d]pyrimidin-2-yl)piperazine-1-carboxylate (450.0 mg, 1.36 mmol) in DCM (10 mL) was added 4 N HCl in dioxane (2.0 mL, 1.36 mmol) at 0° C., and was stirred at 25° C. for 16 h. The reaction mixture was evaporated under reduced pressure and the resulting solids were washed with n-pentane to get the desired compound as HCl salt (326.1 mg, 1.22 mmol). $^1$H NMR (DMSO-d$^6$, 400 MHz): 3.17-3.21 (m, 4H), 3.96-3.99 (m, 4H), 8.08 (d, J=5.3 Hz, 1H), 8.43 (d, J=5.5 Hz, 1H), 8.94 (s, 1H), 9.68 (br s, 2H). MS (EI): m/z=232.1 [M+H]+.

Intermediate: tert-Butyl 4-(4-oxo-3H-pyrido[3,4-d]pyrimidin-2-yl)piperazine-1-carboxylate To a stirred solution of 2-chloro-3H-pyrido[3,4-d]pyrimidin-4-one (250.0 mg, 1.38 mmol, CAS RN 1437435-10-3) in EtOH (3 mL) was added DIPEA (0.72 mL, 4.13 mmol) and 1-BOC-piperazine (307.72 mg, 1.65 mmol, CAS RN 57260-71-6), and was stirred at 110° C. for 16 h. The reaction mixture was concentrated in vacuo. The residue was purified by silica gel column chromatography by using 60-65% EtOAc in n-hexane to get an off-white solid (450 mg, 1.36 mmol). $^1$H NMR (400 MHz, DMSO-d$_6$) δ 11.72 (s, 1H), 8.68 (s, 1H), 8.30 (d, J=5.2 Hz, 1H), 7.72 (d, J=5.1 Hz, 1H), 3.65 (t, J=5.1 Hz, 4H), 3.42 (t, J=5.0 Hz, 4H), 1.42 (s, 9H). MS (EI): m/z=332.1 [M+H]+.

BB16

1-(4-Fluorophenyl)-1H-pyrrolo[2,3-b]pyridine-5-carboxylic acid

To a stirred solution of methyl 1-(4-fluorophenyl)pyrrolo[2,3-b]pyridine-5-carboxylate (589.22 mg, 2.18 mmol) in THF (9 mL), MeOH (3 mL), H$_2$O (3 mL) was added LiOH.H$_2$O (274.44 mg, 6.54 mmol, CAS RN 1310-66-3) and was stirred at 25° C. for 16 h. The reaction mixture was concentrated. The residue was diluted with H$_2$O and neutralized with a citric acid solution. The mixture was extracted with EtOAc (2×50 mL). The combined organic layers were dried over Na$_2$SO$_4$ and concentrated under reduced pressure to get an off-white solid. (510 mg, 1.99 mmol). $^1$H NMR (400 MHz, DMSO-d$_6$) δ 8.88-8.83 (m, 1H), 8.64-8.59 (m, 1H), 8.03 (d, J=3.8 Hz, 1H), 7.91 (dd, J=8.8, 4.9 Hz, 2H), 7.42 (t, J=8.6 Hz, 2H), 6.87 (d, J=3.8 Hz, 1H). MS (ESI): m/z=257.1 [M+H]+.

Intermediate: Methyl 1-(4-fluorophenyl)-1H-pyrrolo[2,3-b]pyridine-5-carboxylate

To a suspension of methyl 1H-pyrrolo[2,3-b]pyridine-5-carboxylate (500.0 mg, 2.84 mmol, CAS RN 849067-96-5) in toluene (15 mL) was added 4-fluoroiodobenzene (0.69 g, 3.12 mmol, CAS RN 352-34-1), trans 1,2N, N-dimethyl cyclohexane diamine (121.11 mg, 0.850 mmol, CAS RN 67579-81-1), K$_3$PO$_4$ (1.81 g, 8.51 mmol, CAS RN 7778-53-2) and CuI (54.05 mg, 0.280 mmol, CAS RN 7681-65-4) successively. The reaction mixture was heated to 110° C. and the reaction was stirred for 6 h. LC-MS of the crude reaction mixture showed the formation of desired mass along with traces of unreacted SM. The reaction mixture was diluted with DCM (50 mL), filtered through the bed of celite and concentrated to dryness. The crude thus obtained was purified by combiflash column using 10% EtOAc in n-hexane as eluent to provide an off-white solid (560 mg, 2.07 mmol). $^1$H NMR (400 MHz, DMSO-d$_6$) δ 8.87 (d, J=2.2 Hz, 1H), 8.66 (d, J=2.1 Hz, 1H), 8.05 (d, J=3.7 Hz, 1H), 7.95-7.86 (m, 2H), 7.43 (t, J=8.8 Hz, 2H), 6.89 (d, J=3.7 Hz, 1H), 3.90 (s, 3H). MS (ESI): m/z=271.2 [M+H]+.

BB17

1-(4-Fluorophenyl)-1H-1,3-benzodiazole-5-carboxylic acid

To a stirred solution of 3-amino-4-(4-fluoroanilino)benzoic acid (400.0 mg, 1.62 mmol) in THF (5 mL) were added triethyl orthoformate (2.5 mL, 1.62 mmol, CAS RN 122-51-0) and PTSA (30.9 mg, 0.160 mmol, CAS RN 104-15-4) under argon atmosphere. The reaction mixture was stirred at 25° C. for 16 h. The reaction mixture was diluted with H$_2$O and was extracted with a mixture of IPA 1:5 chloroform (2×100 mL). The combined organic layers were washed with aq. NaHCO$_3$ solution, brine and H$_2$O, dried over Na$_2$SO$_4$ and concentrated in vacuo. The crude product was purified by silica gel column chromatography by using 10% MeOH in DCM to get a light brown solid (190 mg, 0.740 mmol). $^1$H NMR (400 MHz, DMSO-d$_6$) δ 12.86 (s, 1H), 8.68 (s, 1H), 8.37 (s, 1H), 7.96 (d, J=8.4 Hz, 1H), 7.78 (dd, J=8.7, 4.8 Hz, 2H), 7.62 (d, J=8.8 Hz, 2H), 7.50 (t, J=8.5 Hz, 2H). MS (ESI): m/z=255.2 [M−H]−.

Intermediates a) 3-Amino-4-(4-fluoroanilino)benzoic acid

To a stirred solution of 4-(4-fluoroanilino)-3-nitro-benzoic acid (300 mg, 1.09 mmol) in MeOH (6 mL), THF (15 mL) and H$_2$O (2 mL) were added zinc powder (568 mg, 8.69 mmol) and NH$_4$Cl (697.14 mg, 13.03 mmol) at RT. The reaction mixture was stirred at RT for 6 h. The reaction mixture was filtered through a plug of celite and washed with MeOH (2×15 mL). The filtrate was evaporated under reduced pressure. The residue was diluted with DCM (150 mL) and washed with H$_2$O (5 mL). The organic layer was dried over Na$_2$SO$_4$, filtered and concentrated to get a light brown solid (175 mg, 0.710 mmol). $^1$H NMR (400 MHz, DMSO-d$_6$) δ 7.37 (s, 1H), 7.20 (s, 1H), 7.15 (d, J=7.8 Hz, 1H), 7.05-7.00 (m, 2H), 6.94 (d, J=8.04 Hz, 1H), 6.88-6.86 (m, 2H), 4.80 (brs, 1H).

b) 4-(Fluoroanilino)-3-nitro-benzoic acid

To a stirred solution of 4-fluoro-3-nitrobenzoic acid (1.0 g, 5.4 mmol, CAS RN 453-71-4) and 4-fluoroaniline (0.77 mL, 8.1 mmol, CAS RN 371-40-4) in ACN (60 mL) was added TEA (1.51 mL, 10.8 mmol). The reaction mixture was heated to 110° C. for 16 h. The reaction was cooled down to 25° C., and concentrated under reduced pressure. The residue was suspended in H$_2$O (50 mL) and the pH adjusted to 4 by a 6N aq. HCl solution. The aqueous phase was extracted by DCM (2×100 mL), washed with brine, dried over Na$_2$SO$_4$ and concentrated under reduced pressure. The crude compound was purified by silica gel column (EtOAc) to get a light yellow solid (990 mg, 3.58 mmol). $^1$H NMR (400 MHz, DMSO-d$_6$) δ 13.10 (s, 1H), 9.77 (s, 1H), 8.63 (s, 1H), 7.92 (d, J=9.0 Hz, 1H), 7.41 (t, J=6.8 Hz, 2H), 7.31 (t, J=8.6 Hz, 2H), 7.01 (d, J=9.0 Hz, 1H). MS (ESI): m/z=275.3 [M−H]⁻.

BB18

2-(3-Fluorophenyl)-1,3-benzoxazole-6-carboxylic acid

To a suspension of methyl 2-(3-fluorophenyl)-1,3-benzoxazole-6-carboxylate (366 mg, 1.35 mmol) in H2O (2 mL) and dioxane (2 mL) was added LiOH monohydrate (73.8 mg, 1.76 mmol) and the mixture was stirred at RT for 4 h. Dioxane was removed by evaporation. To the residue was added dropwise aqueous 1 M HCl (1.75 mL, 1.75 mmol). The suspension was filtered and the filter cake was washed with plenty of H₂O to get the desired compound as colorless solid. MS (ESI): m/z=258.1 [M+H]⁺.

Intermediate: Methyl 2-(3-fluorophenyl)-1,3-benzoxazole-6-carboxylate

A mixture of methyl 4-amino-3-hydroxybenzoate (300 mg, 1.76 mmol, CAS RN 63435-16-5), 3-fluorobenzoyl chloride (418 mg, 2.64 mmol, CAS RN 1711-07-5) and dioxane (3 mL) was heated at 210° C. in a microwave oven for 15 min. The reaction mixture was poured on H2O and EtOAc and the layers were separated. The aqueous layer was extracted twice with EtOAc. The organic layers were dried over MgSO₄, filtered, treated with silica gel and evaporated. The compound was purified by silica gel chromatography on a 25 g column using an MPLC system eluting with a gradient of n-heptane:EtOAc (100:0 to 50:50) to get the desired compound as colorless solid (366 mg, 1.35 mmol). MS (ESI): m/z=272.2 [M+H]⁺.

BB19

2-(3-Chlorophenyl)-1,3-benzoxazole-6-carboxylic acid

The desired compound was obtained in analogy to BB18, from methyl 2-(3-chlorophenyl)-1,3-benzoxazole-6-carboxylate (439 mg, 1.53 mmol) as colorless solid. MS (ESI): m/z=274.1 [M+H]⁺.

Intermediate: Methyl 2-(3-chlorophenyl)-1,3-benzoxazole-6-carboxylate

The desired compound was obtained in analogy to intermediate of BB18, from methyl 4-amino-3-hydroxybenzoate (300 mg, 1.76 mmol, CAS RN 63435-16-5) and 3-chlorobenzoyl chloride (462 mg, 338 μl, 2.64 mmol, CAS RN 618-46-2) as a colorless solid (439 mg, 1.53 mmol). MS (ESI): m/z=288.1 [M+H]⁺.

BB20

2-[3-(Trifluoromethyl)phenyl]-1,3-benzoxazole-6-carboxylic acid

The desired compound was obtained in analogy to intermediate BB18, from methyl 2-(3-(trifluoromethyl)phenyl)benzoxazole-6-carboxylate (480 mg, 1.49 mmol) to provide the desired compound as colorless solid. MS (ESI): m/z=308.1 [M+H]⁺.

Intermediate: Methyl 2-[3-(trifluoromethyl)phenyl]-1,3-benzoxazole-6-carboxylate The desired compound was obtained in analogy to an intermediate of BB18, from methyl 4-amino-3-hydroxybenzoate (300 mg, 1.76 mmol, CAS RN 63435-16-5) and 3-(trifluoromethyl)benzoyl chloride (404 mg, 286 μL, 1.93 mmol, CAS RN 2251-65-2) as colorless solid (480 mg, 1.49 mmol). MS (ESI): m/z=322.1 [M+H]⁺.

BB21

3-Chloro-4-[(3-chlorophenyl)methoxy]benzoic acid

To a stirred solution of methyl 3-chloro-4-[(3-chlorophenyl)methoxy]benzoate (868.0 mg, 2.79 mmol) in THF (9 mL), MeOH (3 mL), H₂O (3 mL) was added followed by LiOH.H₂O (351.15 mg, 8.37 mmol). The reaction mixture was stirred at 25° C. for 4 h. The reaction mixture was concentrated in vacuo. The residue was taken up in H₂O (15 mL) and acidified with citric acid. Precipitate was collected by filtration, dried under reduced pressure to get an off-white solid (790 mg, 2.66 mmol). ¹H NMR (400 MHz, DMSO-d₆) δ 7.96-7.84 (m, 2H), 7.55 (s, 1H), 7.45 (s, 2H), 7.49-7.39 (m, 1H), 7.31 (d, J=8.7 Hz, 1H), 5.31 (s, 2H). MS: (ESI): m/z=295.2 [M−H]⁻.

Intermediate: Methyl 3-chloro-4-[(3-chlorophenyl)methoxy]benzoate

To a stirred solution of 3-chlorobenzyl bromide (0.85 mL, 6.43 mmol, CAS RN 766-80-3) and methyl 3-chloro-4-hydroxybenzoate (1.0 g, 5.36 mmol, CAS RN 3964-57-6) in ACN (10 mL) was added K₂CO₃ (1.85 g, 13.4 mmol) and the solution was stirred at 25° C. for 4 h. The reaction mixture was concentrated in vacuo. The residue was taken up in EtOAc (100 mL) and the organic layer was washed with H₂O (2×20 mL) and brine (20 mL). The organic layers were separated; combined; dried over Na₂SO₄; filtered and concentration to dryness. The crude product was purified by flash column chromatography eluting 20-30% EtOAc in n-hexane. The desired fractions were concentrated to dryness in vacuo to get a colorless semisolid (920 mg, 2.96 mmol). ¹H NMR (400 MHz, DMSO-d₆) δ 7.79 (s, 2H), 7.53 (s, 1H), 7.44 (s, 3H), 7.48-7.37 (m, 1H), 7.11 (d, J=8.4 Hz, 1H), 5.23 (s, 2H), 3.80 (s, 3H), 2.24 (s, 3H). MS (ESI): m/z=311.0 [M+H]⁺.

BB22

4-(Azetidin-1-yl)benzoic acid

Methyl 4-(azetidin-1-yl)benzoate (70 mg, 366 μmol) was dissolved in THF (1.8 mL) and H₂O (1.83 mL) at RT, whereupon LiOH (50 mg, 2.09 mmol) was added. The reaction mixture was stirred at RT for 18 h. LiOH (50 mg, 2.09 mmol) was added again and the solution was gently warmed to 40° C. for 3 days. The reaction mixture was acidified to pH 5-6 with 1M HCl solution. It was diluted with EtOAc (10 mL) before being poured into a separating funnel containing EtOAc (25 mL.) The aqueous layer was extracted with EtOAc (2×25 mL), dried over Na₂SO₄, filtered and concentrated in vacuo to yield an orange solid (50.2 mg, 76%). MS (ESI): m/z=178.1 [M+H]⁺.

Intermediate: Methyl 4-(azetidin-1-yl)benzoate

Methyl 4-fluorobenzoate (100 mg, 636 μmol, CAS RN 403-33-8) was dissolved in dry DMF (3 mL) at RT, whereupon azetidine (36.3 mg, 636 μmol, CAS RN 503-29-7) and Cs₂CO₃ (311 mg, 954 μmol, CAS RN 534-17-8) were added. The reaction mixture was then heated in a sealed tube in a microwave reactor at 140° C. for 30 min. The reaction mixture was then diluted with EtOAc and filtered over celite, before pouring into a separating funnel containing EtOAc (50 mL) and H₂O (5 mL). The layers were found to merge and thus the H₂O was removed by Na₂SO₄, and the reaction mixture evaporated to dryness (DMF removed on a high vacuum line) before the residue was taken up in EtOAc and concentrated in a smaller flask to yield a pale yellow solid. The compound was re-dissolved in EtOAc (30 mL) and washed with H₂O (2×30 mL) and concentrated in vacuo to yield a yellow solid (76 mg, 381.6 µmol). ¹H NMR (300 MHz, CHLOROFORM-d) δ 7.88 (d, J=8.80 Hz, 2H), 6.36 (d, J=8.80 Hz, 2H), 3.98 (t, J=7.40 Hz, 4H), 3.85 (s, 3H), 2.41 (quin, J=7.40 Hz, 2H). MS (ESI): m/z=192.1 [M+H]⁺.

BB23

4-[(3-Chlorophenyl)methoxy]-3-(trifluoromethyl)benzoic acid

To a stirred solution of methyl 4-[(3-chlorophenyl)methoxy]-3-(trifluoromethyl)benzoate (1.2 g, 3.48 mmol) in THF (9 mL), MeOH (3 mL) and H₂O (3 mL) was added LiOH. H₂O (438.21 mg, 10.44 mmol) and the solution was stirred at 25° C. for 4 h. The reaction was concentrated to dryness. The residue was taken up in H₂O (15 mL) and acidified with citric acid. The precipitate was collected by filtration, dried under reduced pressure to get an off-white solid (960 mg, 2.9 mmol). ¹H NMR (400 MHz, DMSO-d₆) δ 13.20 (s, 1H), 8.20 (dd, J=8.7, 2.3 Hz, 1H), 8.13 (d, J=2.3 Hz, 1H), 7.52 (s, 1H), 7.43 (dt, J=8.9, 6.1 Hz, 4H), 5.39 (s, 2H).

Intermediate: Methyl 4-[(3-chlorophenyl)methoxy]-3-(trifluoromethyl)benzoate

To a stirred solution of methyl 4-hydroxy-3-(trifluoromethyl)benzoate (1.0 g, 4.54 mmol, CAS RN 115933-50-1) and 3-chlorobenzyl bromide (0.72 mL, 5.45 mmol) in ACN (15 mL) was added K₂CO₃ (1.57 g, 11.36 mmol) and was stirred at 25° C. for 4 h. The reaction was concentrated to dryness. The residue was taken up in EtOAc (100 mL) and the organic layer was washed with H₂O (2×20 mL) then brine (20 mL). The organic layer were separated and dried over Na₂SO₄ before concentrating to dryness. The crude product was purified by flash column chromatography eluting 20-30% EtOAc in n-hexane. The desired fractions were concentrated to dryness in vacuum to get an off-white solid. (1.2 g, 3.48 mmol)¹H NMR (400 MHz, DMSO-d₆) δ 8.23 (dd, J=8.6, 2.4 Hz, 1H), 8.14 (d, J=2.3 Hz, 1H), 7.54-7.38 (m, 5H), 5.40 (s, 2H), 3.32 (s, 3H).

BB24

4-[(3-Chlorophenyl)methoxy]-3-methyl-benzoic acid

To a stirred solution of methyl 4-[(3-chlorophenyl)methoxy]-3-methyl-benzoate (1.7 g, 5.85 mmol) in THF (9 mL), MeOH (3 mL) and H₂O (3 mL) was added LiOH. H₂O (736.04 mg, 17.54 mmol, CAS RN 1310-66-3) and the solution was stirred at RT for 4 h. The reaction was concentrated to dryness and the residue was taken up in H₂O (15 mL), and then acidified with citric acid. The precipitate was collected by filtration and dried in vacuo to yield an off-white solid (1.5 g, 5.42 mmol). ¹H NMR (400 MHz, DMSO-d₆) δ 7.77 (d, J=8.6 Hz, 2H), 7.53 (s, 1H), 7.43 (q, J=6.4, 5.6 Hz, 3H), 7.07 (d, J=8.3 Hz, 1H), 5.22 (s, 2H), 2.24 (s, 3H). MS (ESI): m/z=277.3 [M+H]⁺.

Intermediate: Methyl 4-[(3-chlorophenyl)methoxy]-3-methyl-benzoate

To a stirred solution of methyl 4-hydroxy-3-methyl-benzoate (1.0 g, 6.02 mmol, CAS RN 42113-13-3) and 3-chlorobenzyl bromide (0.95 mL, 7.22 mmol, CAS RN 766-80-3) in ACN (15 mL) was added potassium carbonate (2.08 g, 15.04 mmol, CAS RN 584-08-7) and the reaction was stirred at 25° C. for 16 h. The reaction was concentrated to dryness and the residue was taken up in EtOAc (100 mL) and was washed with H₂O (2×20 mL) followed by brine (20 mL). The organic layers were separated and dried over Na₂SO₄ before concentrating to dryness. The crude product was purified by flash column chromatography eluting 20-30% EtOAc in n-hexane. The desired fractions were concentrated to dryness in vacuo to get a light yellow solid (1.7 g, 5.85 mmol). ¹H NMR (400 MHz, DMSO-d₆) δ 7.79 (s, 2H), 7.53 (s, 1H), 7.44 (s, 1H), 7.48-7.37 (m, 2H), 7.11 (d, J=8.4 Hz, 1H), 5.23 (s, 2H), 3.80 (s, 3H), 2.24 (s, 3H). MS (ESI): m/z=291.1 [M+H]⁺.

BB25

4-[(3-Chlorophenyl)methoxy]-3-(1H-imidazol-2-yl)benzoic acid (5 h)

To a stirred solution of methyl 4-[(3-chlorophenyl)methoxy]-3-(1H-imidazol-2-yl)benzoate (440.0 mg, 1.28 mmol) in THF (6 mL), MeOH (2 mL) and H₂O (2 mL) was added LiOH. H₂O (161.58 mg, 3.85 mmol) and the solution was stirred at 25° C. for 6 h. The reaction mixture was concentrated in vacuo. The residue was taken up in H₂O (15 mL) and was acidified with citric acid. The precipitate was collected by filtration, dried under reduced pressure to get an off-white solid (410 mg, 1.25 mmol). ¹H NMR (400 MHz, DMSO-d₆) δ 12.02 (s, 1H), 8.66 (d, J=2.3 Hz, 1H), 7.81 (dd, J=8.7, 2.3 Hz, 1H), 7.58 (s, 1H), 7.48-7.24 (m, 3H), 7.18 (d, J=8.8 Hz, 3H), 5.48 (s, 2H). MS (ESI): m/z=329.0 [M+H]⁺.

Intermediates a) Methyl 4-[(3-chlorophenyl)methoxy]-3-(1H-imidazol-2-yl)benzoate To a stirred solution of methyl 4-hydroxy-3-(1H-imidazol-2-yl)benzoate (460.0 mg, 2.11 mmol) and 3-chlorobenzyl bromide (0.28 mL, 2.11 mmol, CAS RN 766-80-3) in ACN (15 mL) was added K₂CO₃ (728.37 mg, 5.27 mmol) and the reaction was stirred at 25° C. for 16 h. The reaction mixture was concentrated to dryness and the residue was taken up in EtOAc (100 mL) and the organic layers were washed with H₂O (2×20 mL), then brine (20 mL). The organic layers were separated, dried over Na₂SO₄ and concentrated. The crude product was purified by flash column chromatography eluting 20-30% EtOAc in n-hexane. The desired fractions were concentrated to dryness in vacuum to get a light yellow solid (540 mg, 1.58 mmol). ¹H NMR (400 MHz, DMSO-d₆) δ 12.02 (s, 1H), 8.70 (d, J=2.3 Hz, 1H), 7.84 (dd, J=8.7, 2.4 Hz, 1H), 7.58 (s, 1H), 7.47-7.30 (m, 3H), 7.30-7.19 (m, 2H), 7.09 (s, 1H), 5.51 (s, 2H), 3.83 (s, 3H). MS (ESI): m/z=342.7 [M+H]⁺.

b) Methyl 4-hydroxy-3-(1H-imidazol-2-yl)benzoate

To a stirred solution of methyl 3-formyl-4-hydroxy-benzoate (750.0 mg, 4.16 mmol, CAS RN 24589-99-9) in MeOH (9 mL) was added glyoxal (40% aqueous solution; 0.86 mL, 18.73 mmol, CAS RN 107-22-2) and ammonia (1.26 mL, 54.12 mmol). The mixture was stirred for 3 h, concentrated in vacuum and acidified to pH<1 with 10 mL of 1 N aq. HCl. The aqueous solution was extracted with EtOAc (3×10 mL). The organic extracts were discarded while the aqueous phase was basified by addition of sat NaHCO$_3$ solution. The mixture was extracted with EtOAc (3×10 mL), combined organic extracts were washed with H$_2$O, brine, dried and concentrated in vacuum. The crude product was purified under silica gel column chromatography by using 70-75% EtOAc in n-hexane to get an off-white solid (480 mg, 2.2 mmol). $^1$H NMR (400 MHz, DMSO-d$_6$) δ 13.56 (s, 2H), 8.59 (d, J=2.1 Hz, 1H), 7.84 (dd, J=8.5, 2.2 Hz, 1H), 7.28 (s, 2H), 7.03 (d, J=8.6 Hz, 1H), 5.75 (s, 1H), 3.85 (s, 3H). MS (ESI): m/z=218.8 [M+H]$^+$.

BB26

4-[(3-Chlorophenyl)methoxy]-3-cyano-benzoic acid

To a stirred solution of methyl 4-[(3-chlorophenyl)methoxy]-3-cyano-benzoate (300.0 mg, 0.990 mmol) in THF (10 mL) was added LiOH.H$_2$O (47.43 mg, 1.99 mmol) in H$_2$O (2 mL) dropwise at 0° C. and the reaction mixture was stirred at RT for 16 h. The reaction mixture was concentrated to dryness. H$_2$O was added and the aqueous layer was washed with diethyl ether. The aqueous phase was then acidified by citric acid solution, extracted with EtOAc (2×20 mL). The combined organic layers were dried over Na$_2$SO$_4$ and concentrated to dryness. The crude product was triturated with 30% EtOAc in n-hexane to get an off-white solid (285 mg, 0.990 mmol). $^1$H NMR (400 MHz, DMSO-d$_6$) δ 13.21 (s, 1H), 8.26-8.16 (m, 2H), 7.57 (s, 1H), 7.45 (dd, J=9.4, 5.7 Hz, 4H), 5.39 (s, 2H). MS (ESI): m/z=286.1 [M−H]$^-$.

Intermediate: Methyl 4-[(3-chlorophenyl)methoxy]-3-cyano-benzoate

To a stirred solution of 3-chlorobenzyl bromide (0.3 mL, 2.26 mmol, CAS RN 766-80-3) and methyl 3-cyano-4-hydroxy-benzoate (400 mg, 2.26 mmol, CAS RN 156001-68-2) in ACN (15 mL) was added potassium carbonate (780.1 mg, 5.64 mmol) and was stirred at RT for 16 h. The reaction was concentrated to dryness and the residue was taken up in EtOAc (50 mL) and the organic layers were washed with H$_2$O (2×20 mL) and brine (20 mL). The organics layers were separated and dried over Na$_2$SO$_4$ before concentrating to dryness. The crude product was purified by flash column chromatography eluting 20-30% EtOAc in n-hexane. The desired fractions were concentrated to dryness to get an off-white solid (550 mg, 1.82 mmol). $^1$H NMR (400 MHz, DMSO-d$_6$) δ 8.30-8.19 (m, 2H), 7.58 (s, 1H), 7.52-7.43 (m, 4H), 5.40 (s, 2H), 3.85 (s, 3H). MS (ESI): m/z=302.3 [M+H]$^+$.

BB27

2-(3,4-Dichlorophenyl)-1,3-benzoxazole-6-carboxylic acid

The desired compound was obtained in analogy to BB18, from methyl 2-(3,4-dichlorophenyl)-1,3-benzoxazole-6-carboxylate as a colorless solid. MS (ESI): m/z=308.0 [M+H]$^+$.

Intermediate: Methyl 2-(3,4-dichlorophenyl)-1,3-benzoxazole-6-carboxylate

A mixture of methyl 4-amino-3-hydroxybenzoate (300 mg, 1.76 mmol, CAS RN 63435-16-5), 3,4-dichlorobenzoyl chloride (553 mg, 2.64 mmol, CAS RN 3024-72-4) and dioxane (3 mL) was heated at 210° C. in a microwave oven for 30 min. The reaction mixture was poured on H$_2$O and EtOAc and the layers were separated. The aqueous layer was extracted twice with EtOAc. The combined organic layers were dried over MgSO$_4$, filtered, treated with silica gel and evaporated. The compound was purified by silica gel chromatography on a 12 g column using an MPLC system eluting with a gradient of n-heptane:EtOAc (100:0 to 75:25) to afford a white solid (376 mg, 1.17 mmol). MS (ESI): m/z=322.1 [M+H]$^+$.

BB28

2-(4-Chlorophenyl)-1,3-benzoxazole-6-carboxylic acid

The desired compound was obtained in analogy to BB18, from methyl 2-(4-chlorophenyl)-1,3-benzoxazole-6-carboxylate. MS (ESI): m/z=272.0 [M+H]$^+$.

Intermediate: Methyl 2-(4-chlorophenyl)-1,3-benzoxazole-6-carboxylate

A mixture of methyl 4-amino-3-hydroxybenzoate (300 mg, 1.76 mmol, CAS RN CAS RN 63435-16-5), 4-chlorobenzoyl chloride (462 mg, 2.64 mmol, CAS RN 122-01-0) and dioxane (3 mL) was heated at 210° C. in a microwave oven for 30 min. The reaction mixture was poured on H$_2$O and EtOAc and the layers were separated. The aqueous layer was extracted twice with EtOAc. The organic layers dried over MgSO$_4$, filtered, treated with silica gel and evaporated. The compound was purified by silica gel chromatography on a 12 g column using an MPLC system eluting with a gradient of n-heptane:EtOAc (100:0 to 75:25). MS (ESI): m/z=288.1 [M+H]$^+$.

BB29

4-(2-Azabicyclo[2.2.1]heptan-2-yl)benzoic acid

Methyl 4-(2-azabicyclo[2.2.1]heptan-2-yl)benzoate (270 mg, 1.1 mmol) was dissolved in THF (3.6 mL) whereupon H$_2$O (3.6 mL) and LiOH (158 mg, 6.58 mmol) were added. The reaction mixture was stirred at RT for 20 h followed by heating to 55° C. and stirring for ed for 48 h. Another portion of LiOH (158 mg, 6.58 mmol) was added. After stirring for 7 days the reaction mixture was neutralised to pH 7, the reaction mixture diluted with EtOAc and poured into a separating funnel containing EtOAc (50 mL). The aqueous layer was extracted with EtOAc (2×25 mL), dried over Na$_2$SO$_4$, filtered and concentrated in vacuo to yield a white solid (220 mg, 90%). MS (ESI): m/z=218.2 [M+H]$^+$.

Intermediate: Methyl 4-(2-azabicyclo[2.2.1]heptan-2-yl)benzoate

Methyl 4-fluorobenzoate (706 mg, 593 µl, 4.49 mmol, CAS RN 403-33-8) was dissolved in dry DMF (10 mL) at RT, whereupon 2-azabicyclo[2.2.1]heptane hydrochloride (600 mg, 4.49 mmol) and Cs$_2$CO$_3$ (2.93 g, 8.98 mmol) were added. The reaction mixture was then heated in a sealed tube in a microwave reactor at 140° C. for 30 minutes. The reaction mixture evaporated to dryness (DMF removed on a high vacuum line) before the residue was taken up in EtOAc and washed with H$_2$O (2×30 mL), dried over Na$_2$SO$_4$, filtered and concentrated in vacuo to yield a brown solid (436.5 mg). This was concentrated with silica and purified by flash column chromatography (SiO$_2$, 4 g, Eluent; Hep:

EtOAc 100:0 to 50:50 over 20 mins.) Fractions containing the product were combined and concentrated in vacuo to yield a white solid (279 mg, 25%). MS (ESI): m/z=232.3 [M+H]$^+$.

BB30

4-(2-Azaspiro[3.3]heptan-2-yl)benzoic acid

The desired compound was obtained in analogy to BB29, from methyl 4-(2-azaspiro[3.3]heptan-2-yl)benzoate as a white solid. MS (ESI): m/z=218.2 [M+H]$^+$.

Intermediate: Methyl 4-(2-azaspiro[3.3]heptan-2-yl)benzoate

The desired intermediate was obtained in analogy to an intermediate of BB29, using methyl 4-fluorobenzoate (576 mg, 3.66 mmol, CAS RN 403-33-8), 2-azaspiro[3.3]heptane (400 mg, 3.66 mmol, CAS RN 665-04-3) and Cs$_2$CO$_3$ (2.39 g, 7.33 mmol, CAS RN 534-17-8) to afford a white solid (167.6 mg, 0.71 mmol). MS (ESI): m/z=232.2 [M+H]$^+$.

BB31

2-Phenyl-[1,3]oxazolo[4,5-b]pyridine-6-carboxylic acid

The desired compound was obtained in analogy to BB18, from methyl 2-phenyl-[1,3]oxazolo[4,5-b]pyridine-6-carboxylate. $^1$H NMR (DMSO-d6, 400 MHz): 7.66-7.76 (m, 3H), 8.29 (d, J=7.4 Hz, 2H), 8.63 (d, J=0.8 Hz, 1H), 9.08 (s, 1H), 13.4-13.7 (br s, 1H). MS (ESI): m/z=241 [M+H]$^+$.

Intermediate: Methyl 2-phenyl-[1,3]oxazolo[4,5-b]pyridine-6-carboxylate

A mixture of 6-bromo-2-phenyl-oxazolo[4,5-b]pyridine (1.6 g, 5.82 mmol, CAS RN 174469-41-1), palladium(II) acetate (39.17 mg, 0.170 mmol, CAS RN 3375-31-3), 1,3-bis(diphenylphosphino)propane (95.95 mg, 0.230 mmol, CAS RN 6737-42-4) in DMF (25 mL) and MeOH (25 mL) was purged with nitrogen for 10 min. Then, TEA (3.23 mL, 23.26 mmol, CAS RN 121-44-8) was introduced in one portion and the mixture was stirred under CO atmosphere (70 PSI) at 70° C. for 16 h. The reaction was concentrated to dryness and the residue was taken up in EtOAc (150 mL). The organic layers were washed with H$_2$O (3×30 mL) then brine (30 mL). The organic layers were then collected and dried over Na$_2$SO$_4$ before concentrating to dryness. The crude product was then purified by flash column chromatography eluting 40% EtOAc in n-hexane. The desired fractions were concentrated in vacuo to get a light yellow solid (453 mg, 1.78 mmol). $^1$H NMR (DMSO-d$_6$, 400 MHz): 3.94 (s, 3H), 7.67-7.75 (m, 3H), 8.25-8.30 (m, 2H), 8.70 (s, 1H), 9.10 (s, 1H). MS (ESI): m/z=254.9 [M+H]$^+$.

BB32

4-Cyano-2-phenyl-1,3-benzoxazole-6-carboxylic acid

To a solution of ethyl 4-cyano-2-phenyl-1,3-benzoxazole-6-carboxylate (210.0 mg, 0.720 mmol) in THF (20 mL) was added LiOH (0.01 mL, 0.860 mmol, CAS RN 1310-66-3) in H$_2$O (2 mL) dropwise at 0° C. The reaction mixture was stirred at 25° C. for 8 h. The reaction mixture was concentrated to dryness and H$_2$O was added. The aqueous layer was washed with diethyl ether and then acidified with citric acid. The aqueous layer was extracted with 20% IPA in chloroform (2×50 mL). The combined organic layers were dried over Na$_2$SO$_4$ and concentrated to dryness to get an off-white solid (210.0 mg, 0.720 mmol). $^1$H NMR (DMSO-d$_6$, 400 MHz): 7.66-7.70 (m, 2H), 7.73-7.76 (m, 1H), 8.30 (d, J=7.3 Hz, 2H), 8.40 (d, J=1.1 Hz, 1H), 8.60 (d, J=1.1 Hz, 1H), 13.5-13.8 (br s, 1H). MS (ESI): m/z=264.9 [M+H]$^+$.

Intermediates a) Ethyl 4-cyano-2-phenyl-1,3-benzoxazole-6-carboxylate

To a stirred solution of ethyl 4-iodo-2-phenyl-1,3-benzoxazole-6-carboxylate (700.0 mg, 1.78 mmol) in dry DMF (25 mL) were added zinc cyanide (418.1 mg, 3.56 mmol, CAS RN 557-21-1), 1,1'-bis(diphenylphosphino)ferrocene (98.7 mg, 0.180 mmol, CAS RN 12150-46-8) and zinc (28.93 mg, 0.450 mmol, CAS RN 7440-66-6) and purged with argon for 15 min. Then Pd$_2$(dba)$_3$ (407.59 mg, 0.450 mmol, CAS RN 51364-51-3) was added and reaction mixture was again purged with argon for 10 min. The reaction mixture was stirred at 100° C. for 16 h. After completion of reaction, it was cooled down to 25° C. and filtered. The filtrate was diluted with H$_2$O, extracted with EtOAc (2×10 mL). The combined organic layer was washed with H$_2$O, brine, dried over Na$_2$SO$_4$ and concentrated to dryness. The crude obtained was purified by silica gel column (eluent: 10% EtOAc/n-hexane) to afford a light brown solid (450 mg, 1.54 mmol). $^1$H NMR (DMSO-d$_6$, 400 MHz): 1.37 (t, J=7.1 Hz, 3H), 4.39 (q, J=7.1 Hz, 2H), 7.67-7.70 (m, 2H), 7.73-7.77 (m, 1H), 8.29 (d, J=7.2 Hz, 2H), 8.43 (d, J=1.1 Hz, 1H), 8.63 (d, J=1.1 Hz, 1H). MS (EI): m/z=293.1 [M+H]$^+$.

b) Ethyl 4-iodo-2-phenyl-1,3-benzoxazole-6-carboxylate

To a mixture of benzoylchloride (0.5 mL, 4.3 mmol, CAS RN 98-88-4) and ethyl 4-amino-3-hydroxy-5-iodo-benzoate (1.2 g, 3.91 mmol) in 1,4-dioxane (12 mL) was stirred at 140° C. for 2 h in a microwave. The reaction mixture was concentrated to dryness and diluted with EtOAC. The organic layer was washed with H$_2$O and brine, dried over Na$_2$SO$_4$ and concentrated to dryness. The residue was purified by silica gel column to afford a light brown solid. (1.1 g, 2.8 mmol)$^1$H NMR (DMSO-d$_6$, 400 MHz): 1.36 (t, J=7.1 Hz, 3H), 4.36 (q, J=7.1 Hz, 2H), 7.64-7.73 (m, 3H), 8.24 (d, J=7.0 Hz, 2H), 8.30 (dd, J=1.1, 11.2 Hz, 2H). MS (EI): m/z=394 [M+H]$^+$.

c) Ethyl 4-amino-3-hydroxy-5-iodobenzoate

To a solution of ethyl 4-amino-3-[tert-butyl(dimethyl)silyl]oxy-5-iodobenzoate (180.0 mg, 0.430 mmol) in dry THF (5 mL) was added TBAF (0.85 mL, 0.850 mmol, CAS RN 429-41-4) and was stirred for at 25° C. 16 h. The reaction mixture was concentrated to dryness and the residue was diluted with EtOAc (2×20 mL). The combined organic layer was washed with H$_2$O, brine, dried over Na$_2$SO$_4$ and concentrated to dryness. The crude was purified by silica gel column to afford a light brown solid (76 mg, 0.250 mmol). $^1$H NMR (DMSO-d$_6$, 400 MHz): 1.26 (t, J=7.0 Hz, 3H), 4.20 (q, J=7.0 Hz, 2H), 5.29 (s, 2H), 7.25 (s, 1H), 7.68 (s, 1H), 10.0 (s, 1H). MS (EI): m/z=308.1 [M+H]$^+$.

d) Ethyl 4-amino-3-[(tert-butyldimethylsilyl)oxy]-5-iodobenzoate

A solution of iodine (4.06 g, 15.99 mmol, CAS RN 7553-56-2) in ACN (60 mL) and THF (4 mL) was added dropwise to a mixture of ethyl 4-amino-3-[tert-butyl(dimethyl)silyl]oxy-benzoate (4.5 g, 15.23 mmol), silver nitrate (3.1 g, 18.28 mmol, CAS RN 7761-88-8) and ACN (60 mL) at 0° C. The reaction mixture was stirred for at 25° C. for 2 h. The reaction mixture was filtered through celite bed and filtrate was concentrated under reduced pressure. EtOAc and a sodium thiosulfate solution (CAS RN 7772-98-7) were added to the residue and the organic layer was separated. The obtained organic layer was sequentially washed with $H_2O$, brine, dried over $Na_2SO_4$ and concentrated to dryness. The crude product was purified by silica gel column chromatography to get a dark brown solid (3.7 g, 8.78 mmol). $^1$H NMR (DMSO-$d_6$, 400 MHz): 0.24 (s, 6H), 0.97 (s, 9H), 1.27 (t, J=7.1 Hz, 3H), 4.21 (q, J=7.1 Hz, 2H), 5.23 (s, 2H), 7.24 (d, J=1.5 Hz, 1H), 7.82 (d, J=1.6 Hz, 1H). MS (EI): m/z=422 [M+H]$^+$.

e) Ethyl 4-amino-3-[(tert-butyldimethyl)silyl]oxybenzoate

To a solution of ethyl 3-[(tert-butyldimethylsilyl)oxy]-4-nitrobenzoate (14.0 g, 43.02 mmol) in dry MeOH (150 mL) was added Pd/C (10 wt. %) (2.0 g, 43.02 mmol, CAS RN 7440-05-3) and the reaction mixture was stirred at 25° C. for 7 h under a hydrogen atmosphere. The reaction mixture was filtered through a celite bed and washed with MeOH and concentrated to dryness. The crude product was purified by silica gel column chromatography (30% EtOAc in n-hexane) to provide a colorless gum (8.5 g, 28.77 mmol) which was used as is for the next step. $^1$H NMR (DMSO-$d_6$, 400 MHz): 0.21 (s, 6H), 0.97 (s, 9H), 1.25 (t, J=7.0 Hz, 3H), 4.19 (q, J=7.0 Hz, 2H), 5.35 (s, 2H), 6.69 (d, J=8.2 Hz, 1H), 7.24 (s, 1H), 7.37 (d, J=8.2 Hz, 1H). MS (ESI): m/z=296.2 [M+H]$^+$.

f) Ethyl 3-[(tert-butyldimethylsilyl)oxy]-4-nitrobenzoate

To a solution of ethyl 3-hydroxy-4-nitrobenzoate (1.0 g, 4.74 mmol) in dry DCM (20 mL) was added imidazol (0.48 g, 7.1 mmol, CAS RN 288-32-4) and to this reaction mixture was added tert-butyldimethylsilyl chloride (1.07 g, 7.1 mmol, CAS RN 18162-48-6) in DCM (2 mL) drop wise at 0° C. and the reaction mixture was allowed to stirred at 25° C. for 16 h. After completion of the reaction the reaction mixture was diluted with DCM, organic layer was washed with $H_2O$, brine, dried over $Na_2SO_4$ and concentrated to dryness afforded ethyl 3-[tert-butyl(dimethyl)silyl]oxy-4-nitro-benzoate (1.1 g, 3.38 mmol) as light yellow solid that was used in the next step without purification.

g) Ethyl 3-hydroxy-4-nitrobenzoate

To a solution of 3-hydroxy-4-nitrobenzoic acid (10.0 g, 54.61 mmol, CAS RN 619-14-7) in dry EtOH (60 mL) was added conc. $H_2SO_4$ (5.0 mL, 54.61 mmol, CAS RN 7664-93-9) and the reaction mixture was refluxed for 2 h. The reaction mixture was concentrated to dryness and diluted with EtOAc (100 mL). The combined organic layers were washed with $NaHCO_3$ solution, $H_2O$ and brine, dried over $Na_2SO_4$ and concentrated to dryness to get a light yellow solid (10 g, 47.36 mmol) which was used as is for the next step. $^1$H NMR (DMSO-$d_6$, 400 MHz): 1.32 (t, J=7.0 Hz, 3H), 4.26-4.35 (m, 2H), 7.47 (dd, J=0.96, 8.4 Hz, 1H), 7.67 (s, 1H), 7.94 (d, J=8.5 Hz, 1H), 11.45 (s, 1H). MS (ESI): m/z=209.7 [M−H]$^-$.

BB33

4-(2-Azaspiro[3.4]octan-2-yl)benzoic acid

The desired compound was obtained in analogy to BB29, from methyl 4-(2-azaspiro[3.4]octan-2-yl)benzoate as a white solid. MS (ESI): m/z=232.2 [M+H]$^+$.

Intermediate: Methyl 4-(2-azaspiro[3.4]octan-2-yl)benzoate

The desired intermediate was obtained in analogy to BB29, using methyl 4-fluorobenzoate (495 mg, 3.15 mmol, CAS RN 403-33-8), 2-azaspiro[3.4]octane (350 mg, 3.15 mmol, CAS RN 665-41-8) and $Cs_2CO_3$ (2.05 g, 6.3 mmol, CAS RN 534-17-8) as a white solid (401.8 mg, 1.61 mmol). MS (ESI): m/z=246.3 [M+H]$^+$.

BB34

2-(3,4-Difluorophenyl)-1,3-benzoxazole-6-carboxylic acid

To a suspension of methyl 2-(3,4-difluorophenyl)-1,3-benzoxazole-6-carboxylate (345 mg, 1.19 mmol) in 1,4-dioxane (4 mL) and $H_2O$ (4 mL) was added LiOH monohydrate (62.6 mg, 1.49 mmol) and the mixture was stirred at 50° C. for 16 h. 1M HCl solution (1.49 mL, 1.49 mmol) was added and the reaction was stirred at RT for 3 h. 1,4-Dioxane (4 mL) was removed. The suspension was filtered and the filter cake was washed with plenty of $H_2O$. MS (ESI): m/z=276.2 [M+H]+

Intermediate: Methyl 2-(3,4-difluorophenyl)-1,3-benzoxazole-6-carboxylate

A mixture of methyl 4-amino-3-hydroxybenzoate (300 mg, 1.76 mmol, CAS RN 63435-16-5), 3,4-difluorobenzoyl chloride (466 mg, 332 µl, 2.64 mmol) and dioxane (3 mL) was heated at 210° C. for 30 min in the microwave. The reaction mixture was poured onto $H_2O$ and EtOAc and the layers were separated. The aqueous layer was extracted twice with EtOAc. The organic layers were dried over $MgSO_4$, filtered, treated with silica gel and evaporated. The crude compound was purified by silica gel chromatography on a 12 g column using an MPLC system eluting with a gradient of n-heptane:EtOAc (100:0 to 75:25). MS (ESI): m/z=290.2 [M+H]$^+$.

BB35

2-[4-(Trifluoromethyl)phenyl]-1,3-benzoxazole-6-carboxylic acid

To a suspension of methyl 2-(4-(trifluoromethyl)phenyl)-1,3-benzoxazole-6-carboxylate (274 mg, 853 µmol) in 1,4-dioxane (4 mL) and $H_2O$ (4 mL) was added LiOH monohydrate (44.7 mg, 1.07 mmol) and the mixture was stirred at 50° C. for 16 h. 1M HCl solution (1.07 mL, 1.07 mmol) was added and the reaction mixture was stirred at RT for 3 h. The organic solvent was evaporated, the reaction mixture filtered, the filter cake washed with plenty of $H_2O$ and dried in high vacuum. MS (ESI): m/z=308.2 [M+H]$^+$.

Intermediate: Methyl 2-(4-(trifluoromethyl)phenyl)-1,3-benzoxazole-6-carboxylate A mixture of methyl 4-amino-3-hydroxybenzoate (300 mg, 1.76 mmol, CAS RN 63435-16-5), 4-(trifluoromethyl)

benzoyl chloride (267 μl, 1.76 mmol) and dioxane (3 mL) was heated at 210° C. in the microwave for 30 min. The reaction mixture was poured onto H$_2$O and EtOAc and the layers were separated. The aqueous layer was extracted twice with EtOAc. The organic layers dried over MgSO$_4$, filtered, treated with silica gel and evaporated. The compound was purified by silica gel chromatography on a 12 g column using an MPLC system eluting with a gradient of n-heptane:EtOAc (100:0 to 75:25). MS (ESI): m/z=322.1 [M+H]$^+$.

BB36

2-(3-Fluoro-4-(trifluoromethyl)-1,3-phenyl)benzoxazole-6-carboxylic acid

To a suspension of methyl 2-(3-fluoro-4-(trifluoromethyl) phenyl)-1,3-benzoxazole-6-carboxylate (445 mg, 1.31 mmol) in H$_2$O (4 mL) and 1,4-dioxane (4 mL) was added LiOH monohydrate (68.8 mg, 1.64 mmol) and the mixture was stirred at 50° C. for 16 h., 1M HCl solution (1.64 mL, 1.64 mmol) was added and the reaction was stirred at RT for 3 h. 1,4-Dioxane (4 mL) was removed. The suspension was filtered and the filter cake was washed with plenty of H$_2$O. MS (ESI): m/z=326.1 [M+H]$^+$.

Intermediate: Methyl 2-(3-fluoro-4-(trifluoromethyl) phenyl)-1,3-benzoxazole-6-carboxylate A mixture of methyl 4-amino-3-hydroxybenzoate (300 mg, 1.76 mmol), 3-fluoro-4-(trifluoromethyl)benzoyl chloride (629 mg, 421 μl, 2.64 mmol) and dioxane (3 mL) was heated at 210° C. in the microwave for 30 min. The reaction mixture was poured onto H$_2$O and EtOAc and the layers were separated. The aqueous layer was extracted twice with EtOAc. The organic layers dried over MgSO$_4$, filtered, treated with silica gel and evaporated. The compound was purified by silica gel chromatography on a 12 g column using an MPLC system eluting with a gradient of n-heptane: EtOAc (100:0 to 75:25). MS (ESI): m/z=340.1 [M+H]$^+$.

BB37

2-(4-Fluorophenyl)-1,3-benzoxazole-6-carboxylic acid

To a suspension of methyl 2-(4-fluorophenyl)-1,3-benzoxazole-6-carboxylate (408 mg, 1.5 mmol) in 1,4-dioxane (4 mL) and H$_2$O (4 mL) was added LiOH monohydrate (78.9 mg, 1.88 mmol) and the mixture was stirred at 50° C. for 16 h., 1 M HCl solution (1.88 mL, 1.88 mmol) was added and the reaction mixture was stirred at RT over night. 1,4-Dioxane (4 mL) was removed. The reaction mixture was filtered, the filter cake washed with plenty of H$_2$O and dried to give the desired compound. MS (ESI): m/z=258.2 [M+H]$^+$.

Intermediate: Methyl 2-(4-fluorophenyl)-1,3-benzoxazole-6-carboxylate

A mixture of methyl 4-amino-3-hydroxybenzoate (300 mg, 1.76 mmol), 4-fluorobenzoyl chloride (427 mg, 322 μl, 2.64 mmol) and dioxane (3 mL) was heated at 210° C. under microwave for 30 min. The reaction mixture was poured onto H$_2$O and EtOAc and the layers were separated. The aqueous layer was extracted twice with EtOAc. The organic layers dried over MgSO$_4$, filtered, treated with silica gel and evaporated. The compound was purified by silica gel chromatography on a 12 g column using an MPLC system eluting with a gradient of n-heptane:EtOAc (100:0 to 75:25). MS (ESI): m/z=272.2 [M+H]$^+$.

BB38

6-Fluoro-2-piperazin-1-yl-3H-quinazolin-4-one hydrochloride

To a stirred solution of tert-butyl 4-(6-fluoro-4-oxo-3H-quinazolin-2-yl)piperazine-1-carboxylate (1.1 g, 3.16 mmol) in DCM (20 mL) was added 4 M HCl in dioxane (10.0 mL, 3.16 mmol) at 0° C., and was continued at 25° C. for 16 h. The reaction mixture was concentrated under reduced pressure to get an off-white solid (810 mg, 2.84 mmol). $^1$H NMR (DMSO-d$^6$, 400 MHz): 3.19-3.23 (m, 4H), 3.94-3.98 (m, 4H), 7.60-7.71 (m, 3H), 9.60 (s, 2H). MS (EI): m/z=248.9 [M+H]$^+$.

Intermediates a) tert-Butyl 4-(6-fluoro-4-oxo-3H-quinazolin-2-yl) piperazine-1-carboxylate To a stirred solution of 2-chloro-6-fluoro-3H-quinazolin-4-one (640.0 mg, 3.22 mmol) in EtOH (10 mL) was added DIPEA (1.68 mL, 9.67 mmol) and 1-Boc-piperazine (720.31 mg, 3.87 mmol), and was stirred at 110° C. for 16 h. The reaction mixture was evaporated. The residue was extracted with EtOAc and washed with H$_2$O, dried over Na$_2$SO$_4$ and concentrated under reduced pressure to yield an off-white solid (1.1 g, 3.16 mmol). $^1$H NMR (400 MHz, DMSO-d$_6$) δ 7.62-7.55 (m, 1H), 7.49 (td, J=8.8, 3.2 Hz, 1H), 7.35 (s, 1H), 3.41 (t, J=5.1 Hz, 4H), 3.33 (s, 4H), 1.42 (s, 9H). MS (EI): m/z=349.2 [M+H]$^+$.

b) 2-Chloro-6-fluoro-3H-quinazolin-4-one

A mixture of 1N NaOH (9.0 mL, 3.23 mmol), THF (9 mL), and 2,4-dichloro-6-fluoro-quinazoline (700.0 mg, 3.23 mmol) was stirred at RT under N$_2$ for 16 h at 25° C. The solution was chilled and adjusted to pH 5 with AcOH. Then it was extracted with EtOAc and the obtained organic layer was washed with H$_2$O, dried over Na$_2$SO$_4$ and concentrated under reduced pressure to get an off-white solid (640 mg, 3.22 mmol). $^1$H NMR (400 MHz, DMSO-d$_6$) δ 7.81-7.69 (m, 2H), 7.69 (dd, J=8.9, 5.1 Hz, 1H). MS (EI): m/z=197.4 [M−H]$^−$.

c) 2,4-Dichloro-6-fluoro-quinazoline

To a stirred solution of 6-fluoro-1H-quinazoline-2,4-dione (1.0 g, 5.55 mmol) in phosphoryl chloride (10.0 mL, 5.55 mmol, CAS RN 10025-87-3) were added N,N-dimethyl aniline (0.7 mL, 5.55 mmol, CAS RN 121-69-7). The mixture was heated to reflux for 16 h. The reaction mixture was poured onto ice-water. Formed solids were filtered and the solids were extracted with EtOAc and the organic layer was washed with H$_2$O and dried over Na$_2$SO$_4$ and concentrated under reduced pressure. The crude product was purified under silica gel column chromatography by using 10-15% EtOAc in n-hexane to get a light yellow solid (750 mg, 3.46 mmol). $^1$H NMR (400 MHz, DMSO-d$_6$) δ 8.11 (dtd, J=22.5, 8.9, 3.9 Hz, 3H).

d) 6-Fluoro-1H-quinazoline-2,4-dione

2-Amino-5-fluorobenzoic acid (5.0 g, 32.23 mmol, CAS RN 446-08-2) and urea (19.36 g, 322.31 mmol, CAS RN 57-13-6) were stirred at 160° C. for 6 h. The reaction mixture was cooled to 100° C. and H₂O was added while stirring. A precipitate formed which was filtered off and washed with H₂O to yield a solid that was suspended in a 0.5 N NaOH solution and heated to boil for 5-10 min. The mixture was cooled and the pH was adjusted to 2 with conc. HCl solution. The solids was filtered off and dried under reduced pressure to get an off-white solid (4.6 g, 25.54 mmol). $^1$H NMR (400 MHz, DMSO-d$_6$) δ 11.30 (s, 2H), 7.62-7.49 (m, 2H), 7.19 (dd, J=8.9, 4.5 Hz, 1H), 5.42 (s, 2H).

BB39

7-Fluoro-2-piperazin-1-yl-3H-quinazolin-4-one hydrochloride

To a stirred solution of tert-butyl 4-(7-fluoro-4-oxo-3H-quinazolin-2-yl)piperazine-1-carboxylate (1.2 g, 3.44 mmol) in DCM (10 mL) was added 4 M HCl in dioxane (2.0 mL, 3.44 mmol) at 0° C. and was stirred at 25° C. for 16 h. The reaction mixture was concentrated under reduced pressure to get and as HCl salt (903 mg, 3.17 mmol). $^1$H NMR (DMSO-d$_6$, 400 MHz): 3.21-3.23 (m, 4H), 4.01-4.04 (m, 4H), 7.15 (t, J=7.7 Hz, 1H), 7.51-7.53 (m, 1H), 8.02 (t, J=7.4 Hz, 1H), 9.75 (s, 2H). MS (EI): m/z=249.1 [M+H]⁺.

Intermediates a) tert-Butyl 4-(7-fluoro-4-oxo-3H-quinazolin-2-yl)piperazine-1-carboxylate To a stirred solution of 2-chloro-7-fluoro-3H-quinazolin-4-one (200.0 mg, 1.01 mmol) in EtOH (5 mL) was added DIPEA (0.53 mL, 3.02 mmol) and 1-Boc-piperazine (225.1 mg, 1.21 mmol), and was stirred at 110° C. for 16 h. The reaction mixture was concentrated under reduced pressure to get an off-white solid (321 mg, 0.920 mmol). MS (EI): m/z=349.1 [M+H]⁺.

b) 2-Chloro-7-fluoro-3H-quinazolin-4-one

A mixture of TN NaOH solution (16.0 mL, 3.69 mmol), THF (8 mL) and 2,4-dichloro-7-fluoro-quinazoline (800 mg, 3.69 mmol, CAS RN 174566-15-5) was stirred at RT under nitrogen atmosphere for 4 h. The solution was cooled down and the pH adjusted to 5 by means of adding AcOH, then it was diluted with EtOAc (100 mL). The organic layer was washed with H₂O and dried over Na₂SO₄ and concentrated under reduced pressure to get an off-white solid (705 mg, 3.55 mmol). $^1$H NMR (400 MHz, DMSO-d$_6$) δ 13.40-13.34 (bs, 1H), 8.15-8.11 (m, 1H), 7.47-7.37 (m, 2H). MS (EI): m/z=199.2 [M+H]⁺.

BB40

2-Phenyl-4-(trifluoromethyl)-1,3-benzoxazole-6-carboxylic acid

To a stirred solution of ethyl 2-phenyl-4-(trifluoromethyl)-1,3-benzoxazole-6-carboxylate (260.0 mg, 0.780 mmol) in THF (9 mL) and H₂O (3 mL) was added LiOH.H₂O (32.54 mg, 0.780 mmol, CAS RN 1310-66-3) and was stirred at 25° C. for 2 h. The reaction mixture was concentrated to dryness and the residue was taken up in H₂O (15 mL) and was acidified with citric acid. The precipitate was collected by filtration and dried under reduced pressure to provide an off-white solid (103.2 mg, 0.340 mmol). $^1$H NMR (DMSO-d$_6$, 400 MHz): 7.65-7.73 (m, 3H), 8.23-8.28 (m, 3H), 8.58 (s, 1H), 13.6 (br s, 1H). MS (ESI): m/z=308.2 [M+H]⁺.

Intermediate: Ethyl 2-phenyl-4-(trifluoromethyl)-1,3-benzoxazole-6-carboxylate

A solution of ethyl 4-iodo-2-phenyl-1,3-benzoxazole-6-carboxylate (150.0 mg, 0.380 mmol, intermediate of BB32) in anhydrous DMF (2.5 mL) was added methyl 2,2-difluoro-2-(fluorosulfonyl)acetate (150.0 mg, 0.380 mmol, CAS RN 680-15-9) and CuI (217.97 mg, 1.14 mmol, CAS RN 7681-65-4) at 25° C. The reaction mixture was heated to 110° C. for 2 h in the microwave. After completion of the reaction, the reaction mixture was purified under silica gel column chromatography by using 2-5% EtOAc in n-hexane to furnish an off-white solid (90 mg, 0.270 mmol). $^1$H NMR (DMSO-d$_6$, 400 MHz): 1.37 (t, J=7.1 Hz, 3H), 4.40 (q, J=7.1 Hz, 2H), 7.66-7.76 (m, 3H), 8.23 (m, 3H), 8.62 (s, 1H). MS (EI): m/z=336.1 [M+H]⁺.

BB41

2-Morpholino-1,3-benzoxazole-6-carboxylic acid

To a solution of methyl 2-morpholino-1,3-benzoxazole-6-carboxylate (350.0 mg, 1.33 mmol) in THF (5 mL) was added another solution of NaOH (213.53 mg, 5.34 mmol) in H₂O (5 mL). The reaction mixture was stirred at 20° C. for 4 h. The reaction was acidified (pH 5) with 1N HCl solution. The white precipitate was filtered off and dried under vacuum to give a white solid (220 mg, 0.890 mmol). $^1$H NMR (400 MHz, DMSO-d$_6$) δ ppm 3.55-3.81 (m, 8H) 7.35 (d, J=8.16 Hz, 1H) 7.83 (dd, J=8.22, 1.44 Hz, 1H) 7.88 (d, J=1.13 Hz, 1H) 12.78 (br s, 1H).

Intermediate: Methyl 2-morpholino-1,3-benzoxazole-6-carboxylate

A solution of methyl 2-chloro-1,3-benzoxazole-6-carboxylate (630.0 mg, 2.98 mmol, CAS RN 819076-91-0) and morpholine (1297 mg, 14.89 mmol, CAS RN 110-91-8) in THF (10 mL) was stirred at 20° C. for 1 h. The mixture was concentrated. The residue was suspended in H₂O (30 mL) and extracted with EtOAc (2×20 mL). The organic phase was washed with brine and dried over Na₂SO₄, then concentrated to give an off-white solid (650 mg, 2.48 mmol). $^1$H NMR (400 MHz, DMSO-d$_6$) δ ppm 3.62-3.68 (m, 4H) 3.70-3.77 (m, 4H) 7.37 (d, J=8.28 Hz, 1H) 7.84 (dd, J=8.22, 1.57 Hz, 1H) 7.91 (d, J=1.38 Hz, 1H).

BB42

4-(2,3-Dihydro-1H-pyrrolo[2,3-b]pyridin-1-yl)benzoic acid

The desired compound was obtained in analogy to BB5, using methyl 4-(2,3-dihydro-1H-pyrrolo[2,3-b]pyridin-1-yl)benzoate (162.7 mg, 640 μmol) at a temperature of 55° C. as a white solid (140.8 mg, 576 μmol). $^1$H NMR (300 MHz, DMSO-d$_6$) δ 12.63 (br s, 1H), 8.02-8.06 (m, 1H), 8.00 (d, J=9.05 Hz, 2H), 7.92 (d, J=9.05 Hz, 2H), 7.53 (dd, J=1.51, 7.15 Hz, 1H), 6.79 (dd, J=5.24, 7.25 Hz, 1H), 4.09 (t, J=8.56 Hz, 1H), 3.18 (t, J=8.56 Hz, 2H). MS (ESI): m/z=241.2 [M+H]⁺.

Intermediate: a) Methyl 4-(2,3-dihydro-1H-pyrrolo[2,3-b]pyridin-1-yl)benzoate

Methyl 4-bromobenzoate (447 mg, 2.08 mmol, CAS RN 619-42-1) and 2,3-dihydro-1H-pyrrolo[2,3-b]pyridine (250 mg, 2.08 mmol, CAS RN 10592-27-5) were dissolved in dry dioxane (5 mL) at RT, whereupon xantphos (301 mg, 520 µmol, CAS RN 161265-03-8), Pd$_2$(dba)$_3$ (476 mg, 520 µmol, CAS RN 51364-51-3) and K$_3$PO$_4$ (883 mg, 4.16 mmol, CAS RN 7778-53-2) were added successively. The reaction vessel was flushed with argon and sealed, before being heated to 101° C. for 20 h. The reaction mixture was then cooled to RT and diluted with EtOAc, before being filtered over a celite pad and washed with EtOAc (50 mL). The organic phase was poured into a separating funnel containing H$_2$O (50 mL) and the layers separated. The aqueous layer was extracted with EtOAc (4×45 mL), dried over Na$_2$SO$_4$, filtered and concentrated in vacuo to yield a crude dark brown residue (1.56 g). The crude product was taken up in EtOAc (25 mL) and concentrated in vacuo with silica, before being purified by flash column chromatography (SiO$_2$, 80 g, 100-200 mesh, Eluent: Hep:EtOAc, 100:0 to 1:1 over 25 mins). The fractions containing the product were combined and concentrated in vacuo to yield a pale yellow solid (176.8 mg, 0.69 mmol). $^1$H NMR (300 MHz, CHLOROFORM-d) δ 8.06-8.10 (m, 1H), 8.04 (d, J=9.09 Hz, 2H), 7.91 (d, J=9.09 Hz, 2H), 7.35-7.40 (m, 1H), 6.71 (dd, J=5.24, 7.25 Hz, 1H), 4.04-4.12 (m, 2H), 3.90 (s, 3H), 3.15-3.22 (m, 2H). MS (ESI): m/z=255.2 [M+H]$^+$.

BB43

4-(2-Phenylpyrrolidin-1-yl)benzoic acid

The desired compound was obtained in analogy to BB5, using methyl 4-(2-phenylpyrrolidin-1-yl)benzoate (100 mg, 355 µmol) at a reaction temperature of 55° C. as a white solid (90 mg, 330 µmol). $^1$H NMR (300 MHz, DMSO-d$_6$) δ 12.03 (br s, 1H), 7.65 (d, J=8.86 Hz, 2H), 7.13-7.38 (m, 5H), 6.44 (d, J=8.87 Hz, 2H), 4.89 (br d, J=6.25 Hz, 1H), 3.69-3.78 (m, 1H), 3.38-3.50 (m, 1H), 2.32-2.46 (m, 1H), 1.78-2.04 (m, 3H). MS (ESI): m/z=268.2 [M+H]$^+$.

Intermediate: Methyl 4-(2-phenylpyrrolidin-1-yl)benzoate

The desired compound was obtained in analogy to an intermediate of BB22, using methyl 4-fluorobenzoate (2.13 g, 13.6 mmol, CAS RN 403-33-8), 2-phenylpyrrolidine (2.0 g, 13.6 mmol, CAS RN 1006-64-0) and Cs$_2$CO$_3$ (8.83 g, 27.1 mmol, CAS RN 534-17-8) but required an additional purification step by HPLC as a white solid. $^1$H NMR (300 MHz, CHLOROFORM-d) δ 7.81 (d, J=8.85 Hz, 2H), 7.27-7.33 (m, 2H), 7.16 (s, 3H), 6.45 (d, J=8.85 Hz, 2H), 4.81-4.86 (m, 1H), 3.81 (s, 3H), 3.69-3.80 (m, 1H), 3.45-3.57 (m, 1H), 2.35-2.49 8 (m, 1H), 1.94-2.10 (m, 3H). MS (ESI): m/z=282.3 [M+H]$^+$.

BB44

2-(2-Pyridyl)-1,3-benzoxazole-6-carboxylic acid

A mixture of methyl 3-hydroxy-4-(pyridine-2-carbonylamino)benzoate (300.0 mg, 1.1 mmol) in polyphosphoric acid (2.0 mL, 1.1 mmol, CAS RN 8017-16-1) was stirred at 180° C. for 2 h. The mixture was poured onto an ammonium hydroxide solution (10 mL, CAS RN 1336-21-6) and stirred at 20° C. for 20 min. The reaction mixture was extracted with EtOAc (3×10 mL). The pH of the aqueous layer was adjusted to 6 by adding a 2 M HCl solution and back-extracted with EtOAc (5×20 mL). The combined organic layers were washed with brine (2×20 mL), dried over Na$_2$SO$_4$, filtered and concentrated to give a light yellow solid (80 mg, 0.330 mmol). $^1$H NMR (400 MHz, DMSO-d$_6$) δ ppm 7.68 (ddd, J=7.56, 4.80, 0.94 Hz, 1H) 7.91-8.00 (m, 1H) 8.02-8.12 (m, 2H) 8.32-8.43 (m, 2H) 8.83 (d, J=4.14 Hz, 1H) 13.15 (br s, 1H).

Intermediate: Methyl 3-hydroxy-4-(pyridine-2-carbonylamino)benzoate

A mixture of methyl 4-amino-3-hydroxybenzoate (1.0 g, 5.98 mmol, CAS RN 63435-16-5) and 1,1'-carbonyldiimidazole (969.43 mg, 5.98 mmol, CAS RN 530-62-1) in THF (20 mL) was stirred at 20° C. for 0.5 h. Then 2-pyridinecarboxylic acid (736.48 mg, 5.98 mmol, CAS RN 98-98-6) was added and the mixture was stirred 20° C. for 15 h. The mixture was poured onto H$_2$O (30 mL) and extracted with EtOAc (3×50 mL). The combined organic layers were washed with brine (30 mL), dried over Na$_2$SO$_4$, filtered and concentrated. The crude product was purified by column chromatography (PE:EtOAc=10:1 to 0:1) to give a light yellow solid (1.3 g, 4.77 mmol). MS (ESI): m/z=273.0 [M+H]$^+$.

BB45

N'-hydroxy-4-[4-(4-oxo-3H-quinazolin-2-yl)piperazine-1-carbonyl]benzamidine

To a solution of 4-[4-(4-oxo-3H-quinazolin-2-yl)piperazine-1-carbonyl]benzonitrile (1.0 g, 2.78 mmol) in EtOH (40 mL) was added Na$_2$CO$_3$ (1.77 g, 16.7 mmol) and hydroxylamine hydrochloride (1.16 g, 16.7 mmol, CAS RN 5470-11-1). The reaction mixture was heated at 90° C. for 3 h. The reaction was filtered and concentrated in vacuum to obtain a light yellow solid (820 mg). The crude product was used in the next step without further purification.

Intermediate: 4-[4-(4-Oxo-3H-quinazolin-2-yl)piperazine-1-carbonyl]benzonitrile

To a solution of 4-cyanobenzoic acid (1.0 g, 6.8 mmol, CAS RN 619-65-8) in DMF (30 mL) was added DIPEA (2.63 g, 20.39 mmol, CAS RN 7087-68-5) and HATU (2.84 g, 7.48 mmol, CAS RN 148893-10-1) at 0° C. The mixture was stirred at this temperature for 30 min, then 2-piperazin-1-yl-3H-quinazolin-4-one hydrochloride (1904 mg, 7.14 mmol, CAS RN 591244-85-8) was added and the reaction was warmed up to 25° C. within 0.5 h. After the formation of the desired product, the reaction mixture was quenched with H$_2$O (10 mL), extracted with EtOAc (3×50 mL). The combined organic layers were washed with H$_2$O (2×30 mL) and brine (10 mL), dried over Na$_2$SO$_4$ and concentrated in vacuum to provide alight yellow solid (1.8 g). MS (ESI): m/z=360.1 [M+H]$^+$.

BB46

4-(2-Oxa-6-azaspiro[3.3]heptan-6-yl)benzoic acid

The desired compound was obtained in analogy to BB5, using methyl 4-(2-oxa-6-azaspiro[3.3]heptan-6-yl)benzoate (140.7 mg, 603 µmol) at a reaction temperature of 55° C. as a pale yellow solid (125.6 mg, 561 µmol). $^1$H NMR (300 MHz, DMSO-d$_6$) δ 12.13-12.24 (m, 1H), 7.74 (d, J=8.87 Hz, 2H), 6.42 (d, J=8.87 Hz, 2H), 4.72 (s, 4H), 4.08 (s, 4H). MS (ESI): m/z=220.2 [M+H]$^+$.

Intermediate: Methyl 4-(2-oxa-6-azaspiro[3.3]heptan-6-yl)benzoate

2-Oxa-6-azaspiro[3.3]heptane hemioxalate (250 mg, 867 µmol, CAS RN 1045709-32-7) was suspended in dry toluene (1.73 mL) at RT, whereupon methyl 4-bromobenzoate (280 mg, 1.3 mmol, CAS RN 619-42-1), Pd$_2$(dba)$_3$ (111 mg, 121 μmol, CAS RN 51364-51-3), (R)-(+)-2,2'-bis(diphenylphosphino)-1,1'-binaphthyl (140 mg, 225 μmol, CAS RN 98327-87-8) and Cs$_2$CO$_3$ (424 mg, 1.3 mmol, CAS RN 534-17-8) were added. The reaction mixture was purged with argon and sealed, before being heated to 100° C. for 8 h. The reaction mixture was allowed to cool to RT, before being diluted with EtOAc (10 mL) and filtered through a celite pad. The filter cake was washed with EtOAc (50 mL). The collected organic phase was poured into a separating funnel containing H$_2$O (50 mL) and the layers separated. The aqueous phase was washed with EtOAc (3×20 mL), before the combined organic phases were dried over Na$_2$SO$_4$, filtered and concentrated in vacuo to yield a crude yellow residue (744 mg). The crude product was taken up in EtOAc (30 mL), concentrated in vacuo with silica and purified by flash column chromatography (SiO$_2$, 40 g, 100-200 mesh, Eluent: Hep:EtOAc, 100:0 to 1:1 over 25 mins). Fractions containing the product were combined and concentrated in vacuo to yield a pale yellow solid (144 mg, 607 μmol). $^1$H NMR (300 MHz, CHLOROFORM-d) δ 7.89 (d, J=8.87 Hz, 2H), 6.38 (d, J=7.85 Hz, 2H), 4.85 (s, 4H), 4.12 (s, 4H), 3.85 (s, 3H). MS (ESI): m/z=234.2 [M+H]$^+$.

BB47

2-[4-(4-Bromobenzoyl)piperazin-1-yl]-3H-quinazolin-4-one

4-Bromobenzoic acid (195 mg, 968 μmol, CAS RN 586-76-5), 2-(piperazin-1-yl)quinazolin-4(3H)-one acetate (281 mg, 968 μmol, CAS RN 22587-29-7) and HATU (736 mg, 1.94 mmol) were dissolved in DMF (2 mL) and TEA (490 mg, 675 μl, 4.84 mmol) was added. The reaction mixture was stirred at RT overnight. The reaction mixture was diluted with H$_2$O. The precipitate was filtered and washed with H$_2$O. The filter cake was dissolved in EtOAc and treated with H$_2$O. The resulting two-layer mixture was extracted with EtOAc. The organic layers were washed with H$_2$O and brine, dried over Na$_2$SO$_4$, filtered, treated with silica gel and concentrated in vacuo. The crude compound was purified by flash chromatography on a 12 g column using a MPLC system eluting with a gradient of n-heptane:EtOAc (100:0 to 0:100). The fractions containing the product were pooled and concentrated in vacuo to give a light yellow solid (93.2 mg, 225 μmol). $^1$H NMR (300 MHz, DMSO-d$_6$) δ ppm 3.40-3.86 (m, 8H) 7.11-7.23 (m, 1H) 7.24-7.35 (m, 1H) 7.36-7.47 (m, 2H) 7.60 (ddd, J=8.36, 6.95, 1.61 Hz, 1H) 7.64-7.74 (m, 2H) 7.92 (dd, J=7.96, 1.31 Hz, 1H) 11.44 (br s, 1H). MS (ESI): m/z=415.1[M+H]$^+$.

BB48

6-Chloro-2-piperazin-1-yl-3H-quinazolin-4-one hydrochloride

To a stirred solution of tert-butyl 4-(6-chloro-4-oxo-3H-quinazolin-2-yl) piperazine-1-carboxylate (1.0 g, 2.74 mmol) in DCM (20 mL) was added 4 M HCl in dioxane solution (5.0 mL, 2.74 mmol) at 0° C. and the solution was stirred at 25° C. for 16 h. The reaction mixture was evaporated under reduced pressure. The residue was washed with n-pentane and dried under reduced pressure to yield an off-white solid (809.3 mg, 2.69 mmol). $^1$H NMR (DMSO-d$_6$, 400 MHz): 3.19-3.23 (m, 4H), 3.98-3.99 (m, 4H), 7.69-7.76 (m, 2H), 7.90 (d, J=2.3 Hz, 1H), 9.68 (br s, 2H). MS (EI): m/z=265.0 [M+H]$^+$.

Intermediates a) tert-Butyl 4-(6-chloro-4-oxo-3H-quinazolin-2-yl) piperazine-1-carboxylate To a stirred solution of 1-Boc-piperazine (675.57 mg, 3.63 mmol, CAS RN 57260-71-6) in EtOH (2.5 mL) was added DIPEA (1.58 mL, 9.07 mmol) and 2,6-dichloro-3H-quinazolin-4-one (650.0 mg, 3.02 mmol), and was stirred at 110° C. for 16 h. The reaction mixture was evaporated under reduced pressure. The residue was extracted with EtOAc and washed with H$_2$O and dried over Na$_2$SO$_4$ and concentrated under reduced pressure to get an off-white solid (1.1 g, 3.02 mmol). $^1$H NMR (400 MHz, DMSO-d$_6$) δ 7.83 (d, J=2.6 Hz, 1H), 7.61 (dd, J=8.8, 2.6 Hz, 1H), 7.31 (d, J=8.8 Hz, 1H), 3.62 (t, J=5.2 Hz, 4H), 3.33 (s, 4H), 1.42 (s, 9H). MS (EI): m/z=365.0 [M+H]$^+$.

b) 2,6-Dichloro-3H-quinazolin-4-one

A mixture of 1N NaOH solution (12.0 mL, 4.28 mmol), THF (12 mL), and 2,4,6-trichloroquinazoline (1.0 g, 4.28 mmol) was stirred at RT at 25° C. for 16 h. The solution was cooled and adjusted to pH 5 with AcOH. It was then extracted with EtOAc and the organic layers were washed with H$_2$O, dried over Na$_2$SO$_4$ and concentrated under reduced pressure to get an off-white solid (910 mg, 4.23 mmol). $^1$H NMR (400 MHz, DMSO-d$_6$) δ 8.01 (d, J=2.7 Hz, 1H), 7.86 (dd, J=8.9, 2.6 Hz, 1H), 7.63 (d, J=8.7 Hz, 1H). MS (EI): m/z=214.9 [M+H]$^+$.

c) 2,4,6-Trichloroquinazoline

To a stirred solution of 6-chloro-1H-quinazoline-2,4-dione (500.0 mg, 2.54 mmol) in POCl$_3$ (7.0 mL, 2.54 mmol, CAS RN 10025-87-3) was added N,N-dimethylaniline (0.3 mL, 2.54 mmol, CAS RN 121-69-7) at 0° C. The reaction mixture was stirred at 110° C. for 16 h. The reaction mixture was poured onto an ice-water mixture. Precipitate was filtered through a sintered funnel. The solids were dissolved in EtOAc and washed with H$_2$O, then brine. The combined organic layers were dried over Na$_2$SO$_4$ and concentrated under reduced pressure. The crude product was purified under silica gel column chromatography by using 5-10% EtOAc in n-hexane to get an off-white solid (180 mg, 0.770 mmol). 1H NMR (400 MHz, DMSO-d$_6$) δ 8.32 (d, J=2.3 Hz, 1H), 8.19 (dd, J=9.0, 2.3 Hz, 1H), 8.08 (d, J=9.0 Hz, 1H). MS (EI): m/z=234.9 [M+H]$^+$.

d) 6-Chloro-1H-quinazoline-2,4-dione

2-Amino-5-chlorobenzoic acid (5.0 g, 29.14 mmol, CAS RN 635-21-2) and urea (17.5 g, 291.41 mmol, CAS RN 57-13-6) were stirred at 160° C. for 6 h. The reaction mixture was cooled to 100° C. and H$_2$O was added while stirring for 5 min. The precipitate was filtered off and washed with H$_2$O to yield a solid cake that was suspended in a solution of 0.5 N NaOH and heated to boil for 5-10 min. The mixture was cooled down and the pH adjusted to 2 with a conc. HCl solution; the solids were filtered off. The filter cake was dried under reduced pressure to provide an off-white solid (4.5 g, 22.9 mmol). $^1$H NMR (400 MHz, DMSO-d$_6$) δ 7.78 (s, 1H), 7.62 (d, J=8.7 Hz, 1H), 7.19 (d, J=8.8 Hz, 1H). MS (EI): m/z=197.1 [M+H]$^+$.

BB49

4-[2-[[3-(Trifluoromethyl)phenyl]methylamino]ethyl]benzoic acid; hydrochloride

Ethyl 4-(2-((3-(trifluoromethyl)benzyl)amino)ethyl)benzoate sulfate (55.3 mg, 123 µmol, prepared in a similar fashion as in BB1 (intermediate, step b) using ethyl 4-(2-aminoethyl) benzoate (CAS RN 77266-69-4)) was dissolved in MeOH (410 µL), then NaOH 1M (185 µL, 185 µmol) was added. The reaction mixture was stirred at 70° C. for 3 h. The solvent was evaporated and the residue was diluted with H$_2$O (5 mL). The pH of the aqueous layer was adjusted to pH 2-3 with 1 M HCl solution and the white precipitate was filtered off. The filter cake was dried in vacuo to give a white solid (25.6 mg, 71 µmol). MS (ESI): m/z=324.3 [M+H]$^+$.

BB50

4-(1-Cyanocyclopentyl)benzoic acid

Methyl 4-(1-cyanocyclopentyl)benzoate (208.6 mg, 910 µmol) was dissolved in MeOH (3 mL) and 1 M NaOH solution (1.36 ml, 1.36 mmol). The reaction mixture was stirred at 70° C. for 3 h. The reaction solvents were evaporated and the residue was diluted with H$_2$O (5 mL). The pH of the aqueous layer was adjusted to 2-3 with 1 M HCl solution. The precipitate was filtered off and dried under high vacuum to give a white solid (154.4 mg, 717 µmol). $^1$H NMR (300 MHz, DMSO-d$_6$) δ ppm 1.85-1.98 (m, 4H) 2.04-2.18 (m, 2H) 2.38-2.48 (m, 2H) 7.60-7.68 (m, 2H) 7.94-8.02 (m, 2H) 13.06 (br s, 1H). MS (ESI): m/z=214.3 [M−H]$^−$.

Intermediates a) Methyl 4-(1-cyanocyclopentyl)benzoate

Methyl 4-(cyanomethyl)benzoate (200 mg, 1.14 mmol, CAS RN 76469-88-0) and 1,4-dibromobutane (1.23 g, 673 µl, 5.71 mmol, CAS RN 110-52-1) were combined in THF (5.7 mL) and cooled down to 0° C. To this solution potassium bis(trimethylsilyl)amide (1M solution in THF; 2.28 ml, 2.28 mmol, CAS RN 40949-94-8) was added dropwise over a period of 15 minutes and then allowed to warm up to RT. The reaction mixture was stirred at RT overnight. The reaction mixture was partitioned between EtOAc and H$_2$O. The organic phases were washed with an aqueous solution of NaHCO$_3$ and brine, dried over MgSO$_4$, filtered and concentrated in vacuo. The crude product was purified by flash chromatography on a 12 g column using a MPLC system eluting with a gradient of n-heptane:EtOAc (100:0 to 0:100) to yield a light brown oil (214 mg, 890 µmol). $^1$H NMR (300 MHz, DMSO-d$_6$) δ ppm 1.87-1.95 (m, 4H) 2.04-2.17 (m, 2H) 2.39-2.47 (m, 2H) 3.87 (s, 3H) 7.64-7.70 (m, 2H) 7.97-8.04 (m, 2H). MS (ESI): m/z=230.2 [M+H]$^+$.

BB51

4-Morpholino-2-phenyl-1,3-benzoxazole-6-carboxylic acid

A solution of methyl 4-morpholino-2-phenyl-1,3-benzoxazole-6-carboxylate (287.0 mg, 0.850 mmol) in THF (10 mL) was added NaOH (135.71 mg, 3.39 mmol) in H$_2$O (10 mL). The mixture was stirred at 20° C. for 4 h. The mixture was diluted with H$_2$O and extracted with EtOAc (3×100 mL). The combined organic layers were washed with brine, dried over Na$_2$SO$_4$, filtered and concentrated to give a yellow solid (240.7 mg, 0.74 mmol). MS (ESI): m/z=325.0 [M+H]$^+$.

Intermediates a) Methyl 4-morpholino-2-phenyl-1,3-benzoxazole-6-carboxylate

A solution of methyl 4-bromo-2-phenyl-1,3-benzoxazole-6-carboxylate (1.0 g, 3.01 mmol), morpholine (0.31 g, 3.61 mmol, CAS RN 110-91-8), potassium tert-butoxide (0.51 g, 4.52 mmol, CAS RN 865-47-4) and RuPhos (0.01 g, 0.020 mmol, CAS RN 787618-22-8) in toluene (50 mL) was added palladium(II) acetate (2.2 mg, 0.010 mmol). The mixture was stirred at 80° C. for 15 h under a N$_2$ atmosphere. The solvent were evaporated and the residue diluted with H$_2$O and extracted with EtOAc (100 mL). The combined organic layers were washed with brine, dried over Na$_2$SO$_4$, filtered and concentrated. The crude product was purified by silica gel chromatography (PE/EtOAc=10:1 to 6:1) to give a yellow solid (287 mg, 0.85 mmol). MS (ESI): m/z=339.0 [M+H]$^+$.

b) Methyl 4-bromo-2-phenyl-1,3-benzoxazole-6-carboxylate

A solution of methyl 4-benzamido-3-bromo-5-hydroxy-benzoate (2.1 g, 6 mmol) in toluene (40 mL) was added PTSA (2.07 g, 11.99 mmol). The mixture was stirred at 110° C. for 15 h. The reaction mixture was diluted with H$_2$O and extracted with EtOAc (3×100 mL). The combined organic layers were washed with brine, dried over sodium sulfate, filtered and concentrated. The crude product was purified by silica gel chromatography (PE/EtOAc=1:0 to 5:1) to give a yellow solid (1.5 g, 4.52 mmol). MS (ESI): m/z=331.9 [M+H]$^+$.

c) Methyl 4-benzamido-3-bromo-5-hydroxy-benzoate

A solution of methyl 4-amino-3-bromo-5-hydroxy-benzoate (2.1 g, 8.53 mmol, CAS RN 1246759-65-8) and Na$_2$CO$_3$ (1.81 g, 17.07 mmol) in THF (40 mL) was added benzoylchloride (1.09 mL, 9.39 mmol, CAS RN 98-88-4). The reaction mixture was stirred at 20° C. for 15 h. The mixture was diluted with H$_2$O and extracted with EtOAc (3×100 mL). The combined organic layers were washed with brine, dried over Na$_2$SO$_4$, filtered and concentrated. The crude product was purified by silica gel chromatography (PE/EtOAc=1:0 to 6:1) to give a yellow solid (2.17 g, 6.2 mmol). MS (ESI): m/z=351.0 [M+H]$^+$.

BB52

2-(2-Azaspiro[3.4]octan-2-yl)-1,3-benzoxazole-6-carboxylic acid

To a suspension of methyl 2-(2-azaspiro[3.4]octan-2-yl)-1,3-benzoxazole-6-carboxylate (121 mg, 423 µmol) in dioxane (1 mL) and H$_2$O (1 mL) was added LiOH monohydrate (26.6 mg, 634 µmol) and the suspension was stirred at RT overnight to give a clear, colorless solution. Dioxane was evaporated and the residue was diluted with H$_2$O (approx. 2 mL). To the solution was added dropwise 1M HCl solution (634 µL, 634 µmol) and the resulting suspension was filtered. The filter cake was washed with H$_2$O and dried at high vacuum to get the desired compound as a colorless solid (0.104 g; 382 μmol). MS (ESI): m/z=273.3 [M+H]$^+$.

Intermediate: Methyl 2-(2-azaspiro[3.4]octan-2-yl)-1,3-benzoxazole-6-carboxylate A solution of methyl 2-(methylthio)-1,3-benzoxazole-6-carboxylate (100 mg, 448 μmol, CAS RN 1160490-11-8) and 2-azaspiro[3.4]octane (49.8 mg, 448 μmol, CAS RN 1414885-15-6) in THF (1.5 mL) was stirred at 70° C. for 21 h. Another batch of 2-azaspiro[3.4]octane (24.9 mg, 224 μmol, CAS RN 1414885-15-6) was added and stirring was continued at 70° C. for total of 48 h. The mixture was taken up in H$_2$O and EtOAc and the layers were separated. The aqueous layer was extracted once with EtOAc. The organic layers were dried over MgSO$_4$, filtered and evaporated to get the desired compound as a light brown solid (0.121 g; 94.3%). MS (ESI): m/z=287.3 [M+H]$^+$.

The following building blocks were synthesized in analogy to BB52 in a sealed tube at reflux. In case the amine building block was a salt, DIPEA was added stoichiometrically. The intermediates were either extracted or purified by silica gel chromatography using gradients of n-heptane and EtOAc.

| BB. | Systematic Name | Amine | DIPEA | Reaction time |
|---|---|---|---|---|
| 158 | 2-(7,7-Difluoro-2-azaspiro[3.3]heptan-2-yl)-1,3-benzoxazole-6-carboxylic acid | 5,5-Difluoro-2-azaspiro[3.3]heptane 2,2,2-trifluoroacetate CAS RN 1330765-36-0 | yes | 112 hr |
| 159 | 2-[Methyl(propyl)amino]-1,3-benzoxazole-6-carboxylic acid | N-methylpropan-1-amine CAS RN 627-35-0 | no | 112 hr |
| 74 | 2-(8-Oxa-2-azaspiro[4.5]decan-2-yl)-1,3-benzoxazole-6-carboxylic acid | 8-Oxa-2-azaspiro[4.5]decane (MDL MFCD12028170) | no | 16 hr |
| 75 | 2-(3-Methoxypyrrolidin-1-yl)-1,3-benzoxazole-6-carboxylic acid | 3-Methoxypyrrolidine (CAS RN 62848-20-8) | no | 16 hr |
| 76 | 2-(6,6-Difluoro-2-azaspiro[3.3]heptan-2-yl)-1,3-benzoxazole-6-carboxylic acid | 6,6-Difluoro-2-azaspiro[3.3]heptane 2,2,2-trifluoroacetate (CAS RN 1427367-47-2) | yes | 16 hr |
| 77 | 2-(2-Azaspiro[3.3]heptan-2-yl)-1,3-benzoxazole-6-carboxylic acid | 2-Azaspiro[3.3]heptane hemioxalate (CAS RN 1365639-13-9) | yes | 16 hr |
| 78 | 2-(6-Hydroxy-2-azaspiro[3.3]heptan-2-yl)-1,3-benzoxazole-6-carboxylic acid | 2-Azaspiro[3.3]heptan-6-ol hydrochloride (CAS RN 1630907-10-6) | yes | 15 days |
| 79 | 2-(3-Hydroxy-3-methyl-pyrrolidin-1-yl)-1,3-benzoxazole-6-carboxylic acid | 3-Methylpyrrolidin-3-ol hydrochloride (CAS RN 125032-87-3) | yes | 14 days |
| 80 | 2-(3-Fluoro-3-methyl-pyrrolidin-1-yl)-1,3-benzoxazole-6-carboxylic acid | 3-Fluoro-3-methylpyrrolidine hydrochloride (CAS RN 1427380-91-3) | yes | 144 hr |
| 81 | 2-[3-(1-Hydroxy-1-methyl-ethyl)pyrrolidin-1-yl]-1,3-benzoxazole-6-carboxylic acid | 2-(Pyrrolidin-3-yl)propan-2-ol (CAS RN 351369-41-0) | no | 3 hr |
| 82 | 2-(6-Azaspiro[3.4]octan-6-yl)-1,3-benzoxazole-6-carboxylic acid | 6-Azaspiro[3.4]octane hydrochloride (CAS RN 1414885-18-9) | yes | 10 days |
| 85 | 2-Pyrrolidin-1-yl-1,3-benzoxazole-6-carboxylic acid | Pyrrolidine (CAS RN 123-75-1) | no | 48 hr |
| 86 | 2-(4-Methoxy-1-piperidyl)-1,3-benzoxazole-6-carboxylic acid | 4-Methoxypiperidine (CAS RN 4045-24-3) | no | 112 hr |
| 87 | 2-(4-Hydroxy-1-piperidyl)-1,3-benzoxazole-6-carboxylic acid | Piperidin-4-ol (CAS RN 5382-16-1) | no | 112 hr |

| BB. | Systematic Name | Amine | DIPEA | Reaction time |
|---|---|---|---|---|
| 88 | 2-(3-Methylpyrrolidin-1-yl)-1,3-benzoxazole-6-carboxylic acid | 3-Methylpyrrolidine hydrochloride (CAS RN 186597-29-5) | no | 112 hr |

BB53

2-Piperazin-1-yl-3H-quinazolin-4-one; dihydrochloride salt tert-Butyl 4-(4-oxo-3H-quinazolin-2-yl)piperazine-1-carboxylate (2.69 g, 8.14 mmol) was suspended in DCM (25 mL) and 4M HCl in dioxane (16.3 mL, 65.1 mmol) was added. The reaction mixture was stirred at RT for 18 h and then evaporated. The residue was triturated with n-hexane, filtered and dried in high vacuum to yield the desired compound as a colorless solid (2.36 g, 93.7%). MS (ESI): m/z=231.2 [M+H]$^+$.

Intermediate: tert-Butyl 4-(4-oxo-3H-quinazolin-2-yl)piperazine-1-carboxylate-2-Chloroquinazolin-4(3H)-one (3 g, 13.3 mmol, CAS RN 607-69-2) was suspended in EtOH (16.9 mL) and tert-butyl piperazine-1-carboxylate (2.53 g, 13.3 mmol, CAS RN 57260-71-6) and DIPEA (5.15 g, 7.0 mL, 39.9 mmol) were added. The reaction mixture was purged with argon and stirred in a sealed tube at 110° C. for 18 h. The mixture was cooled to RT, silica gel was added and the suspension concentrated in vacuo. Flash column chromatography (120 g SiO$_2$ column, Eluent: DCM:MeOH, 100:0 to 90:10 over 40 mins) provided the compound as an off-white solid (3.75 g, 85.4%). MS (ESI): m/z=331.3 [M+H]$^+$.

BB53a

2-Piperazin-1-yl-3H-quinazolin-4-one; hydrochloride salt

A solution of tert-butyl 4-(4-oxo-3H-quinazolin-2-yl)piperazine-1-carboxylate (14.5 g, 43.9 mmol, BB53 intermediate) in 4M HCl in EtOAc (300.0 mL, 1200 mmol) was stirred at 20° C. for 2 h. The mixture was evaporated to give the desired compound as a light yellow oil (11 g, 94.0%) which was used in the following step without further purification.

BB54

2-Tetrahydropyran-4-yl-1,3-benzoxazole-6-carboxylic acid

A mixture of methyl 3-hydroxy-4-(tetrahydropyran-4-carbonylamino)benzoate (730.0 mg, 2.61 mmol) in polyphosphoric acid (10.0 mL) was stirred at 175° C. for 3 h. The mixture was poured into ice-cold aqueous NH$_3$ (30 mL) and stirred for 20 min. The mixture was extracted three times with EtOAc (50 mL each). The water layer was adjusted to pH=6 with 2M HCl and extracted three times with EtOAc (50 mL each). The combined organic layer was washed with brine, dried over Na$_2$SO$_4$, filtered and concentrated to give to yield the desired compound as a light yellow solid (270 mg, 41.8%) which was used in the next step without further purification.

Intermediate: Methyl 3-hydroxy-4-(tetrahydropyran-4-carbonylamino)benzoate

A mixture of tetrahydro-2H-pyran-4-carboxylic acid (389.3 mg, 2.99 mmol, CAS RN 5337-03-1) and CDI (484.72 mg, 2.99 mmol) and in THF (10 mL) was stirred at 20° C. for 0.5 h. Then methyl 4-amino-3-hydroxybenzoate (500.0 mg, 2.99 mmol, MDL MFCD00017093) was added and the mixture was stirred 20° C. for 15 h. The mixture was poured into water (30 mL) and extracted three times with EtOAc (50 mL each). The combined organic layers were washed with brine (30 mL), dried over Na$_2$SO$_4$, filtered and concentrated. The crude product was purified by column chromatography (PE:EtOAc=10:1 to 2:3) to yield the desired compound as a light yellow solid (750 mg, 89.8%) which was used in the next step without further purification.

BB55

2-(4-Pyridyl)-1,3-benzoxazole-6-carboxylic acid

The product was obtained in analogy to BB54 starting from methyl 3-hydroxy-4-(pyridine-4-carbonylamino)benzoate (530.0 mg, 1.95 mmol Light yellow solid (220 mg, 47.1%). MS (ESI): m/z=241.0 [M+H]$^+$.

Intermediate: Methyl 3-hydroxy-4-(pyridine-4-carbonylamino)benzoate

The product was obtained in analogy to BB54, intermediate, starting from isonicotinic acid (368.24 mg, 2.99 mmol, CAS RN 55-22-1). Light yellow solid (550 mg, 67.5%). The compound was used in the next step without further purification.

BB56

2-(3-Pyridyl)-1,3-benzoxazole-6-carboxylic acid

The product was obtained in analogy to BB54 starting from methyl 3-hydroxy-4-(pyridine-3-carbonylamino)benzoate (900.0 mg, 3.31 mmol) to yield the desired compound as a light yellow solid (350 mg, 44.1%). The compound was used in the next step without further purification.

Intermediate: Methyl 3-hydroxy-4-(pyridine-3-carbonylamino)benzoate

The product was obtained in analogy to BB54, intermediate, starting from nicotinic acid (368.2 mg, 2.99 mmol, CAS RN 54-86-4) to yield the desired compound as a light yellow solid (550 mg, 67.6%). The compound was used in the next step without further purification.

BB57

2-(3-Cyanophenyl)-1,3-benzoxazole-6-carboxylic acid

To a solution of methyl 2-(3-cyanophenyl)-1,3-benzoxazole-6-carboxylate (220.0 mg, 0.790 mmol) in THF (5 mL) was added NaOH (126.5 mg, 3.16 mmol) in H$_2$O (5 mL). The mixture was stirred at 20° C. for 2 h then diluted with H$_2$O and extracted three times with EtOAc (100 mL each). The combined organic layers were washed with brine, dried over Na$_2$SO$_4$, filtered and concentrated to give the desired compound as a colorless solid (130 mg, 56.3%). MS (ESI): m/z=265.1 [M+H]$^+$.

Intermediates a) Methyl 2-(3-cyanophenyl)-1,3-benzoxazole-6-carboxylate

The product was obtained in analogy to BB54 starting from methyl 4-[(3-cyanobenzoyl)amino]-3-hydroxy-benzoate (500.0 mg, 1.7 mmol) to yield the desired compound as a light yellow solid (230 mg, 90.6% yield). MS (ESI): m/z=279.0 [M+H]$^+$.

b) Methyl 4-[(3-cyanobenzoyl)amino]-3-hydroxy-benzoate

To the solution of methyl 4-amino-3-hydroxybenzoate (2.0 g, 11.96 mmol, MDL MFCD00017093), 3-cyanobenzoic acid (2.11 g, 14.36 mmol, CAS RN 1877-72-1), EDCI (2.79 g, 17.95 mmol) and HOBt (2.75 g, 17.95 mmol) in DMF (20 mL) was added TEA (5.0 mL, 35.89 mmol). The mixture was stirred at 20° C. for 15 h. The mixture was extracted three times with DCM (100 mL each). The combined organic layers were washed with brine, dried over Na$_2$SO$_4$, filtered and concentrated. Purification by silica gel chromatography (PE:EtOAc=10:1 to 4:1) yielded the desired product as a colorless solid (2.81 g, 79.3%) which was used in the next step without further purification.

BB58

4-(6-Azaspiro[3.4]octan-6-yl)benzoic acid

The product was obtained in analogy to BB52 starting from methyl 4-(6-azaspiro[3.4]octan-6-yl)benzoate (120 mg, 489 µmol). Orange solid (108 mg, 94%). MS (ESI): m/z=232.2 [M+H]$^+$.

Intermediate

Methyl 4-(6-azaspiro[3.4]octan-6-yl)benzoate

To a suspension of 6-azaspiro[3.4]octane hydrochloride (250 mg, 1.69 mmol, CAS RN 765-64-0) in dry toluene (3.39 mL) at RT, were added methyl 4-bromobenzoate (401 mg, 1.86 mmol, CAS RN 619-42-1), Pd$_2$(dba)$_3$ (217 mg, 237 µmol, CAS RN 51364-51-3), (R)-(+)-2,2'-bis(diphenylphosphino)-1,1'-binapthyl (274 mg, 440 µmol) and Cs$_2$CO$_3$ (828 mg, 2.54 mmol). The reaction mixture was purged with argon and sealed, before being heated to 100° C. for 72 h. The reaction mixture was allowed to cool to RT, before being diluted with EtOAc (10 mL) and filtered through a celite pad. The filter cake was washed with 50 mL of EtOAc. The collected organic phase was poured into a separating funnel containing H$_2$O (50 mL) and the layers were separated. The aqueous phase was washed three times with EtOAc (30 mL each), before the combined organic phases were dried over Na$_2$SO$_4$, filtered and evaporated. The crude product was taken up in EtOAc (30 mL), concentrated in vacuo with silica and purified by flash column chromatography (SiO$_2$, 80 g, Eluent: n-heptane:EtOAc, 100:0 to 1:1 over 25 mins). Fractions containing the product were combined and concentrated in vacuo to yield the desired compound as a pale yellow solid (242.5 mg, 57%) MS (ESI): m/z=246.2 [M+H]$^+$.

BB59

3,3-Difluoropyrrolidin-1-yl)benzoic acid

The product was obtained in analogy to BB52 starting from methyl 4-(3,3-difluoropyrrolidin-1-yl)benzoate (30 mg, 124 µmol). Colorless solid (29 mg, 100%). MS (ESI): m/z=228.2 [M+H]$^+$.

Intermediates a) Methyl 4-(3,3-difluoropyrrolidin-1-yl)benzoate

Methyl 4-(3-oxopyrrolidin-1-yl)benzoate (25 mg, 108 µmol) was dissolved in DCM (433 µL) and cooled in an ice bath, whereupon deoxofluor in THF (719 mg, 599 µL, 1.62 mmol) was added. The reaction mixture was then allowed to warm up to RT and stirred for 48 h. The reaction mixture was poured into a separating funnel containing EtOAc (20 mL) and H$_2$O (20 mL). The aqueous layer was extracted three times with EtOAc (15 mL each), dried over Na$_2$SO$_4$, filtered and concentrated in vacuo. The residue was taken up in EtOAc (20 mL) and concentrated in vacuo with silica, before being purified by flash column chromatography (SiO$_2$, 12 g, Eluent: n-heptane:EtOAc, 100:0 to 1:1 over 25 mins) to yield a colorless solid (18 mg, 68%). MS (ESI): m/z=242.2 [M+H]$^+$.

b) Methyl 4-(3-oxopyrrolidin-1-yl)benzoate

Methyl 4-(3-hydroxypyrrolidin-1-yl)benzoate (286.3 mg, 1.09 mmol) was suspended in DCM (5.43 mL) at RT, whereupon Dess-Martin periodinane (570 mg, 1.3 mmol, CAS RN 87413-09-0) was added. The reaction mixture was then stirred at RT. A second batch of Dess-Martin periodinane (115 mg, 272 µmol, CAS RN 87413-09-0) was added. After an hour another batch of Dess-Martin periodinane (115 mg, 272 µmol, CAS RN 87413-09-0) was added and the reaction stirred overnight. An aqueous solution of NaHCO$_3$ (10 mL) was added and the mixture poured into a 100 mL separating funnel containing DCM (30 mL), NaHCO$_3$ (25 mL) and H2O (10 mL). The aqueous layer was extracted three times with DCM (25 mL each). The combined organic phases were dried over Na$_2$SO$_4$, filtered and concentrated in vacuo with silica. The crude product was purified by flash column chromatography (SiO$_2$, 80 g, Eluent:n-heptane: EtOAc, 100:1 to 1:1 over 30 mins) to yield a colorless solid (63.5 mg, 26%). MS (ESI): m/z=220.2 [M+H]$^+$.

c) Methyl 4-(3-hydroxypyrrolidin-1-yl)benzoate

Methyl 4-aminobenzoate (1.74 g, 11.5 mmol, CAS RN 619-45-4) was placed into a small reactor vial, whereupon 2-(2-bromoethyl)oxirane (1.52 g, 1 mL, 10.1 mmol, CAS RN 13287-42-8) was added. The reaction mixture was purged with argon, sealed and heated at 120° C. for 2 h. The reaction was dissolved in a mixture of DCM and MeOH (1/1 v/v), and concentrated in vacuo with silica. The crude product was purified by flash column chromatography ($SiO_2$, 40 g, eluent: n-heptane:EtOAc, 100:0 to 1:1 over 35 mins) to yield a colorless solid (759.6 mg, 33%). MS (ESI): m/z=222.2 $[M+H]^+$.

BB60

4-[4-(Trifluoromethyl)-1-piperidyl]benzoic acid

The product was obtained in analogy to BB52 starting from methyl 4-(4-(trifluoromethyl)piperidin-1-yl)benzoate (100 mg, 348 µmol, MDL MFCD29084188). Colorless solid (88.6 mg, 91%). MS (ESI): m/z=274.3 $[M+H]^+$.

BB61

4-(5-Azaspiro[2.4]heptan-5-yl)benzoic acid

The product was obtained in analogy to BB52 starting from methyl 4-(5-azaspiro[2.4]heptan-5-yl)benzoate (101 mg, 437 µmol). Yellow solid (98.6 mg, 98.7%). MS (ESI): m/z=218.2 $[M+H]^+$.

Intermediate

Methyl 4-(5-azaspiro[2.4]heptan-5-yl)benzoate

The product was obtained in analogy to BB58, intermediate starting from 5-azaspiro[2.4]heptane hydrochloride (180.6 mg, 1.35 mmol, CAS RN 3659-21-0). Pale yellow solid (255.6 mg, 79%). MS (ESI): m/z=232.3 $[M+H]^+$.

BB62

2-[4-(3-Chloro-4-hydroxy-benzoyl)piperazin-1-yl]-3H-quinazolin-4-one

The product was obtained in analogy to Method C starting from 2-piperazin-1-yl-3H-quinazolin-4-one hydrochloride (1545.6 mg, 5.79 mmol, BB53a) and 3-chloro-4-hydroxybenzoic acid (1000 mg, 5.79 mmol, CAS RN 3964-58-7). Light yellow solid (800 mg, 35.9%). MS (ESI): m/z=385.0 $[M+H]^+$.

BB63

(4-Chloro-2-pyridyl)methyl methanesulfonate

To a solution of (4-chloro-2-pyridyl)methanol (240.0 mg, 1.67 mmol, CAS RN 63071-10-3) in DCM (5 mL) was added TEA (0.48 mL, 3.34 mmol), the reaction was cooled to 0° C. and methanesulfonyl chloride (0.27 mL, 3.49 mmol) was added dropwise. The reaction was stirred at 25° C. for 12 h. The reaction was quenched with $H_2O$, extracted three times with DCM (10 mL) and the combined organic layers were dried over $Na_2SO_4$ and concentrated to yield 280 mg of a red oil which was used in the next step without further purification.

BB64

3-Chloro-4-[(2-chloro-4-pyridyl)methoxy]benzoic acid

To a solution of NaOH (738.46 mg, 18.46 mmol) in $H_2O$ (32 mL) and THF (80 mL) was added methyl 3-chloro-4-[(2-chloro-4-pyridyl)methoxy]benzoate (600.0 mg, 1.92 mmol) and the reaction was stirred at 25° C. for 1 h. The reaction was evaporated in vacuum and 3M HCl was added to adjust the pH to 6. The mixture was filtered, the filter cake was washed three times with $H_2O$ (4 mL each) and dried in vacuum to yield the desired compound as a light yellow solid (350 mg, 61.1%). MS (ESI): m/z=297.9 $[M+H]^+$.

Intermediate

Methyl 3-chloro-4-[(2-chloro-4-pyridyl)methoxy]benzoate

To a solution of 2-chloro-4-(chloromethyl)pyridine (500.0 mg, 3.09 mmol, CAS RN 101990-73-2) in DMF (20 mL) was added methyl 3-chloro-4-hydroxybenzoate (635 mg, 3.4 mmol, CAS RN 3964-57-6) and $K_2CO_3$ (639.0 mg, 4.66 mmol) and the mixture was heated to 80° C. for 12 h. The reaction was quenched with $H_2O$ (10 mL) and extracted three times with EtOAc (10 mL each). The combined organic layers were washed twice with water (10 mL each) and brine (10 mL), dried over $Na_2SO_4$ and then concentrated in vacuum. The yellow oil was purified with silica gel column (PE:EtOAc=10:1 to 5:1) to provide the desired compound as a colorless solid (700 mg, 53.1%). MS (ESI): m/z=311.9 $[M+H]^+$.

BB65

(6-Chloro-2-pyridyl)methyl methanesulfonate

The product was obtained in analogy to BB63 starting from (6-chloro-2-pyridyl)methanol (240 mg, 1.7 mmol, CAS RN 33674-97-4) to yield the desired product a as colorless oil which was used in next step without further purification.

BB66

2-[4-[2-Methyl-4-[(1-tritylpyrazol-4-yl)methoxy]-1,3-benzoxazole-6-carbonyl]piperazin-1-yl]-3H-quinazolin-4-one To a solution of 2-piperazin-1-yl-3H-quinazolin-4-one hydrochloride (134.5 mg, 0.500 mmol, BB53a) and 2-methyl-4-[(1-tritylpyrazol-4-yl)methoxy]-1,3-benzoxazole-6-carboxylic acid (260.0 mg, 0.500 mmol, BB67), EDCI (117.4 mg, 0.760 mmol), HOBt (115.8 mg, 0.760 mmol) in DMF (10 mL) was added TEA (0.21 mL, 1.51 mmol) and the mixture was stirred at 30° C. for 15 h. The mixture was diluted with $H_2O$ (20 mL), then extracted three times with EtOAc (50 mL each). The combined organic layers were washed with brine, dried over $Na_2SO_4$, filtered and concentrated to give the desired compound as a yellow oil (344 mg, 93.7% yield). MS (ESI): m/z=728.4 $[M+H]^+$.

Intermediates a) 2-Methyl-4-[(1-tritylpyrazol-4-yl)methoxy]-1,3-benzoxazole-6-carboxylic acid To a solution of methyl 2-methyl-4-[(1-tritylpyrazol-4-yl)methoxy]-1,3-benzoxazole-6-carboxylate (550.0 mg, 1.04 mmol) in THF (10 mL) was added NaOH (166.2 mg, 4.15 mmol) in water (10 mL) and the mixture was stirred at 20° C. for 1 h. THF was evaporated and the remaining aqueous phase was extracted three times with EtOAc (100 mL each). The water phase was acidified to pH 3-4 with 1M HCl and extracted three times with EtOAc (100 mL each). The combined organic layers were washed with brine, dried over b) Methyl 2-methyl-4-[(1-tritylpyrazol-4-yl)methoxy]-1,3-benzoxazole-6-carboxylate To a solution of methyl 4-hydroxy-2-methyl-1,3-benzoxazole-6-carboxylate (200.0 mg, 0.970 mmol) and (1-tritylpyrazol-4-yl)methanol (361.5 mg, 1.06 mmol, CAS RN 88529-69-5) in THF (10 mL) was added triphenylphosphine (303.8 mg, 1.16 mmol) and diisopropyl azodicarboxylate (0.23 mL, 1.16 mmol) and the mixture was stirred at 20° C. for 15 h under nitrogen atmosphere. THF was evaporated the residue diluted with H2O (80 mL) and extracted three times with EtOAc (50 mL each). The combined organic layers were washed with brine, dried over $Na_2SO_4$ and concentrated. Purification by silica gel chromatography (PE:EtOAc=3:1) provided the desired compound as a yellow solid (566 mg, 78.7%). MS (ESI): m/z=552.3 $[M+Na]^+$.

c) Methyl 4-hydroxy-2-methyl-1,3-benzoxazole-6-carboxylate

To a solution of (6-methoxycarbonyl-2-methyl-1,3-benzoxazol-4-yl)boronic acid (2.66 g, 4.18 mmol, BB70) in EtOAc (30 mL) was added hydrogen peroxide (1.7 mL, 16.7 mmol) and NaOH (0.7 g, 17.6 mmol) at 5° C. and the mixture was stirred 20° C. for 3 h. The volatiles were removed and the residue purified by reversed phase column chromatography to give the desired compound as a brown solid (360 mg, 41.6% yield). MS (ESI): m/z=208.1 $[M+H]^+$.

d) (6-Methoxycarbonyl-2-methyl-1,3-benzoxazol-4-yl)boronic acid

A solution of methyl 4-bromo-2-methyl-1,3-benzoxazole-6-carboxylate (2.6 g, 9.6 mmol, BB71), bis(pinacolato)diboron (4.89 g, 19.3 mmol, CAS RN 73183-34-3) and potassium acetate (2.5 g, 25.55 mmol) in 1,4-dioxane (20 mL) was added (1,1'-bis(diphenylphosphino)ferrocene)palladium(II) dichloride (232.5 mg, 0.320 mmol, CAS RN 95464-05-4) and the mixture was stirred at 80° C. for 16 h under nitrogen atmosphere. The mixture was concentrated to remove 1,4-dioxane and the residual water phase was extracted three times with EtOAc (200 mL each). The combined organic layers were washed with brine, dried over $Na_2SO_4$ and concentrated to give the desired compound as a brown oil (2.66 g, 43.4% yield). MS (ESI): m/z=236.2 $[M+H]^+$.

e) Methyl 4-bromo-2-methyl-1,3-benzoxazole-6-carboxylate

To a solution of methyl 4-amino-3-bromo-5-hydroxybenzoate (4.0 g, 16.26 mmol, BB72) and triethyl orthoacetate (3.16 g, 19.5 mmol, CAS RN 78-39-7) was added 1,3-dibromo-5,5-dimethylhydantoin (461.5 mg, 1.63 mmol, CAS RN 77-48-5) and the mixture was stirred at 20° C. for 10 min. The mixture was filtered and concentrated under vacuum. The solid was washed with PE and filtered to give the desired compound as an orange solid (2.63 g, 52.3% yield. MS (ESI): m/z=270.1 $[M+H]^+$.

f) Methyl 4-amino-3-bromo-5-hydroxy-benzoate

A solution of methyl 4-amino-3-hydroxybenzoate (10.0 g, 59.8 mmol, CAS RN 63435-16-5) in DCM (200 mL) and DMF (10 mL) was added N-bromosuccinimide (11.7 g, 65.8 mmol). The mixture was stirred at 20° C. for 30 min. The mixture was quenched with saturated sodium sulfite solution, then 1M hydrochloric acid was added and the mixture extracted three times with DCM (100 mL each). The combined organic layers were washed with brine, dried over $Na_2SO_4$, filtered and concentrated. Purification by silica gel chromatography (PE:EtOAc=5:1 to 3:1) provided the desired compound as an orange solid (8 g, 45.4%). MS (ESI): m/z=246.0 $[M+H]^+$.

BB67

N'-Hydroxy-4-[4-(4-oxo-3H-quinazolin-2-yl)piperazine-1-carbonyl]benzamidine

4-[4-(4-Oxo-3H-quinazolin-2-yl)piperazine-1-carbonyl]benzonitrile (136 mg, 378 μmol) was dissolved in EtOH (2 mL) and hydroxylamine solution (5% in $H_2O$, 75 mg, 67 μL, 1.14 mmol) was added and the mixture was heated to 70° C. After 19 h EtOH (2 mL) and another batch of hydroxylamine solution (50% in $H_2O$, 75 mg, 67 μL, 1.14 mmol) were added. The resulting mixture was heated to 70° C. for 3.5 days. After 3.5 days hydroxylamine (0.11 mL) and EtOH (2 mL) were added. After 4.5 days, the reaction mixture was allowed to reach RT and the resulting white suspension was concentrated to give a white solid which was used in the next step without further purification. MS (ESI): m/z=391.4 $[M-H]^-$.

Intermediate

4-[4-(4-Oxo-3H-quinazolin-2-yl)piperazine-1-carbonyl]benzonitrile

The product was obtained in analogy to Method A3 starting from 4-cyanobenzoic acid (121 mg, 825 μmol, CAS RN 619-65-8) and 2-(piperazin-1-yl)quinazolin-4(3H)-one dihydrochloride (250 mg, 825 μmol, BB53) to provide the desired product as an off-white solid (145 mg, 46.5%). MS (ESI): m/z=360.3 $[M+H]^+$.

BB68

2-(3-Chloro-4-cyano-phenyl)-1,3-benzoxazole-6-carboxylic acid

To a solution of methyl 2-(3-chloro-4-cyano-phenyl)-1,3-benzoxazole-6-carboxylate (150.0 mg, 0.480 mmol) in THF (5 mL) was added NaOH (76.7 mg, 1.9 mmol) in H2O (5 mL) and the mixture was stirred at 20° C. for 16 h. The mixture was concentrated to remove THF, and the residual water phase was extracted three times with EtOAc (100 mL each). The combined organic layers were dried over $Na_2SO_4$ and concentrated to give the desired compound as a colorless solid (100 mg, 53.9%). MS (ESI): m/z=298.9 $[M+H]^+$.

Intermediates a) Methyl 2-(3-chloro-4-cyano-phenyl)-1,3-benzoxazole-6-carboxylate

A solution of triphenylphosphine (713.8 mg, 2.72 mmol) and 2,3-dichloro-5,6-dicyano-1,4-benzoquinone (617.7 mg, 2.72 mmol, CAS RN 84-58-2) in toluene (15 mL) was stirred at 20° C. for 3 min. Then methyl 4-[(3-chloro-4-cyano-benzoyl)amino]-3-hydroxy-benzoate (300.0 mg, 0.910 mmol) was added and the mixture stirred at 110° C. for 16 h. The mixture was concentrated, the solid washed with DMF and filtered to give the desired compound as a colorless solid (210 mg, 73.2% yield). MS (ESI): m/z=313 [M+H]⁺.

b) Methyl 4-[(3-chloro-4-cyano-benzoyl)amino]-3-hydroxy-benzoate

The product was obtained in analogy to Method C (using TEA) starting from 3-chloro-4-cyanobenzoic acid (400.0 mg, 2.2 mmol, CAS RN 1261685-26-0) and methyl 4-amino-3-hydroxybenzoate (368.2 mg, 2.2 mmol, CAS RN 63435-16-5). Off-white solid (500 mg, 68.1%). MS (ESI): m/z=331.0 [M+H]⁺.

BB69

(4-(3-(tert-Butyl)-1,2,4-oxadiazol-5-yl)phenyl)(piperazin-1-yl)methanone; hydrochloride To a solution of tert-butyl 4-(4-(3-(tert-butyl)-1,2,4-oxadiazol-5-yl)benzoyl)piperazine-1-carboxylate (345 mg, 832 µmol) in dioxane (4 mL) was added 4M HCl in dioxane (1.04 mL, 4.16 mmol) and the reaction mixture was stirred at RT for 14 h. Volatiles were removed in vacuo to yield 286 mg of a crude residue which was used without further purification. MS (ESI): m/z=315.3 [M+H]⁺.

Intermediates a) tert-Butyl 4-(4-(3-(tert-butyl)-1,2,4-oxadiazol-5-yl)benzoyl)piperazine-1-carboxylate To a solution of 4-(4-(tert-butoxycarbonyl)piperazine-1-carbonyl)benzoic acid (350 mg, 1.05 mmol) in dry DMF (5 mL) was added CDI (187 mg, 1.15 mmol) and the reaction mixture was stirred at RT for 45 min. followed by addition of (Z)—N'-hydroxypivalimidamide (134 mg, 1.15 mmol, MDL MFCD06200902). The reaction was then stirred at 100° C. for 14 h. Volatiles were removed in vacuo and the crude residue was partitioned between EtOAc and 1M aqueous NaHCO₃ solution. The organic phase was collected and the aqueous phase was back-extracted with EtOAc. The combined organic phases were dried over Na₂SO₄ and evaporated down to dryness. The crude product was purified by flash chromatography with a 40 g SiO₂ column using a mixture of n-heptane and EtOAc as eluent to give the desired product as a colorless solid (347 mg, 80.0%). MS (ESI): m/z=359.3 [M-C₄H₈+H]⁺.

b) 4-(4-(tert-Butoxycarbonyl)piperazine-1-carbonyl)benzoic acid

To a solution of tert-butyl 4-(4-(methoxycarbonyl)benzoyl)piperazine-1-carboxylate (930 mg, 2.67 mmol) in MeOH (15 mL) was added 4M aqueous NaOH solution (2 mL, 8.0 mmol) and the reaction mixture was stirred at RT for 14 h. The volatiles were removed in vacuo and the crude residue was partitioned between EtOAc and 1M aqueous HCl solution. The organic phase was collected and the aqueous phase was back-extracted with EtOAc. The combined organic phases were dried over Na₂SO₄, filtered and evaporated to yield the desired compound which was pure enough for the next step without further purification (854 mg, 95.7%). MS (ESI): m/z=333.3 [M-H]⁻.

c) tert-Butyl 4-(4-(methoxycarbonyl)benzoyl)piperazine-1-carboxylate

The product was obtained in analogy to Method A1 (using DIPEA) starting from 4-(methoxycarbonyl)benzoic acid (0.5 g, 2.78 mmol, MDL MFCD00075265) and tert-butyl piperazine-1-carboxylate (543 mg, 2.91 mmol, CAS RN). Colorless solid (934 mg, 96.6%). MS (ESI): m/z=350.3 [M+H]⁺.

BB70

[3-(3-tert-Butyl-1,2,4-oxadiazol-5-yl)-1-bicyclo[1.1.1]pentanyl]-piperazin-1-yl-methanone; hydrochloride The product was obtained in analogy to BB69 starting from tert-butyl 4-(3-(3-(tert-butyl)-1,2,4-oxadiazol-5-yl)bicyclo[1.1.1]pentane-1-carbonyl)piperazine-1-carboxylate (370 mg, 915 µmol). Used without further purification. MS (ESI): m/z=305.3 [M+H]⁺.

Intermediates a) tert-Butyl 4-(3-(3-(tert-butyl)-1,2,4-oxadiazol-5-yl)bicyclo[1.1.1]pentane-1-carbonyl)piperazine-1-carboxylate To a solution of 3-(4-(tert-butoxycarbonyl)piperazine-1-carbonyl)bicyclo[1.1.1]pentane-1-carboxylic acid (300 mg, 925 µmol) in dry DMF (5 mL) was added CDI (165 mg, 1.0 mmol) and the reaction mixture was stirred at RT for 45 min. followed by addition of (Z)—N'-hydroxypivalimidamide (118 mg, 1.02 mmol, MDL MFCD06200902). The reaction was then stirred at 100° C. for 14 h. The volatiles were removed in vacuo and the crude residue was partitioned between EtOAc and 1M aqueous NaHCO₃ solution, the organic phase was collected and the aqueous phase was back-extracted with EtOAc. The combined organic phases were dried over Na₂SO₄ and evaporated. The crude material was purified by flash chromatography with a 40 g SiO₂ column with a mixture of n-heptane and EtOAc as eluent to give the desired product as a colorless oil (553 mg, 70% purity). MS (ESI): m/z=349.3 [M-C₄H₈+H]⁺. The product was used for the next step without further purification.

b) 3-(4-(tert-Butoxycarbonyl)piperazine-1-carbonyl)bicyclo[1.1.1]pentane-1-carboxylic acid To a solution of tert-butyl 4-(3-(ethoxycarbonyl)bicyclo[1.1.1]pentane-1-carbonyl)piperazine-1-carboxylate (800 mg, 2.27 mmol) in MeOH (12 mL) was added 4M aqueous NaOH solution (1.7 mL, 6.8 mmol) and the reaction mixture was stirred at RT for 14 h. The volatiles were removed in vacuo and the crude residue was partitioned between EtOAc and 1M aqueous HCl solution. The organic phase was collected and the aqueous phase was back-extracted with EtOAc. The combined organic phases were dried over Na₂SO₄ and evaporated to give the desired compound as a colorless solid (0.723 mg, 98.2%). MS (ESI): m/z=323.3 [M-H]⁻.

c) tert-Butyl 4-(3-(ethoxycarbonyl)bicyclo[1.1.1]pentane-1-carbonyl)piperazine-1-carboxylate The product was obtained in analogy to Method A1 (using DIPEA) starting from 3-(ethoxycarbonyl)bicyclo[1.1.1]pentane-1-carboxylic acid (0.5 g, 2.71 mmol, CAS RN 1823373-90-5) and tert-butyl piperazine-1-carboxylate (543

BB71

3-((3-Chlorophenyl)sulfonyl)-3,9-diazaspiro[5.5]undecane hydrochloride

To a suspension of tert-butyl 9-((3-chlorophenyl)sulfonyl)-3,9-diazaspiro[5.5]undecane-3-carboxylate (208 mg, 485 µmol) in dioxane (0.5 mL) was added 4M HCl in dioxane (727 mg, 606 µL, 2.42 mmol). The suspension was stirred at RT for 6 h. Ether (2 mL) was added and the suspension filtered. The filter cake was washed with ether to get the desired product as a colorless solid (0.180 g; 99.6%). MS (ESI): m/z=329.2 [M+H]$^+$.

Intermediate: tert-Butyl 9-((3-chlorophenyl)sulfonyl)-3,9-diazaspiro[5.5]undecane-3-carboxylate To a solution of tert-butyl 3,9-diazaspiro[5.5]undecane-3-carboxylate (137 mg, 539 µmol, CAS RN 173405-78-2) and DIPEA (139 mg, 188 µL, 1.08 mmol) in DCM (2 mL) was added dropwise 3-chlorobenzenesulfonyl chloride (114 mg, 75.8 µL, 539 µmol, CAS RN 2888-06-4) and the mixture was stirred at RT for 2 h. The reaction mixture was washed with H$_2$O and the aqueous layer was extracted three times with DCM. The organic layers were dried over MgSO$_4$, filtered, treated with silica gel and evaporated. The compound was purified by silica gel chromatography on a 4 g column using an MPLC (ISCO) system eluting with a gradient of n-heptane:EtOAc (100:0 to 50:50) to get the desired compound as a light brown solid (0.210 g; 90.9%). MS (ESI): m/z=373.2 [M-C$_4$H$_8$]$^-$.

BB72

2-(1-Methylpyrrol-3-yl)-1,3-benzoxazole-6-carboxylic acid

To a solution of methyl 2-(1-methylpyrrol-3-yl)-1,3-benzoxazole-6-carboxylate (150.0 mg, 0.590 mmol) in THF (6 mL) was added NaOH (93.7 mg, 2.34 mmol) in H2O (6 mL) and the mixture was stirred at 20° C. for 1 h. The mixture was concentrated to remove THF, and the residual water phase was extracted three times with EtOAc (50 mL). The pH of the water phase was adjusted to 3-4 with 1M HCl and the water phase was extracted three times with EtOAc (50 mL each). The combined organic layers were washed with brine, dried over Na$_2$SO$_4$ and concentrated to give the desired compound as a brown solid (100 mg, 65.4%). MS (ESI): m/z=243.0 [M+H]$^+$.

Intermediates a) Methyl 2-(1-methylpyrrol-3-yl)-1,3-benzoxazole-6-carboxylate

A solution of phosphorus pentoxide (1035 mg, 7.29 mmol) and methyl 3-hydroxy-4-[(1-methylpyrrole-3-carbonyl)amino]benzoate (400.0 mg, 1.46 mmol) was stirred at 180° C. for 2 h. Then the mixture was added to an ice-cold aqueous ammonium hydroxide solution and extracted three times with EtOAc (100 mL each). The combined organic layers were dried over MgSO$_4$, filtered and evaporated to give the desired compound as a brown solid (230 mg, 0.900 mmol, 53.8% yield). MS (ESI): m/z=257.0 [M+H]$^+$.

b) Methyl 3-hydroxy-4-[(1-methylpyrrole-3-carbonyl)amino]benzoate

The product was obtained in analogy to Method C (using DIPEA) starting from 1-methylpyrrole-3-carboxylic acid (500.0 mg, 4 mmol, CAS RN 36929-61-0) and methyl 4-amino-3-hydroxybenzoate (400.8 mg, 2.4 mmol, CAS RN 63435-16-5). Brown oil (706 mg, 44.3% yield). MS (ESI): m/z=297 [M+Na]$^+$.

BB73

4-[5-(2-Hydroxy-1,1-dimethyl-ethyl)-1,2,4-oxadiazol-3-yl]benzoic acid

The product was obtained in analogy to BB52 starting from methyl 4-(5-(1-hydroxy-2-methylpropan-2-yl)-1,2,4-oxadiazol-3-yl)benzoate (126 mg, 456 µmol Colorless solid (0.099 g; 82.8%). MS (ESI): m/z=263.2 [M+H]$^+$.

Intermediate

Methyl 4-(5-(1-hydroxy-2-methylpropan-2-yl)-1,2,4-oxadiazol-3-yl)benzoate

To a solution of 3-hydroxy-2,2-dimethylpropanoic acid (125 mg, 1.06 mmol, CAS RN 4835-90-9) in DMF (5 mL) were added HOBT.H$_2$O (162 mg, 1.06 mmol) and EDC (406 mg, 2.12 mmol) and the suspension was stirred at RT for 15 min. To this was added methyl (Z)-4-(N'-hydroxycarbamimidoyl)benzoate (205 mg, 1.06 mmol, CAS RN 184778-33-4) and stirring was continued at RT for 15 min followed by stirring at 90° C. for 3 days. The reaction mixture was poured on H$_2$O and EtOAc and the layers were separated. The aqueous layer was extracted twice with EtOAc. The organic layers were washed once with H$_2$O, dried over MgSO$_4$, filtered, treated with silica gel and evaporated. The compound was purified by silica gel chromatography on a 12 g column using an MPLC system eluting with a gradient of n-heptane:EtOAc (100:0 to 50:50) to provide the desired compound as a colorless solid (0.128 g; 43.8%). MS (ESI): m/z=277.2 [M+H]$^+$.

BB83

4-[5-(2-Benzyloxy-1,1-dimethyl-ethyl)-1,2,4-oxadiazol-3-yl]benzoic acid

The product was obtained in analogy to BB52 starting from methyl 4-(5-(1-(benzyloxy)-2-methylpropan-2-yl)-1,2,4-oxadiazol-3-yl)benzoate (48 mg, 131 µmol). Colorless solid (0.038 g; 82.3%). MS (ESI): m/z=353.3 [M+H]$^+$.

Intermediate: 4-(5-(1-(benzyloxy)-2-methylpropan-2-yl)-1,2,4-oxadiazol-3-yl)benzoate To a suspension of methyl (Z)-4-(N'-hydroxycarbamimidoyl)benzoate (308 mg, 1.59 mmol, CAS RN 184778-33-4) in THF (2.5 mL) was added dropwise a suspension of 3-(benzyloxy)-2,2-dimethylpropanoyl chloride (327 mg, 1.44 mmol, CAS RN 36881-15-9) in THF (5 mL). The rapidly formed solution turned into a suspension which was stirred at RT for 15 min. The suspension was refluxed in a sealed vial for 1.5 h. The suspension was then allowed to cool down to RT and was filtered. The filtrate was evaporated. To the residue was added toluene (7.5 mL) and the mixture was stirred at reflux for 2 h. After cooling down the mixture was diluted with MeOH, treated with silica gel and evaporated. The compound was purified by silica gel chromatography on a 12 g column using an MPLC (ISCO) system eluting with a gradient of n-heptane:EtOAc (100:0 to 90:10) to yield the desired compound as a colorless oil (0.049 g; 9.3%). MS (ESI): m/z=367.3 [M+H]⁺.

BB84

2-[4-(2,7-Diazaspiro[4.4]nonane-2-carbonyl)piperazin-1-yl]-3H-quinazolin-4-one

To a solution of tert-butyl 7-(4-(4-oxo-3,4-dihydroquinazolin-2-yl)piperazine-1-carbonyl)-2,7-diazaspiro[4.4]nonane-2-carboxylate (130 mg, 269 μmol) in DCM (1 mL) was added TFA (307 mg, 208 μL, 2.69 mmol) and the mixture was stirred at RT for 3 days. The solution was completely evaporated. The solid residue was suspended in EtOAc, saturated NaHCO₃ solution was added and the layers were separated. The aqueous layer was evaporated and the crude product purified by prep-HPLC (Gemini NX column) using a gradient of ACN:H₂O (containing 0.1% formic acid) (20:80 to 98:2) to furnish the desired compound as a colorless solid (75 mg, 72.8%). MS (ESI): m/z=381.5 [M−H]⁻.

Intermediate: tert-Butyl 7-(4-(4-oxo-3,4-dihydroquinazolin-2-yl)piperazine-1-carbonyl)-2,7-diazaspiro[4.4]nonane-2-carboxylate To a suspension of 2-(piperazin-1-yl)quinazolin-4(3H)-one dihydrochloride (268 mg, 884 μmol, BB53) in DCM (4 mL) was added DIPEA (457 mg, 617 μL, 3.53 mmol). To the formed suspension was added tert-butyl 2,7-diazaspiro[4.4]nonane-2-carboxylate (200 mg, 884 μmol, CAS RN 236406-49-8) followed by bis(trichloromethyl) carbonate (91.8 mg, 309 μmol) and stirring was continued at RT for 4 days. The reaction mixture was poured on H₂O and DCM and the aqueous layer extracted six times with DCM. The combined organic layers were dried over MgSO₄, filtered, treated with silica gel and evaporated. The compound was purified by silica gel chromatography on a 12 g column using an MPLC (ISCO) system eluting with a gradient of DCM:MeOH (100:0 to 90:10) to get the desired compound as a colorless solid (130 mg, 30.5%). MS (ESI): m/z=483.4 [M+H]⁺.

BB89

3-Chloro-4-[(3-chlorophenoxy)methyl]benzoic acid

To a solution of methyl 3-chloro-4-[(3-chlorophenoxy)methyl]benzoate (750.0 mg, 2.41 mmol) in THF (8 mL) was added NaOH (385.6 mg, 9.64 mmol) in H2O (8 mL). The mixture was stirred at 25° C. for 1 h. The mixture was concentrated to remove THF, and the residual water phase was extracted three times with EtOAc (200 mL each). The pH of the water phase was adjusted to 3-4 with 1M HCl and the water phase was extracted three times with EtOAc (200 mL each). The combined organic layers were washed with brine, dried over Na₂SO₄ and concentrated to give the desired compound as a colorless solid (430 mg, 57.6% yield) MS (ESI): m/z=296.9 [M+H]⁺.

Intermediate: Methyl 3-chloro-4-[(3-chlorophenoxy)methyl]benzoate

A solution of methyl 4-(bromomethyl)-3-chloro-benzoate (800.0 mg, 3.04 mmol, CAS RN 74733-30-5) in ACN (40 mL) was added K₂CO₃ (839.1 mg, 6.1 mmol) and 3-chlorophenol (468.3 mg, 3.64 mmol, CAS RN 108-43-0). The mixture was stirred at 90° C. for 12 h. The mixture was diluted with H2O and extracted three times with EtOAc (100 mL each). The combined organic layers were washed with brine, dried over Na₂SO₄, filtered and concentrated. Purification by silica gel chromatography (PE:EtOAc=1:0 to 10:1) provided the desired compound as a yellow solid (750 mg, 79.4% yield).

Example A

A compound of Formula (I) can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of Formula (I) can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:
1. A compound of Formula (I):

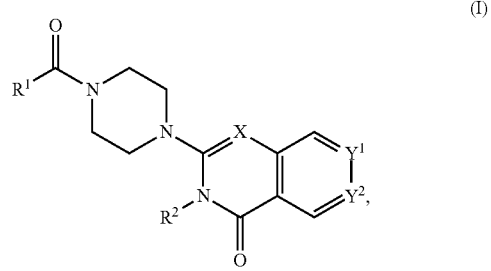

or a pharmaceutically acceptable salt thereof, wherein:
X is C—H or N;
Y¹ is selected from the group consisting of C—H, C—F, C-alkyl, C-haloalkyl, and N;
Y² is selected from the group consisting of C—H, C-halogen, C-alkyl, and C-haloalkyl;
R¹ is selected from the group consisting of:
  i. aryl,
  ii. substituted aryl,
  iii. heteroaryl,
  iv. substituted heteroaryl,
  v. heterocyclyl, vi. substituted heterocyclyl,
vii. cycloalkyl, and
viii. substituted cycloalkyl;
wherein each of said substituted aryl, substituted heteroaryl, substituted heterocyclyl, and substituted cycloalkyl is independently substituted with one or more substituents selected from the group consisting of aminoalkyl, amino, haloalkylaryl, cycloalkyl, cycloalkylaryl, aryl-alkenyl, haloarylalkenyl, cyano(haloaryl), haloarylsulfonyl, alkyl(hydroxyheterocyclyl), alkyl(haloheterocyclyl), arylalkoxyalkylheteroaryl, hydroxyalkynyl, haloalkylaryl-alkoxyalkyl, haloalkylheteroaryl, haloalkylheterocyclyl, alkylheteroaryl, arylcycloalkyl, hydroxyalkylheterocyclyl, alkylsulfanyl, alkoxyheterocyclyl, cycloalkylheteroaryl, alkylcycloalkylheteroaryl, haloalkylcycloalkylheteroaryl, alkoxyalkylheteroaryl, alkoxyalkylheterocyclyl, alkoxyalkylaryl, cycloalkylalkoxy, arylalkoxy, aryloxyalkyl, haloaryloxyalkyl, aryloxyaryl, aryloxyheteroaryl, aryloxy, haloalkylaryloxy, halogen, heterocyclyl, hydroxyheterocyclyl, heterocyclylalkyl, heteroaryl, aryl, aryl-C(O)—, haloaryl, haloheteroaryl, halocycloalkyl, haloalkoxy, hydroxyalkoxy, alkoxyalkoxy, hydroxyalkoxyaryl, hydroxyalkoxyheteroaryl, alkoxy, alkyl, haloalkyl, cyano, cyanoaryl, cyanoheteroaryl, cyanocycloalkyl, cyanoalkylaryl, arylheterocyclyl, alkoxy-(haloalkyl)aryl, alkylaryl, arylalkoxy-(alkyl)aryl, haloaryloxy, hydroxyalkylaryl, hydroxyalkylheteroaryl, alkenyloxy, pentafluoro-lambda6-sulfanyl, heteroarylalkyl, heteroarylalkoxy, haloheteroarylalkoxy, alkoxyaryl, alkoxyheteroaryl, (arylalkoxy)aryl, (arylalkoxy)heteroaryl, carbamoylaryl, alkyl-(alkoxy)aryl, haloalkoxyaryl, haloalkoxyheteroaryl, alkylheterocyclyl, haloheterocyclyl, alkylhaloaryl, haloalkylhaloaryl, and haloarylalkoxy;
wherein said aminoalkyl is substituted on the nitrogen atom with one or two substituents independently selected from the group consisting of H, alkyl, cycloalkyl, alkanoyl, arylalkyl, and haloalkylarylalkyl; and
wherein said amino is substituted on the nitrogen atom with one or two substituents independently selected from the group consisting of H, alkyl, haloalkyl, cycloalkyl, hydroxyalkyl, alkoxyalkyl, haloarylalkyl, haloalkoxyarylalkyl, benzyl and benzyl substituted with a substituent selected from the group consisting of halogen, alkyl, and haloalkyl; and
$R^2$ is selected from the group consisting of hydrogen and alkyl.

2. The compound according to claim 1, or a pharmaceutically acceptable salt thereof, wherein X is N.

3. The compound according to claim 1, or a pharmaceutically acceptable salt thereof, wherein X is C—H.

4. The compound according to claim 1, or a pharmaceutically acceptable salt thereof, wherein $Y^1$ is selected from the group consisting of C—H, C—F, and N.

5. The compound according to claim 1, or a pharmaceutically acceptable salt thereof, wherein $Y^1$ is C—H.

6. The compound according to claim 1, or a pharmaceutically acceptable salt thereof, wherein $Y^2$ is selected from the group consisting of C—H and C-halogen.

7. The compound according to claim 6, or a pharmaceutically acceptable salt thereof, wherein said C-halogen is C—F or C—Cl.

8. The compound according to claim 1, a pharmaceutically acceptable salt thereof, wherein $Y^2$ is C—H.

9. The compound according to claim 1, or a pharmaceutically acceptable salt thereof, wherein $Y^1$ and $Y^2$ are C—H, and X is N.

10. The compound according to claim 1, or a pharmaceutically acceptable salt thereof, wherein $R^1$ is selected from the group consisting of:
i. aryl substituted with one or more substituents selected from the group consisting of aminoalkyl, amino, haloalkylaryl, cycloalkyl, haloaryl-alkenyl, hydroxyalkynyl, haloalkylaryl-alkoxyalkyl, haloalkylaryloxy, haloalkylheteroaryl, alkylheteroaryl, arylcycloalkyl, cycloalkylheteroaryl, cycloalkylalkoxy, arylalkoxy, aryloxy, halogen, heterocyclyl, haloheterocyclyl, hydroxyalkylheterocyclyl, hydroxyalkylheteroaryl, arylalkoxyalkylheteroaryl, haloalkylheterocyclyl, haloaryloxyalkyl, alkoxyalkylheterocyclyl, heteroaryl, haloheteroarylalkoxy, aryl, haloaryl, haloalkoxy, alkoxy, alkyl, haloalkyl, cyano, cyanoaryl, cyanocycloalkyl, cyanoalkylaryl, arylheterocyclyl, alkoxy-(haloalkyl)aryl, arylalkoxy-(alkyl)aryl, haloaryloxy, hydroxyalkylaryl, alkenyloxy, pentafluoro-lambda6-sulfanyl, heteroarylalkyl, alkoxyaryl, (arylalkoxy)aryl, carbamoylaryl, alkyl-(alkoxy)aryl, haloalkoxyaryl, alkylheterocyclyl, alkylcycloalkylheteroaryl, and haloarylalkoxy,
wherein said aminoalkyl is substituted on the nitrogen atom with one or two substituents independently selected from the group consisting of alkanoyl, arylalkyl and haloalkylarylalkyl; and
wherein said amino is substituted on the nitrogen atom with one or two substituents independently selected from the group consisting of alkyl, haloarylalkyl and haloalkoxyarylalkyl;
ii. heteroaryl substituted with one or more substituents selected from the group consisting of alkylsulfanyl, heteroaryl, cycloalkyl, haloaryl, cyano(haloaryl), heterocyclyl, alkoxyheterocyclyl, hydroxyheterocyclyl, alkylheterocyclyl, alkyl(hydroxyheterocyclyl), alkyl(haloheterocyclyl), alkylheteroaryl, hydroxyalkylheterocyclyl, aryl, alkyl, haloalkyl, cyano, cyanoaryl, halogen, arylalkoxy, alkoxy, dialkylamino, haloheterocyclyl, haloalkylhaloaryl, aryloxyalkyl, alkylaryl, heteroarylalkoxy, and haloalkylaryl;
iii. heteroaryl;
iv. cycloalkyl, substituted once with alkylheteroaryl; and
v. heterocyclyl, substituted once with haloarylsulfonyl or haloarylalkyl.

11. The compound according to claim 1, or a pharmaceutically acceptable salt thereof, wherein $R^1$ is selected from the group consisting of:
i. heteroaryl substituted with one or more substituents selected from the group consisting of aryl, alkylaryl, haloaryl, cyano(haloaryl), heterocyclyl, haloheterocyclyl, alkyl(haloheterocyclyl), alkylheterocyclyl, hydroxyalkylheterocyclyl, cycloalkyl, cyano, alkyl and haloalkyl; and
ii. aryl substituted with one or more substituents selected from the group consisting of heterocyclyl, hydroxyalkylheterocyclyl, haloalkylaryl, haloalkylheteroaryl, haloheteroarylalkoxy, haloaryloxyalkyl, arylheterocyclyl, alkylheteroaryl, haloarylalkoxy, halogen, haloalkyl, alkyl, heteroaryl, haloalkoxy, haloalkoxyaryl, hydroxyalkylaryl, alkoxy-(haloalkyl)aryl, alkylheterocyclyl, cycloalkylheteroaryl, alkylcycloalkylheteroaryl and aminoalkyl;
  wherein said aminoalkyl is substituted on the nitrogen atom with two substituents independently selected from the group consisting of alkanoyl and haloalkylarylalkyl.

12. The compound according to claim 1, or a pharmaceutically acceptable salt thereof, wherein $R^1$ is selected from the group consisting of:
  i. monocyclic heteroaryl substituted with one or more alkylaryl substituents;
  ii. bicyclic heteroaryl substituted with one or more substituents selected from the group consisting of aryl, haloaryl, cyano(haloaryl), heterocyclyl, haloheterocyclyl, alkyl(haloheterocyclyl), alkylheterocyclyl, hydroxyalkylheterocyclyl, cycloalkyl, cyano, alkyl, and haloalkyl; and
  iii. monocyclic aryl substituted with one or more substituents selected from the group consisting of heterocyclyl, hydroxyalkylheterocyclyl, haloalkylaryl, haloalkylheteroaryl, haloheteroarylalkoxy, haloaryloxyalkyl, arylheterocyclyl, alkylheteroaryl, haloarylalkoxy, halogen, haloalkyl, alkyl, heteroaryl, haloalkoxy, haloalkoxyaryl, hydroxyalkylaryl, alkoxy-(haloalkyl)aryl, alkylheterocyclyl, cycloalkylheteroaryl, alkylcycloalkylheteroaryl, and aminoalkyl;
  wherein said aminoalkyl is substituted on the nitrogen atom with two substituents independently selected from the group consisting of alkanoyl and haloalkylarylalkyl.

13. The compound according to claim 1, or a pharmaceutically acceptable salt thereof, wherein $R^1$ is selected from the group consisting of:
  i. benzoxazolyl substituted with 1 or 2 substituents selected from the group consisting of methyl, $CF_3$, phenyl, chlorophenyl, cyano-chlorophenyl, 2-azaspiro[3.3]heptanyl, 6-azaspiro[3.4]octanyl, difluoro-2-azaspiro[3.3]heptanyl, 3-fluoro-3-methyl-pyrrolidinyl, 3-(1-hydroxy-1-methyl-ethyl)pyrrolidinyl, fluorophenyl, piperidinyl, cyclohexyl, methylpyrrolidinyl and CN;
  ii. indolyl substituted once with phenyl or fluorophenyl;
  iii. indazolyl substituted once with fluorophenyl;
  iv. phenyl substituted with 1 or 2 substituents selected from the group consisting of Cl, F, methyl, $CF_3$, pyrrolidinyl, hydroxyethylpyrrolidinyl, dimethylpyrrolidinyl, diethylpyrrolidinyl, imidazolyl, dimethylpiperidinyl, trifluoromethylpyridyl, substituted phenyl, phenylcyclopropyl, substituted oxadiazolyl, chlorophenylmethoxy, 2,3-dihydroindolyl, 2-azaspiro[3.3]heptanyl, 5-azaspiro[2.4]heptanyl, (chloropyridyl)methoxy, (chlorophenoxy)methyl, azepanyl, 2,3-dihydropyrrolo[2,3-b]pyridin-1-yl, 2,3-dihydro-1H-pyrrolo[2,3-b]pyridin-4-yl and aminoethyl;
  wherein said substituted phenyl is substituted with 1 or 2 substituents independently selected from the group consisting of $CF_3$, methoxy, trifluoromethoxy, and hydroxymethyl;
  said substituted oxadiazolyl is substituted once with propan-2-yl, trifluoroethyl, 2-fluoro-1,1-dimethylethyl, tert-butyl, cyclopropyl or 1-methylcyclopropyl; and
  said aminoethyl is substituted on the nitrogen atom with acetyl and trifluoromethylbenzyl; and
  v. pyridyl substituted once with tert-butylphenyl.

14. The compound according claim 1, or a pharmaceutically acceptable salt thereof, wherein $R^1$ is selected from the group consisting of:

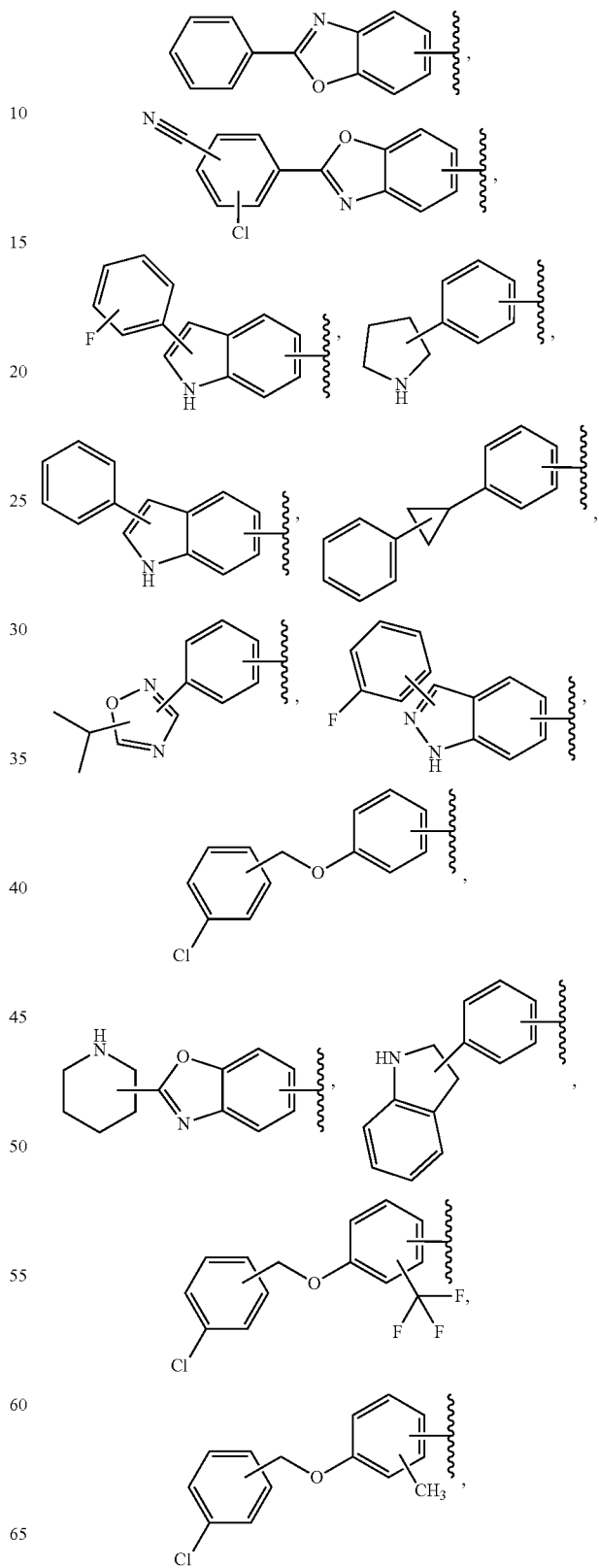

-continued
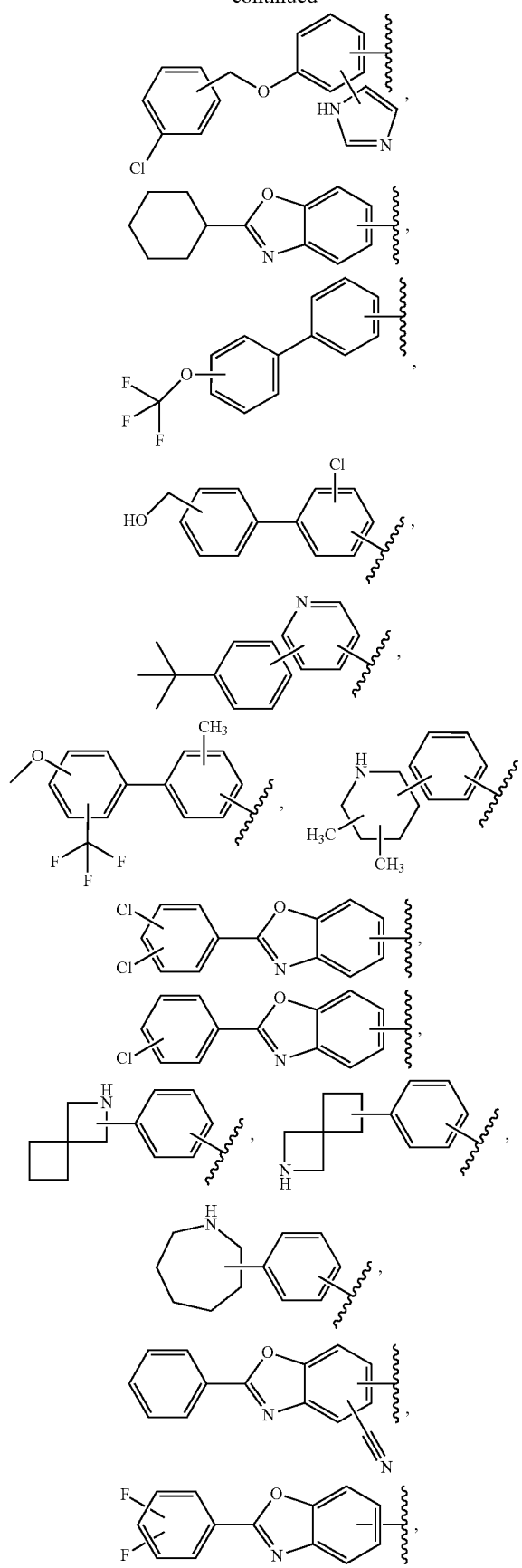
-continued
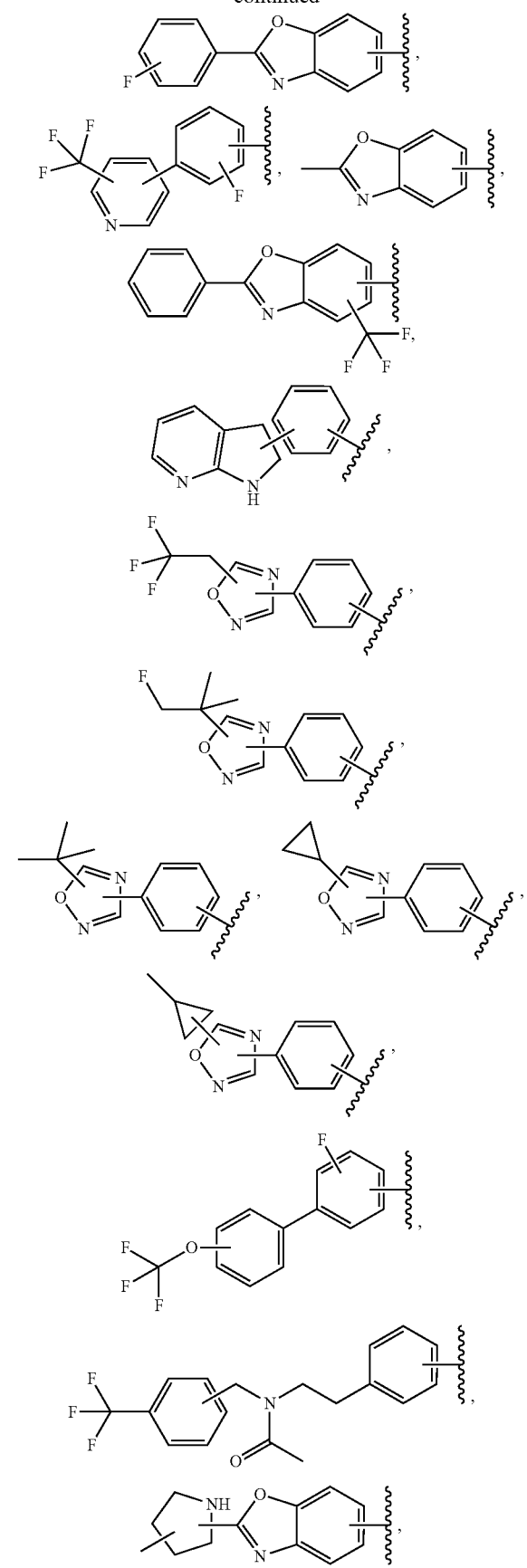

-continued

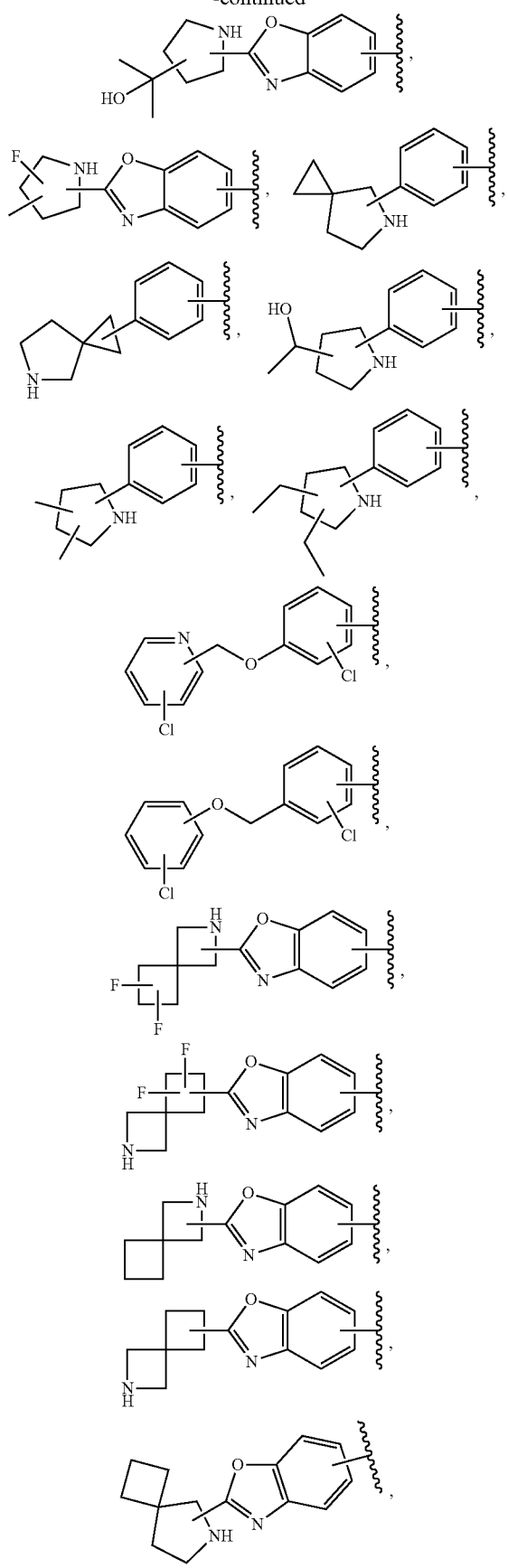

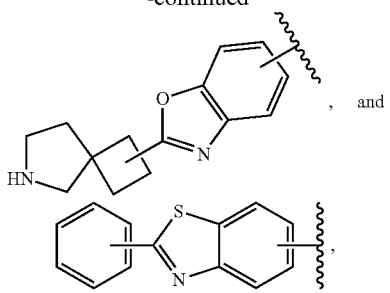

wherein the wavy line indicates the point of attachment of R¹ to the rest of Formula (I).

15. The compound according to claim 1, a pharmaceutically acceptable salt thereof, wherein R¹ is:
  i. heteroaryl substituted with one or more substituents selected from the group consisting of aryl, haloaryl, haloalkylaryl, heterocyclyl, haloheterocyclyl, and dialkylamino; or
  ii. aryl substituted with one or more substituents selected from the group consisting of alkylheteroaryl and heterocyclyl.

16. The compound according to claim 1, or a pharmaceutically acceptable salt thereof, wherein R¹ is:
  i. bicyclic heteroaryl substituted with one or more substituents selected from the group consisting of aryl, haloaryl, haloalkylaryl, heterocyclyl, haloheterocyclyl, and dialkylamino; or
  ii. monocyclic aryl substituted with one or more substituents selected from the group consisting of alkylheteroaryl and heterocyclyl.

17. The compound according to claim 1, or a pharmaceutically acceptable salt thereof, wherein R¹ is selected from the group consisting of:
  i. benzoxazolyl substituted with 1 or 2 substituents selected from the group consisting of:
    phenyl, chlorophenyl, trifluoromethylphenyl, morpholinyl, 2-azaspiro[3.4]octanyl, difluoro-2-azaspiro[3.3]heptanyl and methyl(propyl)amino; and
  ii. phenyl substituted with 1 substituent selected from the group consisting of substituted oxadiazolyl, 2-azaspiro[3.4]octanyl and 6-azaspiro[3.4]octan-yl, wherein:
    said substituted oxadiazolyl is substituted once with 2,2-dimethylpropyl or tert-butyl.

18. The compound according to claim 1, or a pharmaceutically acceptable salt thereof, wherein R¹ is selected from the group consisting of:

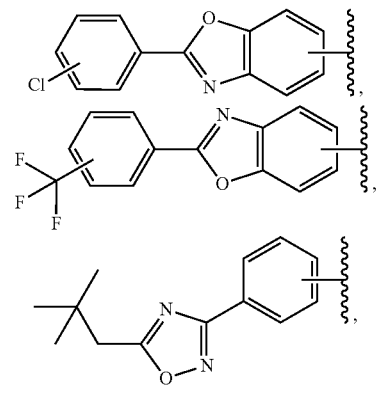

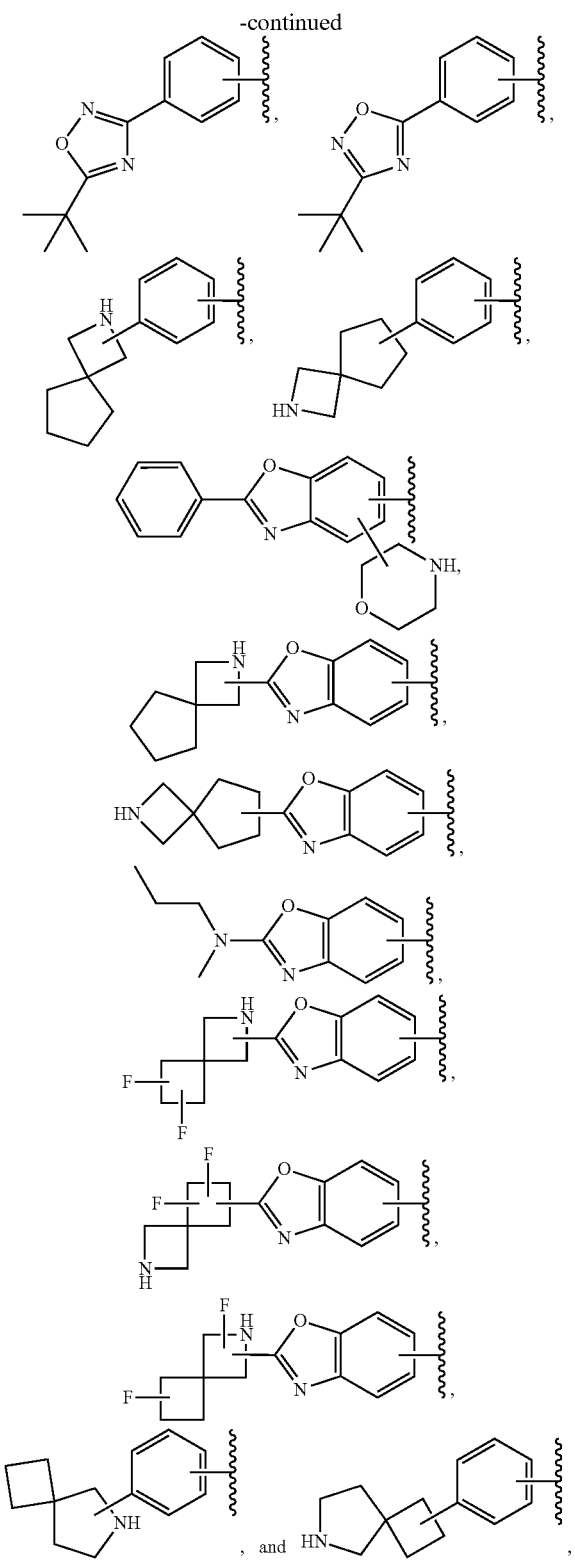

wherein a wavy line indicates the point of attachment of R¹ to the rest of Formula (I).

19. The compound according claim 1, a pharmaceutically acceptable salt thereof, wherein R² is H.

20. The compound according to claim 1, or a pharmaceutically acceptable salt thereof, wherein:

X is C—H or N;
Y¹ is selected from the group consisting of C—H, C—F and N;
Y² is selected from the group consisting of C—H and C-halogen;
R¹ is selected from the group consisting of:
  i. aryl substituted with one or more substituents selected from the group consisting of aminoalkyl, amino, haloalkylaryl, cycloalkyl, haloaryl-alkenyl, alkylcycloalkylheteroaryl, hydroxyalkynyl, haloalkylaryl-alkoxyalkyl, haloalkylaryloxy, haloalkylheteroaryl, alkylheteroaryl, arylcycloalkyl, cycloalkylheteroaryl, cycloalkylalkoxy, arylalkoxy, aryloxy, halogen, heterocyclyl, haloheterocyclyl, hydroxyalkylheterocyclyl, hydroxyalkylheteroaryl, arylalkoxyalkylheteroaryl, haloalkylheterocyclyl, haloaryloxyalkyl, alkoxyalkylheterocyclyl, heteroaryl, haloheteroarylalkoxy, aryl, haloaryl, haloalkoxy, alkoxy, alkyl, haloalkyl, cyano, cyanoaryl, cyanocycloalkyl, cyanoalkylaryl, arylheterocyclyl, alkoxy-(haloalkyl)aryl, arylalkoxy-(alkyl)aryl, haloaryloxy, hydroxyalkylaryl, alkenyloxy, pentafluoro-lambda6-sulfanyl, heteroarylalkyl, alkoxyaryl, (arylalkoxy)aryl, carbamoylaryl, alkyl-(alkoxy)aryl, haloalkoxyaryl, alkylheteroarylalkoxy, and haloarylalkoxy;
    wherein said aminoalkyl is substituted on the nitrogen atom with one or two substituents independently selected from the group consisting of alkanoyl, arylalkyl and haloalkylarylalkyl; and
    wherein said amino is substituted on the nitrogen atom with one or two substituents independently selected from the group consisting of alkyl, haloarylalkyl and haloalkoxyarylalkyl;
  ii. heteroaryl substituted with one or more substituents selected from the group consisting of alkylsulfanyl, heteroaryl, cycloalkyl, haloaryl, cyano(haloaryl), heterocyclyl, alkoxyheterocyclyl, hydroxyheterocyclyl, alkylheterocyclyl, alkyl(hydroxyheterocyclyl), alkyl(haloheterocyclyl), alkylheteroaryl, hydroxyalkylheterocyclyl, aryl, alkyl, haloalkyl, cyano, cyanoaryl, halogen, arylalkoxy, alkoxy, dialkylamino, haloheterocyclyl, haloalkylhaloaryl, aryloxyalkyl, alkylaryl, heteroarylalkoxy, and haloalkylaryl;
  iii. heteroaryl;
  iv. cycloalkyl substituted once with alkylheteroaryl; and
  v. heterocyclyl substituted once with haloarylsulfonyl or haloarylalkyl; and
R² is selected from the group consisting of hydrogen and alkyl.

21. The compound according to claim 1, or a pharmaceutically acceptable salt thereof, wherein:

X is C—H or N;
Y¹ is selected from the group consisting of C—H and C—F;
Y² is selected from the group consisting of C—H and C-halogen;
R¹ is selected from the group consisting of:
  i. heteroaryl substituted with one or more substituents selected from the group consisting of aryl, alkylaryl, haloaryl, cyano(haloaryl), heterocyclyl, haloheterocyclyl, hydroxyalkylheterocyclyl, alkylheterocyclyl, alkyl(haloheterocyclyl), cycloalkyl, cyano, alkyl, and haloalkyl; and
  ii. aryl substituted with one or more substituents selected from the group consisting of heterocyclyl, hydroxyalkylheterocyclyl, haloalkylaryl, haloalkylheteroaryl, haloheteroarylalkoxy, haloaryloxyalkyl, arylheterocyclyl, alkylheteroaryl, haloarylalkoxy, halogen, haloalkyl, alkyl, heteroaryl, haloalkoxy, haloalkoxyaryl, hydroxyalkylaryl, alkoxy-(haloalkyl)aryl, alkylheterocyclyl, cycloalkylheteroaryl, alkylcycloalkylheteroaryl, and aminoalkyl;
  wherein said aminoalkyl is substituted on the nitrogen atom with two substituents independently selected from the group consisting of alkanoyl and haloalkylarylalkyl; and
$R^2$ is selected from the group consisting of hydrogen and alkyl.

22. The compound according to claim 1, or a pharmaceutically acceptable salt thereof, wherein:
X is N;
$Y^1$ and $Y^2$ are each C—H;
$R^1$ is selected from the group consisting of:
  i. heteroaryl substituted with one or more substituents selected from the group consisting of aryl, haloaryl, haloalkylaryl, heterocyclyl, haloheterocyclyl, and dialkylamino; and
  ii. aryl substituted with one or more substituents selected from the group consisting of alkylheteroaryl and heterocyclyl; and
$R^2$ is hydrogen.

23. The compound according to claim 1, or a pharmaceutically acceptable salt thereof, wherein:
X is C—H or N;
$Y^1$ is selected from the group consisting of C—H and C—F;
$Y^2$ is selected from the group consisting of C—H, C—Cl, and C—F;
$R^1$ is selected from the group consisting of:
  i. benzoxazolyl substituted with 1 or 2 substituents selected from the group consisting of methyl, $CF_3$, phenyl, chlorophenyl, cyano-chlorophenyl, 2-azaspiro[3.3]heptanyl, difluoro-2-azaspiro[3.3]heptanyl, 6-azaspiro[3.4]octanyl, 3-fluoro-3-methylpyrrolidinyl, 3-(1-hydroxy-1-methyl-ethyl)pyrrolidinyl, fluorophenyl, piperidinyl, cyclohexyl, methylpyrrolidinyl, and CN;
  ii. indolyl substituted once with phenyl or fluorophenyl;
  iii. indazolyl substituted once with fluorophenyl;
  iv. phenyl substituted with 1 or 2 substituents selected from the group consisting of Cl, F, methyl, $CF_3$, pyrrolidinyl, hydroxyethylpyrrolidinyl, dimethylpyrrolidinyl, diethylpyrrolidinyl, imidazolyl, dimethylpiperidinyl, trifluoromethylpyridyl, substituted phenyl, phenylcyclopropyl, substituted oxadiazolyl, chlorophenylmethoxy, 2,3-dihydroindolyl, 2-azaspiro[3.3]heptanyl, 5-azaspiro[2.4]heptanyl, (chloropyridyl)methoxy, (chlorophenoxy)methyl, azepanyl, 2,3-dihydropyrrolo[2,3-b]pyridin-1-yl, 2,3-dihydro-1H-pyrrolo[2,3-b]pyridin-4-yl, and aminoethyl;
    wherein said substituted phenyl is substituted with 1 or 2 substituents independently selected from the group consisting of $CF_3$, methoxy, trifluoromethoxy, and hydroxymethyl;
    said substituted oxadiazolyl is substituted once with propan-2-yl, trifluoroethyl, 2-fluoro-1,1-dimethylethyl, tert-butyl, cyclopropyl, or 1-methylcyclopropyl; and
    said aminoethyl is substituted on the nitrogen atom with acetyl and trifluoromethylbenzyl; and
  v. pyridyl substituted once with tert-butylphenyl; and
$R^2$ is selected from the group consisting of hydrogen and alkyl.

24. The compound according to claim 1, or a pharmaceutically acceptable salt thereof, wherein:
X is N;
$Y^1$ and $Y^2$ are both C—H;
$R^1$ is selected from the group consisting of:
  i. benzoxazolyl substituted with 1 or 2 substituents selected from the group consisting of phenyl, chlorophenyl, trifluoromethylphenyl, morpholinyl, 2-azaspiro[3.4]octanyl, difluoro-2-azaspiro[3.3]heptanyl and methyl(propyl)amino; and
  ii. phenyl substituted with 1 substituent selected from the group consisting of substituted oxadiazolyl, 2-azaspiro[3.4]octanyl, and 6-azaspiro[3.4]octan-yl, wherein said substituted oxadiazolyl is substituted once with 2,2-dimethylpropyl or tert-butyl; and
$R^2$ is hydrogen.

25. A compound, selected from the group consisting of:
N-[2-[4-[4-(4-oxo-3H-quinazolin-2-yl)piperazine-1-carbonyl]phenyl]ethyl]-N-methyl]acetamide;
2-[4-[4-[(E)-2-(3-fluorophenyl)ethenyl]benzoyl]piperazin-1-yl]-3H-quinazolin-4-one;
2-[4-(4-Phenoxybenzoyl)piperazin-1-yl]-3H-quinazolin-4-one;
2-[4-(3-Phenoxybenzoyl)piperazin-1-yl]-3H-quinazolin-4-one;
2-[4-[4-(Trifluoromethoxy)benzoyl]piperazin-1-yl]-3H-quinazolin-4-one;
2-[4-[3-(Trifluoromethoxy)benzoyl]piperazin-1-yl]-3H-quinazolin-4-one;
2-[4-(2-Phenyl-1,3-benzoxazole-5-carbonyl)piperazin-1-yl]-3H-quinazolin-4-one;
2-[4-(2-Phenyl-1,3-benzoxazole-6-carbonyl)piperazin-1-yl]-3H-quinazolin-4-one;
2-[4-(1H-Indole-5-carbonyl)piperazin-1-yl]-3H-quinazolin-4-one;
2-[4-[1-(4-Fluorophenyl)indole-5-carbonyl]piperazin-1-yl]-3H-quinazolin-4-one;
2-[4-(4-Pyrrolidin-1-ylbenzoyl)piperazin-1-yl]-3H-quinazolin-4-one;
2-[4-[4-[(2-Iodophenyl)methylamino]benzoyl]piperazin-1-yl]-3H-quinazolin-4-one;
2-[4-(3-Phenylmethoxybenzoyl)piperazin-1-yl]-3H-quinazolin-4-one;
2-[4-[4-methylamino]benzoyl]piperazin-1-yl]-3H-quinazolin-4-one;
2-[4-[3-(Cyclopentylmethoxy)benzoyl]piperazin-1-yl]-3H-quinazolin-4-one;
2-[4-(4-Phenylbenzoyl)piperazin-1-yl]-3H-quinazolin-4-one;
2-[4-[4-[3-(Trifluoromethyl)phenyl]benzoyl]piperazin-1-yl]-3H-quinazolin-4-one;
2-[4-[4-(5-Methyl-1,2,4-oxadiazol-3-yl)benzoyl]piperazin-1-yl]-3H-quinazolin-4-one;
2-[4-(3-Phenyl-1,2-oxazole-5-carbonyl)piperazin-1-yl]-3H-quinazolin-4-one;
2-[4-(3-Chloro-4-pyrrolidin-1-ylbenzoyl)piperazin-1-yl]-3H-quinazolin-4-one;
N-benzyl-N-[2-[4-[4-(4-oxo-3H-quinazolin-2-yl)piperazine-1-carbonyl]phenyl]ethyl]acetamide;
2-[4-[3-(Trifluoromethyl)benzoyl]piperazin-1-yl]-3H-quinazolin-4-one;
2-[4-(2-Phenyl-1H-indole-5-carbonyl)piperazin-1-yl]-3H-quinazolin-4-one;
(Rac, cis)-2-[4-[4-[2-phenylcyclopropyl]benzoyl]piperazin-1-yl]-3H-quinazolin-4-one;
(Rac, trans)-2-[4-[4-[2-phenylcyclopropyl]benzoyl]piperazin-1-yl]-3H-quinazolin-4-one;

2-[4-[3-Bromo-5-(trifluoromethoxy)benzoyl]piperazin-1-yl]-3H-quinazolin-4-one;
2-[4-(3-Prop-2-enoxybenzoyl)piperazin-1-yl]-3H-quinazolin-4-one;
2-[4-[4-(2-Methylpropyl)benzoyl]piperazin-1-yl]-3H-quinazolin-4-one;
2-[4-[4-(5-Propan-2-yl-1,2,4-oxadiazol-3-yl)benzoyl]piperazin-1-yl]-3H-quinazolin-4-one;
2-[4-(2-Methyl-1-phenylbenzimidazole-5-carbonyl)piperazin-1-yl]-3H-quinazolin-4-one;
2-[4-[3,5-Bis(trifluoromethyl)benzoyl]piperazin-1-yl]-3H-quinazolin-4-one;
2-[4-[4-[2-methoxy]ethyl]benzoyl]piperazin-1-yl]-3H-quinazolin-4-one;
2-[4-(4-tert-Butyl-3-methoxybenzoyl)piperazin-1-yl]-3H-quinazolin-4-one;
2-[4-[4-(Pentafluoro-λ6-sulfanyl)benzoyl]piperazin-1-yl]-3H-quinazolin-4-one;
2-[4-[1-(4-Fluorophenyl)indazole-5-carbonyl]piperazin-1-yl]-3H-quinazolin-4-one;
2-[4-[4-(2,5-Dimethylpyrrol-1-yl)benzoyl]piperazin-1-yl]-3H-quinazolin-4-one;
2-[4-(Quinoline-7-carbonyl)piperazin-1-yl]-3H-quinazolin-4-one;
2-[4-[3-Bromo-4-(trifluoromethoxy)benzoyl]piperazin-1-yl]-3H-quinazolin-4-one;
2-[4-[4-(Benzimidazol-1-ylmethyl)benzoyl]piperazin-1-yl]-3H-quinazolin-4-one;
2-[4-[4-(1,3-Thiazol-2-yl)benzoyl]piperazin-1-yl]-3H-quinazolin-4-one;
2-[4-[4-(4-Methylpyrazol-1-yl)benzoyl]piperazin-1-yl]-3H-quinazolin-4-one;
2-[4-[4-(3-Methylpyrazol-1-yl)benzoyl]piperazin-1-yl]-3H-quinazolin-4-one;
2-[4-(6-Methoxy-1-benzofuran-2-carbonyl)piperazin-1-yl]-3H-quinazolin-4-one;
2-[4-[5-(2,3-Dihydro-1H-inden-5-yloxymethyl)furan-2-carbonyl]piperazin-1-yl]-3H-quinazolin-4-one;
2-[4-(1,5-Diphenylpyrazole-3-carbonyl)piperazin-1-yl]-3H-quinazolin-4-one;
2-[4-[4-[(3-Chlorophenyl)methoxy]benzoyl]piperazin-1-yl]-3H-quinazolin-4-one;
2-[4-(2-Phenyl-1H-benzimidazole-5-carbonyl)piperazin-1-yl]-3H-quinazolin-4-one;
2-[4-[2-(3-Fluorophenyl)-1H-indole-5-carbonyl]piperazin-1-yl]-3H-quinazolin-4-one;
2-[4-[4-[3-(Trifluoromethyl)phenyl]benzoyl]piperazin-1-yl]-3H-pyrido[3,4-d]pyrimidin-4-one;
2-[4-(2-Phenyl-1,3-benzoxazole-6-carbonyl)piperazin-1-yl]-3H-pyrido[3,4-d]pyrimidin-4-one;
2-[4-[1-(4-Fluorophenyl)pyrrolo[2,3-b]pyridine-5-carbonyl]piperazin-1-yl]-3H-quinazolin-4-one;
2-[4-(4-Piperidin-1-ylbenzoyl)piperazin-1-yl]-3H-quinazolin-4-one;
2-[4-[1-(4-Fluorophenyl)benzimidazole-5-carbonyl]piperazin-1-yl]-3H-quinazolin-4-one;
2-[4-(2-Piperidin-1-yl-1,3-benzoxazole-6-carbonyl)piperazin-1-yl]-3H-quinazolin-4-one;
3-Methyl-2-[4-(2-phenyl-1,3-benzoxazole-6-carbonyl)piperazin-1-yl]quinazolin-4-one;
2-[4-[4-[5-(Trifluoromethyl)-1,2,4-oxadiazol-3-yl]benzoyl]piperazin-1-yl]-3H-quinazolin-4-one;
2-[4-[4-(4-Trifluoromethyl)pyrazol-1-yl]benzoyl]piperazin-1-yl]-3H-quinazolin-4-one;
2-[4-[4-[3-(Trifluoromethyl)pyrazol-1-yl]benzoyl]piperazin-1-yl]-3H-quinazolin-4-one;
2-[4-[4-(5-Cyclopropyl-1,2,4-oxadiazol-3-yl)benzoyl]piperazin-1-yl]-3H-quinazolin-4-one;
2-[4-[2-(3-Fluorophenyl)-1,3-benzoxazole-6-carbonyl]piperazin-1-yl]-3H-quinazolin-4-one;
2-[4-[2-(3-Chlorophenyl)-1,3-benzoxazole-6-carbonyl]piperazin-1-yl]-3H-quinazolin-4-one;
2-[4-[2-[3-(Trifluoromethyl)phenyl]-1,3-benzoxazole-6-carbonyl]piperazin-1-yl]-3H-quinazolin-4-one;
2-[4-(4-Phenylmethoxybenzoyl)piperazin-1-yl]-3H-quinazolin-4-one;
2-[4-[4-(Diethylamino)benzoyl]piperazin-1-yl]-3H-quinazolin-4-one;
2-[4-[3-[(3-Chlorophenyl)methoxy]benzoyl]piperazin-1-yl]-3H-quinazolin-4-one;
2-[4-[3-Chloro-4-[(3-chlorophenyl)methoxy]benzoyl]piperazin-1-yl]-3H-quinazolin-4-one;
2-[4-[4-[5-(2,2-Dimethylpropyl)-1,2,4-oxadiazol-3-yl]benzoyl]piperazin-1-yl]-3H-quinazolin-4-one;
2-[4-[4-[tert-Butyl(methyl)amino]benzoyl]piperazin-1-yl]-3H-quinazolin-4-one;
2-[4-[4-(2,3-Dihydroindol-1-yl)benzoyl]piperazin-1-yl]-3H-quinazolin-4-one;
2-[4-[4-(Azetidin-1-yl)benzoyl]piperazin-1-yl]-3H-quinazolin-4-one;
2-[4-(2-Chloro-4-pyrrolidin-1-ylbenzoyl)piperazin-1-yl]-3H-quinazolin-4-one;
2-[4-[4-[(3-Chlorophenyl)methoxy]-3-(trifluoromethyl)benzoyl]piperazin-1-yl]-3H-quinazolin-4-one;
2-[4-[4-[(3-Chlorophenyl)methoxy]-3-methylbenzoyl]piperazin-1-yl]-3H-quinazolin-4-one;
2-[4-(3-Pyrrolidin-1-ylbenzoyl)piperazin-1-yl]-3H-quinazolin-4-one;
2-[4-[4-(5-tert-Butyl-1,2,4-oxadiazol-3-yl)benzoyl]piperazin-1-yl]-3H-quinazolin-4-one;
2-[4-[4-[(3-Chlorophenyl)methoxy]-3-(1H-imidazol-2-yl)benzoyl]piperazin-1-yl]-3H-quinazolin-4-one;
2-[(3-Chlorophenyl)methoxy]-5-[4-(4-oxo-3H-quinazolin-2-yl)piperazine-1-carbonyl]benzonitrile;
2-[4-(4-Cyclohexylbenzoyl)piperazin-1-yl]-3H-quinazolin-4-one;
2-[4-(2-Cyclohexyl-1,3-benzoxazole-6-carbonyl)piperazin-1-yl]-3H-quinazolin-4-one;
2-[4-[4-(4-Oxo-3H-quinazolin-2-yl)piperazine-1-carbonyl]phenyl]benzonitrile;
2-[4-(1-Butyl-2-methylbenzimidazole-5-carbonyl)piperazin-1-yl]-3H-quinazolin-4-one;
2-[4-[4-[3,5-Bis(trifluoromethyl)phenyl]benzoyl]piperazin-1-yl]-3H-quinazolin-4-one;
2-[4-[4-[3-(Trifluoromethoxy)phenyl]benzoyl]piperazin-1-yl]-3H-quinazolin-4-one;
2-[4-[1-Propan-2-yl-2-(trifluoromethyl)benzimidazole-5-carbonyl]piperazin-1-yl]-3H-quinazolin-4-one;
2-[4-[5-[3-(Trifluoromethyl)phenyl]pyridine-3-carbonyl]piperazin-1-yl]-3H-quinazolin-4-one;
2-[4-[4-(3,4-Difluorophenyl)-2-fluorobenzoyl]piperazin-1-yl]-3H-quinazolin-4-one;
2-[4-[4-(2-Methoxy-5-methylphenyl)benzoyl]piperazin-1-yl]-3H-quinazolin-4-one;
2-[4-(3-Methyl-1-benzofuran-2-carbonyl)piperazin-1-yl]-3H-quinazolin-4-one;
2-[4-[3-[2-(Hydroxymethyl)phenyl]benzoyl]piperazin-1-yl]-3H-quinazolin-4-one;
2-[4-[4-[3-(Hydroxymethyl)phenyl]benzoyl]piperazin-1-yl]-3H-quinazolin-4-one;
2-[4-(3-Bromo-5-propan-2-yloxybenzoyl)piperazin-1-yl]-3H-quinazolin-4-one;

2-[4-[3-Chloro-5-[4-(hydroxymethyl)phenyl]benzoyl]piperazin-1-yl]-3H-quinazolin-4-one;
2-[4-[4-Chloro-3-(2-methylpropoxy)benzoyl]piperazin-1-yl]-3H-quinazolin-4-one;
2-[4-(3-Bromo-5-ethoxybenzoyl)piperazin-1-yl]-3H-quinazolin-4-one;
2-[4-[4-Fluoro-3-[2-(hydroxymethyl)phenyl]benzoyl]piperazin-1-yl]-3H-quinazolin-4-one;
2-[4-[3-Fluoro-4-[3-(trifluoromethyl)phenyl]benzoyl]piperazin-1-yl]-3H-quinazolin-4-one;
2-[4-[3-[2-(Trifluoromethoxy)phenyl]benzoyl]piperazin-1-yl]-3H-quinazolin-4-one;
2-[4-[6-(Trifluoromethyl)quinoline-3-carbonyl]piperazin-1-yl]-3H-quinazolin-4-one;
2-[4-(4,6-Dimethyl-1H-indole-2-carbonyl)piperazin-1-yl]-3H-quinazolin-4-one;
N,N-dimethyl-4-[2-methyl-4-[4-(4-oxo-3H-quinazolin-2-yl)piperazine-1-carbonyl]phenyl]benzamide;
2-[4-[2-(4-tert-Butylphenyl)pyridine-4-carbonyl]piperazin-1-yl]-3H-quinazolin-4-one;
2-[4-[4-(2-Chlorophenoxy)benzoyl]piperazin-1-yl]-3H-quinazolin-4-one;
2-[4-(3-tert-Butyl-5-chlorobenzoyl)piperazin-1-yl]-3H-quinazolin-4-one;
2-[4-[4-(3-Phenylmethoxyphenyl)benzoyl]piperazin-1-yl]-3H-quinazolin-4-one;
2-[4-[3-(2-Methyl-6-phenylmethoxyphenyl)benzoyl]piperazin-1-yl]-3H-quinazolin-4-one;
2-[4-[4-[4-Methoxy-3-(trifluoromethyl)phenyl]-3-methylbenzoyl]piperazin-1-yl]-3H-quinazolin-4-one;
2-[4-(7-Phenylmethoxy-1H-indole-3-carbonyl)piperazin-1-yl]-3H-quinazolin-4-one;
2-[4-[4-(2,6-Difluorophenyl)benzoyl]piperazin-1-yl]-3H-quinazolin-4-one;
2-[4-(1-Cyclopropylbenzimidazole-5-carbonyl)piperazin-1-yl]-3H-quinazolin-4-one;
2-[4-(6-tert-Butyl-1H-indole-2-carbonyl)piperazin-1-yl]-3H-quinazolin-4-one;
2-[4-(4-Chloro-3-ethoxybenzoyl)piperazin-1-yl]-3H-quinazolin-4-one;
2-[4-[4-(4,4-Dimethylpiperidin-1-yl)benzoyl]piperazin-1-yl]-3H-quinazolin-4-one;
2-[4-[5-(Trifluoromethyl)imidazo[1,2-a]pyridine-2-carbonyl]piperazin-1-yl]-3H-quinazolin-4-one;
4-[2-Fluoro-5-[4-(4-oxo-3H-quinazolin-2-yl)piperazine-1-carbonyl]phenyl]-N,N-dimethylbenzamide;
2-[4-[3-(3,5-Difluorophenyl)benzoyl]piperazin-1-yl]-3H-quinazolin-4-one;
2-[4-[2-(3,4-Dichlorophenyl)-1,3-benzoxazole-6-carbonyl]piperazin-1-yl]-3H-quinazolin-4-one;
2-[4-[2-(4-Chlorophenyl)-1,3-benzoxazole-6-carbonyl]piperazin-1-yl]-3H-quinazolin-4-one;
2-[4-[4-(3-Azabicyclo[2.2.1]heptan-3-yl)benzoyl]piperazin-1-yl]-3H-quinazolin-4-one;
2-[4-[4-(2-Azaspiro[3.3]heptan-2-yl)benzoyl]piperazin-1-yl]-3H-quinazolin-4-one;
2-[4-[4-(Azepan-1-yl)benzoyl]piperazin-1-yl]-3H-quinazolin-4-one;
2-[4-(2-Phenyl-[1,3]oxazolo[4,5-b]pyridine-6-carbonyl)piperazin-1-yl]-3H-quinazolin-4-one;
2-[4-[4-(3-Cyclopropyl-1H-1,2,4-triazol-5-yl)benzoyl]piperazin-1-yl]-3H-quinazolin-4-one;
2-[4-[4-(3-Cyclopropyl-1,2,4-oxadiazol-5-yl)benzoyl]piperazin-1-yl]-3H-quinazolin-4-one;
6-[4-(4-Oxo-3H-quinazolin-2-yl)piperazine-1-carbonyl]-2-phenyl-1,3-benzoxazole-4-carbonitrile;
2-[4-[4-(3,4-Dichlorophenyl)benzoyl]piperazin-1-yl]-3H-quinazolin-4-one;
2-[4-(6-Pyrrolidin-1-ylpyridine-3-carbonyl)piperazin-1-yl]-3H-quinazolin-4-one;
2-[4-[3-[5-(2,2-Dimethylpropyl)-1,2,4-oxadiazol-3-yl]benzoyl]piperazin-1-yl]-3H-quinazolin-4-one;
2-[4-[4-(2-Azaspiro[3.4]octan-2-yl)benzoyl]piperazin-1-yl]-3H-quinazolin-4-one;
2-[4-[4-(5-Ethyl-1,2,4-oxadiazol-3-yl)benzoyl]piperazin-1-yl]-3H-quinazolin-4-one;
2-[4-[4-(2-Methyl-1,3-thiazol-4-yl)benzoyl]piperazin-1-yl]-3H-quinazolin-4-one;
2-[4-[2-(3,4-Difluorophenyl)-1,3-benzoxazole-6-carbonyl]piperazin-1-yl]-3H-quinazolin-4-one;
2-[4-[2-[4-(Trifluoromethyl)phenyl]-1,3-benzoxazole-6-carbonyl]piperazin-1-yl]-3H-quinazolin-4-one;
2-[4-[2-[3-Fluoro-4-(trifluoromethyl)phenyl]-1,3-benzoxazole-6-carbonyl]piperazin-1-yl]-3H-quinazolin-4-one;
2-[4-[2-(4-Fluorophenyl)-1,3-benzoxazole-6-carbonyl]piperazin-1-yl]-3H-quinazolin-4-one;
6-Fluoro-2-[4-(2-phenyl-1,3-benzoxazole-6-carbonyl)piperazin-1-yl]-3H-quinazolin-4-one;
7-Fluoro-2-[4-(2-phenyl-1,3-benzoxazole-6-carbonyl)piperazin-1-yl]-3H-quinazolin-4-one;
2-[4-(4-Bromo-3-fluorobenzoyl)piperazin-1-yl]-3H-quinazolin-4-one;
2-[4-(5-Pyrrolidin-1-ylpyridine-2-carbonyl)piperazin-1-yl]-3H-quinazolin-4-one;
2-[4-[3-Fluoro-4-[5-(trifluoromethyl)pyridin-3-yl]benzoyl]piperazin-1-yl]-3H-quinazolin-4-one;
2-[4-(2-Methyl-1,3-benzoxazole-6-carbonyl)piperazin-1-yl]-3H-quinazolin-4-one;
2-[4-[2-Phenyl-4-(trifluoromethyl)-1,3-benzoxazole-6-carbonyl]piperazin-1-yl]-3H-quinazolin-4-one;
2-[4-(4-Bromo-3-methylbenzoyl)piperazin-1-yl]-3H-quinazolin-4-one;
2-[4-(2-Morpholin-4-yl-1,3-benzoxazole-6-carbonyl)piperazin-1-yl]-3H-quinazolin-4-one;
2-[4-[4-(2,3-Dihydropyrrolo[2,3-b]pyridin-1-yl)benzoyl]piperazin-1-yl]-3H-quinazolin-4-one;
2-[4-[4-(2-Phenylpyrrolidin-1-yl)benzoyl]piperazin-1-yl]-3H-quinazolin-4-one;
2-[4-(2-Pyridin-2-yl-1,3-benzoxazole-6-carbonyl)piperazin-1-yl]-3H-quinazolin-4-one;
2-[4-[4-[5-(2,2,2-Trifluoroethyl)-1,2,4-oxadiazol-3-yl]benzoyl]piperazin-1-yl]-3H-quinazolin-4-one;
2-[4-[4-(2-Oxa-6-azaspiro[3.3]heptan-6-yl)benzoyl]piperazin-1-yl]-3H-quinazolin-4-one;
2-[3-[4-[4-(4-oxo-3H-quinazolin-2-yl)piperazine-1-carbonyl]phenyl]phenyl]acetonitrile;
2-[4-[3-Fluoro-4-[3-(trifluoromethoxy)phenyl]benzoyl]piperazin-1-yl]-3H-quinazolin-4-one;
2-[4-[3-Methyl-4-[3-(trifluoromethoxy)phenyl]benzoyl]piperazin-1-yl]-3H-quinazolin-4-one;
2-[4-[4-(3-Ethoxyphenyl)benzoyl]piperazin-1-yl]-3H-quinazolin-4-one;
6-Chloro-2-[4-(2-phenyl-1,3-benzoxazole-6-carbonyl)piperazin-1-yl]-3H-quinazolin-4-one;
2-[4-[4-[2-methylamino]ethyl]benzoyl]piperazin-1-yl]-3H-quinazolin-4-one;
1-[4-[4-(4-Oxo-3H-quinazolin-2-yl)piperazine-1-carbonyl]phenyl]cyclopentane-1-carbonitrile;
2-[4-(4-Morpholin-4-yl-2-phenyl-1,3-benzoxazole-6-carbonyl)piperazin-1-yl]-3H-quinazolin-4-one;
2-[4-[2-(2-Azaspiro[3.4]octan-2-yl)-1,3-benzoxazole-6-carbonyl]piperazin-1-yl]-3H-quinazolin-4-one;

2-[4-[2-(7,7-Difluoro-2-azaspiro[3.3]heptan-2-yl)-1,3-benzoxazole-6-carbonyl]piperazin-1-yl]-3H-quinazolin-4-one;
2-[4-[2-[Methyl(propyl)amino]-1,3-benzoxazole-6-carbonyl]piperazin-1-yl]-3H-quinazolin-4-one;
N-[2-[4-[4-(1-oxo-2H-isoquinolin-3-yl)piperazine-1-carbonyl]phenyl]ethyl]-N-methyl]acetamide;
2-[4-[2-(Oxan-4-yl)-1,3-benzoxazole-6-carbonyl]piperazin-1-yl]-3H-quinazolin-4-one;
2-[4-[2-Pyridin-4-yl-1,3-benzoxazole-6-carbonyl)piperazin-1-yl]-3H-quinazolin-4-one;
2-[4-[2-Pyridin-3-yl-1,3-benzoxazole-6-carbonyl)piperazin-1-yl]-3H-quinazolin-4-one;
3-[6-[4-(4-Oxo-3H-quinazolin-2-yl)piperazine-1-carbonyl]-1,3-benzoxazol-2-yl]benzonitrile;
2-[4-[2-Methylsulfanyl-1,3-benzoxazole-6-carbonyl)piperazin-1-yl]-3H-quinazolin-4-one;
2-[4-[2-Pyrrolidin-1-yl-1,3-benzoxazole-6-carbonyl)piperazin-1-yl]-3H-quinazolin-4-one;
2-[4-[2-(4-Methoxypiperidin-1-yl)-1,3-benzoxazole-6-carbonyl]piperazin-1-yl]-3H-quinazolin-4-one;
2-[4-[2-(4-Hydroxypiperidin-1-yl)-1,3-benzoxazole-6-carbonyl]piperazin-1-yl]-3H-quinazolin-4-one;
2-[4-[2-(3-Methylpyrrolidin-1-yl)-1,3-benzoxazole-6-carbonyl]piperazin-1-yl]-3H-quinazolin-4-one;
2-[4-[4-(6-Azaspiro[3.4]octan-6-yl)benzoyl]piperazin-1-yl]-3H-quinazolin-4-one;
2-[4-[4-(3,3-Difluoropyrrolidin-1-yl)benzoyl]piperazin-1-yl]-3H-quinazolin-4-one;
2-[4-[4-[3-(1-Hydroxyethyl)pyrrolidin-1-yl]benzoyl]piperazin-1-yl]-3H-quinazolin-4-one;
2-[4-[4-[4-(Trifluoromethyl)piperidin-1-yl]benzoyl]piperazin-1-yl]-3H-quinazolin-4-one;
2-[4-[4-(5-Azaspiro[2.4]heptan-5-yl)benzoyl]piperazin-1-yl]-3H-quinazolin-4-one;
2-[4-[3-Chloro-4-[(4-chloropyridin-2-yl)methoxy]benzoyl]piperazin-1-yl]-3H-quinazolin-4-one;
2-[4-[3-Chloro-4-[(2-chloropyridin-4-yl)methoxy]benzoyl]piperazin-1-yl]-3H-quinazolin-4-one;
2-[4-(3-Phenylbenzoyl)piperazin-1-yl]-3H-quinazolin-4-one;
2-[4-[3-Chloro-4-[(6-chloropyridin-2-yl)methoxy]benzoyl]piperazin-1-yl]-3H-quinazolin-4-one;
2-[4-[3-[3-(Trifluoromethyl)phenyl]benzoyl]piperazin-1-yl]-3H-quinazolin-4-one;
2-[4-[4-[3-(Trifluoromethyl)phenoxy]benzoyl]piperazin-1-yl]-3H-quinazolin-4-one;
2-[4-[4-[3-(2,2,2-Trifluoroethyl)-1,2,4-oxadiazol-5-yl]benzoyl]piperazin-1-yl]-3H-quinazolin-4-one;
2-[4-[4-(2,5-Dimethylpyrrolidin-1-yl)benzoyl]piperazin-1-yl]-3H-quinazolin-4-one;
2-[4-[4-(4,4-Difluoropiperidin-1-yl)benzoyl]piperazin-1-yl]-3H-quinazolin-4-one;
2-[4-[3-Chloro-4-[(3-Chlorophenoxy)methyl]benzoyl]piperazin-1-yl]-3H-quinazolin-4-one;
2-[4-(2-Phenyl-1,3-benzothiazole-6-carbonyl)piperazin-1-yl]-3H-quinazolin-4-one;
2-[4-[2-(Oxolan-2-yl)-1,3-benzoxazole-6-carbonyl]piperazin-1-yl]-3H-quinazolin-4-one;
2-[4-[4-[3-(Methoxymethyl)pyrrolidin-1-yl]benzoyl]piperazin-1-yl]-3H-quinazolin-4-one;
2-[4-[2-(2,2,2-Trifluoroethyl)-1,3-benzoxazole-5-carbonyl]piperazin-1-yl]-3H-quinazolin-4-one;
2-[4-[4-[5-(1-methylcyclopropyl)-1,2,4-oxadiazol-3-yl]benzoyl]piperazin-1-yl]-3H-quinazolin-4-one;
2-[4-[4-[5-[1-(trifluoromethyl)cyclopropyl]-1,2,4-oxadiazol-3-yl]benzoyl]piperazin-1-yl]-3H-quinazolin-4-one;
2-[4-[4-[5-[1-(fluoromethyl)cyclopropyl]-1,2,4-oxadiazol-3-yl]benzoyl]piperazin-1-yl]-3H-quinazolin-4-one;
2-[4-[4-[5-(2-hydroxy-1,1-dimethyl-ethyl)-1,2,4-oxadiazol-3-yl]benzoyl]piperazin-1-yl]-3H-quinazolin-4-one;
2-[4-[2-Methyl-4-(1H-pyrazol-4-ylmethoxy)-1,3-benzoxazole-6-carbonyl]piperazin-1-yl]-3H-quinazolin-4-one;
2-[4-[4-[5-(1-Fluoro-2-methylpropan-2-yl)-1,2,4-oxadiazol-3-yl]benzoyl]piperazin-1-yl]-3H-quinazolin-4-one;
2-Chloro-4-[6-[4-(4-oxo-3H-quinazolin-2-yl)piperazine-1-carbonyl]-1,3-benzoxazol-2-yl]benzonitrile;
2-[4-[4-(3-tert-Butyl-1,2,4-oxadiazol-5-yl)benzoyl]piperazin-1-yl]-3H-quinazolin-4-one;
2-[4-[3-(3-tert-Butyl-1,2,4-oxadiazol-5-yl)bicyclo[1.1.1]pentane-1-carbonyl]piperazin-1-yl]-3H-quinazolin-4-one;
2-[4-[3-(3-Chlorophenyl)sulfonyl-3,9-diazaspiro[5.5]undecane-9-carbonyl]piperazin-1-yl]-3H-quinazolin-4-one;
2-[4-[4-(5-tert-Butyl-1,2,4-oxadiazol-3-yl)benzoyl]piperazin-1-yl]-6-chloro-3H-quinazolin-4-one;
2-[4-[4-(3,3-Dimethylpyrrolidin-1-yl)benzoyl]piperazin-1-yl]-3H-quinazolin-4-one;
2-[4-[2-(1-Methylpyrrol-3-yl)-1,3-benzoxazole-6-carbonyl]piperazin-1-yl]-3H-quinazolin-4-one;
2-[4-[4-[5-(1-Hydroxy-2-methylpropan-2-yl)-1,2,4-oxadiazol-3-yl]benzoyl]piperazin-1-yl]-3H-quinazolin-4-one;
2-[4-[2-(8-Oxa-2-azaspiro[4.5]decan-2-yl)-1,3-benzoxazole-6-carbonyl]piperazin-1-yl]-3H-quinazolin-4-one;
2-[4-[2-(3-Methoxypyrrolidin-1-yl)-1,3-benzoxazole-6-carbonyl]piperazin-1-yl]-3H-quinazolin-4-one;
2-[4-[2-(6,6-Difluoro-2-azaspiro[3.3]heptan-2-yl)-1,3-benzoxazole-6-carbonyl]piperazin-1-yl]-3H-quinazolin-4-one;
2-[4-[2-(2-Azaspiro[3.4]octan-2-yl)-1,3-benzoxazole-6-carbonyl]piperazin-1-yl]-3-methylquinazolin-4-one;
2-[4-[2-(2-Azaspiro[3.3]heptan-2-yl)-1,3-benzoxazole-6-carbonyl]piperazin-1-yl]-3H-quinazolin-4-one;
2-[4-[2-(6-Hydroxy-2-azaspiro[3.3]heptan-2-yl)-1,3-benzoxazole-6-carbonyl]piperazin-1-yl]-3H-quinazolin-4-one;
2-[4-[2-(3-Hydroxy-3-methylpyrrolidin-1-yl)-1,3-benzoxazole-6-carbonyl]piperazin-1-yl]-3H-quinazolin-4-one;
2-[4-[2-(3-Fluoro-3-methylpyrrolidin-1-yl)-1,3-benzoxazole-6-carbonyl]piperazin-1-yl]-3H-quinazolin-4-one;
2-[4-[2-[3-(2-Hydroxypropan-2-yl)pyrrolidin-1-yl]-1,3-benzoxazole-6-carbonyl]piperazin-1-yl]-3H-quinazolin-4-one;
2-[4-[2-(6-Azaspiro[3.4]octan-6-yl)-1,3-benzoxazole-6-carbonyl]piperazin-1-yl]-3-methylquinazolin-4-one;
2-[4-[2-(6-Azaspiro[3.4]octan-6-yl)-1,3-benzoxazole-6-carbonyl]piperazin-1-yl]-3H-quinazolin-4-one;
2-[4-[4-[5-(2-Methyl-1-phenylmethoxypropan-2-yl)-1,2,4-oxadiazol-3-yl]benzoyl]piperazin-1-yl]-3H-quinazolin-4-one;
2-[4-[4-(3-Hydroxy-3-methylbut-1-ynyl)benzoyl]piperazin-1-yl]-3H-quinazolin-4-one;
2-[4-[4-(3,3-Diethylpyrrolidin-1-yl)benzoyl]piperazin-1-yl]-3H-quinazolin-4-one;

2-[4-[2-(4-Chlorophenyl)sulfonyl-2,7-diazaspiro[4.4]
nonane-7-carbonyl]piperazin-1-yl]-3H-quinazolin-4-
one;
2-[4-[2-(3-Chlorophenyl)sulfonyl-2,7-diazaspiro[4.4]
nonane-7-carbonyl]piperazin-1-yl]-3H-quinazolin-4-
one; and
2-[4-[7-[(3-Chlorophenyl)methyl]-2,7-diazaspiro[4.4]
nonane-2-carbonyl]piperazin-1-yl]-3H-quinazolin-4-
one;
or a pharmaceutically acceptable salt thereof.

26. The compound of claim 25, selected from the group consisting of:
2-[4-(2-Phenyl-1,3-benzoxazole-5-carbonyl)piperazin-1-yl]-3H-quinazolin-4-one;
2-[4-(2-Phenyl-1,3-benzoxazole-6-carbonyl)piperazin-1-yl]-3H-quinazolin-4-one;
2-[4-[1-(4-Fluorophenyl)indole-5-carbonyl]piperazin-1-yl]-3H-quinazolin-4-one;
2-[4-(4-Pyrrolidin-1-ylbenzoyl)piperazin-1-yl]-3H-quinazolin-4-one;
2-[4-[4-[3-(Trifluoromethyl)phenyl]benzoyl]piperazin-1-yl]-3H-quinazolin-4-one;
2-[4-(2-Phenyl-1H-indole-5-carbonyl)piperazin-1-yl]-3H-quinazolin-4-one;
(Rac, trans)-2-[4-[4-[2-phenylcyclopropyl]benzoyl]piperazin-1-yl]-3H-quinazolin-4-one;
2-[4-[4-(5-Propan-2-yl-1,2,4-oxadiazol-3-yl)benzoyl]piperazin-1-yl]-3H-quinazolin-4-one;
2-[4-[1-(4-Fluorophenyl)indazole-5-carbonyl]piperazin-1-yl]-3H-quinazolin-4-one;
2-[4-[4-[(3-Chlorophenyl)methoxy]benzoyl]piperazin-1-yl]-3H-quinazolin-4-one;
2-[4-[2-(3-Fluorophenyl)-1H-indole-5-carbonyl]piperazin-1-yl]-3H-quinazolin-4-one;
2-[4-(2-Piperidin-1-yl-1,3-benzoxazole-6-carbonyl)piperazin-1-yl]-3H-quinazolin-4-one;
3-Methyl-2-[4-(2-phenyl-1,3-benzoxazole-6-carbonyl)piperazin-1-yl]quinazolin-4-one;
2-[4-[3-Chloro-4-[(3-chlorophenyl)methoxy]benzoyl]piperazin-1-yl]-3H-quinazolin-4-one;
2-[4-[4-(2,3-Dihydroindol-1-yl)benzoyl]piperazin-1-yl]-3H-quinazolin-4-one;
2-[4-[4-[(3-Chlorophenyl)methoxy]-3-(trifluoromethyl)benzoyl]piperazin-1-yl]-3H-quinazolin-4-one;
2-[4-[4-[(3-Chlorophenyl)methoxy]-3-methylbenzoyl]piperazin-1-yl]-3H-quinazolin-4-one;
2-[4-[4-[(3-Chlorophenyl)methoxy]-3-(1H-imidazol-2-yl)benzoyl]piperazin-1-yl]-3H-quinazolin-4-one;
2-[4-(2-Cyclohexyl-1,3-benzoxazole-6-carbonyl)piperazin-1-yl]-3H-quinazolin-4-one;
2-[4-[4-[3-(Trifluoromethoxy)phenyl]benzoyl]piperazin-1-yl]-3H-quinazolin-4-one;
2-[4-[3-Chloro-5-[4-(hydroxymethyl)phenyl]benzoyl]piperazin-1-yl]-3H-quinazolin-4-one;
2-[4-[3-Fluoro-4-[3-(trifluoromethyl)phenyl]benzoyl]piperazin-1-yl]-3H-quinazolin-4-one;
2-[4-[2-(4-tert-Butylphenyl)pyridine-4-carbonyl]piperazin-1-yl]-3H-quinazolin-4-one;
2-[4-[4-[4-Methoxy-3-(trifluoromethyl)phenyl]-3-methylbenzoyl]piperazin-1-yl]-3H-quinazolin-4-one;
2-[4-[4-(4,4-Dimethylpiperidin-1-yl)benzoyl]piperazin-1-yl]-3H-quinazolin-4-one;
2-[4-[2-(3,4-Dichlorophenyl)-1,3-benzoxazole-6-carbonyl]piperazin-1-yl]-3H-quinazolin-4-one;
2-[4-[2-(4-Chlorophenyl)-1,3-benzoxazole-6-carbonyl]piperazin-1-yl]-3H-quinazolin-4-one;
2-[4-[4-(2-Azaspiro[3.3]heptan-2-yl)benzoyl]piperazin-1-yl]-3H-quinazolin-4-one;
2-[4-[4-(Azepan-1-yl)benzoyl]piperazin-1-yl]-3H-quinazolin-4-one;
2-[4-[4-(3-Cyclopropyl-1,2,4-oxadiazol-5-yl)benzoyl]piperazin-1-yl]-3H-quinazolin-4-one;
6-[4-(4-Oxo-3H-quinazolin-2-yl)piperazine-1-carbonyl]-2-phenyl-1,3-benzoxazole-4-carbonitrile;
2-[4-[2-(3,4-Difluorophenyl)-1,3-benzoxazole-6-carbonyl]piperazin-1-yl]-3H-quinazolin-4-one;
2-[4-[2-(4-Fluorophenyl)-1,3-benzoxazole-6-carbonyl]piperazin-1-yl]-3H-quinazolin-4-one;
6-Fluoro-2-[4-(2-phenyl-1,3-benzoxazole-6-carbonyl)piperazin-1-yl]-3H-quinazolin-4-one;
7-Fluoro-2-[4-(2-phenyl-1,3-benzoxazole-6-carbonyl)piperazin-1-yl]-3H-quinazolin-4-one;
2-[4-[3-Fluoro-4-[5-(trifluoromethyl)pyridin-3-yl]benzoyl]piperazin-1-yl]-3H-quinazolin-4-one;
2-[4-(2-Methyl-1,3-benzoxazole-6-carbonyl)piperazin-1-yl]-3H-quinazolin-4-one;
2-[4-[2-Phenyl-4-(trifluoromethyl)-1,3-benzoxazole-6-carbonyl]piperazin-1-yl]-3H-quinazolin-4-one;
2-[4-[4-(2,3-Dihydropyrrolo[2,3-b]pyridin-1-yl)benzoyl]piperazin-1-yl]-3H-quinazolin-4-one;
2-[4-[4-[5-(2,2,2-Trifluoroethyl)-1,2,4-oxadiazol-3-yl]benzoyl]piperazin-1-yl]-3H-quinazolin-4-one;
2-[4-[3-Fluoro-4-[3-(trifluoromethoxy)phenyl]benzoyl]piperazin-1-yl]-3H-quinazolin-4-one;
6-Chloro-2-[4-(2-phenyl-1,3-benzoxazole-6-carbonyl)piperazin-1-yl]-3H-quinazolin-4-one;
N-[2-[4-[4-(1-oxo-2H-isoquinolin-3-yl)piperazine-1-carbonyl]phenyl]ethyl]-N-methyl]acetamide;
2-[4-[2-(3-Methylpyrrolidin-1-yl)-1,3-benzoxazole-6-carbonyl]piperazin-1-yl]-3H-quinazolin-4-one;
2-[4-[4-[3-(1-Hydroxyethyl)pyrrolidin-1-yl]benzoyl]piperazin-1-yl]-3H-quinazolin-4-one;
2-[4-[4-(5-Azaspiro[2.4]heptan-5-yl)benzoyl]piperazin-1-yl]-3H-quinazolin-4-one;
2-[4-[3-Chloro-4-[(4-chloropyridin-2-yl)methoxy]benzoyl]piperazin-1-yl]-3H-quinazolin-4-one;
2-[4-[3-Chloro-4-[(3-Chlorophenoxy)methyl]benzoyl]piperazin-1-yl]-3H-quinazolin-4-one;
2-[4-(2-Phenyl-1,3-benzothiazole-6-carbonyl)piperazin-1-yl]-3H-quinazolin-4-one;
2-[4-[4-[5-(1-Methylcyclopropyl)-1,2,4-oxadiazol-3-yl]benzoyl]piperazin-1-yl]-3H-quinazolin-4-one;
2-[4-[4-[5-(1-Fluoro-2-methylpropan-2-yl)-1,2,4-oxadiazol-3-yl]benzoyl]piperazin-1-yl]-3H-quinazolin-4-one;
2-Chloro-4-[6-[4-(4-oxo-3H-quinazolin-2-yl)piperazine-1-carbonyl]-1,3-benzoxazol-2-yl]benzonitrile;
2-[4-[4-(5-tert-Butyl-1,2,4-oxadiazol-3-yl)benzoyl]piperazin-1-yl]-6-chloro-3H-quinazolin-4-one;
2-[4-[4-(3,3-Dimethylpyrrolidin-1-yl)benzoyl]piperazin-1-yl]-3H-quinazolin-4-one;
2-[4-[2-(2-Azaspiro[3.3]heptan-2-yl)-1,3-benzoxazole-6-carbonyl]piperazin-1-yl]-3H-quinazolin-4-one;
2-[4-[2-(3-Fluoro-3-methylpyrrolidin-1-yl)-1,3-benzoxazole-6-carbonyl]piperazin-1-yl]-3H-quinazolin-4-one;
2-[4-[2-[3-(2-Hydroxypropan-2-yl)pyrrolidin-1-yl]-1,3-benzoxazole-6-carbonyl]piperazin-1-yl]-3H-quinazolin-4-one;
2-[4-[2-(6-Azaspiro[3.4]octan-6-yl)-1,3-benzoxazole-6-carbonyl]piperazin-1-yl]-3H-quinazolin-4-one;
2-[4-[4-(3,3-Diethylpyrrolidin-1-yl)benzoyl]piperazin-1-yl]-3H-quinazolin-4-one;

2-[4-[4-(3-tert-Butyl-1,2,4-oxadiazol-5-yl)benzoyl]piperazin-1-yl]-3H-quinazolin-4-one; and
2-[4-[2-(6,6-Difluoro-2-azaspiro[3.3]heptan-2-yl)-1,3-benzoxazole-6-carbonyl]piperazin-1-yl]-3H-quinazolin-4-one;

or a pharmaceutically acceptable salt thereof.

27. The compound of claim 25, selected from the group consisting of:
2-[4-[2-(3-Chlorophenyl)-1,3-benzoxazole-6-carbonyl]piperazin-1-yl]-3H-quinazolin-4-one;
2-[4-[2-[3-(Trifluoromethyl)phenyl]-1,3-benzoxazole-6-carbonyl]piperazin-1-yl]-3H-quinazolin-4-one;
2-[4-[4-[5-(2,2-Dimethylpropyl)-1,2,4-oxadiazol-3-yl]benzoyl]piperazin-1-yl]-3H-quinazolin-4-one;
2-[4-[4-(5-tert-Butyl-1,2,4-oxadiazol-3-yl)benzoyl]piperazin-1-yl]-3H-quinazolin-4-one;
2-[4-[3-[5-(2,2-Dimethylpropyl)-1,2,4-oxadiazol-3-yl]benzoyl]piperazin-1-yl]-3H-quinazolin-4-one;
2-[4-[4-(2-Azaspiro[3.4]octan-2-yl)benzoyl]piperazin-1-yl]-3H-quinazolin-4-one;
2-[4-(4-Morpholin-4-yl-2-phenyl-1,3-benzoxazole-6-carbonyl)piperazin-1-yl]-3H-quinazolin-4-one;
2-[4-[2-(2-Azaspiro[3.4]octan-2-yl)-1,3-benzoxazole-6-carbonyl]piperazin-1-yl]-3H-quinazolin-4-one;
2-[4-[2-(7,7-Difluoro-2-azaspiro[3.3]heptan-2-yl)-1,3-benzoxazole-6-carbonyl]piperazin-1-yl]-3H-quinazolin-4-one;
2-[4-[2-[Methyl(propyl)amino]-1,3-benzoxazole-6-carbonyl]piperazin-1-yl]-3H-quinazolin-4-one;
2-[4-[4-(6-Azaspiro[3.4]octan-6-yl)benzoyl]piperazin-1-yl]-3H-quinazolin-4-one;
2-[4-[4-(3-tert-Butyl-1,2,4-oxadiazol-5-yl)benzoyl]piperazin-1-yl]-3H-quinazolin-4-one; and
2-[4-[2-(6,6-Difluoro-2-azaspiro[3.3]heptan-2-yl)-1,3-benzoxazole-6-carbonyl]piperazin-1-yl]-3H-quinazolin-4-one;

or a pharmaceutically acceptable salt thereof.

28. A process of manufacturing a compound according claim 1, or a pharmaceutically acceptable salt thereof, the process comprising:
a) reacting an amine 1, wherein $R^2$, X, $Y^1$ and $Y^2$ are as defined for Formula (I),

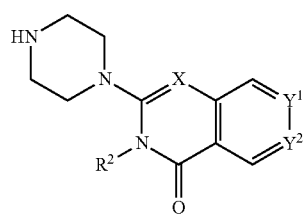

1 with an acid 2, wherein $R^1$ is as defined for Formula (I),

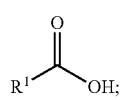

2 or
b) reacting an amine 1, wherein $R^2$, X, $Y^1$ and $Y^2$ are as defined for Formula (I),

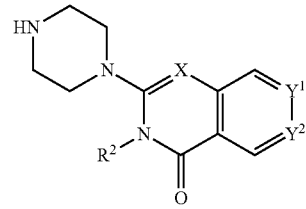

1 with an acid chloride 2a, wherein $R^1$ is as defined for Formula (I),

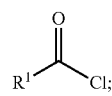

2a or
c) reacting a compound of formula 3, wherein $R^2$, X, $Y^1$ and $Y^2$ are as defined for Formula (I),

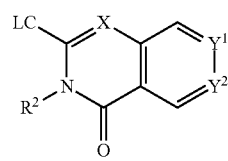

3 with a piperazine derivative 4, wherein $R^1$ is as defined for Formula (I),

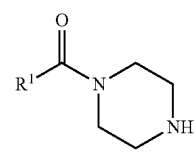

4 to form said compound of Formula (I), or a pharmaceutically acceptable salt thereof.

29. A compound according to claim 1, or a pharmaceutically acceptable salt thereof, wherein the compound is manufactured according to a process comprising:
a) reacting an amine 1, wherein $R^2$, X, $Y^1$ and $Y^2$ are as defined for Formula (I),

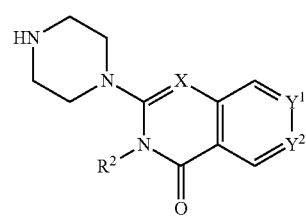

1 with an acid 2, wherein $R^1$ is as defined for Formula (I),

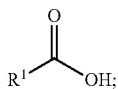

2 or b) reacting an amine 1, wherein $R^2$, X, $Y^1$ and $Y^2$ are as defined for Formula (I),

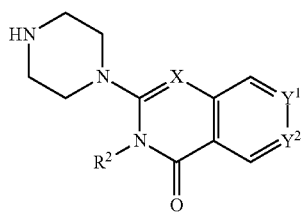

1 with an acid chloride 2a, wherein $R^1$ is as defined for Formula (I),

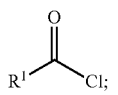

2a or c) reacting a compound of formula 3, wherein $R^2$, X, $Y^1$ and $Y^2$ are as defined for Formula (I),

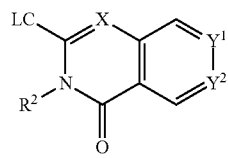

3 with a piperazine derivative 4, wherein $R^1$ is as defined for Formula (I),

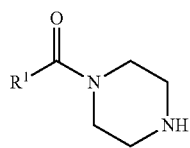

4 to form said compound of Formula (I), or a pharmaceutically acceptable salt thereof.

30. The compound according to claim 1, or a pharmaceutically acceptable salt thereof, wherein said compound or pharmaceutically acceptable salt thereof has an $IC_{50}$ for monoacylglycerol lipase below 10 µM as measured in an assay comprising the steps of:
a) providing a solution of the compound or pharmaceutically acceptable salt thereof in DMSO;
b) providing a solution of monoacylglycerol lipase (recombinant wild-type) in assay buffer (50 mM tris(hydroxymethyl)aminomethane; 1 mM ethylenediaminetetraacetic acid);
c) adding 1 µL of compound solution from step a) to 19 µL of monoacylglycerol lipase solution from step b);
d) shaking the mixture for 1 min at 2000 rpm;
e) incubating for 15 min at RT;
f) adding 20 µL of a solution of 4-nitrophenlyacetate in assay buffer (50 mM tris(hydroxymethyl)aminomethane; 1 mM ethylenediaminetetraacetic acid, 6% EtOH);
g) shaking the mixture for 1 min at 2000 rpm;
h) incubating for 5 min at RT;
i) measuring the absorbance of the mixture at 405 nm a first time;
j) incubating a further 80 min at RT;
k) measuring the absorbance of the mixture at 405 nm a second time;
l) subtracting the absorbance measured under i) from the absorbance measured under k) and calculating the slope of absorbance;
wherein:
i) the concentration of the compound or pharmaceutically acceptable salt thereof in the assay after step f) is in the range of 25 µM to 1.7 nM;
ii) the concentration of monoacylglycerol lipase in the assay after step f) is 1 nM;
iii) the concentration of 4-nitrophenylacetate in the assay after step f) is 300 µM; and
iv) steps a) to l) are repeated for at least 3 times, each time with a different concentration of the compound or pharmaceutically acceptable salt thereof in the assay.

31. A pharmaceutical composition, comprising a compound of claim 1, or a pharmaceutically acceptable salt thereof, and a pharmaceutically acceptable excipient.

32. A pharmaceutical composition, comprising a compound of claim 25, or a pharmaceutically acceptable salt thereof, and a pharmaceutically acceptable excipient.

33. A method for inhibiting monoacylglycerol lipase in a mammal, the method comprising administering to the mammal an effective amount of a compound of claim 1, or a pharmaceutically acceptable salt thereof.

34. A method for inhibiting monoacylglycerol lipase in a mammal, the method comprising administering to the mammal an effective amount of a compound of claim 25, or a pharmaceutically acceptable salt thereof.

35. A method for the treatment of a condition in a mammal, wherein the condition is neuroinflammation, a neurodegenerative disease, pain, cancer, or a mental disorder, or any combination thereof, the method comprising administering to the mammal an effective amount of a compound of claim 1, or a pharmaceutically acceptable salt thereof.

36. A method for the treatment of a condition in a mammal, wherein the condition is neuroinflammation, a neurodegenerative disease, pain, cancer, or a mental disorder, or any combination thereof, the method comprising administering to the mammal an effective amount of a compound of claim 25, or a pharmaceutically acceptable salt thereof.

37. A method for the treatment of a condition in a mammal, wherein the condition is multiple sclerosis, Alzheimer's disease, Parkinson's disease, amyotrophic lateral sclerosis, traumatic brain injury, neurotoxicity, stroke, epilepsy, anxiety, migraine, depression, cancer, or pain, or any combination thereof, the method comprising administering to the mammal an effective amount of a compound of claim 1, or a pharmaceutically acceptable salt thereof.

38. A method for the treatment of a condition in a mammal, wherein the condition is multiple sclerosis, Alzheimer's disease, Parkinson's disease, amyotrophic lateral sclerosis, traumatic brain injury, neurotoxicity, stroke, epilepsy, anxiety, migraine, depression, cancer, or pain, or any combination thereof, the method comprising administering to the mammal an effective amount of a compound of claim 25, or a pharmaceutically acceptable salt thereof.

\* \* \* \* \*